US011203768B2

(12) United States Patent
Uchida et al.

(10) Patent No.: US 11,203,768 B2
(45) Date of Patent: Dec. 21, 2021

(54) LENTIVIRAL PROTEIN DELIVERY SYSTEM FOR RNA-GUIDED GENOME EDITING

(71) Applicant: The United States of America, as represented by the Secretary, Department of Health and Human Services, Bethesda, MD (US)

(72) Inventors: Naoya Uchida, Rockville, MD (US); Juan J. Haro Mora, Washington, DC (US); John F. Tisdale, Washington, DC (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 28 days.

(21) Appl. No.: 15/942,673

(22) Filed: Apr. 2, 2018

(65) Prior Publication Data

US 2018/0223313 A1    Aug. 9, 2018

Related U.S. Application Data

(63) Continuation of application No. PCT/US2016/054759, filed on Sep. 30, 2016.

(60) Provisional application No. 62/236,223, filed on Oct. 2, 2015.

(51) Int. Cl.
| | |
|---|---|
| *C12N 15/86* | (2006.01) |
| *C12N 9/22* | (2006.01) |
| *C12Q 1/68* | (2018.01) |
| *C07K 7/64* | (2006.01) |
| *C12N 15/90* | (2006.01) |
| *C12N 15/10* | (2006.01) |
| *C07K 14/155* | (2006.01) |
| *C07K 14/47* | (2006.01) |
| *C12N 9/90* | (2006.01) |
| *C12N 15/11* | (2006.01) |

(52) U.S. Cl.
CPC ............ *C12N 15/86* (2013.01); *C07K 7/645* (2013.01); *C07K 14/155* (2013.01); *C07K 14/4717* (2013.01); *C12N 9/22* (2013.01); *C12N 9/90* (2013.01); *C12N 15/102* (2013.01); *C12N 15/11* (2013.01); *C12N 15/907* (2013.01); *C12Y 502/01008* (2013.01); *C07K 2319/00* (2013.01); *C12N 2310/20* (2017.05); *C12N 2740/15011* (2013.01); *C12N 2740/15023* (2013.01); *C12N 2740/15032* (2013.01); *C12N 2740/15041* (2013.01); *C12N 2740/15042* (2013.01); *C12N 2740/15043* (2013.01); *C12N 2740/16011* (2013.01); *C12N 2740/16023* (2013.01); *C12N 2740/16031* (2013.01); *C12N 2740/16041* (2013.01); *C12N 2740/16043* (2013.01); *C12N 2800/80* (2013.01)

(58) Field of Classification Search
CPC ............ C12N 15/86; C12N 9/22; C12Q 1/68
See application file for complete search history.

(56) References Cited

U.S. PATENT DOCUMENTS

| | | | |
|---|---|---|---|
| 5,861,488 A | 1/1999 | LeBoulch et al. | |
| 8,697,359 B1 | 4/2014 | Zhang | |
| 8,771,945 B1 | 7/2014 | Zhang | |
| 8,895,308 B1 | 11/2014 | Zhang et al. | |
| 8,945,839 B2 | 2/2015 | Zhang | |
| 9,855,297 B2 * | 1/2018 | Duchateau | ............ C12N 5/0637 |
| 11,078,483 B1 * | 8/2021 | Kryukov | ............ C12N 15/1082 |
| 11,078,495 B2 * | 8/2021 | Kafri | .................... C12N 15/113 |
| 2012/0272348 A1 | 10/2012 | Danos et al. | |
| 2014/0068797 A1 | 3/2014 | Doudna et al. | |
| 2017/0296630 A1 | 10/2017 | Uchida et al. | |
| 2021/0230638 A1 * | 7/2021 | Aupepin De Lamothe-Dreuzy | ................ C12N 15/113 |

FOREIGN PATENT DOCUMENTS

| | | |
|---|---|---|
| WO | WO 2011/007193 A1 | 1/2011 |
| WO | WO 2014/191128 A1 | 12/2014 |
| WO | WO 2016/039933 A1 | 3/2016 |

OTHER PUBLICATIONS

Skipper et al. Human Gene Therapy, vol. 26, No. 8, pp. 487-497 (Year: 2015).*
Blasco et al., Simple and Rapid In Vivo Generation of Chromosomal Rearrangements using CRISPR/Cas9 Technology. Cell Reports 9: 1219-1227 (Year: 2014).*
Choi et al., Lentivirus pre-packed with Cas9 protein for safer gene editing. Gene Therapy 23 : 627 (Year: 2016).*

(Continued)

*Primary Examiner* — Ethan C Whisenant

(74) *Attorney, Agent, or Firm* — Leydig, Voit & Mayer, Ltd.

(57) ABSTRACT

The invention is directed to a system comprising a lentivirus vector particle which encodes at least one guide RNA sequence that is complementary to a first DNA sequence in a host cell genome, a Cas9 protein, and optionally a donor nucleic acid molecule comprising a second DNA sequence. The invention also is directed to a method of altering a DNA sequence in a host cell using such a system, where the host cell can be in a human and the altered DNA can be of the human β-globin gene. The invention also is directed to a fusion protein comprising a Cas9 protein and a cyclophilin A (CypA) protein. The invention also is directed to sequences of vectors that can be used in the system and method.

20 Claims, 21 Drawing Sheets

Specification includes a Sequence Listing.

(56) References Cited

OTHER PUBLICATIONS

Navarro-Guerrero et al., Genome-wide CRISPR/Cas9-knockout in human induced Pluripotent Stem Cell (iPSC)-derived macrophages. Scientific Reports 11: 4245 (Year: 2021).*
Platt et al., CRISPR-Cas9 Knockin Mice for Genome Editing and Cancer Modeling. Cell 159 :440-455 (Year: 2014).*
Xie et al., Seamless gene correction of b-thalassemia mutations in patient-specific iPSCs using CRISPR/Cas9 and piggyBac.Genome Research 24 : 1526-1533 (Year: 2014).*
U.S. Appl. No. 15/510,014, filed Mar. 9, 2017.
Wang et al., "CCR5 gene disruption via lentiviral vectors expressing Cas9 and single guided RNA renders cells resistant to HIV-1 infection," PLoS One, 9(12), 26 pp., (Dec. 26, 2014).
Song et al., "Improved Hematopoietic Differentiation Efficiency of Gene-Corrected Beta-Thalassemia Induced Pluripotent Stem Cells by CRISPR/Cas9 System," Stem Cells and Development, 24(9): 1053-1065 (2015).
Xu et al., "Both TALENs and CRISPR/Cas$_9$ Directly Target the HBB IVS$_2$-6$_{54}$ (C>T) Mutation in β-thalassemia-derived iPSCs," Scientific Reports, 5(1): 1-12 (published Jul. 9, 2015).
U.S. Appl. No. 62/048,881, Uchida et al., filed Sep. 11, 2014.
"Sangamo BioSciences Announces FDA Acceptance of IND to Initiate Clinical Trial of its Novel ZFP Therapeutic® for Beta-Thalassemia," Sangamo Biosciences, 2 pp. (2015).
Abrahimi et al., "Efficient Gene Disruption in Cultured Primary Human Endothelial Cells by CRISPR/Cas9," Circulation Research, 117(2), 121-128 (2015).
Aubrey et al., "An Inducible Lentiviral Guide RNA Platform Enables the Identification of Tumor-Essential Genes and Tumor-Promoting Mutations In Vivo," Cell Reports, 10, 1422-1432 (2015).
Bhaya et al., "CRISPR-Cas systems in bacteria and archaea: versatile small RNAs for adaptive defense and regulation," Annu Rev Genet, 45, 273-297 (2011).
Cai et al., "Targeted genome editing by lentiviral protein transduction of zinc-finger and TAL-effector nucleases," eLife, 3:01911, 19 pp. (2014).
Chan et al., "Lentiviral Gene Therapy Against Human Immunodeficiency Virus Type 1, Using a Novel Human TRIM21-Cyclophilin A Restriction Factor," Human Gene Therapy, 23, 1176-1185 (2012).
Cong et al., "Multiplex Genome Engineering Using CRISPR/Cas Systems," Science, 339, 819-823 (2013).
Cradick et al., "CRISPR/Cas9 systems targeting β-globin and CCR5 genes have substantial off-target activity," Nucleic Acids Res., 41(20), 9584-9592 (2013).
Deveau et al., "CRISPR/Cas system and its role in phage-bacteria interactions," Annu Rev Microbiol, 64, 475-493 (2010).
Donello et al., "Woodchuck hepatitis virus contains a tripartite posttranscriptional regulatory element," J Virol, 72(6), 5085-5092 (1998).
Forrester et al., "A developmentally stable chromatin structure in the human beta-globin gene cluster," Proc Natl Acad Sci USA, 83(5), 1359-1363 (1986).
Garneau et al., "The CRISPR/Cas bacterial immune system cleaves bacteriophage and plasmid DNA," Nature, 468(7320), 67-71 (2010).
Gasiunas et al., "Cas9-crRNA ribonucleoprotein complex mediates specific DNA cleavage for adaptive immunity in bacteria," Proc Natl Acad Sci USA, 109(39), E2579-E2586 (2012).
Goomer et al., "The transcriptional start site for a human U6 small nuclear RNA gene is dictated by a compound promoter element consisting of the PSE and the TATA box," Nucleic Acids Res., 20(18), 4903-4912 (1992).
Haft et al., "A guild of 45 CRISPR-associated (Cas) protein families and multiple CRISPR/Cas subtypes exist in prokaryotic genomes," PLoS Comput Biol, 1(6), 10 pp. (2005).
Hanawa et al., "Comparison of Various Envelope Proteins for Their Ability to Pseudotype Lentiviral Vectors and Transduce Primitive Hematopoietic Cells from Human Blood," Molecular Therapy, 5(3), 242-251 (2002).

Hardison et al., "Locus control regions of mammalian beta-globin gene clusters: combining phylogenetic analyses and experimental results to gain functional insights," Gene, 205(1-2), 73-94 (1997).
Hargrove et al., "Globin Lentiviral Vector Insertions Can Perturb the Expression of Endogenous Genes in β-thalassemic Hematopoietic Cells," Mol Ther, 16(3), 525-533 (2008).
He et al., "Lentiviral protein delivery of meganucleases in human cells mediates gene targeting and alleviates toxicity," Gene Therapy, 21(8), 759-766 (2014).
Horvath et al., "CRISPR/Cas, the immune system of bacteria and archaea," Science, 327(5962), 167-170 (2010).
Huang et al., "Production of Gene-Corrected Adult Beta Globin Protein in Human Erythrocytes Differentiated from Patient iPSCs After Genome Editing of the Sickle Point Mutation," Stem Cells, 33(5), 1470-1479 (2015).
International Preliminary Report on Patentability, Application No. PCT/US2016/054759, dated Apr. 12, 2018, 13 pp.
International Search Report, Application No. PCT/US2016/054759, dated Feb. 1, 2017, 13 pp.
Izmiryan et al., "Efficient gene targeting mediated by a lentiviral vector-associated meganuclease," Nucleic Acids Res., 39(17), 7610-7619 (2011).
Jackson et al., "Beta-globin locus control region HS2 and HS3 interact structurally and functionally," Nucleic Acids Res., 31(4), 1180-1190 (2003).
Jinek et al., "A programmable dual-RNA-guided DNA endonuclease in adaptive bacterial immunity," Science, 337(6096), 816-821 (2012).
Kabadi et al., "Multiplex CRISPR/Cas9-based genome engineering from a single lentiviral vector," Nucleic Acids Research, 42(19), 11 pp. (2014).
Levasseur et al., "A recombinant human hemoglobin with anti-sickling properties greater than fetal hemoglobin," J Biol Chem, 279(26), 27518-27524 (2004).
Li et al., "Locus control regions," Blood, 100(9), 3077-3086 (2002).
Li et al., "Locus control regions: coming of age at a decade plus," Trends Genet, 15(10), 403-408 (1999).
Logan et al., "Advances in lentiviral vector design for gene-modification of hematopoietic stem cells," Curr Opin Biotechnol, 13(5), 429-436 (2002).
Luban et al., "Human immunodeficiency virus type 1 Gag protein binds to cyclophilins A and B," Cell, 73(6), 1067-1078 (1993).
Ma et al., "Pol III Promoters to Express Small RNAs: Delineation of Transcription Initiation," Mol Ther Nucleic Acids, 6, 11 pp. (2014).
Makarova et al., "Evolution and classification of the CRISPR-Cas systems," Nat Rev Microbiol, 9(6), 467-477 (2011).
Mali et al., "Cas9 as a versatile tool for engineering biology," Nat. Methods, 70(10), 957-963 (2013).
Mascarenhas et al., "The capsid protein of human immunodeficiency virus: interactions of HIV-1 capsid with host protein factors," FEBS J., 276(21), 6118-6127 (2009).
Matrai et al., "Recent advances in lentiviral vector development and applications," Molecular Therapy, 18(3), 477-490 (2010).
Myslinski et al., "An unusually compact external promoter for RNA polymerase III transcription of the human H1RNA gene," Nucleic Acids Research, 29(12), 2502-2509 (2001).
Naldini et al., "In vivo gene delivery and stable transduction of nondividing cells by a lentiviral vector," Science, 272(5259), 263-267 (1996).
Neagu et al., "Potent inhibition of HIV-1 by TRIM5-cyclophilin fusion proteins engineered from human components," J. Clin. Invest, 179(10), 3035-3047 (2009).
Nigro et al., "Cyclophilin A: a key player for human disease," Cell Death and Disease, 4, 10pp. (2013).
Oh et al., "Expression of an anti-sickling beta-globin in human erythroblasts derived from retrovirally transduced primitive normal and sickle cell disease hematopoietic cells," Exp Hematol, 32(5), 461-469 (2004).
Persons et al., "The degree of phenotypic correction of murine beta-thalassemia intermedia following lentiviral-mediated transfer of a human gamma-globin gene is influenced by chromosomal position effects and vector copy number," Blood, 101(6), 2175-2183 (2003).

(56) References Cited

OTHER PUBLICATIONS

Popplewell et al., "Gene Correction of a Duchenne Muscular Dystrophy Mutation by Meganuclease-Enhanced Exon Knock-In," *Human Gene Therapy*, 24, 692-701 (2013).
Qing et al., "Cyclophilin A associates with enterovirus-71 virus capsid and plays an essential role in viral infection as an uncoating regulator," *PLoS Pathog*, 10(10), 15 pp. (2014).
Reik et al., "The locus control region is necessary for gene expression in the human beta-globin locus but not the maintenance of an open chromatin structure in erythroid cells," *Mol Cell Biol*, 18(10), 5992-6000 (1998).
Reyon et al., "FLASH assembly of TALENs for high-throughput genome editing," *Nat. Biotechnol.*, 30(5), 460-465 (2012).
Romero et al., "β-globin gene transfer to human bone marrow for sickle cell disease," *J. Clin. Invest.*, 123(8), 3317-3330 (2013).
Sander et al., "CRISPR-Cas systems for editing, regulating and targeting genomes," *Nat. Biotechnol.*, 32(4), 347-355 (2014).
Sander et al., "Selection-free zinc-finger-nuclease engineering by context-dependent assembly (CoDA)," *Nature Methods*, 8(1), 67-69 (2011).
Sankaran et al., "Human fetal hemoglobin expression is regulated by the developmental stage-specific repressor BCL11A," *Science*, 322(5909), 1839-1842 (2008).
Sarkis et al., "Non-Integrating Lentiviral Vectors," *Current Gene Therapy*, 8(6), 430-438 (2008).
Schmidt et al., "CRISPR genome engineering and viral gene delivery: a case of mutual attraction," *Biotechnol. J.*, 10(2), 258-272 (2015).
Smith et al., "Efficient and Allele-Specific Genome Editing of Disease Loci in Human iPSCs," *Molecular Therapy*, 23(3), 570-577 (2015).
Steinberg et al., "Genetic modifiers of sickle cell disease," *Am J Hematol*, 87(8), 795-803 (2012).
Stoddard, "Homing endonuclease structure and function," *Q Rev Biophys*, 38(1), 49-95 (2005).
Terns et al., "CRISPR-based adaptive immune systems," *Curr Opin Microbiol*, 14(3), 321-327 (2011).
Thomas et al., "Efficient Transduction of Hematopoietic Stem Cells and Its Potential for Gene Correction of Hematopoietic Diseases," *Methods in Molecular Biology*, 1114, 441-450 (2014).
Tuan et al., "The 'beta-like-globin' gene domain in human erythroid cells," *Proc Natl Acad Sci USA*, 82(19), 6384-6388 (1985).
Uchida et al., "Development of a Cas9 Protein Delivery System with Lentiviral Vectors for RNA-Guided Genome Editing," *Molecular Therapy*, 24(Suppl. 1), Abstract (2016).
Vigna et al., "Lentiviral vectors: excellent tools for experimental gene transfer and promising candidates for gene therapy," *J Gene Med*, 2(5), 308-316 (2000).
Voelkel et al., "Protein transduction from retroviral Gag precursors," *Proc Natl Acad Sci USA*, 107(17), 7805-7810 (2010).
Wang et al., "CCR5 gene disruption via lentiviral vectors expressing Cas9 and single guided RNA renders cells resistant to HIV-1 infection," *PLoS One*, 9(12).
Written Opinion of the International Searching Authority, Application No. PCT/US2016/054759, dated Feb. 14, 2017, 11 pp.
Wu et al., "Generation of Healthy Mice from Gene-Corrected Disease-Specific Induced Pluripotent Stem Cells," *PLoS Biology*, 9(7), 14 pp. (2011).
Xiao-Jie et al., "CRISPR-Cas9: a new and promising player in gene therapy," *J. Med. Genet.*, 52(5), 289-296 (2015).
Xie et al., "Seamless gene correction of β-thalassemia mutations in patient-specific iPSCs using CRISPR/Cas9 and *piggyBac*," *Genome Research*, 24(9), 1526-1533 (2014).
Zhang et al., "Efficient construction of sequence-specific TAL effectors for modulating mammalian transcription," *Nat. Biotechnol.*, 29(2), 149-153 (2011).
Zufferey et al., "Woodchuck hepatitis virus posttranscriptional regulatory element enhances expression of transgenes delivered by retroviral vectors," *J Virol*, 73(4), 2886-2892 (1999).

\* cited by examiner

Fig. 1
(1): H1p-gRNA Cas9 vector
(2): U6p-gRNA Cas9 vector
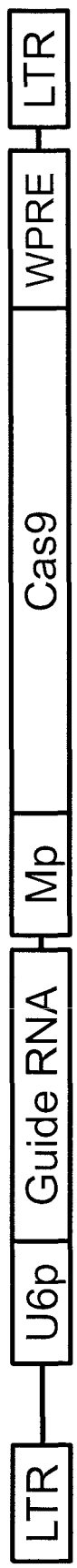
(3): U6p-gRNA Cas9 WPRE vector Fig. 9A
Cas9 protein delivery with guide RNA vector or template vector
(A): All-in-one vector (guide RNA and YFP template vector with packaged Cas9 protein)
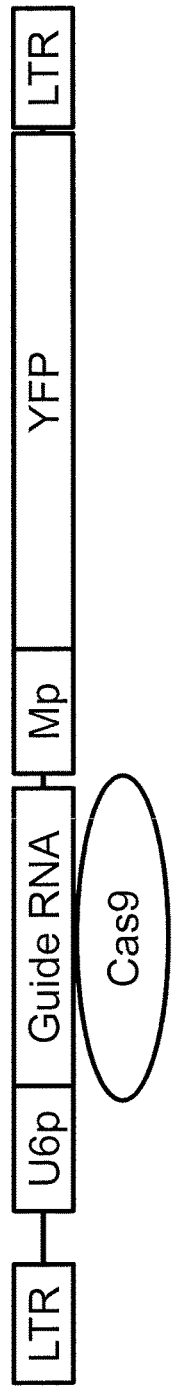
(B): Guide RNA vector and YFP template vector with packaged Cas9 protein
(C): Guide RNA vector with packaged Cas9 protein and YFP template vector
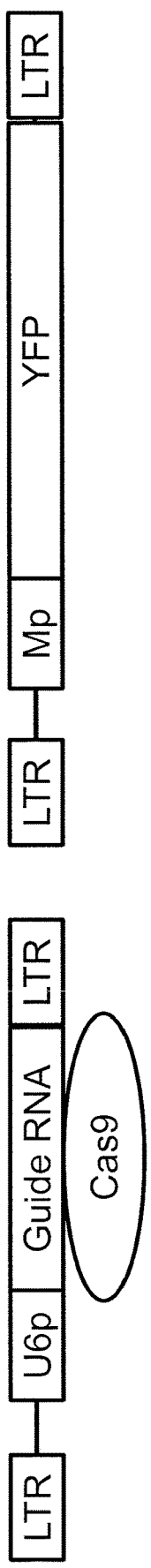

Fig. 9B
Cas9 protein delivery with guide RNA vector or template vector
(D): YFP template vector with packaged Cas9 protein
(E): YFP template vector

Fig. 12
β-globin gene template vector with recombination-specific GFP expression
(a): Recombination-specific GFP-expressing β-globin gene template vector
(b): GFP-expressing β-globin gene template vector

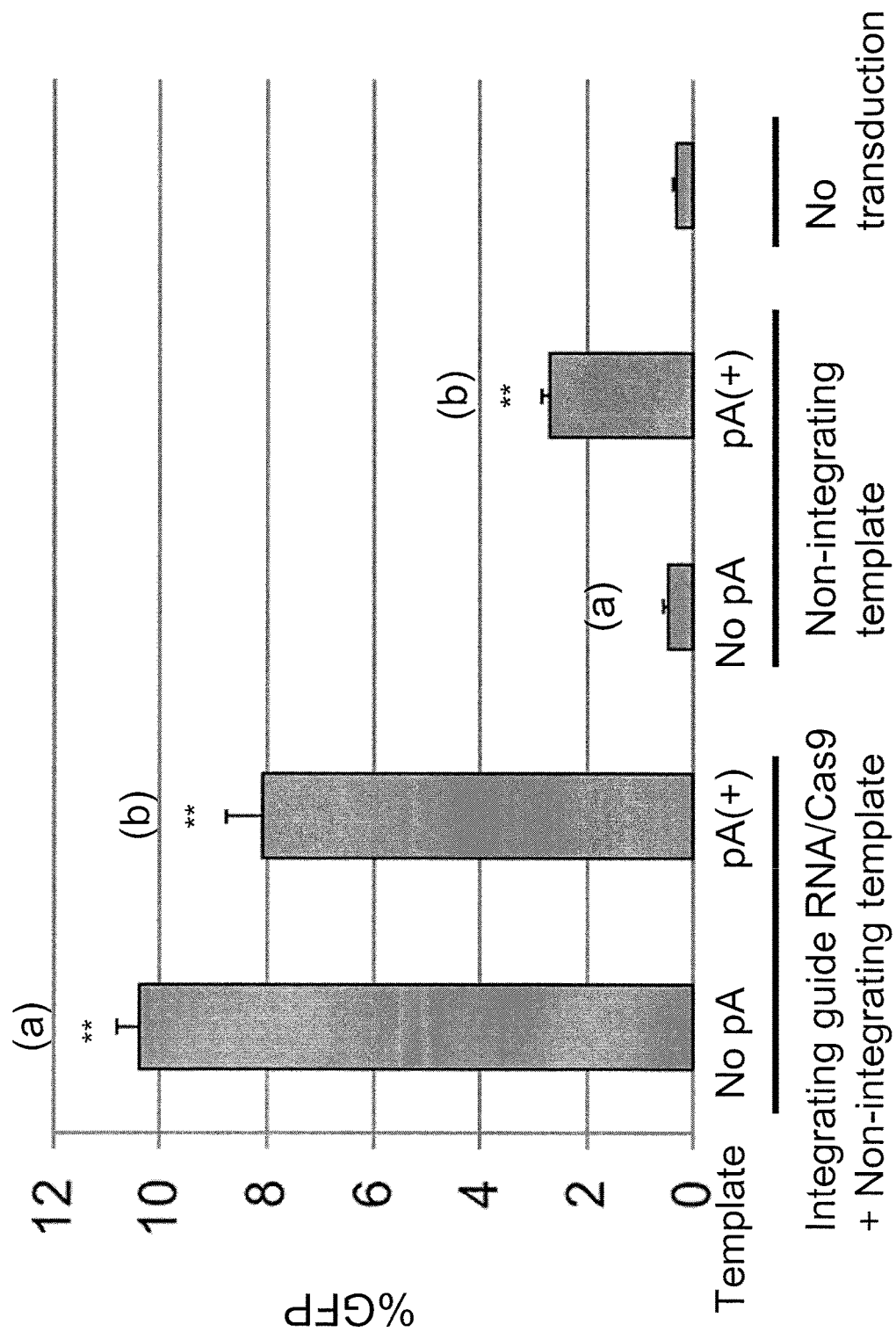

Fig. 14A
Cas9 protein delivery with lentiviral vectors for β-globin genome editing
(I) Integrating vector encoding both guide RNA and Cas9
and
Non-integrating β-globin template vector containing a GFP marker
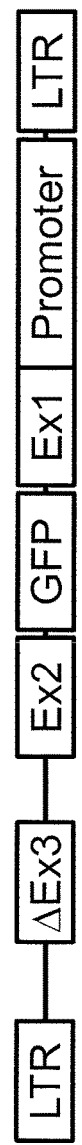
(II): Integrating guide RNA vector with Cas9 protein
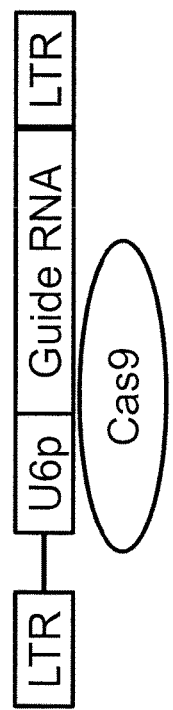
and
Non-integrating β-globin template vector containing a GFP marker
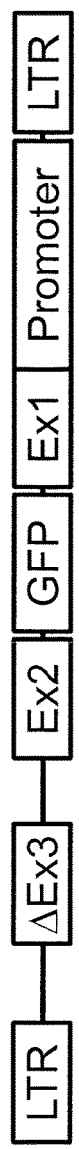

Fig. 14B
Cas9 protein delivery with lentiviral vectors for β-globin genome editing
(III): Non-integrating guide RNA vector with Cas9 protein
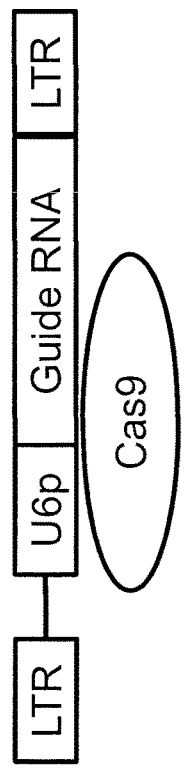
and
Non-integrating β-globin template vector containing a GFP marker
(IV): Non-integrating all-in-one vector (guide RNA and template vector with Cas9 protein)
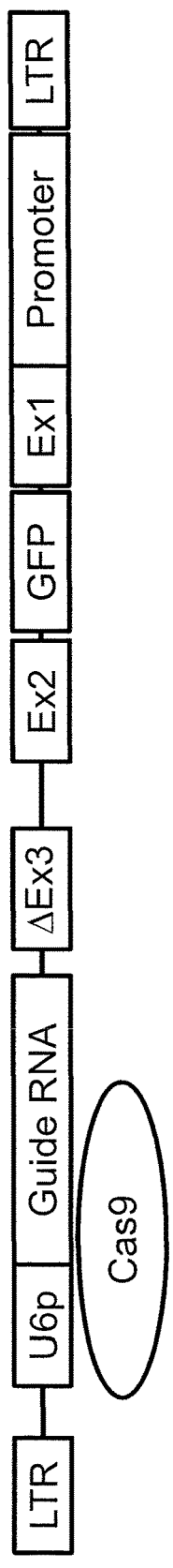

Fig. 16A
(1): All-in-one vector (guide RNA and YFP template vector with packaged Cas9 protein)
(2): 2xgR multiple guide RNA and YFP template vector with packaged Cas9 protein
(3): 4xgR multiple guide RNA and YFP template vector with packaged Cas9 protein Fig. 16B
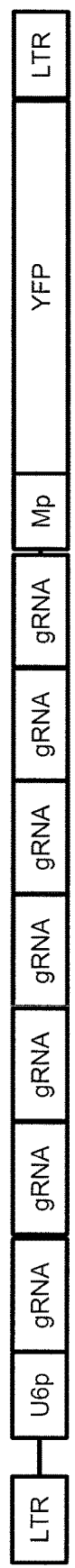
(4): 6xgR multiple guide RNA and YFP template vector with packaged Cas9 protein
(5): 9xgR multiple guide RNA and YFP template vector with packaged Cas9 protein
(6): YFP template vector

SEQUENCE LISTING

<160> NUMBER OF SEQ ID NOS: 39

<210> SEQ ID NO 1
<211> LENGTH: 1423
<212> TYPE: PRT
<213> ORGANISM: Streptococcus pyogenes

<400> SEQUENCE: 1

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Asp Lys Lys Tyr Ser Ile Gly Leu
        35                  40                  45

```
Asp Ile Gly Thr Asn Ser Val Gly Trp Ala Val Ile Thr Asp Glu Tyr
 50                  55                  60
Lys Val Pro Ser Lys Lys Phe Lys Val Leu Gly Asn Thr Asp Arg His
 65                  70                  75                  80
Ser Ile Lys Lys Asn Leu Ile Gly Ala Leu Leu Phe Asp Ser Gly Glu
                 85                  90                  95
Thr Ala Glu Ala Thr Arg Leu Lys Arg Thr Ala Arg Arg Arg Tyr Thr
                100                 105                 110
Arg Arg Lys Asn Arg Ile Cys Tyr Leu Gln Glu Ile Phe Ser Asn Glu
                115                 120                 125
Met Ala Lys Val Asp Asp Ser Phe Phe His Arg Leu Glu Glu Ser Phe
130                 135                 140
Leu Val Glu Glu Asp Lys Lys His Glu Arg His Pro Ile Phe Gly Asn
145                 150                 155                 160
Ile Val Asp Glu Val Ala Tyr His Glu Lys Tyr Pro Thr Ile Tyr His
                165                 170                 175
Leu Arg Lys Lys Leu Val Asp Ser Thr Asp Lys Ala Asp Leu Arg Leu
                180                 185                 190
Ile Tyr Leu Ala Leu Ala His Met Ile Lys Phe Arg Gly His Phe Leu
                195                 200                 205
Ile Glu Gly Asp Leu Asn Pro Asp Asn Ser Asp Val Asp Lys Leu Phe
                210                 215                 220
Ile Gln Leu Val Gln Thr Tyr Asn Gln Leu Phe Glu Glu Asn Pro Ile
225                 230                 235                 240
Asn Ala Ser Gly Val Asp Ala Lys Ala Ile Leu Ser Ala Arg Leu Ser
                245                 250                 255
Lys Ser Arg Arg Leu Glu Asn Leu Ile Ala Gln Leu Pro Gly Glu Lys
                260                 265                 270
Lys Asn Gly Leu Phe Gly Asn Leu Ile Ala Leu Ser Leu Gly Leu Thr
                275                 280                 285
Pro Asn Phe Lys Ser Asn Phe Asp Leu Ala Glu Asp Ala Lys Leu Gln
                290                 295                 300
Leu Ser Lys Asp Thr Tyr Asp Asp Asp Leu Asp Asn Leu Leu Ala Gln
305                 310                 315                 320
Ile Gly Asp Gln Tyr Ala Asp Leu Phe Leu Ala Ala Lys Asn Leu Ser
                325                 330                 335
Asp Ala Ile Leu Leu Ser Asp Ile Leu Arg Val Asn Thr Glu Ile Thr
                340                 345                 350
Lys Ala Pro Leu Ser Ala Ser Met Ile Lys Arg Tyr Asp Glu His His
                355                 360                 365
Gln Asp Leu Thr Leu Leu Lys Ala Leu Val Arg Gln Gln Leu Pro Glu
                370                 375                 380
Lys Tyr Lys Glu Ile Phe Phe Asp Gln Ser Lys Asn Gly Tyr Ala Gly
385                 390                 395                 400
Tyr Ile Asp Gly Gly Ala Ser Gln Glu Glu Phe Tyr Lys Phe Ile Lys
                405                 410                 415
Pro Ile Leu Glu Lys Met Asp Gly Thr Glu Glu Leu Leu Val Lys Leu
                420                 425                 430
Asn Arg Glu Asp Leu Leu Arg Lys Gln Arg Thr Phe Asp Asn Gly Ser
                435                 440                 445
Ile Pro His Gln Ile His Leu Gly Glu Leu His Ala Ile Leu Arg Arg
450                 455                 460
Gln Glu Asp Phe Tyr Pro Phe Leu Lys Asp Asn Arg Glu Lys Ile Glu
```

```
            465                 470                 475                 480
Lys Ile Leu Thr Phe Arg Ile Pro Tyr Tyr Val Gly Pro Leu Ala Arg
                    485                 490                 495

Gly Asn Ser Arg Phe Ala Trp Met Thr Arg Lys Ser Glu Glu Thr Ile
                500                 505                 510

Thr Pro Trp Asn Phe Glu Glu Val Asp Lys Gly Ala Ser Ala Gln
            515                 520                 525

Ser Phe Ile Glu Arg Met Thr Asn Phe Asp Lys Asn Leu Pro Asn Glu
            530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
                580                 585                 590

Lys Thr Asn Arg Lys Val Thr Val Lys Gln Leu Lys Glu Asp Tyr Phe
                595                 600                 605

Lys Lys Ile Glu Cys Phe Asp Ser Val Glu Ile Ser Gly Val Glu Asp
            610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
                660                 665                 670

Glu Arg Leu Lys Thr Tyr Ala His Leu Phe Asp Asp Lys Val Met Lys
            675                 680                 685

Gln Leu Lys Arg Arg Arg Tyr Thr Gly Trp Gly Arg Leu Ser Arg Lys
            690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
            755                 760                 765

Ser Pro Ala Ile Lys Lys Gly Ile Leu Gln Thr Val Lys Val Val Asp
            770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
                820                 825                 830

Gln Ile Leu Lys Glu His Pro Val Glu Asn Thr Gln Leu Gln Asn Glu
            835                 840                 845

Lys Leu Tyr Leu Tyr Tyr Leu Gln Asn Gly Arg Asp Met Tyr Val Asp
            850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                885                 890                 895
```

-continued

```
Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
            915                 920                 925

Lys Leu Ile Thr Gln Arg Lys Phe Asp Asn Leu Thr Lys Ala Glu Arg
        930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
            980                 985                 990

Lys Val Ile Thr Leu Lys Ser Lys Leu Val Ser Asp Phe Arg Lys Asp
            995                 1000                1005

Phe Gln Phe Tyr Lys Val Arg Glu Ile Asn Asn Tyr His His Ala
    1010                1015                1020

His Asp Ala Tyr Leu Asn Ala Val Val Gly Thr Ala Leu Ile Lys
    1025                1030                1035

Lys Tyr Pro Lys Leu Glu Ser Glu Phe Val Tyr Gly Asp Tyr Lys
    1040                1045                1050

Val Tyr Asp Val Arg Lys Met Ile Ala Lys Ser Glu Gln Glu Ile
    1055                1060                1065

Gly Lys Ala Thr Ala Lys Tyr Phe Phe Tyr Ser Asn Ile Met Asn
    1070                1075                1080

Phe Phe Lys Thr Glu Ile Thr Leu Ala Asn Gly Glu Ile Arg Lys
    1085                1090                1095

Arg Pro Leu Ile Glu Thr Asn Gly Glu Thr Gly Glu Ile Val Trp
    1100                1105                1110

Asp Lys Gly Arg Asp Phe Ala Thr Val Arg Lys Val Leu Ser Met
    1115                1120                1125

Pro Gln Val Asn Ile Val Lys Lys Thr Glu Val Gln Thr Gly Gly
    1130                1135                1140

Phe Ser Lys Glu Ser Ile Leu Pro Lys Arg Asn Ser Asp Lys Leu
    1145                1150                1155

Ile Ala Arg Lys Lys Asp Trp Asp Pro Lys Lys Tyr Gly Gly Phe
    1160                1165                1170

Asp Ser Pro Thr Val Ala Tyr Ser Val Leu Val Val Ala Lys Val
    1175                1180                1185

Glu Lys Gly Lys Ser Lys Lys Leu Lys Ser Val Lys Glu Leu Leu
    1190                1195                1200

Gly Ile Thr Ile Met Glu Arg Ser Ser Phe Glu Lys Asn Pro Ile
    1205                1210                1215

Asp Phe Leu Glu Ala Lys Gly Tyr Lys Glu Val Lys Lys Asp Leu
    1220                1225                1230

Ile Ile Lys Leu Pro Lys Tyr Ser Leu Phe Glu Leu Glu Asn Gly
    1235                1240                1245

Arg Lys Arg Met Leu Ala Ser Ala Gly Glu Leu Gln Lys Gly Asn
    1250                1255                1260

Glu Leu Ala Leu Pro Ser Lys Tyr Val Asn Phe Leu Tyr Leu Ala
    1265                1270                1275

Ser His Tyr Glu Lys Leu Lys Gly Ser Pro Glu Asp Asn Glu Gln
    1280                1285                1290
```

```
Lys Gln Leu Phe Val Glu Gln His Lys His Tyr Leu Asp Glu Ile
    1295                1300                1305

Ile Glu Gln Ile Ser Glu Phe Ser Lys Arg Val Ile Leu Ala Asp
    1310                1315                1320

Ala Asn Leu Asp Lys Val Leu Ser Ala Tyr Asn Lys His Arg Asp
    1325                1330                1335

Lys Pro Ile Arg Glu Gln Ala Glu Asn Ile Ile His Leu Phe Thr
    1340                1345                1350

Leu Thr Asn Leu Gly Ala Pro Ala Ala Phe Lys Tyr Phe Asp Thr
    1355                1360                1365

Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
    1385                1390                1395

Ile Asp Leu Ser Gln Leu Gly Gly Asp Lys Arg Pro Ala Ala Thr
    1400                1405                1410

Lys Lys Ala Gly Gln Ala Lys Lys Lys Lys
    1415                1420
```

<210> SEQ ID NO 2
<211> LENGTH: 1587
<212> TYPE: PRT
<213> ORGANISM: Artificial Sequence
<220> FEATURE:
<223> OTHER INFORMATION: Synthetic

<400> SEQUENCE: 2

```
Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
                20                  25                  30

Ala Glu Asn Phe Arg Ala Leu Ser Thr Gly Glu Lys Gly Phe Gly Tyr
            35                  40                  45

Lys Gly Ser Cys Phe His Arg Ile Ile Pro Gly Phe Met Cys Gln Gly
        50                  55                  60

Gly Asp Phe Thr Arg His Asn Gly Thr Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu Asp Tyr Lys Asp His Asp Gly Asp Tyr Lys Asp
                165                 170                 175

His Asp Ile Asp Tyr Lys Asp Asp Asp Lys Met Ala Pro Lys Lys
            180                 185                 190

Lys Arg Lys Val Gly Ile His Gly Val Pro Ala Ala Asp Lys Lys Tyr
        195                 200                 205

Ser Ile Gly Leu Asp Ile Gly Thr Asn Ser Val Gly Trp Ala Val Ile
    210                 215                 220
```

```
Thr Asp Glu Tyr Lys Val Pro Ser Lys Lys Phe Lys Val Leu Gly Asn
225                 230                 235                 240

Thr Asp Arg His Ser Ile Lys Lys Asn Leu Ile Gly Ala Leu Leu Phe
            245                 250                 255

Asp Ser Gly Glu Thr Ala Glu Ala Thr Arg Leu Lys Arg Thr Ala Arg
            260                 265                 270

Arg Arg Tyr Thr Arg Arg Lys Asn Arg Ile Cys Tyr Leu Gln Glu Ile
        275                 280                 285

Phe Ser Asn Glu Met Ala Lys Val Asp Asp Ser Phe Phe His Arg Leu
290                 295                 300

Glu Glu Ser Phe Leu Val Glu Glu Asp Lys Lys His Glu Arg His Pro
305                 310                 315                 320

Ile Phe Gly Asn Ile Val Asp Glu Val Ala Tyr His Glu Lys Tyr Pro
                325                 330                 335

Thr Ile Tyr His Leu Arg Lys Lys Leu Val Asp Ser Thr Asp Lys Ala
                340                 345                 350

Asp Leu Arg Leu Ile Tyr Leu Ala Leu Ala His Met Ile Lys Phe Arg
            355                 360                 365

Gly His Phe Leu Ile Glu Gly Asp Leu Asn Pro Asp Asn Ser Asp Val
370                 375                 380

Asp Lys Leu Phe Ile Gln Leu Val Gln Thr Tyr Asn Gln Leu Phe Glu
385                 390                 395                 400

Glu Asn Pro Ile Asn Ala Ser Gly Val Asp Ala Lys Ala Ile Leu Ser
                405                 410                 415

Ala Arg Leu Ser Lys Ser Arg Arg Leu Glu Asn Leu Ile Ala Gln Leu
            420                 425                 430

Pro Gly Glu Lys Lys Asn Gly Leu Phe Gly Asn Leu Ile Ala Leu Ser
            435                 440                 445

Leu Gly Leu Thr Pro Asn Phe Lys Ser Asn Phe Asp Leu Ala Glu Asp
            450                 455                 460

Ala Lys Leu Gln Leu Ser Lys Asp Thr Tyr Asp Asp Asp Leu Asp Asn
465                 470                 475                 480

Leu Leu Ala Gln Ile Gly Asp Gln Tyr Ala Asp Leu Phe Leu Ala Ala
                485                 490                 495

Lys Asn Leu Ser Asp Ala Ile Leu Leu Ser Asp Ile Leu Arg Val Asn
            500                 505                 510

Thr Glu Ile Thr Lys Ala Pro Leu Ser Ala Ser Met Ile Lys Arg Tyr
            515                 520                 525

Asp Glu His His Gln Asp Leu Thr Leu Leu Lys Ala Leu Val Arg Gln
530                 535                 540

Gln Leu Pro Glu Lys Tyr Lys Glu Ile Phe Phe Asp Gln Ser Lys Asn
545                 550                 555                 560

Gly Tyr Ala Gly Tyr Ile Asp Gly Gly Ala Ser Gln Glu Glu Phe Tyr
                565                 570                 575

Lys Phe Ile Lys Pro Ile Leu Glu Lys Met Asp Gly Thr Glu Glu Leu
            580                 585                 590

Leu Val Lys Leu Asn Arg Glu Asp Leu Leu Arg Lys Gln Arg Thr Phe
            595                 600                 605

Asp Asn Gly Ser Ile Pro His Gln Ile His Leu Gly Glu Leu His Ala
            610                 615                 620

Ile Leu Arg Arg Gln Glu Asp Phe Tyr Pro Phe Leu Lys Asp Asn Arg
625                 630                 635                 640

Glu Lys Ile Glu Lys Ile Leu Thr Phe Arg Ile Pro Tyr Tyr Val Gly
```

-continued

```
            645                 650                 655
Pro Leu Ala Arg Gly Asn Ser Arg Phe Ala Trp Met Thr Arg Lys Ser
            660                 665                 670

Glu Glu Thr Ile Thr Pro Trp Asn Phe Glu Glu Val Val Asp Lys Gly
            675                 680                 685

Ala Ser Ala Gln Ser Phe Ile Glu Arg Met Thr Asn Phe Asp Lys Asn
            690                 695                 700

Leu Pro Asn Glu Lys Val Leu Pro Lys His Ser Leu Leu Tyr Glu Tyr
705                 710                 715                 720

Phe Thr Val Tyr Asn Glu Leu Thr Lys Val Lys Tyr Val Thr Glu Gly
                725                 730                 735

Met Arg Lys Pro Ala Phe Leu Ser Gly Glu Gln Lys Lys Ala Ile Val
            740                 745                 750

Asp Leu Leu Phe Lys Thr Asn Arg Lys Val Thr Val Lys Gln Leu Lys
                755                 760                 765

Glu Asp Tyr Phe Lys Lys Ile Glu Cys Phe Asp Ser Val Glu Ile Ser
770                 775                 780

Gly Val Glu Asp Arg Phe Asn Ala Ser Leu Gly Thr Tyr His Asp Leu
785                 790                 795                 800

Leu Lys Ile Ile Lys Asp Lys Asp Phe Leu Asp Asn Glu Glu Asn Glu
                805                 810                 815

Asp Ile Leu Glu Asp Ile Val Leu Thr Leu Thr Leu Phe Glu Asp Arg
                820                 825                 830

Glu Met Ile Glu Glu Arg Leu Lys Thr Tyr Ala His Leu Phe Asp Asp
            835                 840                 845

Lys Val Met Lys Gln Leu Lys Arg Arg Arg Tyr Thr Gly Trp Gly Arg
850                 855                 860

Leu Ser Arg Lys Leu Ile Asn Gly Ile Arg Asp Lys Gln Ser Gly Lys
865                 870                 875                 880

Thr Ile Leu Asp Phe Leu Lys Ser Asp Gly Phe Ala Asn Arg Asn Phe
                885                 890                 895

Met Gln Leu Ile His Asp Asp Ser Leu Thr Phe Lys Glu Asp Ile Gln
            900                 905                 910

Lys Ala Gln Val Ser Gly Gln Gly Asp Ser Leu His Glu His Ile Ala
            915                 920                 925

Asn Leu Ala Gly Ser Pro Ala Ile Lys Lys Gly Ile Leu Gln Thr Val
            930                 935                 940

Lys Val Val Asp Glu Leu Val Lys Val Met Gly Arg His Lys Pro Glu
945                 950                 955                 960

Asn Ile Val Ile Glu Met Ala Arg Glu Asn Gln Thr Thr Gln Lys Gly
                965                 970                 975

Gln Lys Asn Ser Arg Glu Arg Met Lys Arg Ile Glu Glu Gly Ile Lys
            980                 985                 990

Glu Leu Gly Ser Gln Ile Leu Lys  Glu His Pro Val Glu  Asn Thr Gln
            995                 1000                1005

Leu Gln  Asn Glu Lys Leu Tyr  Leu Tyr Tyr Leu Gln  Asn Gly Arg
    1010                1015                1020

Asp Met  Tyr Val Asp Gln Glu  Leu Asp Ile Asn Arg  Leu Ser Asp
    1025                1030                1035

Tyr Asp  Val Asp His Ile Val  Pro Gln Ser Phe Leu  Lys Asp Asp
    1040                1045                1050

Ser Ile  Asp Asn Lys Val Leu  Thr Arg Ser Asp Lys  Asn Arg Gly
    1055                1060                1065
```

```
Lys Ser Asp Asn Val Pro Ser Glu Val Val Lys Lys Met Lys
    1070            1075            1080

Asn Tyr Trp Arg Gln Leu Leu Asn Ala Lys Leu Ile Thr Gln Arg
    1085            1090            1095

Lys Phe Asp Asn Leu Thr Lys Ala Glu Arg Gly Gly Leu Ser Glu
    1100            1105            1110

Leu Asp Lys Ala Gly Phe Ile Lys Arg Gln Leu Val Glu Thr Arg
    1115            1120            1125

Gln Ile Thr Lys His Val Ala Gln Ile Leu Asp Ser Arg Met Asn
    1130            1135            1140

Thr Lys Tyr Asp Glu Asn Asp Lys Leu Ile Arg Glu Val Lys Val
    1145            1150            1155

Ile Thr Leu Lys Ser Lys Leu Val Ser Asp Phe Arg Lys Asp Phe
    1160            1165            1170

Gln Phe Tyr Lys Val Arg Glu Ile Asn Asn Tyr His His Ala His
    1175            1180            1185

Asp Ala Tyr Leu Asn Ala Val Val Gly Thr Ala Leu Ile Lys Lys
    1190            1195            1200

Tyr Pro Lys Leu Glu Ser Glu Phe Val Tyr Gly Asp Tyr Lys Val
    1205            1210            1215

Tyr Asp Val Arg Lys Met Ile Ala Lys Ser Glu Gln Glu Ile Gly
    1220            1225            1230

Lys Ala Thr Ala Lys Tyr Phe Phe Tyr Ser Asn Ile Met Asn Phe
    1235            1240            1245

Phe Lys Thr Glu Ile Thr Leu Ala Asn Gly Glu Ile Arg Lys Arg
    1250            1255            1260

Pro Leu Ile Glu Thr Asn Gly Glu Thr Gly Glu Ile Val Trp Asp
    1265            1270            1275

Lys Gly Arg Asp Phe Ala Thr Val Arg Lys Val Leu Ser Met Pro
    1280            1285            1290

Gln Val Asn Ile Val Lys Lys Thr Glu Val Gln Thr Gly Gly Phe
    1295            1300            1305

Ser Lys Glu Ser Ile Leu Pro Lys Arg Asn Ser Asp Lys Leu Ile
    1310            1315            1320

Ala Arg Lys Lys Asp Trp Asp Pro Lys Lys Tyr Gly Gly Phe Asp
    1325            1330            1335

Ser Pro Thr Val Ala Tyr Ser Val Leu Val Val Ala Lys Val Glu
    1340            1345            1350

Lys Gly Lys Ser Lys Lys Leu Lys Ser Val Lys Glu Leu Leu Gly
    1355            1360            1365

Ile Thr Ile Met Glu Arg Ser Ser Phe Glu Lys Asn Pro Ile Asp
    1370            1375            1380

Phe Leu Glu Ala Lys Gly Tyr Lys Glu Val Lys Lys Asp Leu Ile
    1385            1390            1395

Ile Lys Leu Pro Lys Tyr Ser Leu Phe Glu Leu Glu Asn Gly Arg
    1400            1405            1410

Lys Arg Met Leu Ala Ser Ala Gly Glu Leu Gln Lys Gly Asn Glu
    1415            1420            1425

Leu Ala Leu Pro Ser Lys Tyr Val Asn Phe Leu Tyr Leu Ala Ser
    1430            1435            1440

His Tyr Glu Lys Leu Lys Gly Ser Pro Glu Asp Asn Glu Gln Lys
    1445            1450            1455
```

-continued

Gln Leu Phe Val Glu Gln His Lys His Tyr Leu Asp Glu Ile Ile
1460            1465                1470

Glu Gln Ile Ser Glu Phe Ser Lys Arg Val Ile Leu Ala Asp Ala
1475            1480                1485

Asn Leu Asp Lys Val Leu Ser Ala Tyr Asn Lys His Arg Asp Lys
1490            1495                1500

Pro Ile Arg Glu Gln Ala Glu Asn Ile Ile His Leu Phe Thr Leu
1505            1510                1515

Thr Asn Leu Gly Ala Pro Ala Ala Phe Lys Tyr Phe Asp Thr Thr
1520            1525                1530

Ile Asp Arg Lys Arg Tyr Thr Ser Thr Lys Glu Val Leu Asp Ala
1535            1540                1545

Thr Leu Ile His Gln Ser Ile Thr Gly Leu Tyr Glu Thr Arg Ile
1550            1555                1560

Asp Leu Ser Gln Leu Gly Gly Asp Lys Arg Pro Ala Ala Thr Lys
1565            1570                1575

Lys Ala Gly Gln Ala Lys Lys Lys Lys
1580            1585

<210> SEQ ID NO 3
<211> LENGTH: 1587
<212> TYPE: PRT
<213> ORGANISM: Artificial Sequence
<220> FEATURE:
<223> OTHER INFORMATION: Synthetic

<400> SEQUENCE: 3

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Asp Lys Lys Tyr Ser Ile Gly Leu
            35                  40                  45

Asp Ile Gly Thr Asn Ser Val Gly Trp Ala Val Ile Thr Asp Glu Tyr
50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
        115                 120                 125

Met Ala Lys Val Asp Asp Ser Phe Phe His Arg Leu Glu Glu Ser Phe
130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
            245                 250                 255

Lys Ser Arg Arg Leu Glu Asn Leu Ile Ala Gln Leu Pro Gly Glu Lys
        260                 265                 270

Lys Asn Gly Leu Phe Gly Asn Leu Ile Ala Leu Ser Leu Gly Leu Thr
    275                 280                 285

Pro Asn Phe Lys Ser Asn Phe Asp Leu Ala Glu Asp Ala Lys Leu Gln
290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
            325                 330                 335

Asp Ala Ile Leu Leu Ser Asp Ile Leu Arg Val Asn Thr Glu Ile Thr
        340                 345                 350

Lys Ala Pro Leu Ser Ala Ser Met Ile Lys Arg Tyr Asp Glu His His
    355                 360                 365

Gln Asp Leu Thr Leu Leu Lys Ala Leu Val Arg Gln Gln Leu Pro Glu
370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
            405                 410                 415

Pro Ile Leu Glu Lys Met Asp Gly Thr Glu Glu Leu Leu Val Lys Leu
        420                 425                 430

Asn Arg Glu Asp Leu Leu Arg Lys Gln Arg Thr Phe Asp Asn Gly Ser
    435                 440                 445

Ile Pro His Gln Ile His Leu Gly Glu Leu His Ala Ile Leu Arg Arg
450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
            485                 490                 495

Gly Asn Ser Arg Phe Ala Trp Met Thr Arg Lys Ser Glu Glu Thr Ile
        500                 505                 510

Thr Pro Trp Asn Phe Glu Glu Val Val Asp Lys Gly Ala Ser Ala Gln
    515                 520                 525

Ser Phe Ile Glu Arg Met Thr Asn Phe Asp Lys Asn Leu Pro Asn Glu
530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
            565                 570                 575

Ala Phe Leu Ser Gly Glu Gln Lys Lys Ala Ile Val Asp Leu Leu Phe
        580                 585                 590

Lys Thr Asn Arg Lys Val Thr Val Lys Gln Leu Lys Glu Asp Tyr Phe
    595                 600                 605

Lys Lys Ile Glu Cys Phe Asp Ser Val Glu Ile Ser Gly Val Glu Asp
610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu

-continued

```
                645                 650                 655
Asp Ile Val Leu Thr Leu Thr Leu Phe Glu Asp Arg Glu Met Ile Glu
                660                 665                 670

Glu Arg Leu Lys Thr Tyr Ala His Leu Phe Asp Lys Val Met Lys
                675                 680                 685

Gln Leu Lys Arg Arg Tyr Thr Gly Trp Gly Arg Leu Ser Arg Lys
                690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
                740                 745                 750

Ser Gly Gln Gly Asp Ser Leu His Glu His Ile Ala Asn Leu Ala Gly
                755                 760                 765

Ser Pro Ala Ile Lys Lys Gly Ile Leu Gln Thr Val Lys Val Val Asp
                770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
                820                 825                 830

Gln Ile Leu Lys Glu His Pro Val Glu Asn Thr Gln Leu Gln Asn Glu
                835                 840                 845

Lys Leu Tyr Leu Tyr Tyr Leu Gln Asn Gly Arg Asp Met Tyr Val Asp
                850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                885                 890                 895

Thr Arg Ser Asp Lys Asn Arg Gly Lys Ser Asp Asn Val Pro Ser Glu
                900                 905                 910

Glu Val Val Lys Lys Met Lys Asn Tyr Trp Arg Gln Leu Leu Asn Ala
                915                 920                 925

Lys Leu Ile Thr Gln Arg Lys Phe Asp Asn Leu Thr Lys Ala Glu Arg
930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
                980                 985                 990

Lys Val Ile Thr Leu Lys Ser Lys Leu Val Ser Asp Phe Arg Lys Asp
                995                 1000                1005

Phe Gln Phe Tyr Lys Val Arg Glu Ile Asn Asn Tyr His His Ala
                1010                1015                1020

His Asp Ala Tyr Leu Asn Ala Val Val Gly Thr Ala Leu Ile Lys
                1025                1030                1035

Lys Tyr Pro Lys Leu Glu Ser Glu Phe Val Tyr Gly Asp Tyr Lys
                1040                1045                1050

Val Tyr Asp Val Arg Lys Met Ile Ala Lys Ser Glu Gln Glu Ile
                1055                1060                1065
```

```
Gly Lys Ala Thr Ala Lys Tyr Phe Phe Tyr Ser Asn Ile Met Asn
1070                1075                1080

Phe Phe Lys Thr Glu Ile Thr Leu Ala Asn Gly Glu Ile Arg Lys
1085                1090                1095

Arg Pro Leu Ile Glu Thr Asn Gly Glu Thr Gly Glu Ile Val Trp
1100                1105                1110

Asp Lys Gly Arg Asp Phe Ala Thr Val Arg Lys Val Leu Ser Met
1115                1120                1125

Pro Gln Val Asn Ile Val Lys Lys Thr Glu Val Gln Thr Gly Gly
1130                1135                1140

Phe Ser Lys Glu Ser Ile Leu Pro Lys Arg Asn Ser Asp Lys Leu
1145                1150                1155

Ile Ala Arg Lys Lys Asp Trp Asp Pro Lys Lys Tyr Gly Gly Phe
1160                1165                1170

Asp Ser Pro Thr Val Ala Tyr Ser Val Leu Val Val Ala Lys Val
1175                1180                1185

Glu Lys Gly Lys Ser Lys Lys Leu Lys Ser Val Lys Glu Leu Leu
1190                1195                1200

Gly Ile Thr Ile Met Glu Arg Ser Ser Phe Glu Lys Asn Pro Ile
1205                1210                1215

Asp Phe Leu Glu Ala Lys Gly Tyr Lys Glu Val Lys Lys Asp Leu
1220                1225                1230

Ile Ile Lys Leu Pro Lys Tyr Ser Leu Phe Glu Leu Glu Asn Gly
1235                1240                1245

Arg Lys Arg Met Leu Ala Ser Ala Gly Glu Leu Gln Lys Gly Asn
1250                1255                1260

Glu Leu Ala Leu Pro Ser Lys Tyr Val Asn Phe Leu Tyr Leu Ala
1265                1270                1275

Ser His Tyr Glu Lys Leu Lys Gly Ser Pro Glu Asp Asn Glu Gln
1280                1285                1290

Lys Gln Leu Phe Val Glu Gln His Lys His Tyr Leu Asp Glu Ile
1295                1300                1305

Ile Glu Gln Ile Ser Glu Phe Ser Lys Arg Val Ile Leu Ala Asp
1310                1315                1320

Ala Asn Leu Asp Lys Val Leu Ser Ala Tyr Asn Lys His Arg Asp
1325                1330                1335

Lys Pro Ile Arg Glu Gln Ala Glu Asn Ile Ile His Leu Phe Thr
1340                1345                1350

Leu Thr Asn Leu Gly Ala Pro Ala Ala Phe Lys Tyr Phe Asp Thr
1355                1360                1365

Thr Ile Asp Arg Lys Arg Tyr Thr Ser Thr Lys Glu Val Leu Asp
1370                1375                1380

Ala Thr Leu Ile His Gln Ser Ile Thr Gly Leu Tyr Glu Thr Arg
1385                1390                1395

Ile Asp Leu Ser Gln Leu Gly Gly Asp Lys Arg Pro Ala Ala Thr
1400                1405                1410

Lys Lys Ala Gly Gln Ala Lys Lys Lys Lys Val Asn Pro Thr Val
1415                1420                1425

Phe Phe Asp Ile Ala Val Asp Gly Glu Pro Leu Gly Arg Val Ser
1430                1435                1440

Phe Glu Leu Phe Ala Asp Lys Val Pro Lys Thr Ala Glu Asn Phe
1445                1450                1455
```

```
Arg Ala Leu Ser Thr Gly Glu Lys Gly Phe Gly Tyr Lys Gly Ser
    1460            1465                1470

Cys Phe His Arg Ile Ile Pro Gly Phe Met Cys Gln Gly Gly Asp
    1475            1480                1485

Phe Thr Arg His Asn Gly Thr Gly Gly Lys Ser Ile Tyr Gly Glu
    1490            1495                1500

Lys Phe Glu Asp Glu Asn Phe Ile Leu Lys His Thr Gly Pro Gly
    1505            1510                1515

Ile Leu Ser Met Ala Asn Ala Gly Pro Asn Thr Asn Gly Ser Gln
    1520            1525                1530

Phe Phe Ile Cys Thr Ala Lys Thr Glu Trp Leu Asp Gly Lys His
    1535            1540                1545

Val Val Phe Gly Lys Val Lys Glu Gly Met Asn Ile Val Glu Ala
    1550            1555                1560

Met Glu Arg Phe Gly Ser Arg Asn Gly Lys Thr Ser Lys Lys Ile
    1565            1570                1575

Thr Ile Ala Asp Cys Gly Gln Leu Glu
    1580            1585

<210> SEQ ID NO 4
<211> LENGTH: 81706
<212> TYPE: DNA
<213> ORGANISM: Homo sapiens

<400> SEQUENCE: 4
ggatcctcac atgagttcag tatataattg taacagaata aaaatcaat tatgtattca    60 agttgctagt gtcttaagag gttcacattt ttatctaact gattatcaca aaaatacttc   120
gagttacttt tcattataat tcctgactac acatgaagag actgacacgt aggtgcctta   180
cttaggtagg ttaagtaatt tatccaaaac cacacaatgt agaacctaag ctgattcggc   240
catagaaaca caatatgtgg tataaatgag acagagggat ttctctcctt cctatgctgt   300
cagatgaata ctgagataga atatttagtt catctatcac acattaaacg ggactttaca   360
tttctgtctg ttgaagattt gggtgtgggg ataactcaag gtatcatatc caagggatgg   420
atgaaggcag gtgactctaa cagaaaggga aggatgttg gcaaggctat gttcatgaaa    480
gtatatgtaa aatccacatt aagcttcttt ctgcatgcat tggcaatgtt tatgaataat   540
gtgtatgtaa aagtgtgctg tatattcaaa agtgtttcat gtgcctaggg gtgtcaaata   600
ctttgagttt gtaagtatat acttctctgt aatgtgtctg aatatctcta tttacttgat   660
tctcaataag taggtatcat agtgaacatc tgacaaatgt ttgaggaaca atttagtgtt   720
tacctattca ccaaaattta ttaaatgcct aatctgtatc agatatacaa ttatctggcg   780
aaatctgtaa ttcctaattt aaacagctgt gtagcctaat tagggataaa ggcatgcaaa   840
cccataattt gtgtaggttg aaatgagcta tagaaaaatg cagtatattt atcagaagtc   900
tttagggtca tgaaaaggaa tggtcaactg acactgccag ggactcatat gtaagagata   960
actaatgtga agtgacttta aaggagaaat tagcagaagt tttcttttcca tgtctcctca  1020 tcatgttaca ataacggaag agattaaaac aacaaataca tttagacagc aatgtttatc  1080
ctggttagat gttttaatct aaatctatct tggagtgtta aatgcatttt gctcacctac  1140
tttaaaatat aaatgaaggt aggaacctgt agatacaaaa agttggagaa aaaaagacaa  1200
taaagatgac aaaaatctat taatccttga tagaaaatga gaagagataa aacactggtt  1260
tacataaaga aaataagatg gatagatagc agatccttat aaaagtgata atttgagaaa  1320
```

```
aaaaatactc catattctga gtttcttcac ataaaataat acaaatctgc tgtggtaagt    1380
tacaaagaga tagatttttt atcattatat aaaagatatt ttaaacagag ttatacaaca    1440
aaggaacaga ctatgtcata tattctcact tatcactata aacatctcag aaaaatctgc    1500
aaaatcattt catagcattt taaatagtta ggaataatgt agaaaactga acagttcta     1560 agtttcccac aaacttagag tctcaaatgt tgcattacct aacttacctg caaatatttt    1620
atacaaattt gcacatgcta ctctagtcaa aaatatatgt acattatggg tattttctgt    1680
gtgtaacttg gttctagttg cttctttcag aaatagcctc tattttgat ttacctgata     1740 aaatcacatt cctctccaaa gccttctaaa tacttccaga ctaactactt tttagtacat    1800
ctaagaagaa aagagttttg tctcttatcc acctctgagt caaaaagcag catgtccatc    1860
aattggtaca tagttcccac agccccactt agctctggat tggagttcta cttggcattg    1920
tttgcaacta catggacgta aaatgcatgg attctcttga aaaaatgttt ctgccatgat    1980
gttctctgaa agagactaac cttccctcgc tttgcagaga aagactcgtg taatccttga    2040
caatgtcatc tcatctattt attcccatgt ctacccatat gtgaccttca tgtctttgct    2100
ctaagcccct acatcctcaa tctacacact aggatagtat aaaagtaata gtaataatag    2160
tagtaatagt aataacaata caatgattat ggcttatact atacacaaga cactgttgat    2220
atattatttc atttagtatt cacagtaact ctgtgcctca agtactattg taatacccctt   2280 taagaggagg aaactgaggc acagggccct aaagtaatat tccaagatga agtggcact     2340 aactgacaga gggcataatt caactcatga tatttggctc tagaatacat gctctgaatc    2400
attatacaat aataattcat gaggaaacat tttttaaagc ctaagttatt tgctctgaaa    2460
taagacataa tttggggtga gaaagcttag attccatgaa gtattacagc atttggtagt    2520 cttttttgcac tccaggtctt atttttactg cttaaacata ataaacata tggttcagta    2580 tgcctttgat tttacaataa tattcctgtt attttggaa gcacagggtg tgggataatg     2640
ctaattacta gtgattagta ttgagaggtg acagcgtgct ggcagtcctc acagccctcg    2700
ctcgctcttg gcgcctcctc tgcctgggct cccacattgg tggcacttga ggagcccttc    2760
agccggccgc tgcactgtgg gagccctttt ctgggctggc caaggccaga gccggctccc    2820
tcagcttgcc aggaggtgtg gagggacaga cgcgggcagg aaccgggctg tgcgccgtgc    2880
ttgagggagt tccgggtggg catgggctcc gaggaccccg cactcggagc cgccagccgg    2940
ccccaccggc cgcgggcagt gaggggctta gcacctgggc cagcagctgc tgtgctcaat    3000
tcctcgccgg gccttagctg ccttcctgcg gggcagggct cgggacctgc agcgcgccat    3060
gcctgagcct ccccaccttc atgggctcct gtgcggcccg agcctcgccg acgagcgccg    3120 cccctgctc cagggcaccc agtcccatcg accacccaag ggctgaagag tgcgggcgca    3180
cggcagggga ctggcaggca gctccccctg cagcccaggt gcgggatcca ctgggtgaag    3240
ccggctaggc tcctgagttt gctggggatg cgaagaaccc ttatgtctag ataagggatt    3300
gtaaatacac caattggcac tctgtatcta gctcaaggtt tgtaaacaca ccaatcagca    3360
ccctgtgtct agctcagggt ttgtgaatgc accaatcaac actctatcta gctactctgg    3420
tggggccttg gagaacctt atgtctagct caggattgt aaatacacca atcggcagtc     3480
tgtatctagc tcaaggtttg taaacacacc aatcagcacc ctgtgtctag ctcagggttt    3540
gtgaatgcac caatcaacac tctgtatcta gctactctgg tggggacgtg gagaaccttt    3600
atgtctagct caggattgt aaatacacca ctcggcagtc tgtatctagc tcaaggtttg     3660
taaacacacc aatcagcacc ctgtgtctag ctcagggttt gtgaatgcac caatcaacac    3720
```

```
tctgtatcta gctactctgg tggggacttg gagaaccttt gtgtggacac tctgtatcta    3780
gctaatctgg tggggacgtg gagaaccttt gtgtctagct catggattgt aaatgcacca    3840
atcagtgccc tgtcaaaaca gaccactggg ctctaccaat cagcaggatg tgggtggggc    3900
cagataagag aataaaagca ggctgcccga gccagcagtg caacccgct cgggtccct     3960 tccacactgt ggaagctttg ttctttcgct ctttgcaata aatcttgctg ctgctcactg    4020
tttgggtcta cactgccttt atgagctgta acgctcaccg cgaaggtctg cagcttcact    4080
cttgaagcca gcgagaccac gaacccaccg ggaggaacga caactccag aggcgccgcc     4140 ttaagagctg aacgttcac tgtgaaggtc tgcagcttca ctcctgagcc agcgagacca    4200
cgaacccatc agaaggaaga aactccgaac acatccaaac atcagaacga caaactcca     4260 cacacgcagc ctttaagaac tgtaacactc accacgaggg tccccggctt cattcttgaa    4320
gtcagtgaaa ccaagaaccc accaattccg gacacagtat gtcagaaaca atatgagtca    4380
ctaaatcaat atacttctca acaatttcca acagcccttg caattaactt ggccatgtga    4440
ctggttgtga ctaaaataat gtggagataa taatgtgtta ctccctaagg cagagtgccc    4500
ttctatcatt ctcttccct tcctctatgt ggcagaaagt aaaagattct gaaatgataa      4560
agtcaatcac aggaaggcac ctggactcct ggcccactgc ttggaggaga gcactcagga    4620
ccatgaacat ctgactgtga cgtagcaata aagaaaccca cgtttcatat gaaactgctt    4680
aaaattaatg gcacaagtca tgttttgat gttgcacatt tgtctttatt tgtggcttgt     4740
tttgcttcca catcaatcca ctcaaggcct acattctgct ataatgcaat ttcaagttct    4800
ttacaggccg agaaaaatga atctgaattc ctgacctcca aaagtgatca agatattttt    4860
agttcaggct ccaaaatttt ctcattttca taggttttcc tcgattgatc attattcatg    4920
atttgcaagg aatcattcaa tgttttctaa atctattact gcatcctgac acatatgaca    4980
ttttaactat gttccagatt tttgaatgaa gagtgtaaat tttaaatgtt ttcaccacaa    5040
aaaataagta tgtgaagtgg tggatttgtt aattagcctt atttaaccat ttaatattgt    5100
acacgtacac caaagcatca tgttgtaccc catgaataca cacaattatt atttgtcaat    5160
ttaaaatgaa ataataaaaa ataacaaagg cattagcctc tgcattgcct ttaccggtca    5220
tcctcacggt gactaacgca aaaaacgttc tatttcatcc ttacaaacat ccctatcttt    5280
gatgcctctt tgtctagatc tctatcccct cctgttttct ctacgttatt tatatgggta    5340
tcatcaccat cctggacaac atcaggacag atatccctca ccaagccaat gttcctctct    5400
atgttggctc aaatgtcctt gaactttcct ttcaccaccc tttccacagt caaaggata     5460 ttgtagttta atgcctcaga gttcagcttt taagcttctg acaaattatt cttcctcttt    5520
aggttctcct ttatggaatc ttctgtactg atggccatgt cctttaacta ctatgtagat    5580
atctgctact acctgtatta tgcctctacc tttattagca gagttatctg tactgttggc    5640
atgacaatca tttgttaata tgacttgcct ttccttttc tgctattctt gatcaaatgg      5700
ctcctctttc ttgctcctct catttctcct gccttcactt ggacgtgctt cacgtagtct    5760
gtgcttatga ctggattaaa aattgatatg gacttatcct aatgttgttc gtcataatat    5820 gggtttatg gtccattatt atttcctatg cattgatctg gagaaggctt caatcctttt    5880
actctttgtg gaaaatatct gtaaaccttc tggttcactc tgctatagca atttcagttt    5940
aggctagtaa gcatgaggat gcctccttct ctgattttc ccacagtctg ttggtcacag     6000
aataacctga gtgattactg atgaaagagt gagaatgtta ttgatagtca caatgacaaa    6060
```

-continued

```
aaacaaacaa ctacagtcaa aatgtttctc tttttattag tggattatat ttcctgacct    6120
atatctggca ggactcttta gagaggtagc tgaagctgct gttatgacca ctagagggaa    6180
gaagatacct gtggagctaa tggtccaaga tggtggagcc ccaagcaagg aagttgttaa    6240
ggagcccttt tgattgaagg tgggtgcccc caccttacag ggacaggaca tctggatact    6300
cctcccagtt tctccagttt ccctttttcc taatatatct cctgataaaa tgtctatact    6360
cacttcccca tttctaataa taaagcaaag gctagttagt aagacatcac cttgcatttt    6420
gaaaatgcca tagactttca aaattatttc atacatcggt cttctttat ttcaagagtc     6480
cagaaatggc aacattacct ttgattcaat gtaatggaaa gagctctttc aagagacaga    6540
gaaaagaata atttaatttc tttccccaca cctccttccc tgtctcttac cctatcttcc    6600
ttccttctac cctccccatt tctctctctc atttctcaga agtatatttt gaaaggattc    6660
atagcagaca gctaaggctg gttttttcta agtgaagaag tgatattgag aaggtagggt    6720
tgcatgagcc ctttcagttt tttagtttat atacatctgt attgttagaa tgttttataa    6780
tataaataaa attatttctc agttatatac tagctatgta acctgtggat atttccttaa    6840
gtattacaag ctatacttaa ctcacttgga aaactcaaat aaatacctgc ttcatagtta    6900
ttaataagga ttaagtgaga taatgcccat aagattccta ttaataacag ataaatacat    6960
acacacacac acacattgaa aggattctta ctttgtgcta ggaactataa taagttcatt    7020
gatgcattat atcattaagt tctaatttca acactagaag gcaggtatta tctaaatttc    7080
atactggata cctccaaact cataaagata attaaattgc cttttgtcat atatttattc    7140
aaaagggtaa actcaaacta tggcttgtct aattttatat atcaccctac tgaacatgac    7200
cctattgtga tattttataa aattattctc aagttattat gaggatgttg aaagacagag    7260
aggatggggt gctatgcccc aaatcagcct cacaattaag ctaagcagct aagagtcttg    7320
cagggtagtg tagggaccac agggttaagg gggcagtaga attatactcc cactttagtt    7380
tcatttcaaa caatccatac acacacagcc ctgagcactt acaaattata ctacgctcta    7440
tactttttgt ttaaatgtat aaataagtgg atgaaagaat agatagatag atagacagat    7500
agatgataga tagaataaat gcttgccttc atagctgtct ccctaccttg ttcaaaatgt    7560
tcctgtccag accaaagtac cttgccttca cttaagtaat caattcctag gttatattct    7620
gatgtcaaag gaagtcaaaa gatgtgaaaa acaatttctg acccacaact catgctttgt    7680
agatgactag atcaaaaaat ttcagccata tcttaacagt gagtgaacag gaaatctcct    7740
cttttcccta catctgagat cccagcttct aagaccttca attctcactc ttgatgcaac    7800
agaccttgga agcatacagg agagctgaac ttggtcaaca aaggagaaaa gtttgttggc    7860
ctccaaaggc acagctcaaa cttttcaagc cttctctaat cttaaaggta acaagggtc     7920
tcatttcttt gagaacttca gggaaaatag acaaggactt gcctggtgct tttggtaggg    7980
gagcttgcac tttccccctt tctggaggaa atatttatcc ccaggtagtt ccctttttgc    8040
accagtggtt ctttgaagag acttccacct gggaacagtt aaacagcaac tacagggcct    8100
tgaactgcac actttcagtc cggtcctcac agttgaaaag acctaagctt gtgcctgatt    8160
taagcctttt tggtcataaa acattgaatt ctaatctccc tctcaaccct acagtcaccc    8220
atttggtata ttaaagatgt gttgtctact gtctagtatc cctcaagtag tgtcaggaat    8280
tagtcattta aatagtctgc aagccaggag tggtggctca tgtctgtaat tccagcactt    8340
gagaggtaga agtgggagga ctgcttgagc tcaagagttt gatattatcc tggacaacat    8400
agcaagacct cgtctctact taaaaaaaaa aaaaaaatta gccaggcatg tgatgtacac    8460
```

```
ctgtagtccc agctactcag gaggccgaaa tgggaggatc ccttgagctc aggaggtcaa    8520
ggctgcagtg agacatgatc ttgccactgc actccagcct ggacagcaga gtgaaacctt    8580
gcctcacgaa acagaataca aaaacaaaca aacaaaaaac tgctccgcaa tgcgcttcct    8640
tgatgctcta ccacataggt ctgggtactt tgtacacatt atctcattgc tgttcataat    8700
tgttagatta attttgtaat attgatatta ttcctagaaa gctgaggcct caagatgata    8760
acttttattt tctggacttg taatagcttt ctcttgtatt caccatgttg taactttctt    8820
agagtagtaa caatataaag ttattgtgag tttttgcaaa cacagcaaac acaacgaccc    8880
atatagacat tgatgtgaaa ttgtctattg tcaatttatg ggaaaacaag tatgtacttt    8940
ttctactaag ccattgaaac aggaataaca gaacaagatt gaaagaatac attttccgaa    9000
attacttgag tattatacaa agacaagcac gtggacctgg gaggagggtt attgtccatg    9060
actggtgtgt ggagacaaat gcaggtttat aatagatggg atggcatcta gcgcaatgac    9120
tttgccatca cttttagaga gctcttgggg accccagtac acaagagggg acgcagggta    9180
tatgtagaca tctcattctt tttcttagtg tgagaataag aatagccatg acctgagttt    9240
atagacaatg agccctttc tctctcccac tcagcagcta tgagatggct tgccctgcct    9300
ctctactagg ctgactcact ccaaggccca gcaatgggca gggctctgtc agggctttga    9360
tagcactatc tgcagagcca gggccgagaa ggggtggact ccagagactc tccctcccat    9420
tcccgagcag ggtttgctta tttatgcatt taaatgatat atttatttta aagaaataa     9480 caggagactg cccagccctg gctgtgacat ggaaactatg tagaatattt tgggttccat    9540
ttttttttcc ttctttcagt tagaggaaaa ggggctcact gcacatacac tagacagaaa    9600
gtcaggagct ttgaatccaa gcctgatcat ttccatgtca tactgagaaa gtccccaccc    9660
ttctctgagc ctcagtttct cttttttataa gtaggagtct ggagtaaatg atttccaatg    9720
gctctcattt caatacaaaa tttccgttta ttaaatgcat gagcttctgt tactccaaga    9780
ctgagaagga aattgaacct gagactcatt gactggcaag atgtccccag aggctctcat    9840
tcagcaataa aattctcacc ttcacccagg cccactgagt gtcagatttg catgcactag    9900
ttcacgtgtg taaaaggag gatgcttctt tcctttgtat tctcacatac ctttaggaaa     9960
gaacttagca cccttcccac acagccatcc caataactca tttcagtgac tcaacccttg   10020
actttataaa agtcttgggc agtatagagc agagattaag agtacagatg ctggagccaa   10080
accacctgag tgattagtga ctcagtttct cttagtagtt gtatgactca gtttcttcat   10140
ctgtaaaatg gagggttttt taattagttt gttttgaga aagggtctca ctctgtcacc     10200
caaatgggag tgtagtggca aaatctcggc tcactgcaac ttgcacttcc caggctcaag   10260
cggtcctccc acctcaacat cctgagtagc tggaaccaca ggtacacacc accataccctc   10320 gctaattttt tgtatttttg gtagagatgg ggtttcacat gttacacagg atggtctcag   10380
actccggagc tcaagcaatc tgcccacctc agccttccaa agtgctggga ttataagcat   10440
gattacagga gttttaacag gctcataaga ttgttctgca gcccgagtga gttaatacat   10500
gcaaagagtt taaagcagtg acttataaat gctaactact ctagaaatgt tgctagtat    10560 tttttgttta actgcaatca ttcttgctgc aggtgaaaac tagtgttctg tacttttatgc   10620 ccattcatct ttaactgtaa taataaaaat aactgacatt tattgaaggc tatcagagac   10680
tgtaattagt gctttgcata attaatcata tttaatactc ttggattctt tcaggtagat    10740
actattatta tccccatttt actacagtta aaaaactac ctctcaactt gctcaagcat     10800
```

```
acactctcac acacacaaac ataaactact agcaaatagt agaattgaga tttggtccta   10860
attatgtctt tgctcactat ccaataaata tttattgaca tgtacttctt ggcagtctgt   10920
atgctggatg ctggggatac aaagatgttt aaatttaagc tccagtctct gcttccaaag   10980
gcctcccagg ccaagttatc cattcagaaa gcatttttta ctctttgcat tccactgttt   11040
ttcctaagtg actaaaaaat tacactttat tcgtctgtgt cctgctctgg gatgatagtc   11100
tgactttcct aacctgagcc taacatccct gacatcagga aagactacac catgtggaga   11160
aggggtggtg gttttgattg ctgctgtctt cagttagatg gttaactttg tgaagttgaa   11220
aactgtggct ctctggttga ctgttagagt tctggcactt gtcactatgc ctattattta   11280
acaaatgcat gaatgcttca gaatatggga atattatctt ctggaatagg gaatcaagtt   11340
atattatgta acccaggatt agaagattct tctgtgtgta agaatttcat aaacattaag   11400
ctgtctagca aaagcaaggg cttggaaaat ctgtgagctc ctcaccatat agaaagcttt   11460
taacccatca ttgaataaat ccctataggg gatttctacc ctgagcaaaa ggctggtctt   11520
gattaattcc caaactcata tagctctgag aaagtctatg ctgttaacgt tttcttgtct   11580
gctaccccat catatgcaca acaataaatg caggcctagg catgactgaa ggctctctca   11640
taattcttgg ttgcatgaat cagattatca acagaaatgt tgagacaaac tatggggaag   11700
cagggtatga aagagctctg aatgaaatgg aaaccgcaat gcttcctgcc cattcagggc   11760
tccagcatgt agaaatctgg ggcttttgtga agactggctt aaaatcagaa gccccattgg   11820
ataagagtag ggaagaacct agagcctacg ctgagcaggt ttccttcatg tgacagggag   11880
cctcctgccc cgaacttcca gggatcctct cttaagtgtt tcctgctgga atctcctcac   11940
ttctatctgg aaatggtttc tccacagtcc agcccctggc tagttgaaag agttacccat   12000
gcagaggccc tcctagcatc cagagactag tgcttagatt cctactttca gcgttggaca   12060
acctggatcc acttgcccag tgttcttcct tagttcctac cttcgacctt gatcctcctt   12120
tatcttcctg aaccctgctg agatgatcta tgtggggaga atggcttctt tgagaaacat   12180
cttcttcgtt agtggcctgc ccctcattcc cactttaata tccagaatca ctataagaag   12240
aatataataa gaggaataac tcttattata ggtaagggaa aattaagagg catacgtgat   12300
gggatgagta agagaggaga gggaaggatt aatggacgat aaaatctact actatttgtt   12360
gagacccttt atagtctaat caattttgct attgttttcc atcctcacgc taactccata   12420
aaaaaacact attattatct ttatttgcc atgacaagac tgagctcaga agagtcaagc    12480
atttgcctaa ggtcggacat gtcagaggca gtgccagacc tatgtgagac tctgcagcta   12540
ctgctcatgg gccctgtgct gcactgatga ggaggatcag atggatgggg caatgaagca   12600
aaggaatcat tctgtggata aaggagacag ccatgaagaa gtctatgact gtaaatttgg   12660
gagcaggagt ctctaaggac ttggatttca aggaattttg actcagcaaa cacaagaccc   12720
tcacggtgac tttgcgagct ggtgtgccag atgtgtctat cagaggttcc agggagggtg   12780
gggtggggtc agggctggcc accagctatc agggcccaga tgggttatag ctggcaggc    12840
tcagataggt ggttaggtca ggttggtggt gctgggtgga gtccatgact cccaggagcc   12900
aggagagata gaccatgagt agagggcaga catgggaaag gtggggagg cacagcatag    12960
cagcattttt cattctacta ctacatggga ctgctcccct ataccccag ctaggggcaa    13020
gtgccttgac tcctatgttt tcaggatcat catctataaa gtaagagtaa taattgtgtc   13080
tatctcatag ggttattatg aggatcaaag gagatgcaca ctctctggac cagtggccta   13140
acagttcagg acagagctat gggcttccta tgtatgggtc agtggtctca atgtagcagg   13200
```

```
caagttccag aagatagcat caaccactgt tagagatata ctgccagtct cagagcctga    13260
tgttaattta gcaatgggct gggaccctcc tccagtagaa ccttctaacc agctgctgca    13320
gtcaaagtcg aatgcagctg gttagacttt ttttaatgaa agcttagctt tcattaaaga    13380
ttaagctcct aagcagggca cagatgaaat tgtctaacag caactttgcc atctaaaaaa    13440
atctgacttc actggaaaca tggaagccca aggttctgaa catgagaaat ttttaggaat    13500
ctgcacagga gttgagaggg aaacaagatg gtgaagggac tagaaaccac atgagagaca    13560
cgaggaaata gtgtagattt aggctggagg taaatgaaag agaagtggga attaatactt    13620
actgaaatct ttctatatgt caggtgccat tttatgatat ttaataatct cattacatat    13680
ggtaattctg tgagatatgt attattgaac atactataat taatactaat gataagtaac    13740
acctcttgag tacttagtat atgctagaat caaatttaag tttatcatat gaggccgggc    13800
acggtggctc atatatggga ttacatgcct gtaatcccag cactttggga ggccaaggca    13860
attggatcac ctgaggtcag gagttccaga ccagcctggc caacatggtg aaacccttc     13920 tctactaaaa aatacaaaaa atcagccagg tgtggtggca cgcgtctata atcccagcta    13980
ctcaggaggc tgaggcagga gaatcacttg aacccaggag gtggaggttg cagtgagcta    14040
agattgcacc actgcactcc agcctaggcg acagagtgag actccatctc aaaaaaaaaa    14100
aaagaagttt attatatgaa ttaacttagt tttactcaca ccaatactca gaagtagatt    14160
attacctcat ttattgatga ggagcccaat gtacttgtag tgtagatcaa cttattgaaa    14220
gcacaagcta ataagtagac aattagtaat tagaagtcag atggtctgag ctctcctact    14280
gtctacatta catgagctct tattaactgg ggactcgaaa atcaaagaca tgaaataatt    14340
tgtccaagct tacagaacca ccaagtagta aggctaggat gtagacccag ttctgctacc    14400
tctgaagaca gtgttttttc cacagcaaaa cacaaactca gatattgtgg atgcgagaaa    14460
ttagaagtag atattcctgc cctgtggccc ttgcttctta cttttacttc ttgtcgattg    14520
gaagttgtgg tccaagccac agttgcagac catacttcct caaccataat tgcatttctt    14580
caggaaagtt tgagggagaa aaaggtaaag aaaaatttag aaacaacttc agaataaaga    14640
gattttctct tgggttacag agattgtcat atgcacaatt ataagcagac acttgagaaa    14700
actgaaggcc catgcctgcc caaattaccc tttgaccect tggtcaagct gcaactttgg    14760
ttaaagggag tgtttatgtg ttatagtgtt catttactct tctggtctaa cccattggct    14820
ccgtcttcat cctgcagtga cctcagtgcc tcagaaacat acatatgttt gtctagttta    14880
agtttgtgtg aaattctaac tagcgtcaag aactgagggc cctaaactat gctaggaata    14940
gtgctgtggt gctgtgatag gtacacaaga aatgagaaga aactgcagat tctctgcatc    15000 tcccttgcc gggtctgaca acaaagtttc cccaaatttt accaatgcaa gccatttctc     15060
catatgctaa ctactttaaa atcatttggg gcttcacatt gtctttctca tctgtaaaaa    15120
gaatggaaga actcattcct acagaactcc ctatgtcttc cctgatgggc tagagttcct    15180
ctttctcaaa aattagccat tatttgtattt ccttctaagc caaagctcag aggtcttgta    15240
ttgcccagtg acatgcacac tggtcaaaag taggctaagt agaagggtac tttcacagga    15300
acagagagca aaagaggtgg gtgaatgaga gggtaagtga gaaaagacaa atgagaagtt    15360
acaacatgat ggcttgttgt ctaaatatct cctagggaat tattgtgaga ggtctgaata    15420
gtgttgtaaa ataagctgaa tctgctgcca acattaacag tcaagaaata cctccgaata    15480
actgtacctc caattattct ttaaggtagc atgcaactgt aatagttgca tgtatatatt    15540
```

```
tatcataata ctgtaacaga aaacacttac tgaatatata ctgtgtccct agttctttac   15600
acaataaact aatctcatcc tcataattct attagctaat acatattatc atcctatatt   15660
tcagagactt caagaagtta agcaacttgc tcaagatcat ctaagaagta ggtggtattt   15720
ctgggctcat ttggcccctc ctaatctctc atggcaacat ggctgcctaa agtgttgatt   15780
gccttaattc atcagggatg ggctcatact cactgcagac cttaactggc atcctctttt   15840
cttatgtgat ctgcctgacc ctagtagact tatgaaattt ctgatgagaa aggagagagg   15900
agaaaggcag agctgactgt gatgagtgat gaaggtgcct tctcatctgg gtaccagtgg   15960
ggcctctaag actaagtcac tctgtctcac tgtgtcttag ccagttcctt acagcttgcc   16020
ctgatgggag atagagaatg ggtatcctcc aacaaaaaaa taaattttca tttctcaagg   16080
tccaacttat gttttcttaa tttttaaaaa aatcttgacc attctccact ctctaaaata   16140
atccacagtg agagaaacat tcttttcccc catcccataa atacctctat taaatatgga   16200
aaatctgggc atggtgtctc acacctgtaa tcccagcact ttgggaggct gaggtgggtg   16260
gactgcttgg agctcaggag ttcaagacca tcttggacaa catggtgata ccctgcctct   16320
acaaaaagta caaaaattag cctggcatgg tggtgtgcac ctgtaatccc agctattagg   16380
gtggctgagc aggagaatt gcttgaaccc gggaggcgga ggttgcagtg agctgagatc   16440
gtgccactgc actccagcct gggggacaga gcacattata attaactgtt attttttact   16500
tggactcttg tggggaataa gatacatgtt ttattcttat ttatgattca agcactgaaa   16560
atagtgttta gcatccagca ggtgcttcaa aaccatttgc tgaatgatta ctatactttt   16620
tacaagctca gctccctcta tcccttccag catcctcatc tctgattaaa taagcttcag   16680
ttttccctta gttcctgtta catttctgtg tgtctccatt agtgacctcc catagtccaa   16740
gcatgagcag ttctggccag gccctgtcg gggtcagtgc cccaccccg ccttctggtt    16800 ctgtgtaacc ttctaagcaa accttctggc tcaagcacag caatgctgag tcatgatgag   16860
tcatgctgag gcttagggtg tgtgcccaga tgttctcagc ctagagtgat gactcctatc   16920
tgggtcccca gcaggatgct tacagggcag atggcaaaaa aaaggagaag ctgaccacct   16980
gactaaaact ccacctcaaa cggcatcata aagaaaatgg atgcctgaga cagaatgtga   17040
catattctag aatatattat ttcctgaata tatatatata tatacacata tacgtatata   17100
tatatatata tatatatttg ttgttatcaa ttgccataga atgattagtt attgtgaatc   17160
aaatatttat cttgcaggtg gcctctatac ctagaagcgg cagaatcagg ctttattaat   17220
acatgtgtat agattttag gatctataca catgtattaa tatgaaacaa ggatatggaa    17280
gaggaaggca tgaaaacagg aaaagaaaac aaaccttgtt tgccatttta aggcacccct   17340
ggacagctag gtggcaaaag gcctgtgctg ttagaggaca catgctcaca tacgggtca    17400 gatctgactt ggggtgctac tgggaagctc tcatcttaag gatacatctc aggccagtct   17460
tggtgcatta ggaagatgta ggcaactctg atcctgagag gaagaaaca ttcctccagg    17520 agagctaaaa gggttcacct gtgtgggtaa ctgtgaagga ctacaagagg atgaaaaaca   17580
atgacagaca gacataatgc ttgtgggaga aaaaacagga ggtcaagggg atagagaagg   17640
cttccagaag aatggctttg aagctggctt ctgtaggagt tcacagtggc aaagatgttt   17700
cagaaatgtg acatgactta aggaactata caaaaaggaa caaatttaag gagaggcaga   17760
taaattagtt caacagacat gcaaggaatt ttcagatgaa tgttatgtct ccactgagct   17820
tcttgaggtt agcagctgtg agggttttgc aggcccagga cccattacag gacctcacgt   17880
atacttgaca ctgttttttg tattcatttg tgaatgaatg acctcttgtc agtctactcg   17940
```

```
gtttcgctgt gaatgaatga tgtcttgtca gcctacttgg tttcgctaag agcacagaga    18000
gaagatttag tgatgctatg taaaaacttc cttttggtt caagtgtatg tttgtgatag    18060
aaatgaagac aggctacatg atgcatatct aacataaaca caaacattaa gaaaggaaat    18120
caacctgaag agtatttata cagataacaa atacagaga gtgagttaaa tgtgtaataa    18180
ctgtggcaca ggctggaata tgagccattt aaatcacaaa ttaattagaa aaaaaacagt    18240
ggggaaaaaa ttccatggat gggtctagaa agactagcat tgttttaggt tgagtggcag    18300
tgtttaaagg gtgatatcag actaaacttg aaatatgtgg ctaaataact agaatactct    18360 ttatttttc gtatcatgaa tagcagatat agcttgatgg ccccatgctt ggtttaacat    18420
ccttgctgtt cctgacatga aatccttaat ttttgacaaa ggggctattc attttcattt    18480
tatattgggc ctagaaatta tgtagatggt cctgaggaaa agtttatagc ttgtctattt    18540
ctctctctaa catagttgtc agcacaatgc ctaggctata ggaagtactc aaagcttgtt    18600
aaattgaatt ctatccttct tattcaattc tacacatgga ggaaaaactc atcagggatg    18660
gaggcacgcc tctaaggaag gcaggtgtgg ctctgcagtg tgattgggta cttgcaggac    18720
gaagggtggg gtgggagtgg ctaaccttcc attcctagtg cagaggtcac agcctaaaca    18780
tcaaattcct tgaggtgcgg tggctcactc ctgtaatcac agcagtttgg gacgccaagg    18840
tgggcagatc acttgaggtc aggagttgga caccagccca gccaacatag tgaaacctgg    18900
tctctgctta aaatataaa aattagctgg acgtggtgac gggagcctgt aatccaacta    18960
cttgggaggc tgaggcagga gaatcgcttg aaccggggag gtggagtttg cactgagcag    19020
agatcatgcc attgcactcc agcctccaga gcgagactct gtctaaagaa aaacgaaaac    19080
aaacaaacaa acaaacaaac aaacccatc aaattccctg accgaacaga attctgtctg    19140
attgttctct gacttatcta ccattttccc tccttaaaga aactgtgaac ttccttcagc    19200
tagaggggcc tggctcagaa gcctctggtc agcatccaag aaatacttga tgtcactttg    19260
gctaaaggta tgatgtgtag acaagctcca gagatggttt ctcatttcca tatccaccca    19320
cccagctttc caattttaaa gccaattctg aggtagagac tgtgatgaac aaacaccttg    19380
acaaaattca acccaaagac tcactttgcc tagcttcaaa atccttactc tgacatatac    19440
tcacagccag aaattagcat gcactagagt gtgcatgagt gcaacacaca cacacaccaa    19500
ttccatattc tctgtcagaa atcctgttg gttttttcgtg aaaggatgtt ttcagaggct    19560
gaccccttgc cttcacctcc aatgctacca ctctggtcta agtcactgtc accaccacct    19620
aaattatagc tgttgactca taacaatctt cctgcttcta ccactgcccc actacaattt    19680
cttcccaata tactatccaa attagtcttt tcaaaatgta agtcatatat ggtcacctct    19740
ttgttcaaag tcttctgata gtttcctata tcatttataa taaaaccaaa tccttacaat    19800
tctctacaat agttgttcat gcatatatta tgtttattac agatacatat atatagctct    19860
catataaata aatatatata tttatgtgta tgtgtgtaga gtgtttttc ttacaactct    19920 atgatgtagg tattattagt gtcccaaatt ttataattta ggacttctat gatctcatct    19980
tttattctcc ccttcaccga atctcatcct acattggcct tattgatatt ccttgaaaat    20040
tctaagcatc ttacatcttt agggtattta catttgccat tccctatgcc ctaaatattt    20100
aatcatagtt tcatataaat gggttcctca tcatctatgg gtactctctc aggtgttaac    20160
tttatagtga ggactttcct gccatactac ttaaagtagc gataccctt cacctgtcc    20220 taatcacact ctggccttca tttcagtttt ttttttttct ccatagcacc taatctcatt    20280
```

-continued

```
ggtatataac atgtttcatt tgcttattta atgtcaagct ctttccacta tcaagtccat    20340
gaaaacagga actttattcc tctattctgt ttttgtgctg tattcttagc aattttacaa    20400
ttttgaatga atgaatgagc agtcaaacac atatacaact ataattaaaa ggatgtatgc    20460
tgacacatcc actgctatgc acacacaaag aaatcagtgg agtagagctg gaagtgctaa    20520
gcctgcatag agctagttag ccctccgcag gcagagcctt gatgggatta ctgagttcta    20580
gaattggact catttgtttt gtaggctgag atttgctctt gaaaacttgt tctgaccaaa    20640
ataaaaggct caaaagatga atatcgaaac cagggtgttt tttacactgg aatttataac    20700
tagagcactc atgtttatgt aagcaattaa ttgtttcatc agtcaggtaa aagtaaagaa    20760
aaactgtgcc aaggcaggta gcctaatgca atatgccact aaagtaaaca ttatttcata    20820
ggtgtcagat atggcttatt catccatctt catgggaagg atggccttgg cctggacatc    20880
agtgttatgt gaggttcaaa acacctctag gctataaggc aacagagctc cttttttttt    20940
tttctgtgct ttcctggctg tccaaatctc taatgataag catacttcta ttcaatgaga    21000
atattctgta agattatagt taagaattgt gggagccatt ccgtctctta tagttaaatt    21060
tgagcttctt ttatgatcac tgttttttta atatgcttta agttctgggg tacatgtgcc    21120
atggtggttt gctgcaccca tcaacccgtc atctacatta ggtatttctc ctaatgctat    21180 ccttcccccta gcccccacc cccaacaggc cccagtgtgt gatgttcccc tccctgtgtc    21240
catggatcac tggtttttt ttgtttttt ttttttta aagtctcagt taaattttg    21300
```
(partial — note: above line had minor format)

```
gaatgtaatt tattttcctg gtatcctagg acttgcaagt tatctggtca ctttagccct    21360
cacgttttga tgataatcac atatttgtaa acacaacaca cacacacaca cacacacaca    21420
tatatatata tataaaacat atatatacat aaacacacat aacatattta tcgggcattt    21480
ctgagcaact aatcatgcag gactctcaaa cactaaccta tagccttttc tatgtatcta    21540
cttgtgtaga aaccaagcgt ggggactgag aaggcaatag caggagcatt ctgactctca    21600
ctgcctttag ctaggcccct ccctcatcac agctcagcat agtcctgagc tcttatctat    21660
atccacacac agtttctgac gctgcccagc tatcaccatc ccaagtctaa agaaaaaaat    21720
aatgggtttg cccatctctg ttgattagaa acaaaacaa aataaaataa gccctaagc    21780 tcccagaaaa catgactaaa ccagcaagaa gaagaaaata caataggtat atgaggagac    21840
tggtgacact agtgtctgaa tgaggcttga gtacagaaaa gaggctctag cagcatagtg    21900
gtttagagga gatgtttctt tccttcacag atgccttagc ctcaataagc ttgcggttgt    21960
ggaagtttac tttcagaaca aactcctgtg gggctgaaat tattgatggc taaaagaagc    22020
ccgggggagg gaaaaatcat tcagcatcct cacccttagt gacacaaaac agagggggcc    22080
tggttttcca tatttcctca tgatggatga tctcgttaat gaaggtggtc tgacgagatc    22140
attgcttctt ccatttaagc cttgctcact tgccaatcct cagttttaac cttctccaga    22200
gaaatacaca ttttttattc aggaaacata ctatgttata gtttcaatac taaataatca    22260
aagtactgaa gatagcatgc ataggcaaga aaaagtcctt agctttatgt tgctgttgtt    22320
tcagaattta aaaagatca ccaagtcaag gacttctcag ttctagcact agaggtggaa    22380
tcttagcata taatcagagg ttttttcaaaa tttctagaca taagattcaa agccctgcac    22440
ttaaaatagt ctcatttgaa ttaactcttt atataaattg aaagcacatt ctgaactact    22500
tcagagtatt gttttatttc tatgttctta gttcataaat acattaggca atgcaattta    22560
attaaaaaaa cccaagaatt tcttagaatt ttaatcatga aaataaatga aggcatcttt    22620
acttactcaa ggtcccaaaa ggtcaaagaa accaggaaag taaagctata tttcagcgga    22680
```

```
aaatgggata tttatgagtt ttctaagttg acagactcaa gttttaacct tcagtgccca   22740
tcatgtagga aagtgtggca taactggctg attctggctt tctactcctt tttcccatta   22800
aagatccctc ctgcttaatt aacattcaca agtaactctg gttgtacttt aggcacagtg   22860
gctcccgagg tcagtcacac aataggatgt ctgtgctcca agttgccaga gagagagatt   22920
actcttgaga atgagcctca gccctggctc aaactcacct gcaaacttcg tgagagatga   22980
ggcagaggta cactacgaaa gcaacagtta gaagctaaat gatgagaaca catggactca   23040
tagagggaaa caacgcatac tggggcctat cagagggtgg agggtgagag aaggagagga   23100
tcaggaaaaa tcactaatgg atgctaagcg taatacctga gtgatgagat catctataca   23160
acaaaccccc ttgacattca tttatctatg taacaaacct gcacatcctg tacatgtacc   23220
cctgaactta aaataaaagt tgaaaacaag aaagcaacag tttgaacact tgttatggtc   23280
tattctctca ttctttacaa ttacactaga aaatagccac aggcttcctg caaggcagcc   23340
acagaattta tgacttgtga tatccaagtc attcctggat aatgcaaaat ctaacacaaa   23400
atctagtaga atcatttgct tacatctatt tttgttctga aatatagat ttagatacat    23460 aatggaagca gaataattta aaatctggct aatttagaat cctaagcagc tcttttccta   23520
tcagtggttt acaagccttg tttatatttt tcctatttta aaaataaaaa taagtaagt    23580 tatttgtggt aaagaatatt cattaaagta tttatttctt agataatacc atgaaaaaca   23640
ttcagtgaag tgaagggcct actttactta acaagaatct aatttatata attttcata   23700 ctaatagcat ctaagaacag tacaatattt gactcttcag gttaaacata tgtcataaat   23760
tagccagaaa gatttaagaa aatattggat gtttccttgt ttaaattagg catcttacag   23820
tttttagaat cctgcataga acttaagaaa ttacaaatgc taaagcaaac ccaaacaggc   23880
aggaattaat cttcatcgaa tttgggtgtt tctttctaaa agtcctttat acttaaatgt   23940
cttaagacat acatagattt tattttacta attttaatta tatagacaat aaatgaatat   24000
tcttactgat tacttttct gactgtctaa tctttctgat ctatcctgga tggccataac    24060
acttatctct ctgaactttg ggcttttaat ataggaaaga aaagcaataa tccattttc    24120 atggtatctc atatgataaa caaataaaat gcttaaaaat gagcaggtga agcaatttat   24180
cttgaaccaa caagcatcga agcaataatg agactgcccg cagcctacct gacttctgag   24240
tcaggattta taagccttgt tactgagaca caaacctggg cctttcaatg ctataacctt   24300
tcttgaagct cctccctacc acctttagcc ataaggaaac atggaatggg tcagatccct   24360
ggatgcaagc caggtctgga accataggca gtaaggagag aagaaaatgt gggctctgca   24420
actggctccg agggagcagg agaggatcaa ccccatactc tgaatctaag agaagactgg   24480
tgtccatact ctgaatggga agaatgatgg gattacccat agggcttgtt ttagggaaa    24540 acctgttctc caaactcttg gccttgagat acctggtcct tattccttgg actttggcaa   24600
tgtctgaccc tcacattcaa gttctgagga agggccactg ccttcatact gtggatctgt   24660
agcaaattcc ccctgaaaac ccagagctgt atcttaattg gttaaaaaaa attatattat   24720
ctcaacgact gttcttctct gagtagccaa gctcagcttg gttcaagcta caagcagctg   24780
agctgctttt tgtctagtca ttgttctttt atttcagtgg atcaaatacg ttcttttccaa  24840 acctaggatc ttgtcttcct aggctatata ttttgtccca ggaagtctta atctggggtc   24900
cacagaacac taggggggctg gtgaagttta tagaaaaaaa atctgtattt ttacttacat   24960
gtaactgaaa tttagcattt tcttctactt tgaatgcaaa ggacaaacta gaatgacatc   25020
```

```
atcagtacct attgcatagt tataaagaga aaccacagat attttcatac tacaccatag   25080
gtattgcaga tcttttttgtt tttgttttg tttgagatgg agtttcgctc ttattgccca   25140
ggctggagtg cagtggcatg atttcggctc actgcaacct cccttcctg cattcaagca    25200 attctcctgc cttggcctcc tgagtagctg gggattacag gcacctgcca ccatgccagt   25260 ctaattttg tattttagt agagatgggg tttcgccatg ttggccaggc tggtcttgaa    25320
ctcctgacct cagatgatct gcccgccttg gcctcctgaa gtgctgggat taggtgtg     25380 agccaccacg cctggcccat tgcagatatt tttaattcac atttatctgc atcactactt   25440
ggatcttaag gtagctgtag acccaatcct agatctaatg ctttcataaa gaagcaaata   25500
taataaatac tataccacaa atgtaatgtt tgatgtctga taatgatatt tcagtgtaat   25560
taaacttagc actcctatgt atattatttg atgcaataaa aacatatttt tttagcactt   25620
acagtctgcc aaactggcct gtgacacaaa aaaagtttag gaattcctgg ttttgtctgt   25680
gttagccaat ggttagaata tatgctcaga aagataccat tggttaatag ctaaaagaaa   25740
atggagtaga aattcagtgg cctggaataa taacaatttg ggcagtcatt aagtcaggtg   25800
aagacttctg gaatcatggg agaaaagcaa gggagacatt cttacttgcc acaagtgttt   25860 ttttttttt ttttttttat cacaaacata agaaaatata ataaataaca aagtcaggtt    25920
atagaagaga gaaacgctct tagtaaactt ggaatatgga atccccaaag gcacttgact   25980
tgggagacag gagccatact gctaagtgaa aaagacgaag aacctctagg gcctgaacat   26040
acaggaaatt gtaggaacag aaattcctag atctggtggg gcaaggggag ccataggaga   26100
aagaaatggt agaaatggat ggagacggag gcagaggtgg gcagatcatg aggtcaagag   26160
atcgagacca tcctggcaaa catggtgaaa tcccgtctct actaaaaata aaaaaattag   26220
ctgggcatgg tggcatgcgc ctgtagtccc agctgctcgg gaggctgagg caggagaatc   26280
gtttgaaccc aggaggcgaa ggttgcagtg agctgagata gtgccattgc actccagtct   26340
ggcaacagag tgagactccg tctcaaaaaa aaaaaaaaa gaaagaaaga aagaaaaag    26400 aaaaagaaa aataaatgg atgtagaaca agccagaagg aggaactggg ctgggcaat     26460 gagattatgg tgatgtaagg gactttata gaattaacaa tgctggaatt tgtggaactc    26520
tgcttctatt attcccccaa tcattacttc tgtcacattg atagttaaat aatttctgtg   26580
aatttattcc ttgattctaa aatatgagga taatgacaat ggtattataa gggcagatta   26640
agtgatatag catgagcaat attcttcagg cacatggatc gaattgaata cactgtaaat   26700
cccaacttcc agtttcagct ctaccaagta aagagctagc aagtcatcaa aatgggggaca  26760 tacagaaaaa aaaaggaca ctagaggaat aatatacct gactcctagc ctgattaata    26820
tatcgattca cttttttctc tgtttgatga caaattctgg cttaaataa ttttaggatt    26880 ttaggcttct cagctcccctt cccagtgaga agtataagca ggacagacag gcaagcaaga  26940
agagagcccc aggcaatact cacaaagtag ccaatgtccc ctgtggtcat agagaaatga   27000
aaagagagag gattctctgg aagcactgga tgtaatcttt tctgtctgtc ctctctaggg   27060
aatcacccca aggtactgta ctttgggatt aaggctttag tcccactgtg gactacttgc   27120
tattctgttc agtttctaga aggaactatg tacggttttt gtctccctag agaaactaag   27180
gtacagaagt tttgtttaca atgcactcct taagagagct agaactgggt gagattctgt   27240
tttaacagct ttatttctct ttccttggcc ctgttttgt cactgtcacc acctttaagg    27300
caaatgttaa atgcgctttg gctgaaactt ttttcctat tttgagattt gctccttat     27360 atgaggcttt cttggaaaag gagaatggga gagatggata tcatttggga agatgatgaa   27420
```

```
gagggtaaaa aaggggacaa atggaaattt gtgttgcaga tagatgagga gccaacaaaa    27480
aagagcctca ggatccagca cacattatca caaacttagt gtccatccat cactgctgac    27540
cctctccgga cctgactcca cccctgaggg acacaggtca gccttgacca atgactttta    27600
agtaccatgg agaacagggg gccagaactt cggcagtaaa gaataaaagg ccagacagag    27660
aggcagcagc acatatctgc ttccgacaca gctgcaatca ctagcaagct ctcaggcctg    27720
gcatcatggt gcattttact gctgaggaga aggctgccgt cactagcctg tggagcaaga    27780
tgaatgtgga agaggctgga ggtgaagcct tgggcaggta agcattggtt ctcaatgcat    27840
gggaatgaag ggtgaatatt accctagcaa gttgattggg aaagtcctca agatttttg    27900 catctctaat tttgtatctg atatggtgtc atttcataga ctcctcgttg tttacccctg    27960
gacccagaga ttttttgaca gctttggaaa cctgtcgtct ccctctgcca tcctgggcaa    28020
ccccaaggtc aaggcccatg gcaagaaggt gctgacttcc tttggagatg ctattaaaaa    28080 catgacaac ctcaagcccg cctttgctaa gctgagtgag ctgcactgtg acaagctgca    28140
tgtggatcct gagaacttca aggtgagttc aggtgctggt gatgtgattt tttggcttta    28200
tattttgaca ttaattgaag ctcataatct tattggaaag accaacaaag atctcagaaa    28260
tcatgggtcg agcttgatgt tagaacagca gacttctagt gagcataacc aaaacttaca    28320
tgattcagaa ctagtgacag taaaggacta ctaacagcct gaattggctt aacttttcag    28380
gaaatcttgc cagaacttga tgtgtttatc ccagagaatt gtattataga attgtagact    28440
tgtgaaagaa gaatgaaatt tggcttttgg tagatgaaag tccatttcaa ggaaatagaa    28500
atgccttatt ttatgtgggt catgataatt gaggtttaga aagagatttt tgcaaaaaaa    28560 ataaagatt tgctcaaaga aaaataagac acattttcta aaatatgtta aatttcccat    28620
cagtattgtg accaagtgaa ggcttgtttc cgaatttgtt ggggattta aactcccgct    28680 gagaactctt gcagcactca cattctacat ttacaaaaat tagacaattg cttaaagaaa    28740
aacagggaga gagggaaccc aataatactg gtaaaatggg gaagggggtg agggtgtagg    28800
taggtagaat gttgaatgta gggctcatag aataaaattg aacctaagct catctgaatt    28860
ttttgggtgg gcacaaacct tggaacagtt tgaggtcagg gttgtctagg aatgtaggta    28920
taaagccgtt tttgtttgtt tgtttgtttt ttcatcaagt tgttttcgga aacttctact    28980
caacatgcct gtgtgttatt ttgtcttttg cctaacagct cctgggtaac gtgatggtga    29040
ttattctggc tactcacttt ggcaaggagt tcacccctga agtgcaggct gcctggcaga    29100
agctggtgtc tgctgtcgcc attgccctgg cccataagta ccactgagtt ctcttccagt    29160
ttgcaggtgt tcctgtgacc ctgacaccct ccttctgcac atgggactg ggcttggcct    29220 tgagagaaag ccttctgttt aataaagtac attttcttca gtaatcaaaa attgcaattt    29280
tatcttctcc atcttttact cttgtgttaa aaggaaaaag tgttcatggg ctgagggatg    29340
gagagaaaca taggaagaac caagagcttc cttaagaaat gtatggggc ttgtaaaatt    29400 aatgtggatg ttatgggaga attccaggat tccaaggagg atgatatgat ggagaaaaat    29460
ctttatcggg gtgggaaaat ggttaattaa gtggacagag actcctaggc agttttact    29520 gcaccgggga aagaaggagc tgttagtggt acctgagaaa gcagatttgt ggtacatgtc    29580
acttttcatt aaaaacaaaa acaaaacaaa acaaaacttc atagatatcc aagatatagg    29640
ctagaattac tattttaatt tactcttatt tacattttga agtagctagc ttgtcacatg    29700
ttttatgaaa ttgatttgga gataagatga gtgtgtatca acaatagcct gctctttcca    29760
```

```
tgaaggattc cattatttca tgggttagct gaagctaaga cacatgatat cattgtgcat    29820
tatcttctga tagaatgtaa catgcactaa aataaagtta gagttaggac ctgagtggga    29880
aagttttggg agagtgtgat gaagactttc cgtgggagat agaatactaa taaaggctta    29940
aattctaaaa ccagcaagct agggcttcgt gacttgcatg aaactggctc tctggaagta    30000
gaagggagag taagacatac gtagaggact aggaaagacc agatagtaca gggcctggct    30060
acaaaaatac aagcttttac tatgctattg caatactaaa cgataagcat taggatgtta    30120
agtgactcag gaaataagat tttgggaaaa agtaatctgc ttatgtgcac aaaatggatt    30180
caagtttgca gataaaataa aatatggatg atgattcaag gggacagata caatggttca    30240
aacccaagag gagcagtgag tctgtggaat ttgaaggatg acaaaggtg gggtgagaaa    30300 gacatagtat tcgactgact gtgggagatg agaaggaaga aggaggtgat aaatgactga    30360
aagctcccag actggtgaag ataacaggag gaaaccatgc actgacctgg tgactctcat    30420
gtgtgaaggg tagagggata ttaacagatt tactttttag gaagtgctag attggtcagg    30480
gagttttgac cttcaggtct tgtgtctttc atatcaagga acctttgcat tttccaagtt    30540
agagtgccat attttggcaa atataacttt attagtaatt ttatagtgct ctcacattga    30600
tcagactttt tcctgtgaat tacttttgaa tttggctgta tatatccaga atatgggaga    30660
gagacaaata attattgtag ttgcaggcta tcaacaatac tggtctctct gagccttata    30720 accttttcaat atgcccataa acagagtaaa cagggattat tcatggcact aaatattttc    30780
acctagtcag tcaacaaatg ggagcaatgt gcatttttg atacatattt ttatatattt    30840
atggggtaca tgtgatactt acatgcctag aacatgtgat gattaagtct agatatttag    30900
gatatccatt gctttgagca tttatcattt ctatgtattg agaaaatttc aaatcctcat    30960
ttctagccat tttgaaatat ataataaata gtaattaact atagtcaccc tactcaaata    31020
tcaaacatta tggcttaatc cttctatcca actgtgtttg tacctattaa ccaacatctc    31080
ttaaatcccc tcccatacac actcacactt tttccagcct ctgataacta tcattctact    31140
ctctaccacc atgagaccca cttttttagc tcccacagat gaataaaaac atgtgatatt    31200
tgactttctg tatctggctt attttattat ctatctcttt ggcataccaa gagtttgttt    31260
ttgttctgct tcagggcttt caattaacat aatgacctct ggttccatcc atgttgctac    31320
aaatgacaag atttcattct ttttcatggc aaaatagtac tgtgcaaaaa tacaattttt    31380
taatccgttc atctgttgat agacacttag gttgatccca aaccttaact attgtgaata    31440
gtgcttcaat aaacatgagt gtaatgtgtc cattggatat actgatttcc tttcttttgg    31500
ataaataacc actagtgaga ttgctggatt gtatgatagt tctgttttta gtttactgag    31560
aaatcttcat actgttttcc ataatggttg tactattta cattcccacc aacagtgtgt    31620
aagaaagagt tccctttttct ccatatcctc acaaggatct gttatttttt gtcttttttg    31680
ttaatagccg ttttaactag agtaagtaga tatctcattg tagttttgat ttgcatttcc    31740
ctgatcatta gtgatgttga aattttttc atatgtttgt tggtcatttg tatatctttt    31800
tctgagaatt gtctgttcat gtccttagcc tactttttat tgggattgtt tgttattttc    31860
ttgataatct atttgtgttc attttagagc ctggatatta ttcttttgtc agatgtatag    31920
attgtgaaga ttttctccca ctctgtgggt tgtctgttta ttctgcagac tcttcctttt    31980
gccatgcaaa agctctttag tttaatttag tcccagatat tttctttgtt tttatgtatt    32040
tgcatttgtg ttcttggtca tgaaatcctt tcctaagcca atgtgtagaa gggttttttcc   32100 gatgttattt tctagaattg ttacagtttc agggcttaga tttaagtcct tgatccatct   32160
```

```
tgagttgatt tttgtataag gtgagagatg aagatccagt ttcattctcc tacatgtagc    32220
ttgccagcta tccccgcacc atttgttgaa tagggtgccc tttccccact ttatgttttt    32280
gtttgctttg tcaaagatca gttggatgta agtatttgag tttatttctg ggttctctat    32340
tctgttccat tggtcgatgt gcctatttgt acaccagcat catgctgttt tggtgactat    32400
ggccttattg tatagtttga aatgaggtaa tgtaatgcct tcagatttgt tcttttttt     32460 agacttgctt gtttattggg ctctttttg gttccataag aatttagga ttgtttttc       32520 tagttctgtg aagactaatg gtggtatttt gatgggaatt gcaatgaatt tgtaggttgc    32580
ttctggcatt atggccattt tcacaatatt gattctaccc atctatgaga atggcatgtg    32640
tttccatttg tttgtgtctt atatgattac tttcagccgt gttttgtagt tttccttgta    32700
gatgtctttc acctccttgg ttaggtatat attcctaagt ttttgttttg ttttgttttg    32760 tttttttgcag ctattgtaaa aggggttgag ttcttgattt tattctcagc ttggtcattg   32820
ctggtatgta agaaagcaac tcattggtgt acgttaattt tgtatccaga aactttgctg    32880
aattatttta tcagttctag ggggttttgg aggagtcttt agagttttct acatacacaa    32940
tcatatcatc agcaaacagt gacagtttga cttttctcttt aacaatttgg atgtgcttta   33000
cttgtttctc ttgtctgatt gctcttgcta ggacttccag taatatgtta aagagaagtg    33060
gtgagagtgg gtatccttgt ctcattccag ttttcagaca gaatgctttt aactttttcc    33120
cattcaatat aatgttggct gtgtgtttac catagctggc ttttattaca ttgaggtatg    33180
tcctttgtaa accgattttg ctgagttttta gtcataaagt gatgttgaat tttgttgaat   33240
gcagtttctg tggctattga gataatcaca tgattttgt ttccaattct ctttatgttg    33300
tgtatcacac ttattgactt gcgtatgtta aaccatccgt gcatccctcg catgaaaccc    33360
acttgatcat gggttttgat atgctgtcgg atgctattag ctagtatttt gtcaaggatg    33420
ttggcatcta tgttcatcag ggatattgat ctgtagtgtt ttttttttt ggttatgttc    33480 tttcccagtt ttggtattaa ggtgatactg gcttcataga atgatttagg gaggattctc    33540
tctttctcta tcttgtagaa tactgtcaat aggattggta tcaattcttc tttgaatgtc    33600
tggtagaatt cagctgtgaa tctatctggt cctggacttt tttgttgttg gtaaatttt    33660 attatcattt cagtcttgct gcttattact ggtctgttca gggtatctaa ttcttcctga    33720
cttaagctag agccctgtat cttttccagga attcgaacgt ctccttagg ttttctagtt    33780 tatgcatgta aaggtgttca tagtagcctt gaataatctt ttgtatttct gtggtatcag    33840
taatagtatc tcctgttttg tttctaattg agtttatttg cacttctctc ctctttttctt   33900 ggttaatctt gctaatggtc tatcagtttt atttatcttt tcaaagaacc agcttttat    33960 ttcatttagc ttttgtattt ttttgcagtt gtttaatt catttagttc tcctcttatc    34020
ttagttattc ccttctttt gctgggtttt ggttctgttt gttttgttt ctctagtttc    34080 ttgtggtgtg accttatatt gtctgtctgt cctctttcag actctttgac atcgacattt    34140
agggctgtga actttccttt tagcaccatc tttgctgtat cctagaggtt ttgataggtt    34200
gtgtcactat tgtcggtcag ttcaagtaat tttgttgttc ttattatact ttaagttctg    34260
ggatacatgt gcagaatgtg caggtttgtt acataggtat agatgtgcca tggtggtttg    34320
ctgcacccat caacctgtca tctacattag gtatttcttt taatgttatc cctctcctaa    34380
ccccctcacc ccccgacagg ccctggtgtg tgatgttccc ctccctgtgt ccatgtgttc    34440
tcattgttca actcccactt atgagtgaga acgtgtggtg tttggtttct ctgttcctgt    34500
```

```
gttagtttgc tcagaatgat ggtttccacc ttcatccatg tccctgcaaa gacatgaact    34560
catcattttt atggctgcat agtattccat ggtgtatatg tgccacattt tctttatcca    34620
ttatatcgct gatggccatt tgggttggtt ccaagtcttt gctattgtga atagtgccac    34680
aataaacata cgtgtgcacg tgtcttata gtagaatgat ttctaattct ttgggtatat     34740
acccagtaat gggattgctg ggtcaaacag tatttctggt tctagatcct tgaggaatcg    34800
ccacactgtc ttccacaatg gttgaactaa tttacacacc catcaacagt gtaaaatttt    34860
tcctattctt ccacatcctc tccagcacct tttgtttcct gactttttaa taattgccat    34920
tctaactggc atgagatggt atctcattgt ggttttgatt tgcatttctc taatgaccag    34980
tgatgatgag cttcttttca tgtgtttctt ggccacataa atgacttctt tagagaagca    35040
tctgttcata tcctttgtcc acttttgat ggggtcgtta ggtttttct tgtaaatttg      35100 ttgaagttct ttgtagattt tggatgttag ccctttgtca gatggataga ttgcaaaaat    35160
tttctcccat tctgtaggtt gcctgttcac tctgatgata gtcttttgct gtgcagaagc    35220
tctttagttt aattagatcc catatgtcaa ttttggcctt tgttgtcatt gcttttgatg    35280
ttttagtcgt gaattttgc ccatgcctat gtcctgaatg gtattgccta ggttatcttc     35340 taggatttt atggttttag gttgcacatt taagtcttta atccaccttg agttaatttt     35400
tgtataaggt gtaaggaagg ggtacagttt cagttttatg catattgcta gccagttttt    35460
ccagcaccat ttattaaata gggaattctt tctccattgc ttttgtgatg tttgtcaaag    35520
atcagatggt cgtagatgtg tggcattatt tctgaggctt ctgttctgtt ccactggtct    35580
atatatctgt tttggtacca gtaccatgct gttttttgtta ctgtagcctt gtagtatagt   35640
ttgaagtcag gtagcatcat gcctccagct ttgttctttt tgtttaggat tgtcttggct    35700
atatgggctc ttttttgatt ccatatgaca tttaaagtag ttttttctaa ttctttgaaa    35760
aaagtcagtg gtagcttgat ggggatagca ttgaatctat aaattacttt gggcagtatg    35820
gccattttaa agatattgat tctttctatc tatgagcatg gaatgttttt ccatttgttt    35880
gtgtcctctc ttatttcctt gagcagtgag tggtttgtag ctctccttga agaggttctt    35940
cacatccctt agaagttgta tttctaggta ttttatttta ttctctttgc agcaattgtg    36000
aatgggagtt cacccatgat ttggctctct gcttgtctat tattggtgta taggaacgct    36060
tgtgatttct gcacactgat tttgtatctt gagactttgc tgaagctgtt tatcagctta    36120
agattttggg ctgagatgac agggtcttct aaatatacaa tcatgtcatc tgcaaacaga    36180
gacaatttga cttcctctct tcctatttga atatgcttta tttctttctc ttgcctgatt    36240
gtcctggcga gaacttccaa tactatgttg agtaagagtg gcgagagggc atccttgtct    36300
tgtgccggtt tcaaagcaa atgattttta aatttccatc ttgatttcat tgttgaccca     36360
atgatcattc aggagcaggt tatttaattt ccctgtattt gcatggtttt gaaggttcct    36420
tttgtagttg atttccaatt ttattctact gtggtctgag agagtgcttg ataaatttc     36480 aattttaaa aatttattga ggcttgtttt gtggcatatc atatggccta tcttggagaa    36540
agttccatgt gctgatgaat agaatgtgta ttctgcagtt gttgggtaga atgtcctgta    36600
aatatctgtt aagtccattt gttctttaaa tccattgttt ctttgtagac tgtccttgatg   36660 acctgcctag tgcagtcagt ggagtattga agtcccccac tattattatg ttgctgtcta   36720
gtctagtagt aattgtttta taaatttggg atctccagta ttagatgcat atatattaag   36780
aattgtaata ttctcccatt ggacaagggc ttttatcatt tatgatgtc cctctttgtc     36840 ttttttaact gctgtttctt taaagtttgt tttgtctgac ataagaatag ctgctttggc    36900
```

```
tcgcttttgg tgtccatttg tgtggaatgt cattttccac ccctttacct taagtttatg    36960
tgagtcctta tgtgttaggt gagtctcctg aaggcggcag ataactggtt ggtgaattct    37020
tattcattct gcaattctgt atcttttaag tggagcattt agtccattta cattcaacat    37080
cagtattgag gtgtgaggta ctattccatt cttcgtggta tttgttgcct gtgtatcttt    37140
ttatctgtat ttttgttgta tatgtcctat gggatttatg ctttaaagag gttctgtttt    37200
gatgtgcttc cagggtttat ttcaagattt agagctcctt ttatcagttc ttgtagtgtt    37260
ggcttggtag tgccgaattc tctcagcatt tgttttctg aaaaacactg tgtattttct     37320
tcatttgtga agcttagttt cactggatat aaaattcttg gctgataatt gttttgttta    37380
agaaggctga agatagggcc atattcactt ctagctttta cggtttctgc tgagaaatct    37440
gctgttaatc tgataggttt tctttcatag gttacctggt agtttcacct cacagctctt    37500
aagattctct tgtctttag ataactttgg atactctgat gacaatgtac ctaggcaatg     37560 atattttgc aatgaatttc ccaggtgttt attgagcttc ttgtatttgg atatctaggt     37620
ctctagcaag gtgggggaag ttttccttga ttatttccct ggataagttt tccaaacttt    37680
tagatttctc ttctttctca ggaatgctga ttattcttag gtttgattgt ttaacataat    37740
cccagatttc ttggaggctt tgttcatatt ttcttattct ttttctttg tctttgttgg     37800 attgggttaa ttcaaaaact ttgtcttcaa gctctgaatt tcttctgctt ggattctatt    37860
gctgagactt tctagagcat tttgcatttc tataagtgca tccattcatc cattgtttcc    37920
tgaagttttg aatgttttt atttatgcta tctctttaac tgaagatttc tcccctcatt     37980
tcttgtatca tattttggt ttttttaaaa ttggacttca ccttcctcgg atgcctcctt     38040
gattagctta ataactgacc ttctgaatta ttttcaggt aaatcaggga tttcttcttg     38100
gtttggatgc attgctggtg agctagtatg atttttggg gggtgttaaa gaaccttgtt    38160
tttcatatta ccagagttag ttttctggtt ccttctcact tgggtaggct ctgtcagagg    38220
gaaagtctag gcctcaaggc tgagactttt gtcccatgag gtgttccctt gatgtagcac    38280
agtccccctt ttcctaggcg tggggcttcc tgagagccga actgtagtga ttgttatctc    38340
tcttctggat ctagccaccc atcaggtcta ccagactcca ggctggtact ggggtttgtc    38400
tgcacagagt cttgtgacgt gaaccatctg tgggtctctc agccatagat acaaccacct    38460
gctccaatgg aggtggcaga ggatgaaatg gactctgtga gggtccttac ttttggttgt    38520
tcaatgcact attttgtgc tggttggcct cctgccagga ggtggcactt tctagaaagc     38580
atcagcagag gcagtcaggt ggtggtggct gggggggctg gggcaccta gaactcccaa     38640 gaatatatgc cctttgtctt cagctaccag ggtgagtaag gaaggaccat caggtggggg    38700
caggactagt cgtgtctgag ctcagagtct ccttgggcag gtctttctgt ggctactgtg    38760
ggaggatggg ggtgtagttt ccaggtcaat ggatttatgt tcctaggaca attatggctg    38820
cctctgctgt gtcatgcagg tcatcaggaa agtgggggaa agcaagcagt cacgtgactt    38880
gcccagctcc catgcaactc aaaaggttgg tctcacttcc agcgtgcacc ctcccccgca    38940
acagcaccga atctgtttcc atgcagtcag tgagcaaggc tgagaacttg ccccaggcta    39000
ccagctgcga aaccaagtag ggctgtccta cttccctgcc agtggagtct gcacaccaaa    39060
ttcatgtccc cccaccaacc cccccactgc ccagccccta gatctggcca ggtggagatt    39120
ttctttttcc tgtcatcttt tcccagttcc tctggcagcc ctcccaaatg acccctgtga    39180
ggcaaggcag aaatggcttc ctaggggacc cagagagccc acaggctttt tcccgctgct    39240
```

```
tcctctaccc ctgtattttg cttggccctc taaattgact cagctccagg taaggtcaga    39300
atcttctcct gtggtctaga tcttcaggtt ccccagtgag gatgtgtgtt tgggggtaga    39360 cggtcccct tttccacttc cacagtttgg gcactcacaa tatttggggt gtttcccggg     39420
tcctgcagga gcaatctgct tctttcagag ggtgtgtgcg ttctctcagc tttcttgatt    39480
tatttctgca ggtggttctg caaaaaaaat tcctgatggg agacttcaca tgctgctctg    39540
tgcatccgag tgggagctgc aatgtacttc tgctgcctcc catctgccat caccctctaa    39600
tttgtcggta atatgcattt ttaatcaatc ttttttttctc tctctctctt tttcttctcc   39660
cccaaaacta tactgccctt tgatatcaag gaatcaagga cgtgatgttg aggggtgggc    39720
agtggataca ctctttaccc cttagggagc tatatctaga tttagatatt gccaattcaa    39780
gataacttaa ttgaaagcaa attcataatg aatacacaca cacacacaca catctgcatg    39840
acaagatttt taatagttga agaataact aataattgtc cacaggcaat aagggctttt     39900
taagcaaaac agttgtgata aacaggtcat tcttagaata gtaatccagc caatagtaca    39960
ggttgcttag agattatgtc attaccagag ttaaaattct ataatggctt ctcactccct    40020
accactgagg acaagtttat gtccttaggt ttatgcttcc ctgaaacaat accacctgct    40080
attctccact ttacatatca acggcactgg ttctttatct aactctctgg cacagcagga    40140
gtttgttttc ttctgcttca gagctttgaa tttactattt cagcttctaa actttatttg    40200
gcaatgcctt cccatggcag attccttctg tcattttgcc tctgttcgaa tactttctcc    40260
ttaatttcat tcttagttaa taatatctga aattattttg ttgtttaact taattattaa    40320
ttttatgtat gttctaccta gattataatc ttcagaggaa agttttattc tctgacttat    40380
ttaacttaaa tgcccactac tttaaaaatt atgacattta tttaacagat atttgctgaa    40440
caaatgtttg aaaatacatg ggaagaatg cttgaaaaca cttgaaattg cttgtgtaaa     40500
gaaacagttt tatcagttag gatttaatca atgtcagaag caatgatata ggaaaaatcg    40560
aggaataaga cagttatgga taaggagaaa tcaacaaact cttaaaagat attgcctcaa    40620
aagcataaga ggaaataagg gttatacat gactttaga acactgcctt ggttttttgga     40680 taaatgggga agttgtttga aaacaggagg atcctagat attccttagt ctgaggagga     40740
gcaattaaga ttcacttgtt tagaggctgg gagtggtggc tcacgcctgt aatcccagaa    40800
ttttgggagg ccaaggcagg cagatcacct gaggtcaaga gttcaagacc aacctggcca    40860
acatggtgaa atcccatctc tacaaaaata caaaaattag acaggcatga tggcaagtgc    40920
ctgtaatccc agctacttgg gaggctgagg aaggagaatt gcttgaacct ggaaggcagg    40980
agttgcagtg agccgagatc ataccactgc actccagcct gggtgacaga acaagactct    41040
gtctcaaaaa aaaaaagag agattcaaaa gattcacttg tttaggcctt agcgggctta    41100
gacaccagtc tctgacacat tcttaaaggt caggctctac aaatggaacc caaccagact    41160
ctcagatatg gccaaagatc tatacacacc catctcacag atcccctatc ttaaagagac    41220
cctaatttgg gttcacctca gtctctataa tctgtaccag cataccaata aaaatctttc    41280
tcacccatcc ttagattgag agaagtcact tattattatg tgagtaactg gaagatactg    41340
ataagttgac aaatctttt cttttccttc ttattcaact tttatttaa cttccaaaga      41400 acaagtgcaa tatgtgcagc tttgttgcgc aggtcaacat gtatctttct ggtctttag    41460 ccgcctaaca ctttgagcag atataagcct tacacaggat tatgaagtct gaaaggattc    41520
caccaatatt attataattc ctatcaacct gataggttag gggaaggtag agctctcctc    41580
caataagcca gatttccaga gtttctgacg tcataatcta ccaaggtcat ggatcgagtt    41640
```

```
cagagaaaaa acaaaagcaa aaccaaacct accaaaaaat aaaaatccca aagaaaaaat   41700
aaagaaaaaa acagcatgaa tacttcctgc catgttaagt ggccaatatg tcagaaacag   41760
cactgagtta cagataaaga tgtctaaact acagtgacat cccagctgtc acagtgtgtg   41820
gactattagt caataaaaca gtccctgcct cttaagagtt gttttccatg caaatacatg   41880
tcttatgtct tagaataaga ttccctaaga agtgaaccta gcatttatac aagataatta   41940
attctaatcc atagtatctg gtaaagagca ttctaccatc atctttaccg agcatagaag   42000
agctacacca aaaccctggg tcatcagcca gcacatacac ttatccagtg ataaatacac   42060
atcatcgggt gcctacatac ataccctgaat ataaaaaaaa tacttttgct gagatgaaac   42120
aggcgtgatt tatttcaaat aggtacggat aagtagatat tgaagtaagg attcagtctt   42180
atattatatt acataacatt aatctattcc tgcactgaaa ctgttgcttt ataggatttt   42240
tcactacact aatgagaact taagagataa tggcctaaaa ccacagagag tatattcaaa   42300
gataagtata gcacttctta tttggaaacc aatgcttact aaatgagact aagacgtgtc   42360
ccatcaaaaa tcctggacct atgcctaaaa cacatttcac aatccctgaa cttttcaaaa   42420
attggtacat gctttaactt taaactacag gcctcactgg agctacagac aagaaggtga   42480
aaaacggctg acaaaagaag tcctggtatc ttctatggtg ggagaagaaa actagctaaa   42540
gggaagaata aattagagaa aaattggaat gactgaatcg gaacaaggca aaggctataa   42600
aaaaaattaa gcagcagtat cctcttgggg gccccttccc cacactatct caatgcaaat   42660
atctgtctga aacggtccct ggctaaactc cacccatggg ttggccagcc ttgccttgac   42720
caatagcctt gacaaggcaa acttgaccaa tagtcttaga gtatccagtg aggccagggg   42780
ccggcggctg gctagggatg aagaataaaa ggaagcaccc ttcagcagtt ccacacactc   42840
gcttctggaa cgtctgaggt tatcaataag ctcctagtcc agacgccatg ggtcatttca   42900
cagaggagga caaggctact atcacaagcc tgtggggcaa ggtgaatgtg gaagatgctg   42960
gaggagaaac cctgggaagg taggctctgg tgaccaggac aagggaggga aggaaggacc   43020
ctgtgcctgg caaagtccca ggtcgcttct caggatttgt ggcaccttct gactgtcaaa   43080
ctgttcttgt caatctcaca ggctcctggt tgtctaccca tggacccaga ggttctttga   43140
cagctttggc aacctgtcct ctgcctctgc catcatgggc aaccccaaag tcaaggcaca   43200
tggcaagaag gtgctgactt ccttgggaga tgccataaag cacctggatg atctcaaggg   43260
cacctttgcc cagctgagtg aactgcactg tgacaagctg catgtggatc ctgagaactt   43320
caaggtgagt ccaggagatg tttcagcact gttgccttta gtctcgaggc aacttagaca   43380
actgagtatt gatctgagca cagcagggtg tgagctgttt gaagatactg gggttgggag   43440
tgaagaaact gcagaggact aactgggctg agacccagtg gcaatgtttt agggcctaag   43500
gagtgcctct gaaaatctag atggacaact ttgactttga gaaagagag gtggaaatga   43560 ggaaaatgac ttttctttat tagatttcgg tagaaagaac tttcaccttt ccctattttt   43620
tgttattcgt tttaaaacat ctatctggag gcaggacaag tatggtcatt aaaaagatgc   43680
aggcagaagg catatattgg ctcagtcaaa gtggggaact ttggtggcca aacatacatt   43740
gctaaggcta ttcctatatc agctggacac atataaaatg ctgctaatgc ttcattacaa   43800
acttatatcc tttaattcca gatggggca aagtatgtcc aggggtgagg aacaattgaa   43860
acatttgggc tggagtagat tttgaaagtc agctctgtgt gtgtgtgtgt gtgtgtcgc   43920 gcgtgtgttt gtgtgtgtgt gagagcgtgt gtttcttta acgttttcag cctacagcat   43980
```

```
acagggttca tggtggcaag aagataacaa gatttaaatt atggccagtg actagtgctg    44040
caagaagaac aactacctgc atttaatggg aaagcaaaat ctcaggcttt gagggaagtt    44100
aacataggct tgattctggg tggaagcttg gtgtgtagtt atctggaggc caggctggag    44160
ctctcagctc actatgggtt catctttatt gtctcctttc atctcaacag ctcctgggaa    44220
atgtgctggt gaccgttttg gcaatccatt tcggcaaaga attcacccct gaggtgcagg    44280
cttcctggca gaagatggtg actggagtgg ccagtgccct gtcctccaga taccactgag    44340
ctcactgccc atgatgcaga gctttcaagg ataggcttta ttctgcaagc aatcaaataa    44400
taaatctatt ctgctaagag atcacacatg gttgtcttca gttcttttt tatgtctttt    44460 taaatatatg agccacaaag ggttttatgt tgagggatgt gtttatgtgt atttatacat    44520
ggctatgtgt gtttgtgtca tgtgcacact ccacactttt ttgtttacgt tagatgtggg    44580
ttttgatgag caaataaaag aactaggcaa taaagaaact tgtacatggg agttctgcaa    44640
gtgggagtaa aaggtgcagg agaaatctgg ttggaagaaa gacctctata ggacaggact    44700
cctcagaaac agatgttttg gaagagatgg ggaaaggttc agtgaagggg gctgaacccc    44760
cttccctgga ttgcagcaca gcagcgagga aggggctcaa cgaagaaaaa gtgttccaag    44820
ctttaggaag tcaaggttta ggcagggata gccattctat tttattaggg gcaatactat    44880
ttccaacggc atctggcttt tctcagccct tgtgaggctc tacagggagg ttgaggtgtt    44940
agagatcaga gcaggaaaca ggttttctt tccacggtaa ctacaatgaa gtgatcctta    45000
ctttactaag gaacttttca ttttaagtgt tgacgcatgc ctaaagaggt gaaattaatc    45060
ccataccctt aagtctacag actggtcaca gcatttcaag gaggagacct cattgtaagc    45120
ttctagggag gtggggactt aggtgaagga aatgagccag cagaagctca caagtcagca    45180
tcagcgtgtc atgtctcagc agcagaacag cacggtcaga tgaaaatata gtgtgaagaa    45240
tttgtataac attaattgag aaggcagatt cactggagtt cttatataat tgaaagttaa    45300
tgcacgttaa taagcaagag tttagtttaa tgtgatggtg ttatgaactt aacgcttgtg    45360
tctccagaaa attcacatgc tgaatcccca actcccaatt ggctccattt gtggggagg    45420 ctttggaaaa gtaatcaggt ttagaggagc tcatgagagc agatccccat catagaatta    45480
ttttcctcat cagaagcaga gagattagcc atttctcttc cttctggtga ggacacagtg    45540
ggaagtcagc cacctgcaac ccaggaagag agccctgacc aggaaccagc agaaaagtga    45600
gaaaaaatcc tgttgttgaa gtcacccagt ctatgctatt ttgttatagc accttgcact    45660
aagtaaggca gatgaagaaa gagaaaaaaa taagcttcgg tgttcagtgg attagaaacc    45720
atgtttatct caggtttaca aatctccact tgtcctctgt gtttcagaat aaaataccaa    45780
ctctactact ctcatctgta agatgcaaat agtaagcctg agcccttctg tctaactttg    45840
aattctattt tttcttcaac gtactttagg cttgtaatgt gtttatatac agtgaaatgt    45900
caagttcttt cttatatttt cttctttct tttttttcct cagcctcaga gttttccaca    45960
tgcccttcct actttcagga acttctttct ccaaacgtct tctgcctggc tccatcaaat    46020
cataaaggac ccacttcaaa tgccatcact cactaccatt tcacaattcg cactttcttt    46080
ctttgtcctt ttttttttta gtaaaacaag tttataaaaa attgaaggaa taatgaatg    46140 gctacttcat aggcagagta gacgcaaggg ctactggttg ccgattttta ttgttatttt    46200
tcaatagtat gctaaacaag gggtagatta tttatgctgc ccattttag accataaaag    46260 ataacttcct gatgttgcca tggcattttt ttccttttaa ttttatttca tttcatttta    46320
atttcgaagg tacatgtgca ggatgtgcag gcttgttaca tgggtaaatg tgtgtctttc    46380
```

```
tggccttttta gccatctgta tcaatgagca gatataagct ttacacagga tcatgaagga   46440
tgaaagaatt tcaccaatat tataataatt tcaatcaacc tgatagctta ggggataaac   46500
taatttgaag atacagcttg cctccgataa gccagaattc cagagcttct ggcattataa   46560
tctagcaagg ttagagatca tggatcactt tcagagaaaa acaaaaacaa actaaccaaa   46620
agcaaaacag aaccaaaaaa ccaccataaa tacttcctac cctgttaatg gtccaatatg   46680
tcagaaacag cactgtgtta gaaataaagc tgtctaaagt acactaatat tcgagttata   46740
atagtgtgtg gactattagt caataaaaac aacccttgcc tctttagagt tgttttccat   46800
gtacacgcac atcttatgtc ttagagtaag attccctgag aagtgaacct agcatttata   46860
caagataatt aattctaatc cacagtacct gccaaagaac attctaccat catctttact   46920
gagcatagaa gagctacgcc aaaccctgg gtcatcagcc agcacacaca cttatccagt   46980
ggtaaataca catcatctgg tgtatacata catacctgaa tatggaatca aatattttc    47040 taagatgaaa cagtcatgat ttatttcaaa taggtacgga taagtagata ttgaggtaag   47100
cattaggtct tatattatgt aacactaatc tattactgcg ctgaaactgt ggctttatag   47160
aaattgtttt cactgcacta ttgagaaatt aagagataat ggcaaaagtc acaaagagta   47220
tattcaaaaa gaagtatagc acttttcct tagaaaccac tgctaactga aagagactaa    47280
gatttgtccc gtcaaaaatc ctggacctat gcctaaaaca catttcacaa tccctgaact   47340
tttcaaaaat tggtacatgc tttagcttta aactacaggc ctcactggag ctagagacaa   47400
gaaggtaaaa aacggctgac aaaagaagtc ctggtatcct ctatgatggg agaaggaaac   47460
tagctaaagg gaagaataaa ttagagaaaa actggaatga ctgaatcgga acaaggcaaa   47520
ggctataaaa aaaattagca gtatcctctt gggggcccct tccccacact atctcaatgc   47580
aaatatctgt ctgaaacggt ccctggctaa actccaccca tgggttggcc agccttgcct   47640
tgaccaatag ccttgacaag gcaaacttga ccaatagtct tagagtatcc agtgaggcca   47700
ggggccggcg gctggctagg gatgaagaat aaaaggaagc acccttcagc agttccacac   47760
actcgcttct ggaacgtctg aggttatcaa taagctccta gtccagacgc catgggtcat   47820
ttcacagagg aggacaaggc tactatcaca agcctgtggg gcaaggtgaa tgtggaagat   47880
gctggaggag aaaccctggg aaggtaggct ctggtgacca ggacaaggga gggaaggaag   47940
gaccctgtgc ctggcaaaag tccaggtcgc ttctcaggat ttgtggcacc ttctgactgt   48000
caaactgttc ttgtcaatct cacaggctcc tggttgtcta cccatggacc cagaggttct   48060
ttgacagctt tggcaacctg tcctctgcct ctgccatcat gggcaacccc aaagtcaagg   48120
cacatggcaa gaaggtgctg acttccttgg gagatgccac aaagcacctg gatgatctca   48180
agggcacctt tgcccagctg agtgaactgc actgtgacaa gctgcatgtg gatcctgaga   48240
acttcaaggt gagtccagga gatgtttcag ccctgttgcc tttagtctcg aggcaactta   48300
gacaacggag tattgatctg agcacagcag ggtgtgagct gttgaagat actgggggttg   48360 ggggtgaaga aactgcagag gactaactgg gctgagaccc agtggtaatg ttttagggcc   48420
taaggagtgc ctctaaaaat ctagatggac aattttgact ttgagaaaag agaggtggaa   48480
atgaggaaaa tgacttttct ttattagatt ccagtagaaa gaactttcat ctttccctca   48540
tttttgttgt tttaaaacat ctatctggag gcaggacaag tatggtcgtt aaaaagatgc   48600
aggcagaagg catatattgg ctcagtcaaa gtggggaact ttggtggcca aacatacatt   48660
gctaaggcta ttcctatatc agctggacac atataaaatg ctgctaatgc ttcattacaa   48720
```

```
acttatatcc tttaattcca gatgggggca aagtatgtcc aggggtgagg aacaattgaa   48780
acatttgggc tggagtagat tttgaaagtc agctctgtgt gtgtgtgtgt gtgtgcgcgc   48840
gcgcgtgtgt gtgtgtgtgt cagcgtgtgt ttcttttaac gtcttcagcc tacaacatac   48900
agggttcatg gtggcaagaa gatagcaaga tttaaattat ggccagtgac tagtgcttga   48960
aggggaacaa ctacctgcat ttaatgggaa ggcaaaatct caggctttga gggaagttaa   49020
cataggcttg attctgggtg gaagcttggt gtgtagttat ctggaggcca ggctggagct   49080
ctcagctcac tatgggttca tctttattgt ctcctttcat ctcaacagct cctgggaaat   49140
gtgctggtga ccgttttggc aatccatttc ggcaaagaat tcacccctga ggtgcaggct   49200
tcctggcaga agatggtgac tgcagtggcc agtgccctgt cctccagata ccactgagct   49260
cactgcccat gattcagagc tttcaaggat aggcttatt ctgcaagcaa tacaaataat   49320
aaatctattc tgctgagaga tcacacatga ttttcttcag ctcttttttt tacatctttt   49380
taaatatatg agccacaaag ggtttatatt gagggaagtg tgtatgtgta tttctgcatg   49440
cctgtttgtg tttgtggtgt gtgcatgctc ctcatttatt tttatatgag atgtgcattt   49500
tgatgagcaa ataaaagcag taaagacact tgtacacggg agttctgcaa gtgggagtaa   49560
atggtgtagg agaaatccgg tgggaagaaa gacctctata ggacaggact tctcagaaac   49620
agatgttttg gaagagatgg gaaaaggttc agtgaagacc tggggctgg attgattgca   49680 gctgagtagc aaggatggtt cttaaggaag ggaaagtgtt ccaagcttta ggaattcaag   49740
gtttagtcag gtgtagcaat tctattttat taggaggaat actatttcta atggcactta   49800
gcttttcaca gcccttgtgg atgcctaaga aagtgaaatt aatcccatgc cctcaagtgt   49860
gcagattggt cacagcattt caagggagag acctcattgt aagactctgg gggaggtggg   49920
gacttaggtg taagaaatga atcagcagag gctcacaagt cagcatgagc atgttatgtc   49980
tgagaaacag accagcactg tgagatcaaa atgtagtggg aagaatttgt acaacattaa   50040
ttggaaggct tacttaatgg aattttgta tagttggatg ttagtgcatc tctataagta   50100
agagtttaat atgatggtgt tacggaccta atgtttgtgt ctcctcaaaa ttcacatgct   50160
gaatccccaa ctcccaactg accttatctg tgggggaggc ttttgaaaag taattaggtt   50220
tagatgagct cataagagca gatccccatc ataaaattat tttccttatc agaagcagag   50280
agacaagcca tttctctttc ctcccggtga ggacacagtg agaagtccgc catctgcaat   50340
ccaggaagag aaccctgacc acgagtcagc cttcagaaat gtgagaaaaa actctgttgt   50400
tgaagccacc cagtctttg tattttgtta tagcaccttg cactgagtaa ggcagatgaa   50460
gaaggagaaa aaaataagct tgggttttga gtggactaca gaccatgttt atctcaggtt   50520
tgcaaagctc ccctcgtccc ctatgtttca gtataaaata cctactctac tactctcatc   50580
tataagaccc aaataataag cctgcgccct tctctctaac tttgatttct cctatttta   50640 cttcaacatg ctttactcta gccttgtaat gtctttacat acagtgaaat gtaaagttct   50700
ttattctttt tttctttctt tcttttttct cctcagcctc agaatttggc acatgccctt   50760
ccttctttca ggaacttctc caacatctct gcctggctcc atcatatcat aaaggtccca   50820
cttcaaatgc agtcactacc gtttcagaat atgcactttc tttctttttt gtttttttgtt   50880 tttttaagt caaagcaaat ttcttgagag agtaaagaaa taaacgaatg actactgcat   50940
aggcagagca gccccgaggg ccgctggttg ttccttttat ggttatttct tgatgatatg   51000
ttaaacaagt tttggattat ttatgccttc tcttttagg ccatataggg taactttctg   51060
acattgccat ggcattttc ttttaattta atttactgtt accttaaatt cagggtaca   51120
```

```
cgtacaggat atgcaggttt gttttatagg taaaagtgtg ccatggtttt aatgggtttt    51180 tttttcttg taaagttgtt taagtttctt gtttactctg gatattaggc ctttgtcaga    51240
agaatagatt ggaaaatctt tttcccattc tgtagattgt ctttcgctct gatggtagtt    51300
tcttttgctg agcaggagct ctttagttta attagattcc attggtcaat ttttgctttt    51360
gctgcaattg cttttcacgc tttcatcatg aaatctgtgc ccgtgtttat atcatgaata    51420
gtattgcctt gatttttttc taggcttttt atagtttggg gttttcatt taagtctcta    51480 atccatctgg agttaatttt ggataaggta taaggaagga gtccagtttc atttttcagc    51540
atatggctag ccagttctcc cccatcattt attaaattga aaatcctttc cccattgctt    51600
gcttttgtca ggtttctaaa agaccagatg gttgtaggta caatatgcag tttcttcaag    51660
tcatataata ccatctgaaa tctcttatta attcatttct tttagtatgt atgctggtct    51720
cctctgctca ctatagtgag ggcaccatta gccagagaat ctgtctgtct agttcatgta    51780
agattctcag aattaagaaa aatggatggc atatgaatga aacttcatgg atgacatatg    51840
gaatctaata tgtatttgtt gaattaatgc ataagatgca acagagagaa gttgacaact    51900
gcaatgataa cctggtattg atgatataag agtctataga tcacagtaga agcaataatc    51960
atggaaaaca attggaaatg gggaacagcc acaaacaaga aagaatcaat acttccagga    52020
aagtgactgc aggtcacttt tcctggagcg ggtgagagaa aagtggaagt tagcagtaac    52080
tgctgaattc ctggttggct gatggaaaga tggggcagct gttcactggt acgcagggtt    52140
ttagatgtat gtacctaagg atatgaggta tggcaatgaa cagaaattct tttgggaatg    52200
agttttaggg ccattaaagg acatgacctg aagtttcctc tgaggccagt ccccacaact    52260
caatataaat gtgtttcctg catatagtca aagttgccac ttctttttct tcatatcatc    52320
gatctctgct cttaaagata atcttggttt tgcctcaaac tgtttgtcac tacaaacttt    52380
ccccatgttc ctaagtaaaa caggtaactg cctctcaact atatcaagta gactaaaata    52440
ttgtgtctct aatatcagaa attcagcttt aatatattgg gtttaactct ttgaaattta    52500
gagtctcctt gaaatacaca tggggtgat ttcctaaact ttatttcttg taaggattta    52560
tctcaggggt aacacacaaa ccagcatcct gaacctctaa gtatgaggac agtaagcctt    52620
aagaatataa aataaactgt tcttctctct gccggtggaa gtgtgccctg tctattcctg    52680
aaattgcttg tttgagacgc atgagacgtg cagcacatga gacacgtgca gcagcctgtg    52740
gaatattgtc agtgaagaat gtctttgcct gattagatat aaagacaagt taaacacagc    52800
attagactat agatcaagcc tgtgccagac acaaatgacc taatgcccag cacgggccac    52860
ggaatctcct atcctcttgc ttgaacagag cagcacactt ctcccccaac actattagat    52920
gttctggcat aattttgtag atatgtagga tttgacatgg actattgttc aatgattcag    52980
aggaaatctc ctttgttcag ataagtacac tgactactaa atggattaaa aaacacagta    53040
ataaaaccca gttttcccct tacttcccta gtttgtttct tattctgctt tcttccaagt    53100
tgatgctgga tagaggtgtt tatttctatt ctaaaaagtg atgaaattgg ccgggcgcgg    53160
tggctcacac ctgtaatccc agcactttgg gaggctgagg tgggcggatc acgaggtcag    53220
gagatcaaga ccatcctggc taacatggtg aaaccccatc tctactaaaa atacaaaaaa    53280
ttagccagag acagtggcgg gtgcctgtag tcccagctac tcgggaggct gaggcaggag    53340
aatggcgtga acctgggagg cagagcttgc ggtgagcaga gatcgcgcca ctgcacactc    53400
cagcctgggt gacaaagcga gactccatct caaaaaaaaa aaaaaaaaaa agaaaaagaa    53460
```

```
agaaagaaag aaaaaaaaac tgatgaaatt gtgtattcaa tgtagtctca agagaattga    53520
aaaccaagaa aggctgtggc ttcttccaca taaagcctgg atgaataaca ggataacacg    53580
ttgttacatt gtcacaactc ctgatccagg aattgatggc taagatattc gtaattctta    53640
tccttttcag ttgtaactta ttcctatttg tcagcattca ggttattagc ggctgctggc    53700
gaagtccttg agaaataaac tgcacactgg atggtggggg tagtgtagga aaatggaggg    53760
gaaggaagta aagtttcaaa ttaagcctga acagcaaagt tcccctgaga aggccacctg    53820
gattctatca gaaactcgaa tgtccatctt gcaaaacttc cttgcccaaa ccccaccccc    53880
ggagtcacaa cccacccttg accaatagat tcattttact gagggaggca aagggctggt    53940
caatagattc atttcactgg gagaggcaaa gggctggggg ccagagagga gaagtaaaaa    54000
gccacacatg aagcagcaat gcaggcatgc ttctggctca tctgtgatca ccaggaaact    54060
cccagatctg acactgtagt gcatttcact gctgacaaga aggctgctgc caccagcctg    54120
tgaagcaagg ttaaggtgag aaggctggag gtgagattct gggcaggtag gtactggaag    54180
ccgggacaag gtgcagaaag gcagaaagtg tttctgaaag agggattagc ccgttgtctt    54240
acatagtctg actttgcacc tgctctgtga ttatgactat cccacagtct cctggttgtc    54300
tacccatgga cctagaggta cttttgaaagt tttggatatc tgggctctga ctgtgcaata    54360
atgggcaacc ccaaagtcaa ggcacatggc aagaaggtgc tgatctcctt cggaaaagct    54420
gttatgctca cggatgacct caaaggcacc tttgctacac tgagtgacct gcactgtaac    54480
aagctgcacg tggaccctga aacttcctg gtgagtagta agtacactca cgctttcttc    54540 tttacccctta gatatttgca ctatgggtac ttttgaaagc agaggtggct ttctcttgtg    54600
ttatgagtca gctatgggat atgatatttc agcagtggga ttttgagagt tatgttgctg    54660
taaataacat aactaaaatt tggtagagca aggactatga ataatggaag gccacttacc    54720
atttgatagc tctgaaaaac acatcttata aaaaattctg gccaaaatca aactgagtgt    54780
ttttggatga gggaacagaa gttgagatag agaaaataac atctttcctt tggtcagcga    54840
aattttctat aaaaattaat agtcactttt ctgcatagtc ctggaggtta gaaaaagatc    54900
aactgaacaa agtagtggga agctgttaaa aagaggattg tttccctccg aatgatgatg    54960 gtatacttt gtacgcatgg tacaggattc tttgttatga gtgtttggga aaattgtatg    55020
tatgtatgta tgtatgtatg tgatgactgg ggacttatcc tatccattac tgttccttga    55080
agtactatta tcctacttt taaaaggacg aagtctctaa aaaaaaaatg aaacaatcac    55140
aatatgttgg ggtagtgagt tggcatagca agtaagagaa ggataggaca caatgggagg    55200
tgcagggctg ccagtcatat tgaagctgat atctagccca taatggtgag agttgctcaa    55260
actctggtga aaaaggatgt aagtgttata tctatttact gcaagtccag cttgaggcct    55320
tctattcact atgtaccatt ttcttttta tcttcactcc ctccccagct cttaggcaac    55380
gtgatattga ttgttttggc aacccacttc agcgaggatt ttaccctaca gatacaggct    55440
tcttggcagt aactaacaaa tgctgtggtt aatgctgtag cccacaagac cactgagttc    55500
cctgtccact atgtttgtac ctatggtcca ctatgtttgt acctatgtcc caaaatctca    55560
tctcctttag atgggggagg ttggggagaa gagcagtatc ctgcctgctg attcagttcc    55620
tgcatgataa aaatagaata agaaatatg ctctctaaga aatatcattg tactctttt    55680 ctgtctttat attttaccct gattcagcca aaggacgca ctatttctga tggaaatgag    55740
aatgttggag aatgggagtt taaggacaga gaagatactt tcttgcaatc ctgcaagaaa    55800
agagagaact cgtgggtgga tttagtgggg tagttactcc taggaagggg aaatcgtctc    55860
```

```
tagaataaga caatgttttt acagaaaggg aggtcaatgg aggtactctt tggaggtgta    55920
agaggattgt tggtagtgtg tagaggtatg ttaggactca aattagaagt tctgtatagg    55980
ctattatttg tatgaaactc aggatatagc tcatttggtg actgcagttc acttctactt    56040
attttaaaca acatattttt tattatttat aatgaagtgg ggatggggct tcctagagac    56100
caatcaaggg ccaaaccttg aactttctct taacgtcttc aatggtatta atagagaatt    56160
atctctaagg catgtgaact ggctgtcttg gttttcatct gtacttcatc tgctacctct    56220
gtgacctgaa acatatttat aattccatta agctgtgcat atgatagatt tatcatatgt    56280
attttcctta aaggattttt gtaagaacta attgaattga tacctgtaaa gtctttatca    56340
cactacccaa taaataataa atctctttgt tcagctctct gtttctataa atatgtacaa    56400
gttttattgt ttttagtggt agtgatttta ttctctttct atatatatac acacacatgt    56460
gtgcattcat aaatatatac aattttatg aataaaaaat tattagcaat caatattgaa    56520
aaccactgat ttttgtttat gtgagcaaac agcagattaa aaggctgaga tttaggaaac    56580
agcacgttaa gtcaagttga tagaggagaa tatggacatt taaaagaggc aggatgatat    56640
aaaattaggg aaactggatg cagagaccag atgaagtaag aaaaatagct atcgttttga    56700
gcaaaaatca ctgaagtttc ttgcatatga gagtgacata ataaataggg aaacgtagaa    56760
aattgattca catgtatata tatatataga actgattaga caaagtctaa cttgggtata    56820
gtcagaggag cttgctgtaa ttatattgag gtgatggata aagaactgaa gttgatggaa    56880
acaatgaagt taagaaaaaa aatcgagtaa gagaccattg tggcagtgat tgcacagaac    56940
tggaaaacat tgtgaaacag agagtcagag atgacagcta aaatccctgt ctgtgaatga    57000
aaagaaggaa attattgac agaacagcaa atgcctacaa gcccctgtt tggatctggc      57060
aatgaacgta gccattctgt ggcaatcact tcaaactcct gtacccaaga cccttaggaa    57120
gtatgtagca ccctcaaacc taaaacctca agaaagagg ttttagaaga tataataccc     57180
tttcttctcc agtttcatta atcccaaaac ctctttctca aagtatttcc tctatgtgtc    57240
caccccaaag agctcacctc accatatctc ttgagtggga gcacatagat aggcggtgct    57300
accatctaac agcttctgaa attcctttgt catattttg agtccccact aataacccac     57360
aaagcagaat aaataccagt tgctcatgta caataatcac tcaactgctg tcttgtagca    57420
tacattaatt aagcacattc tttgaataat tactgtgtcc aaacaatcac actttaaaat    57480
ctcacacttg tgctatccct tgcccttctg aatgtcactc tgtattttaa atgaagagat    57540
gagggttgaa tttcctgtgt tacttattgt tcatttctcg atgaggagtt ttcacattca    57600
cctttagtgg aaaacacata agtacacatc ttacaggaaa aatataccaa actgacatgt    57660
agcatgaatg cttgtgcatg tagtcatata aaatcttgta gcaatgtaaa cattctctga    57720
tatacacata cagatgtgtc tatatgtcta cacaatttct tatgctccat gaacaaacat    57780
tccatgcaca cataagaaca cacactgtta cagatgcata cttgagtgca ttgacaaaat    57840
taccccagtc aatctagaga atttggattt ctgcatttga ctctgttagc tttgtacatg    57900
ctgttcattt actctgggtg atgtcttttcc ctcattttgc cttgtctatc ttgtactcat   57960
actttaagtc ctaacttata tgttatctca actaagaagc tatttttttt taattttaac    58020
tgggcttaaa gccctgtcta taaactctgc tacaattatg ggctctttct tataatattt    58080
agtgttttttc ctactaatgt acttaatctg ctcattgtat attcctacca ctaaattta    58140
acctctttta tggtagagac attgtcttgt aaactcttat ttccctagta tttggagatg    58200
```

```
aaaaaaaaga ttaaattatc caaaattaga tctctcttt  ctacattatg agtattacac   58260
tatccataga gaagtttgtt tgagacctaa actgaggaac ctttggttct aaaatgacta   58320
tgtgatatct tagtatttat aggtcatgag gttccttcct ctgcctctgc tatagtttga   58380
ttagtcaaca agcatgtgtc atgcatttat tcacatcaga atttcataca ctaataagac   58440
atagtatcag aagtcagttt attagttata tcagttaggg tccatcaagg aaaggacaaa   58500
ccattatcag ttactcaacc tagaattaaa tacagctctt aatagttaat tatccttgta   58560
ttggaagagc taaaatatca aataaaggac agtgcagaaa tctagatgtt agtaacatca   58620
gaaaacctct tccgccatta ggcctagaag ggcagaagga gaaaatgttt ataccaccag   58680
agtccagaac cagagcccat aaccagaggt ccactggatt cagtgagcta gtgggtgctc   58740
cttggagaga gccagaactg tctaatgggg gcatcaaagt atcagccata aaaaaccata   58800
aaaaagactg tctgctgtag gagatccgtt cagagagaga gagagaccag aaataatctt   58860
gcttatgctt tccctcagcc agtgtttacc attgcagaat gtacatgcga ctgaaagggt   58920
gaggaaacct gggaaatgtc agttcctcaa atacagagaa cactgaggga aggatgagaa   58980
ataaatgtga aagcagacat gaatggtaat tgacagaagg aaactaggat gtgtccagta   59040
aatgaataat tacagtgtgc agtgattatt gcaatgatta atgtattgat aagataatat   59100
gaaaacacag aattcaaaca gcagtgaact gagattagaa ttgtggagag cactggcatt   59160
taagaatgtc acacttagaa tgtgtctcta ggcattgttc tgtgcatata tcatctcaat   59220
attcattatc tgaaaattat gaattaggta caaagctcaa ataatttatt ttttcaggtt   59280
agcaagaact tttttttttt ttttctgaga tagagcattg ctatggttgc ccaggctgga   59340
gtgcaatggc atgatccagg ctcactgcaa catctgcctc ccaggttcaa gcgattctcc   59400
tgcctcagcc tcccaagtag ctggcactac aggcatgtgc caccaccatg cctggctaat   59460
tttctatttt tagtagatag ggggtttcac catgttggtc aggctgatct cgaactccta   59520
acatcaggtg atccaccctc ctcggcctct gaaagtgctg ggatcacagg cgtgagccac   59580
cacacccagc caagaatgtg aattttgtag aaggatataa cccatatttc tctgacccta   59640
gagtccttag tatacctccc ataccatgtg gctcatcctc cttacataca tttcccatct   59700
ttcaccctac cttttccttt ttgtttcagc ttttcactgt gtcaaaatct agaaccttat   59760
ctcctacctg ctctgaaacc aacagcaagt tgacttccat tctaacccac attggcatta   59820
cactaattaa aatcgatact gagttctaaa atcatcgggg attttgggga ctatgtctta   59880
cttcatactt ccttgagatt tcacattaaa tgttggtgtt cattaaaggt ccttcattta   59940
actttgtatt catcacactc ttggattcac agttatatct aaactcttaa atacagcctg   60000
tataatccca attcccaact ctgatttcta acctctgacc tccaacctca gtgccaaacc   60060
catatatcaa acaatgtact gggcttattt atatagatgt cctataggca cctcagactc   60120
agcatgggta tttcacttgt tatactaaaa ctgtttctct tccagtgttt tccattttag   60180
tcattagata gctacttgcc cattcaccaa ggtcacagat taaaatcatt tccctacctc   60240
taatcaacag ttcgattctg cttcaatttg tccctatcta ttaatcacca ctcttactgc   60300
ccagtcaggt cctcattgtt tcctgaacaa gagtagatgc tattctttcc acttttagac   60360
cttatcctgg ctggatgcgg tggctcaggc ttgtaaaccc agcactttgg gaggccaagg   60420
caggcagatc acttgaggtc aggagttcaa gaccagcctg accaacatgg tgaaacccca   60480
tctctactaa aaatacaaaa tcagccgggc gtgtggtgca tgcctgcagt cccagctatt   60540
caggtggctg aggcaggaga attgcttgaa cccaggaggc agaggttgcg gtgagcctag   60600
```

```
attgcaccat tgcactctag cttgggcaat agggatgaaa ctccatctca gaagagaaaa    60660 gaaaaaaga ccttattctg ttatacaaat cctctcaatg caatccatat agaataaaca    60720
tgtaaccaga tctcccaatg tgtaaaatca tttcaggtag aacagaatta aagtgaaaag    60780
ccaagtcttt ggaattaaca gacaaagatc aaataacagt cctcatggcc ttaagaattt    60840
acctaacatt ttttttagaa tcaattttct tatatatgaa ttggaaacat aattcctccc    60900
tcacaaacac attctaagat tttaaggaga tattgatgaa gtacatcatc tgtcattttt    60960
aacaggtagt ggtagtgatt cacacagcac attatgatct gttcttgtat gttctgttcc    61020
attctgtatt cttgacctgg ttgtattctt tctgagctcc agatccacat atctaagtac    61080 atcttttgc attttacaag agtgcataca atacaatgta tccaagactg tatttctgat    61140
tttatcgtac cactaaactc acaaatgtgg ccctattctt gtgttcacga ctgcatcac    61200 cgtcatggtc caagtctgat aatagaaatg gcattgtcac tttcttccct actgcaacag    61260
aagcccagct atttgtctcc catttttctct acttctaaaa tacatttctt cactaagtga    61320
gaataatctt ttaaagacac aaatcaaacc atgccaccac cttttcttgaa ttattcaata    61380 tctttcgttg gcttccaggt tacagaaaaa taacttgtaa caaagtttaa aggtcattca    61440
tggctcctct ctaccctatt ttataacatt tcccccttgtg atcagaatct caggcacatc    61500
atccatcttt ctatatacaa ataaagtcat atagttgaa ctcacctctg gttactttta    61560
atcaaccaaa tgctgtaaaa tgcatttgta tcgctacgtg ttaagcagta gttgattctt    61620
ttcatttctg tgtaatattc tattctttga ctataccgta atttatcaat tctactgttg    61680
gtaagcattt aagtggctac cggtttgagg tttttatgat tattgctgtc ataagcattt    61740
ctatacatgt ctttggatac acacatgcat gtgtttctga atatctaaaa atgtaattgc    61800
taggtaatag acttatcaag catccagcat ttgtggatac tattaaaggt tttccaaagg    61860
ggttatacta ttgtacagtg tcaccaacag agtttgagtt tctattgatc catatcacca    61920
ccaaaatttg aactgtcagt cttatctctt ctcttgtctc ttttttcctc ttttttttcc    61980
ttcccttccc ctctcttcgt ttcttttctc tcctcttctc ttctttcctc tcttcccttc    62040
cctttctctt tctcttccct atcccttctc ctctcctctc ccctcctttt ttctcctctc    62100
ctctccatta tttattttc cttcttctcc tccatcccctt ccatcctctc tcttcccctc    62160
ttccttcctt cctttctcca tttcttcctc ctctttcctt caatccttcc ttttggatat    62220
gctcatgggt gtgtatttgt ctgccattgt ggcattattt gaattcagaa aagagtgaaa    62280
aactactggg atcttcattc ctgggtctaa ttccacattt tttttaaga acacatctgt    62340 aaaaatgttc tgtactagca tattcccagg aacttcgtta aatttaatct ggctgaatat    62400
ggtaaatcta cttttcactt tgcattcttt ctttagtcat accataattt taaacattca    62460
aaatatttgt atataatatt tgattttatc tgtcattaaa atgttaaccct taaaattcat    62520 gtttccagaa cctatttcaa taactggtaa ataaacacta ttcatttttt aaatattctt    62580
ttaatggata tttatttcaa tataataaaa aattagagtt ttattatagg aagaatttac    62640
caaaagaagg aggaagcaag caagtttaaa ctgcagcaat agatttgtcc attccaacct    62700
ctcaaaattc ccttggagac aaaaatctct agaggcaaag aagaacttta tattgagtca    62760
acttgttaaa acatctgctt ttagataagt tttcttagta taaagtgaca gaaacaaata    62820
agttaaactc taagatacat tccactatat tagcctaaaa cacttctgca aaaatgaaac    62880
taggaggata ttttagaaaa caactgctga aagagatgcg gtggggagat atgtagagga    62940
```

```
gaacagggtt tctgagtcaa gacacacatg acagaacagc caatctcagg gcaagttaag    63000
ggaatagtgg aatgaaggtt cattttttcat tctcacaaac taatgaaacc ctgcttatct    63060
taaaccaacc tgctcactgg agcagggagg acaggaccag cataaaaggc agggcagagt    63120
cgactgttgc ttacactttc ttctgacata acagtgttca ctagcaacct caaacagaca    63180
ccatggtgca tctgactcct gaggagaaga ctgctgtcaa tgccctgtgg ggcaaagtga    63240
acgtggatgc agttggtggt gaggccctgg gcaggttggt atcaaggtta taagagaggc    63300
tcaaggaggc aaatggaaac tgggcatgtg tagacagaga agactcttgg gtttctgata    63360
ggcactgact ctctgtccct tgggctgttt tcctaccctc agattactgg tggtctaccc    63420
ttggacccag aggttctttg agtcctttgg ggatctgtcc tctcctgatg ctgttatggg    63480
caaccctaag gtgaaggctc atggcaagaa ggtgctaggt gcctttagtg atggcctggc    63540
tcacctggac aacctcaagg gcactttttc tcagctgagt gagctgcact gtgacaagct    63600
gcacgtggat cctgagaact tcagggtgag tccaggagat gcttcacttt tctcttttta    63660
ctttctaatc ttacattttg gttcttttac ctacctgctc ttctcccaca ttttttgtcat   63720 tttactatat tttatcattt aatgcttcta aaattttgtt aattttttat ttaaatattc    63780
tgcatttttt ccttcctcac aatcttgcta ttttaaatta tttaatatcc tgtctttctc    63840
tcccaacccc ctcccttcat ttttccttct ctaacaacaa ctcaaattat gcataccagc    63900
tctcacctgc taattctgca cttagaataa tccttttgtc tctccacatg ggtatgggag    63960
aggctccaac tcaaagatga gaggcataga atactgtttt agaggctata aatcatttta    64020
caataaggaa taattggaat tttataaatt ctgtagtaaa tggaatggaa aggaaagtga    64080
atatttgatt atgaaagact aggcagttac actggaggtg gggcagaagt cgttgctagg    64140
agacagccca tcatcacact gattaatcaa ttaatttgta tctattaatc tgtttatagt    64200
aattaatttg tatatgctat atacacatac aaaattaaaa ctaatttgga attaatttgt    64260
atatagtatt atacagcata tatagcatat atgtacatat atagactaca tgctagttaa    64320
gtacatagag gatgtgtgtg tatagatata tgttatatgt atgcattcat atatgtactt    64380
atttatgctg atgggaataa cctggggatc agttttgtct aagatttggg cagaaaaaaa    64440
tgggtgttgg ctcagtttct cagaagccag tctttatttc tctgttaacc atatgcatgt    64500
atctgcctac ctcttctccg cagctcttgg gcaatgtgct ggtgtgtgtg ctggcccgca    64560
actttggcaa ggaattcacc ccacaaatgc aggctgccta tcagaaggtg gtggctggtg    64620
tggctaatgc cctggctcac aagtaccatt gagatcctgg actgttttcct gataaccata    64680 agaagaccct atttccctag attctatttt ctgaacttgg gaacacaatg cctacttcaa    64740
gggtatggct tctgcctaat aaagaatgtt cagctcaact tcctgattaa tttcacttat    64800
ttcatttttt tgtccaggtg tgtaagaagg ttcctgaggc tctacagata gggagcactt    64860
gtttatttta caaagagtac atgggaaaag agaaaagcaa gggaaccgta caaggcatta    64920
atgggtgaca cttctacctc caaagagcag aaattatcaa gaactcttga tacaaagata    64980
atactggcac tgcagaggtt ctagggaaga cctcaaccct aagacatagc ctcaagggta    65040
atgctacgat taaactccaa caattactga gaaaataatg tgctcaatta aaggcataat    65100
gattactcaa gacaatgtta tgttgtcttt cttcctcctt cctttgcctg cacattgtag    65160
cccataatac tataccccat caagtgttcc tgctccaaga aatagcttcc tcctcttact    65220
tgccccagaa catctctgta aagaatttcc tcttatcttc ccatatttca gtcaagattc    65280
attgctcacg tattacttgt gacctctctt gaccccagcc acaataaact tctctatact    65340
```

```
acccaaaaaa tctttccaaa ccctccccca caccattttt tatattttta tattttcctt    65400
atttatttca tgcacacaca cacactccgt gctttataag caattctgcc tattctctac    65460
cttcttacat gcctactgtg cctcatatta aattcatcaa tgggcagaaa gaaatatttt    65520
attcaagaaa acagtgaatg aatgaacgaa tgagtaaatg agtaaatgaa ggaatgatta    65580
ttccttgctt tagaacttct ggaattagag gacaatatta ataataccat cgcacagtgt    65640
ttctttgttg ttaatgctac aacatacaaa gaggaagcat gcagtaaaca accgaacagt    65700
tatttccttt ctgatcatag gagtaatatt ttttccttg agcaccattt ttgccatagg     65760
taaaattaga aggattttta gaactttctc agttgtatac attttaaaa atctgtatta     65820 tatgcatgtt gattaatttt aaacttactt gaatacctaa acagaatctg ttgtttcctt    65880
gtgtttgaaa gtgctttcac agtaactctg tctgtactgc cagaatatac tgacaatgtg    65940
ttatagttaa ctgttttgat cacaacattt tgaattgact ggcagcagaa gctcttttat    66000
atccatgtgt tttccttaag tcattataca tagtaggcac tgagaactct ttatatctga    66060
ataagatatt taggaaccac tggtttacat atcagaagca gagctactca gggcattttg    66120
gggaagatca ctttcacatt cctgagcata gggaagttct cataagagta agatattaaa    66180
aggagatact tgtgtggtat tcgaaagaca gtaagagaga ttgtagacct tatgatcttg    66240
atagggaaaa caaactacat tcctttctcc aaaagtcaaa aaaaaagagc aaatatagct    66300
tactatacct tctattccta caccattaga agtagtcagt gagtctaggc aagatgttgg    66360
ccctaaaaat ccaaatacca gagaattcat gagaacatca cctggatggg acatgtgccg    66420
agcacacaca attactatat gctaggcatt gctatcttca tattgaagat gaggaggtca    66480
agagatgaaa aaagacttgg caccttgttg ttatattaaa attatttgtt agagtagagc    66540
ttttgtaaga gtctaggagt gtgggagcta aatgatgata cacatggaca caaaaaatag    66600
atcaacagac acccaggcct acttgagggt tgagggtggg aagagggaga cgatgaaaaa    66660
gaacctattg ggtattaagt tcatcactga gtgatgaaat aatctgtaca tcaagaccca    66720
gtgatatgca atttacctat ataacttgta catgtacccc caaatttaaa atgaaagtta    66780
aaacaaagta taggaatgga attaattcct caagatttgg ctttaatttt atttgataat    66840
ttatcaaatg gttgttttc ttttctcact atggcgttgc tttataaact atgttcagta    66900
tgtctgaatg aaagggtgtg tgtgtgtgtg aagagaggg agagaggaag ggaagagagg     66960
acgtaataat gtgaatttga gttcatgaaa attttcaat aaaataattt aatgtcagga     67020
gaattaagcc taatagtctc ctaaatcatc catctcttga gcttcagagc agtcctctga    67080
attaatgcct acatgtttgt aaagggtgtt cagactgaag ccaagattct acctctaaag    67140
agatgcaatc tcaaatttat ctgaagactg tacctctgct ctccataaat tgacaccatg    67200
gcccacttaa tgaggttaaa aaaaagctaa ttctgaatga aaatctgagc ccagtggagg    67260
aaatattaat gaacaaggtg cagactgaaa tataaatttt tctgtaataa ttatgcatat    67320
actttagcaa agttctgtct atgttgactt tattgctttt tggtaagaaa tacaactttt    67380
taaagtgaac taaactatcc tatttccaaa ctattttgtg tgtgtgcggt ttgtttctat    67440
gggttctggt tttcttggag cattttatt tcattttaat taattaattc tgagagctgc    67500
tgagttgtgt ttactgagag attgtgtatc tgcgagagaa gtctgtagca agtagctaga    67560
ctgtgcttga cctaggaaca tatacagtag attgctaaaa tgtctcactt ggggaatttt    67620
agactaaaca gtagagcatg tataaaaata ctctagtcaa gtgctgcttt tgaaacaaat    67680
```

```
gataaaacca cactcccata gatgagtgtc atgattttca tggaggaagt taatattcat   67740
cctctaagta tacccagact agggccattc tgatataaaa cattaggact taagaaagat   67800
taatagactg gagtaaagga aatggacctc tgtctctctc gctgtctctt ttttgaggac   67860
ttgtgtgtgt gtgtgtgtgt gtgtgtgtgt gtgtgttgtg gtcagtgggg ctggaataaa   67920
agtagaatag acctgcacct gctgtggcat ccattcacag agtagaagca agctcacaat   67980
agtgaagatc tcagtaagct tgaatagttt ttcaggaact ttgaatgctg atttagattt   68040
gaaactgagg ctctgaccat aaccaaattt gcactattta ttgcttcttg aaacttattt   68100
gcctggtatg cctgggcttt tgatggtctt agtatagctt gcagccttgt ccctgcaggg   68160
tattatgggt aatagaaaga aaagtctgcg ttacactcta gtcacactaa gtaactacca   68220
ttggaaaagc aaccccctgcc ttgaagccag gatgatggta tctgcagcag ttgccaacac   68280
aagagaagga tccatagttc atcatttaaa aaagaaaaca aaatagaaaa aggaaaacta   68340
tttctgagca taagaagttg tagggtaagt ctttaagaag gtgacaattt ctgccaatca   68400
ggatttcaaa gctcttgctt tgacaatttt ggtctttcag aatactataa ataaaccta    68460 tattataatt tcataaagtc tgtgcatttt ctttgaccca ggatatttgc aaaagacata   68520
ttcaaacttc cgcagaacac tttatttcac atatacatgc ctcttatatc agggatgtga   68580
aacagggtct tgaaaactgt ctaaatctaa acaatgcta atgcaggttt aaatttaata    68640
aaataaaatc caaatctaa cagccaagtc aaatctgcat gttttaacat ttaaatatt    68700 ttaaagacgt cttttcccag gattcaacat gtgaaatctt ttctcaggga tacacgtgtg   68760
cctagatcct cattgcttta gttttttaca gaggaatgaa tataaaaga aaatacttaa    68820 attttatccc tcttacctct ataatcatac ataggcataa ttttttaacc taggctccag   68880
atagccatag aagaaccaaa cactttctgc gtgtgtgaga ataatcagag tgagattttt   68940
tcacaagtac ctgatgaggg ttgagacagg tagaaaagt gagagatctc tatttattta    69000 gcaataataag agaaagcatt taagagaata aagcaatgaa aataagaaat ttgtaaattt   69060
ccttctgata actagaaata gaggatccag tttcttttgg ttaacctaaa ttttatttca   69120
ttttattgtt ttatttttatt ttattttatt ttatttttgtg taatcgtagt ttcagagtgt   69180
tagagctgaa aggaagaagt aggagaaaca tgcaaagtaa aagtataaca cttccttac   69240 taaaccgaca tgggtttcca ggtaggggca ggattcagga tgactgacag ggcccttagg   69300
gaacactgag accctacgct gacctcataa atgcttgcta cctttgctgt tttaattaca   69360
tcttttaata gcaggaagca gaactctgca cttcaaagt ttttcctcac ctgaggagtt   69420
aatttagtac aaggggaaaa agtacagggg gatgggagaa aggcgatcac gttgggaagc   69480
tatagagaaa gaagagtaaa ttttagtaaa ggaggtttaa acaaacaaaa tataaagaga   69540
aataggaact tgaatcaagg aaatgatttt aaaacgcagt attcttagtg gactagagga   69600 aaaaataat ctgagccaag tagaagacct tttcccctcc tacccctact ttctaagtca    69660
cagaggcttt ttgttccccc agacactctt gcagattagt ccaggcagaa acagttagat   69720
gtccccagtt aacctcctat ttgacaccac tgattacccc attgatagtc acactttggg   69780
ttgtaagtga ctttttattt attttgtattt ttgactgcat taagaggtct ctagtttttt   69840
atctcttgtt tcccaaaacc taataagtaa ctaatgcaca gagcacattg atttgtattt   69900
attctatttt tagacataat ttattagcat gcatgagcaa attaagaaaa acaacaacaa   69960
atgaatgcat atatatgtat atgtatgtgt gtatatatac acacatatat atatatattt   70020
tttcttttct taccagaagg ttttaatcca aataaggaga agatatgctt agaaccgagg   70080
```

```
tagagttttc atccattctg tcctgtaagt attttgcata ttctggagac gcaggaagag   70140
atccatctac atatcccaaa gctgaattat ggtagacaaa actcttccac ttttagtgca   70200
tcaacttctt atttgtgtaa taagaaaatt gggaaaacga tcttcaatat gcttaccaag   70260
ctgtgattcc aaatattacg taaatacact tgcaaggag gatgttttta gtagcaattt    70320
gtactgatgg tatggggcca agagatatat cttagaggga gggctgaggg tttgaagtcc   70380
aactcctaag ccagtgccag aagagccaag gacaggtacg gctgtcatca cttagacctc   70440
accctgtgga gccacaccct agggttggcc aatctactcc caggagcagg gagggcagga   70500
gccagggctg ggcataaaag tcagggcaga gccatctatt gcttacattt gcttctgaca   70560
caactgtgtt cactagcaac ctcaaacaga caccatggtg catctgactc ctgaggagaa   70620
gtctgccgtt actgccctgt ggggcaaggt gaacgtggat gaagttggtg gtgaggccct   70680
gggcaggttg gtatcaaggt tacaagacag gtttaaggag accaatagaa actgggcatg   70740
tggagacaga gaagactctt gggtttctga taggcactga ctctctctgc ctattggtct   70800
attttcccac ccttaggctg ctggtggtct acccttggac ccagaggttc tttgagtcct   70860
ttggggatct gtccactcct gatgctgtta tgggcaaccc taaggtgaag gctcatggca   70920
agaaagtgct cggtgccttt agtgatggcc tggctcacct ggacaacctc aagggcacct   70980
ttgccacact gagtgagctg cactgtgaca agctgcacgt ggatcctgag aacttcaggg   71040
tgagtctatg gacgcttga tgttttcttt ccccttcttt tctatggtta agttcatgtc    71100
ataggaaggg gataagtaac agggtacagt ttagaatggg aaacagacga atgattgcat   71160
cagtgtggaa gtctcaggat cgttttagtt tcttttattt gctgttcata acaattgttt   71220
tcttttgttt aattcttgct ttcttttttt ttcttctccg caattttac tattatactt     71280
aatgccttaa cattgtgtat aacaaaagga aatatctctg agatacatta agtaacttaa   71340
aaaaaaactt tacacagtct gcctagtaca ttactatttg gaatatatgt gtgcttattt   71400
gcatattcat aatctcccta cttttattttc ttttattttt aattgataca taatcattat   71460
acatatttat gggttaaagt gtaatgtttt aatatgtgta cacatattga ccaaatcagg   71520
gtaattttgc atttgtaatt ttaaaaaatg ctttcttctt ttaatatact ttttgttta    71580
tcttatttct aatactttcc ctaatctctt tctttcaggg caataatgat acaatgtatc   71640
atgcctcttt gcaccattct aaagaataac agtgataatt tctgggttaa ggcaatagca   71700
atatctctgc atataaatat ttctgcatat aaattgtaac tgatgtaaga ggtttcatat   71760
tgctaatagc agctacaatc cagctaccat tctgctttta ttttatggtt gggataaggc   71820
tggattattc tgagtccaag ctaggccctt ttgctaatca tgttcatacc tcttatcttc   71880
ctcccacagc tcctgggcaa cgtgctggtc tgtgtgctgg cccatcactt ggcaaagaa    71940
ttcaccccac cagtgcaggc tgcctatcag aaagtggtgg ctggtgtggc taatgccctg   72000
gcccacaagt atcactaagc tcgctttctt gctgtccaat ttctattaaa ggttcctttg   72060
ttccctaagt ccaactacta aactgggga tattatgaag ggccttgagc atctggattc    72120
tgcctaataa aaaacattta ttttcattgc aatgatgtat ttaaattatt ctgaatatt    72180
ttactaaaaa gggaatgtgg gaggtcagtg catttaaaac ataagaaat gaagagctag    72240
ttcaaacctt gggaaaatac actatatctt aaactccatg aaagaaggtg aggctgcaaa   72300
cagctaatgc acattggcaa cagccccctga tgcatatgcc ttattcatcc ctcagaaaag   72360
gattcaagta gaggcttgat ttggaggtta aagttttgct atgctgtatt ttacattact   72420
```

```
tattgtttta gctgtcctca tgaatgtctt ttcactaccc atttgcttat cctgcatctc    72480
tcagccttga ctccactcag ttctcttgct tagagatacc acctttcccc tgaagtgttc    72540
cttccatgtt ttacggcgag atggtttctc ctcgcctggc cactcagcct tagttgtctc    72600
tgttgtctta tagaggtcta cttgaagaag gaaaaacagg ggtcatggtt tgactgtcct    72660
gtgagccctt cttccctgcc tcccccactc acagtgaccc ggaatctgca gtgctagtct    72720
cccggaacta tcactctttc acagtctgct ttggaaggac tgggcttagt atgaaaagtt    72780
aggactgaga agaatttgaa aggcggcttt ttgtagcttg atattcacta ctgtcttatt    72840
accctgtcat aggcccaccc caaatggaag tcccattctt cctcaggatg tttaagatta    72900
gcattcagga agagatcaga ggtctgctgg ctcccttatc atgtcccctta tggtgcttct    72960 ggctctgcag ttattagcat agtgttacca tcaaccacct taacttcatt tttcttattc    73020
aatacctagg taggtagatg ctagattctg gaaataaaat atgagtctca agtggtcctt    73080
gtcctctctc ccagtcaaat tctgaatcta gttggcaaga ttctgaaatc aaggcatata    73140
atcagtaata agtgatgata gaagggtata tagaagaatt ttattatatg agagggtgaa    73200
accctcaaaa tgaaatgaaa tcagaccctt gtcttacacc ataaacaaaa ataaatttga    73260
atgggttaaa gaattaaact aagacctaaa accataaaaa ttttttaaaga aatcaaaaga    73320 agaaaattct aatattcacg ttgcagccgt ttttttgaatt tgatatgaga agcaaaggca    73380
acaaaaggaa aaataaagaa gtgaggctac atcaaactaa aaaatttcca cacaaaaaac    73440
aaaacaatga acaaatgaaa ggtgaaccat gaaatggcat atttgcaaac caaatatttc    73500
ttaaatattt tggttaatat ccaaaatata taagaaacac agatgattca ataacaaaca    73560
aaaaattaaa aataggaaaa taaaaaaatt aaaagaaga aaatcctgcc atttatggca    73620
gaattgatga acctggagga tgtaaaacta agaaaaataa gcctgacaca aaagacaaa    73680 tactacacaa ccttgctcat atgtgaaaca taaaaaagtc actctcatgg aaacagacag    73740
tagaggtatg gtttccaggg gttgggggtg ggagaatcag gaaactatta ctcaaagggt    73800
ataaaatttc agttatgtgg gatgaataaa ttctagatat ctaatgtaca gcatcgtgac    73860
tgtagttaat tgtactgtaa gtatatttaa aatttgcaaa gagagtagat ttttttttttt    73920 ttttagatgg agttttgctc ttgttgtcca ggctggagtg caatggcaag atcttggctc    73980
actgcaacct ccgcctcctg ggttcaagca aatctcctgc ctcagcctcc cgagtagctg    74040
ggattacagg catgcgacac catgcccagc taattttgta ttttttagtag agacggggtt    74100 tctccatgtt ggtcaggctg atccgcctgc ctcggccacc caaagggctg ggattacagg    74160
cgtgagccac cgggcctggc cgagagtaga tcttaaaagc atttaccaca agaaaaaggt    74220
aactatgtga gataatgggt atgttaatta gcttgattgt ggtaatcatt tcacaaggta    74280
tacatatatt aaaacatcat gttgtacacc ttaaatatat acaattttta tttgtgaatg    74340
atacctcaat aaagttgaag aataataaaa aagaatagac atcacatgaa ttaaaaaact    74400
aaaaaataaa aaatgcatc ttgatgatta gaattgcatt cttgatttttt cagatacaaa    74460 tatccatttg actgtttact cttttccaaa acaatacaat aaattttagc actttatctt    74520
cattttcccc ttcccaatct ataattatat atatatatat tttagatatt ttgtatagtt    74580
ttactcccta gattttctag tgttattatt aaatagtgaa gaaatgttta cacttatgta    74640
caaaatgttt tgcatgcttt tcttcatttc taacattctc tctaagttta ttctattttt    74700
ttctgattat ccttaatatt atctctttct gctggaaata cattgttact tttggtttat    74760
ctaaaaatgg cttcatttttc ttcattctaa aatcatgtta aattaatacc actcatgtgt    74820
```

-continued

```
aagtaagata gtggaataaa tagaaatcca aaaactaaat ctcactaaaa tataataatg    74880
tgatatataa aaatatagct tttaaattta gcttggaaat aaaaaacaaa cagtaattga    74940
acaactatac tttttgaaaa gagtaaagtg aaatgcttaa ctgcatatac cacaatcgat    75000
tacacaatta ggtgtgaagg taaaattcag tcacgaaaaa actagaataa aaatatggga    75060
agacatgtat ataatcttag agataacact gttatttaat tatcaaccca aagtagaaac    75120
tatcaaggga gaaataaatt cagtcaacaa taaaagcatt taagaagtta ttctaggctg    75180
ggagcggtgg ctcacacctg caattgcagc actttgggag gcctagacag gcggatcacg    75240
acgtcaggag ttcaagatca gcctggccaa catagtgaaa cctcatcgct actaaaaata    75300
taaaaactta gcctggcgtg gtggcaggca tgtgtaatcc cagcaatttg ggaggctgag    75360
gcaggagaat cgcttgatcc tgggaggcag aggttgcagt gagccaagat tgtgccactg    75420
cattccagcc caggtgacag catgagactc cgtcacaaaa aaaaagaaa aaaaaagggg    75480 gggggggagc ggtggagcca agatgaccga ataggaacag ctccagtcta tagctcccat    75540
cgtgagtgac gcagaagacg ggtgatttct gcatttccaa ctgaggtacc aggttcatct    75600
cacagggaag tgccaggcag tgggtgcagg acagtaggtg cagtgcactg tgcatgagcc    75660
aaagcagggc gaggcatcac ctcacccggg aagcacaagg ggtcagggaa ttccctttcc    75720
tagtcaaaga aaagggtgac agatggcacc tggaaaatcg ggtcactccc gccctaatac    75780
tgcgctcttc caacaagctt aacaaatggc acaccaggag attatatccc atgcctggct    75840
cagagggtcc tacgcccatg gagcctcgct cattgctagc acagcagtct gaggtcaaac    75900
tgcaaggtgg cagtgaggct ggggggaggggg tgcccaccat tgtccaggct tgagcaggta    75960
aacaaagccg cctggaagct cgaactgggt ggagcccacc acagctcaag gaggcctgcc    76020
tgcctctgta ggctccacct ctaggggcag ggcacagaca aacaaagac aacaagaacc    76080 tctgcagact taaatgtccc tgtctgacag ctttgaagag agtagtggtt ctcccagcac    76140
atagcttcag atctgagaac aggcagactg cctcctcaag tgggtccctg accccgagt    76200 agcctaactg ggaggcatcc cccagtaggg gcagactgac acctcacatg gctggtactc    76260
ctctaagaca aaacttccag aggaatgatc aggcagcagc atttgcggtt caccaatatc    76320
cactgttctg cagccaccgc tgttgatacc caggaaaaca gcttctggag tggacctcca    76380
gtaaactcca acagacctgc agctgagggt cctgactgtt agaaggaaaa ctaacaaaca    76440
gaaaggacat ccacaccaaa aacccatctg tacatcgcca tcatcaaaga ccaaaggtag    76500
ataaaaccat aaagatgggg aaaaagcaga gcagaaaaac tggacactct aaaaatgaga    76560
gtgcctctcc tcctccaaag taacgcagct cctcaccagc aatggaacaa agctgggcag    76620
agaatgactt tgacgagttg agagaggaag gcttcagaag atcaaactac tccaagctaa    76680
aggaggaagt tcgaacaaac ggcaaagaag taaaaaactt tgaaaaaaaa ttagatgaat    76740
ggataactag aataaccaat gcacagaagt ccttaaagga cctgatggag ctgaaaacca    76800
aggcaggaga actacgtgac aaatacacaa gcctcagtaa ccgatgagat caactggaag    76860
aaagggtatc aatgacgaaa gatgaaatga atgaaatgaa gcatgaagag aagtttagag    76920 aaaaagaat aaaaagaaac gaacaaagcc tccaagaaat atgggactat gtgaaaagac    76980
caaatctaca tctaattggt gtagctgaaa gtgatgggga gaatggaacc aagttggaaa    77040
acactctgca ggatattatc caggagaact tccccaatct agcaaggcaa gcccaaattc    77100
acattcagga aatacagaga acgccacaaa gatactccta gagaaaagca actccaagac    77160
```

```
acataactgt cagattcacc aaagttgaaa tgaaggaaaa aatgttaagg gcagccagag    77220
agaaaggtcg ggttacccac aaagggaagc ccatcagact aacagctgat ctatcggcag    77280
aaactctaca agccagaaga aagtgggggc caatattcaa cattgttaaa gaaaagaatt    77340
ttcaacccag aatttcatat ccagccaaac taagcttcat aagtgaagga gaaataaaat    77400
cctttacaga caagcaaatg ctgagagatt ttgtcaccac caggcctgcc ctacaagagc    77460
tcctgaagga agcactaaac atggaaagga acaactagta tcagccactg caaaaacatg    77520
ccaaattgta aagaccatca aggctaggaa gaaactgcat caacgagcaa ataaccagc     77580 taacatcata atgacaggat caaattcata cataacaata ctcaccttaa atgtaaatag    77640
gctaaatgct ccaattaaaa gacacagact ggcaaattgg ataaggagtc aagacccatc    77700
tgtgttctgt attcaggaaa cccatctcac gtgcagagac acataggc tcgaaataaa      77760 aggatggagg aatatctacc aagcaaatgg aaaacaaaaa aaggcagggg ttgcaatcct    77820
agtctctgat aaaacagatt ttaaaccaac aaagatcaaa agagacaaag aaggccatta    77880
cataatggca aagggatcta ttcaagaaga gaactaact atactaaata tatatgcacc     77940
caatacagga gcacccagat tcataaaaca agtcctgagt gacctacaaa gagacttaga    78000
tgcccacaca ataataatgg gagactttaa cacccactg tcaacattag acagatcaac     78060
gagacagaaa gttaacaagg atatccagga attggactca gctctgcacc aagcagacct    78120
aatagacatc tacagaactc tccaccccaa atcaacagaa tatacattct tttcagcacc    78180
acaccacacc tattccaaaa ctgaccacat agttggaagt aaagctctcc tcagcaaatg    78240
taaaagaaca gaaactataa caaactgtct ctcagaccac agtgcaatca aactagaact    78300
caggattaag aaactcactc aaaccactc agctacatgg aaactgaaca gcctgctcct     78360
gaatgactac tgggtacata acaaaatgaa ggcagaaata aagatgttct ttgaaaccaa    78420
cgagaacaaa gacacaacac accagaatct ctgagacaca ttcaaagcag tgtgtagagg    78480
gaaatttata gcactaaatg cccacaaggg aaagcaggaa agatctaaaa ttgacaccct    78540
aacatcacaa ttaaaaaact agagaagcag gagcaaacac attcaaaagc taacagaaga    78600
caagaaataa ctaagatcag agcagaagtg aaggacatag agacacaaaa aaaccccttca   78660 aaaaaatcaa tgaatccaga agctgttttt ttgaaaagat caacaaaatt gatagactgc    78720
tagcaagact aataaagaag aaaagagaga agaatcaaat agacgcaata aaaaatgaca    78780
cggggtatca ccactgatcc cacagaaata caaactaccg tcagagaata ctataaacac    78840
ctctacgcaa ataaactaga aaatctagaa gaaatggata aattcctcga cacatacact    78900
ctgccaagac taaaccagga agaagttgta tctctgaata gaccaataac aggctctgaa    78960
attgaggcaa taattaatag cttatcaacc aaaaaaagtc cgggaccagt aggattcata    79020
gccgaattct accagaggta caaggaggag ctggtaccat tccttctgaa actattccaa    79080
tcaatagaaa aagagggaat cctccctaac tcattttatg aggccagcat catcctgata    79140
ccaaagcctg acagagacac aacaaaaaaa gagaatgtta caccaatatc cttgatgaac    79200
attgatgcaa aaatcctcaa taaaatactg gcaaactgat ccaccatgat caagtgggct    79260
tcatccctgc catgcaaggc tggttcaaca tacgaaaatc aataaacata tccagcata    79320 taaacagaac caaagacaca aaccatatga ttatctcaat agatgcagaa aaggcctttg    79380
acaaaattca acaacgcttc atgctaaaaa ctctcaataa attaggtatt gatgggacat    79440
atctcaaaat aataagagct atctatgaca aacccacagc caatatcata ctgagtggac    79500
aaaaactgga agcattccct ttgaaaactg gcacaaggca gggatgccct ctctcaccac    79560
```

```
tcctattcaa catagtgttg taagttctgg ccagggcaat caggcaggag aaggaaataa    79620
agggcattca attaggaaaa gaggaagtga aattgtccct gtttgcagat gacatgattg    79680
tatatctaga aaaccccatt gtctcagccc aaaatctcct taagctgata agcaacttca    79740
gcaaagtctc aggatataaa atcagtgtgc aaaaatcaca agtattccta tgcaccaata    79800
acagacaaac agagagccaa atcatgagtg aactcccatt cacaattgct tcaaagagaa    79860
taaaatacct aggaatccaa cttacaaggg atgtgaagga cctcttcaag gagaactaca    79920
aaccactgct caatgaaata aaagaggata caaacaaatg gaagaacatt ccatgctcat    79980
gggtaggaag aatcaatatc gtgaaaatgg tcatactgcc caaggtaatt tatagattca    80040
atgccatccc catcaagcta ccaatgactt tcttcacaga actggaaaaa actactttaa    80100
agttcatatg gaaccaaaaa agagcccaca tcaccaaggc aatcctaagc caaaagaaca    80160
aagctggagg catcacgcta cctgacttca aactatacta caatgctacg gtaaccaaaa    80220
cagcatggta ctggtaccaa aacagagatc tagaccaatg gaacagaaca gagccctcag    80280
aaataatgcc gcatatctac aactatctga tctttgacaa acctgagaga aacaagcaat    80340
ggggaaagga ttccctattt aataaatggt gctgggaaaa ctggctagcc atatgtagaa    80400
agctgaaact ggatcccttc cttacacctt atacaaaaat taattcaaga tggattaaag    80460
acttacatgt tagacctaaa accataaaaa ccctagaaaa aacctaggc aataccattc    80520 aggacatagg catgggcaag gacttcatgt ctaaaacacc aaaagcaatg gcaacaaaag    80580
acaaaatgga caaacgggat ctaattaaac тaaagagcттт ctgcacagct aaagaaacta    80640
ccatcagagt gaacaggcaa cctacaaaat gggagaaaat ttttgcaatc tactcatctg    80700
acaaagggct aatatccaga atctacaatg aactcaaaca aatttacaag aaaaaacaaa    80760
caaccccatc aaaaagtggg caaggatat gaacagacac ttcgcaaaag aagacattta    80820

tgtaatcaaa aaacacatga aaaaatgctc atcatcacta gccatcagag aaatgcaaat    80880
caaaaccaca atgagatacc atctcacacc agttagaatg gcgatcatta aaaagtcagg    80940
aaacaacagg tgctggagag gatgtggaga acaggaaca acttttacac tgttggtggg    81000
actgtaaact agttcaacca ttgcggaagt cagtgtggca attcctcagg aatctagaac    81060

tagaaatacc atttgaccca gccatcccat tactgggtac atacccaaag gattataaat    81120
catgctgcta taaagacaca tgcacacgta tgtttattgc agcactattc acaatagcaa    81180
agacttggaa ccaacccaaa tgtccaacaa cgatagactg gattaagaaa atgtggcaca    81240

tatacaccat ggaatactat gcagccataa aaaatgatga gttcatgtcc tttgtaggga    81300
catggatgaa gctggaaact atcattctca gcaaactatc acaaggagaa taaaccaaac    81360
accgcatgtt ctcactcata ggtgggaatt gaacaatgag aacacatgga cacatgaaga    81420
ggaacatcac actctgggga ctgttatggg gtggggggca gggcaggga tagcactagg    81480 agatatacct aatgctaaat gacgagttaa tgggtcagc acaccaacat ggcacatgta    81540

tacatatata acaaacctgc atgttgtgca catgtaccct aaaacttgaa gtataataat    81600
aaaaaaaagt tatcctatta aaactgatct cacacatccg tagagccatt atcaagtctt    81660

tctctttgaa atagacagaa atttagtgtt ttctcagtca gttaac                 81706

<210> SEQ ID NO 5
<211> LENGTH: 1606
<212> TYPE: DNA
<213> ORGANISM: Homo sapiens
```

<400> SEQUENCE: 5

```
gcaatgaaaa taaatgtttt ttattaggca gaatccagat gctcaaggcc cttcataata      60
tcccccagtt tagtagttgg acttagggaa caaaggaacc tttaatagaa attggacagc     120
aagaaagcga gcttagtgat acttgtgggc cagggcatta gccacaccag ccaccacttt     180
ctgataggca gcctgcactg gtggggtgaa ttctttgcca aagtgatggg ccagcacaca     240
gaccagcacg ttgcccagga gctgtgggag gaagataaga ggtatgaaca tgattagcaa     300
aagggcctag cttggactca gaataatcca gccttatccc aaccataaaa taaaagcaga     360
atggtagctg gattgtagct gctattagca atatgaaacc tcttacatca gttacaattt     420
atatgcagaa atatttatat gcagagatat tgctattgcc ttaacccaga aattatcact     480
gttattcttt agaatggtgc aaagaggcat gatacattgt atcattattg ccctgaaaga     540
aagagattag ggaaagtatt agaaataaga taaacaaaaa agtatattaa aagaagaaag     600
cattttttaa aattacaaat gcaaaattac cctgatttgg tcaatatgtg tacacatatt     660
aaaacattac actttaaccc ataaatatgt ataatgatta tgtatcaatt aaaaataaaa     720
gaaaataaag tagggagatt atgaaatatgc aaataagcac acatatattc caaatagtaa     780
tgtactaggc agactgtgta aagtttttttt ttaagttact taatgtatct cagagatatt     840
tccttttgtt atacacaatg ttaaggcatt aagtataata gtaaaaattg cggagaagaa     900
aaaaaagaa agcaagaatt aaacaaaaga aaacaattgt tatgaacagc aaataaaaga     960
aactaaaacg atcctgagac ttccacactg atgcaatcat tcgtctgttt cccattctaa    1020
actgtacccct gttacttatc cccttcctat gacatgaact taaccataga aaagaagggg    1080
aaagaaaaca tcaagcgtcc catagactca ccctgaagtt ctcaggatcc acgtgcagct    1140
tgtcacagtg cagctcactc agtgtggcaa aggtgcccctt gaggttgtcc aggtgagcca    1200
ggccatcact aaaggcaccg agcactttct tgccatgagc cttcacctta gggttgccca    1260
taacagcatc aggagtggac agatccccaa aggactcaaa gaacctctgg gtccaagggt    1320
agaccaccag cagcctaagg gtgggaaaat agaccaatag gcagagagag tcagtgccta    1380
tcagaaaccc aagagtcttc tctgtctcca catgcccagt ttctattggt ctccttaaac    1440
ctgtcttgta accttgatac caacctgccc agggcctcac caccaacttc atccacgttc    1500
accttgcccc acagggcagt aacggcgaga ttctcctcag gagtcagatg caccatggtg    1560
tctgtttgag gttgctagtg aacacagttg tgtcagaagc aaatgt                    1606
```

<210> SEQ ID NO 6
<211> LENGTH: 1586
<212> TYPE: DNA
<213> ORGANISM: Homo sapiens

<400> SEQUENCE: 6

```
gtgatctctc agcagaatag atttattatt tgtattgctt gcagaataaa gcctatcctt      60
gaaagctctg aatcatgggc agtgagctca gtggtatctg gaggacaggg cactggccac     120
tgcagtcacc atcttctgcc aggaagcctg cacctcaggg gtgaattctt tgccgaaatg     180
gattgccaaa acgtcaccga gcacatttcc caggagctgt tgagatgaaa ggagacaata     240
aagatgaacc catagtgagc tgagagctcc agcctggcct ccagataact acacaccaag     300
cttccaccca gaatcaagcc tatgttaact tccctcaaag cctgagattt gccttcccca     360
ttaaatgcag gtagttgttc cccttcaagc actagtcact ggccataatt taaatcttgc     420
tatcttcttg ccaccatgaa ccctgtatgt tgtaggctga agacgttaaa agaaacacac     480
```

```
gctgacacac acacacacac gcgcgcgcgc acacacacac acacacacag agctgacttt    540
caaaatctac tccagcccaa atgtttcaat tgttcctcac ccctggacat actttgcccc    600
catctggaat taaaggatat aagtttgtaa tgaagcatta gcagcatttt atatgtgtcc    660
agctgatata ggaatagcct tagcaatgta tgtttggcca ccaaagttcc ccactttgac    720
tgagccaata tatgccttct gcctgcatct ttttaacgac catacttgtc ctgcctccag    780
atagatgttt taaaacaaca aaaatgaggg aaagatgaaa gttctttcta ctggaatcta    840
ataaagaaaa gtcatttttcc tcatttccac ctctcttttc tcaaagtcaa aattgtccat    900
ctagattttt agaggcactc cttaggcccct aaaacattac cactgggtct cagcccagtt    960
agtcctctgc agtttcttca ccccaacccc cagtatcttc aaacagctca caccctgctg   1020
tgctcagatc aatactccgt tgtctaagtt gcctcgagac taaaggcaac agggctgaaa   1080
catctcctgg actcaccttg aagttctcag gatccacatg cagcttgtca cagtgcagtt   1140
cactcagctg ggcaaaggtg cccttgagat catccaggtg cttttgtggca tctcccaagg   1200 aagtcagcac cttcttgcca tgtgccttga ctttggggtt gcccatgatg gcagaggcag   1260
aggacaggtt gccaaagctg tcaaagaacc tctgggtcca tgggtagaca accaggagcc   1320
tgtgagattg acaagaacag tttgacagtc agaaggtgcc acaaatcctg agaagcgacc   1380 tggactttttg ccaggcacag ggtccttcct tccctccctt gtcctggtca ccagagccta   1440
ccttcccagg gtttctcctc cagcatcttc cacattcacc ttgccccaca ggcttgtgat   1500
agtagccttg tcctcctctg tgaaatgacc catggcgtct ggactaggag cttattgata   1560
acctcagacg ttccagaagc gagtgt                                         1586

<210> SEQ ID NO 7
<211> LENGTH: 1591
<212> TYPE: DNA
<213> ORGANISM: Homo sapiens

<400> SEQUENCE: 7
gtgatctctt agcagaatag atttattatt tgattgcttg cagaataaag cctatccttg     60
aaagctctgc atcatgggca gtgagctcag tggtatctgg aggacagggc actggccact    120
ccagtcacca tcttctgcca ggaagcctgc acctcagggg tgaattcttt gccgaaatgg    180
attgccaaaa cggtcaccag cacatttccc aggagctgtt gagatgaaag gagacaataa    240
agatgaaccc atagtgagct gagagctcca gcctggcctc cagataacta cacaccaagc    300
ttccacccag aatcaagcct atgttaactt ccctcaaagc ctgagatttt gctttcccat    360
taaatgcagg tagttgttct tcttgcagca ctagtcactg gccataattt aaatcttgtt    420
atcttcttgc caccatgaac cctgtatgct gtaggctgaa aacgttaaaa gaaacacacg    480
ctctcacaca cacacaaaca cacgcgcgca cacacacaca cacacacaca gagctgactt    540
tcaaaatcta ctccagccca atgtttcaa ttgttcctca ccctggaca tactttgccc     600 ccatctggaa ttaaaggata aagtttgta atgaagcatt agcagcattt tatatgtgtc    660
cagctgatat aggaatagcc ttagcaatgt atgtttggcc accaaagttc cccactttga    720
ctgagccaat atatgccttc tgcctgcatc ttttttaatga ccatacttgt cctgcctcca    780
gatagatgtt ttaaaacgaa taacaaaaat aggggaaagg tgaaagttct ttctaccgaa    840
atctaataaa gaaagtcat tttcctcatt tccacctctc ttttctcaaa gtcaaagttg    900
tccatctaga ttttcagagg cactccttag gccctaaaac attgccactg ggtctcagcc    960
```

| | |
|---|---|
| cagttagtcc tctgcagttt cttcactccc aaccccagta tcttcaaaca gctcacaccc | 1020 |
| tgctgtgctc agatcaatac tcagttgtct aagttgcctc gagactaaag caacagtgc | 1080 |
| tgaaacatct cctggactca ccttgaagtt ctcaggatcc acatgcagct tgtcacagtg | 1140 |
| cagttcactc agctgggcaa aggtgccctt gagatcatcc aggtgcttta tggcatctcc | 1200 |
| caaggaagtc agcaccttct tgccatgtgc cttgactttg gggttgccca tgatggcaga | 1260 |
| ggcagaggac aggttgccaa agctgtcaaa gaacctctgg gtccatgggt agacaaccag | 1320 |
| gagcctgtga gattgacaag aacagtttga cagtcagaag gtgccacaaa tcctgagaag | 1380 |
| cgacctggac ttttgccagg cacagggtcc ttccttccct cccttgtcct ggtcaccaga | 1440 |
| gcctaccttc cagggtttc tcctccagca tcttccacat tcaccttgcc ccacaggctt | 1500 |
| gtgatagtag ccttgtcctc ctctgtgaaa tgacccatgg cgtctggact aggagcttat | 1560 |
| tgataaccte agacgttcca gaagcgagtg t | 1591 |

<210> SEQ ID NO 8
<211> LENGTH: 4954
<212> TYPE: DNA
<213> ORGANISM: Artificial Sequence
<220> FEATURE:
<223> OTHER INFORMATION: Synthetic

<400> SEQUENCE: 8

| | |
|---|---|
| atatttgcat gtcgctatgt gttctgggaa atcaccataa acgtgaaatg tctttggatt | 60 |
| tgggaatctt ataagttctg tatgagacca ctcacccggt gaacaccggg cacgggcagc | 120 |
| ttgccgggtt ttagagctag aaatagcaag ttaaaataag gctagtccgt tatcaacttg | 180 |
| aaaaagtggc accgagtcgg tgcttttttt aagcttgtta acgggcccag cttcgataaa | 240 |
| ataaagatt ttatttagtc tccagaaaaa gggggaatg aaagacccca cctgtaggtt | 300 |
| tggcaagcta gcttaagtaa cgccatttttg caaggcatgg aaaatacata actgagaata | 360 |
| gagaagttca gatcaaggtt aggaacagag agacagcaga atatgggcca aacaggatat | 420 |
| ctgtggtaag cagttcctgc cccggctcag ggccaagaac agatggtccc cagatgcggt | 480 |
| cccgccctca gcagttttcta gagaaccatc agatgtttcc agggtgcccc aaggacctga | 540 |
| aaatgaccct gtgccttatt tgaactaacc aatcagttcg cttctcgctt ctgttcgcgc | 600 |
| gcttctgctc cccgagctca ataaaagagc ccacaacccc tcactcggcg cgccagtcct | 660 |
| ccgatagact gccggtgcca ccatggacta aaggaccac gacggagact acaaggatca | 720 |
| tgatattgat tacaaagacg atgacgtaaa gatggcccca agaagaagc ggaaggtcgg | 780 |
| tatccacgga gtcccagcag ccgacaagaa gtacagcatc ggcctggaca tcggcaccaa | 840 |
| ctctgtgggc tgggccgtga tcaccgacga gtacaaggtg cccagcaaga aattcaaggt | 900 |
| gctgggcaac accgaccggc acagcatcaa gaagaacctg atcggagccc tgctgttcga | 960 |
| cagcggcgaa acagccgagg ccacccggct gaagagaacc gccagaagaa gatacaccag | 1020 |
| acggaagaac cggatctgct atctgcaaga gatcttcagc aacgagatgg ccaaggtgga | 1080 |
| cgacagcttc ttccacagac tggaagagtc cttcctggtg gaagaggata agaagcacga | 1140 |
| gcggcacccc atcttcggca acatcgtgga cgaggtggcc taccacgaga gtaccccac | 1200 |
| catctaccac ctgagaaaga aactggtgga cagcaccgac aaggccgacc tgcggctgat | 1260 |
| ctatctggcc ctggcccaca tgatcaagtt ccggggccac ttcctgatcg agggcgacct | 1320 |
| gaaccccgac aacagcgacg tggacaagct gttcatccag ctggtgcaga cctacaacca | 1380 |
| gctgttcgag gaaaacccca tcaacgccag cggcgtggac gccaaggcca tcctgtctgc | 1440 |

```
cagactgagc aagagcagac ggctggaaaa tctgatcgcc cagctgcccg gcgagaagaa    1500
gaatggcctg ttcggaaacc tgattgccct gagcctgggc ctgaccccca acttcaagag    1560
caacttcgac ctggccgagg atgccaaact gcagctgagc aaggacacct acgacgacga    1620
cctggacaac ctgctggccc agatcggcga ccagtacgcc gacctgtttc tggccgccaa    1680
gaacctgtcc gacgccatcc tgctgagcga catcctgaga gtgaacaccg agatcaccaa    1740 ggccccctg agcgcctcta tgatcaagag atacgacgag caccaccagg acctgaccct    1800
gctgaaagct ctcgtgcggc agcagctgcc tgagaagtac aaagagattt tcttcgacca    1860
gagcaagaac ggctacgccg gctacattga cggcggagcc agccaggaag agttctacaa    1920
gttcatcaag cccatcctgg aaaagatgga cggcaccgag gaactgctcg tgaagctgaa    1980
cagagaggac ctgctgcgga agcagcggac cttcgacaac ggcagcatcc ccaccagat    2040 ccacctggga gagctgcacg ccattctgcg gcggcaggaa gattttttacc cattcctgaa    2100 ggacaaccgg aaaagatcg agaagatcct gaccttccgc atccctact acgtgggccc    2160 tctggccagg ggaaacagca gattcgcctg gatgaccaga aagagcgagg aaaccatcac    2220
cccctggaac ttcgaggaag tggtggacaa gggcgcttcc gcccagagct tcatcgagcg    2280
gatgaccaac ttcgataaga acctgcccaa cgagaaggtg ctgcccaagc acagcctgct    2340
gtacgagtac ttcaccgtgt ataacgagct gaccaaagtg aaatacgtga ccgagggaat    2400
gagaaagccc gccttcctga gcggcgagca gaaaaaggcc atcgtggacc tgctgttcaa    2460
gaccaaccgg aaagtgaccg tgaagcagct gaaagaggac tacttcaaga aaatcgagtg    2520
cttcgactcc gtggaaatct ccggcgtgga agatcggttc aacgcctccc tgggcacata    2580
ccacgatctg ctgaaaatta tcaaggacaa ggacttcctg gacaatgagg aaaacgagga    2640
cattctggaa gatatcgtgc tgaccctgac actgtttgag gacagagaga tgatcgagga    2700
acggctgaaa acctatgccc acctgttcga cgacaaagtg atgaagcagc tgaagcggcg    2760
gagatacacc ggctggggca ggctgagccg gaagctgatc aacggcatcc gggacaagca    2820
gtccggcaag acaatcctgg atttcctgaa gtccgacggc ttcgccaaca gaaacttcat    2880
gcagctgatc cacgacgaca gcctgacctt taaagaggac atccagaaag cccaggtgtc    2940
cggccagggc gatagcctgc acgagcacat tgccaatctg gccggcagcc ccgccattaa    3000
gaagggcatc ctgcagacag tgaaggtggt ggacgagctc gtgaaagtga tgggccggca    3060
caagcccgag aacatcgtga tcgaaatggc cagagagaac cagaccaccc agaagggaca    3120
gaagaacagc cgcgagagaa tgaagcggat cgaagagggc atcaaagagc tgggcagcca    3180
gatcctgaaa gaacacccg tggaaaacac ccagctgcag aacgagaagc tgtacctgta    3240
ctacctgcag aatgggcggg atatgtacgt ggaccaggaa ctggacatca accggctgtc    3300
cgactacgat gtggaccata tcgtgcctca gagctttctg aaggacgact ccatcgacaa    3360
caaggtgctg accagaagcg acaagaaccg gggcaagagc gacaacgtgc cctccgaaga    3420
ggtcgtgaag aagatgaaga actactggcg gcagctgctg aacgccaagc tgattaccca    3480
gagaaagttc gacaatctga ccaaggccga gagaggcggc ctgagcgaac tggataaggc    3540
cggcttcatc aagagacagc tggtggaaac ccggcagatc acaaagcacg tggcacagat    3600
cctggactcc cggatgaaca ctaagtacga cgagaatgac aagctgatcc gggaagtgaa    3660
agtgatcacc ctgaagtcca gctggtgtc cgatttccgg aaggatttcc agttttacaa    3720
agtgcgcgag atcaacaact accaccacgc ccacgacgcc tacctgaacg ccgtcgtggg    3780
```

```
aaccgccctg atcaaaaagt accctaagct ggaaagcgag ttcgtgtacg gcgactacaa    3840
ggtgtacgac gtgcggaaga tgatcgccaa gagcgagcag gaaatcggca aggctaccgc    3900
caagtacttc ttctacagca acatcatgaa cttttttcaag accgagatta ccctggccaa    3960
cggcgagatc cggaagcggc ctctgatcga gacaaacggc gaaaccgggg agatcgtgtg    4020
ggataagggc cgggattttg ccaccgtgcg gaaagtgctg agcatgcccc aagtgaatat    4080
cgtgaaaaag accgaggtgc agacaggcgg cttcagcaaa gagtctatcc tgcccaagag    4140
gaacagcgat aagctgatcg ccagaaagaa ggactgggac cctaagaagt acggcggctt    4200
cgacagcccc accgtggcct attctgtgct ggtggtggcc aaagtggaaa agggcaagtc    4260
caagaaactg aagagtgtga aagagctgct ggggatcacc atcatggaaa gaagcagctt    4320
cgagaagaat cccatcgact ttctggaagc caagggctac aaagaagtga aaaaggacct    4380
gatcatcaag ctgcctaagt actccctgtt cgagctggaa aacggccgga gagaatgct    4440
ggcctctgcc ggcgaactgc agaagggaaa cgaactggcc ctgccctcca aatatgtgaa    4500
cttcctgtac ctggccagcc actatgagaa gctgaagggc tcccccgagg ataatgagca    4560
gaaacagctg tttgtggaac agcacaagca ctacctggac gagatcatcg agcagatcag    4620
cgagttctcc aagagagtga tcctggccga cgctaatctg gacaaagtgc tgtccgccta    4680
caacaagcac cgggataagc ccatcagaga gcaggccgag aatatcatcc acctgtttac    4740
cctgaccaat ctgggagccc ctgccgcctt caagtacttt gacaccacca tcgaccggaa    4800
gaggtacacc agcaccaaag aggtgctgga cgccaccctg atccaccaga gcatcaccgg    4860
cctgtacgag acacggatcg acctgtctca gctgggaggc gacaaaaggc cggcggccac    4920
gaaaaaggcc ggccaggcaa aaagaaaaa gtaa                                4954

<210> SEQ ID NO 9
<211> LENGTH: 5126
<212> TYPE: DNA
<213> ORGANISM: Artificial Sequence
<220> FEATURE:
<223> OTHER INFORMATION: Synthetic

<400> SEQUENCE: 9
aaggtcgggc aggaagaggg cctatttccc atgattcctt catatttgca tatacgatac      60
aaggctgtta gagagataat tagaattaat ttgactgtaa acacaaagat attagtacaa     120
aatacgtgac gtagaaagta ataatttctt gggtagtttg cagttttaaa attatgtttt     180
aaaatggact atcatatgct taccgtaact tgaaagtatt tcgatttctt ggctttatat     240
atcttgtgga aaggacgaaa caccgggcac gggcagcttg ccgggtttta gagctagaaa     300
tagcaagtta aaataaggct agtccgttat caacttgaaa aagtggcacc gagtcggtgc     360
ttttttttaag cttgggccgc tcgagcgcgt taacgggccc agcttcgata aaataaaaga     420
ttttatttag tctccagaaa aaggggggaa tgaaagaccc cacctgtagg tttggcaagc     480
tagcttaagt aacgccattt tgcaaggcat ggaaaataca taactgagaa tagagaagtt     540
cagatcaagg ttaggaacag agagacagca gaatatgggc caaacaggat atctgtggta     600
agcagttcct gccccggctc agggccaaga acagatggtc cccagatgcg gtcccgccct     660
cagcagtttc tagagaacca tcagatgttt ccagggtgcc ccaaggacct gaaaatgacc     720
ctgtgcctta tttgaactaa ccaatcagtt cgcttctcgc ttctgttcgc gcgcttctgc     780
tccccgagct caataaaaga gcccacaacc cctcactcgg cgcgccagtc ctccgataga     840
ctgccggtgc caccatggac tataaggacc acgacggaga ctacaaggat catgatattg     900
```

```
attacaaaga cgatgacgat aagatggccc caaagaagaa gcggaaggtc ggtatccacg    960
gagtcccagc agccgacaag aagtacagca tcggcctgga catcggcacc aactctgtgg   1020
gctgggccgt gatcaccgac gagtacaagg tgcccagcaa gaaattcaag gtgctgggca   1080
acaccgaccg gcacagcatc aagaagaacc tgatcggagc cctgctgttc gacagcggcg   1140
aaacagccga ggccacccgg ctgaagagaa ccgccagaag aagatacacc agacggaaga   1200
accggatctg ctatctgcaa gagatcttca gcaacgagat ggccaaggtg gacgacagct   1260
tcttccacag actggaagag tccttcctgg tggaagagga taagaagcac gagcggcacc   1320
ccatcttcgg caacatcgtg gacgaggtgg cctaccacga aagtacccc accatctacc    1380
acctgagaaa gaaactggtg gacagcaccg acaaggccga cctgcggctg atctatctgg   1440
ccctggccca catgatcaag ttccggggcc acttcctgat cgagggcgac ctgaaccccg   1500
acaacagcga cgtggacaag ctgttcatcc agctggtgca gacctacaac cagctgttcg   1560
aggaaaaccc catcaacgcc agcggcgtgg acgccaaggc catcctgtct gccagactga   1620
gcaagagcag acggctggaa atctgatcg cccagctgcc cggcgagaag aagaatggcc    1680
tgttcggaaa cctgattgcc ctgagcctgg gcctgacccc caacttcaag agcaacttcg   1740
acctggccga ggatgccaaa ctgcagctga gcaaggacac ctacgacgac gacctggaca   1800
acctgctggc ccagatcggc gaccagtacg ccgacctgtt tctggccgcc aagaacctgt   1860
ccgacgccat cctgctgagc gacatcctga gagtgaacac cgagatcacc aaggccccc    1920
tgagcgcctc tatgatcaag agatacgacg agcaccacca ggacctgacc ctgctgaaag   1980
ctctcgtgcg gcagcagctg cctgagaagt acaaagagat tttcttcgac cagagcaaga   2040
acggctacgc cggctacatt gacggcggag ccagccagga gagttctac aagttcatca    2100
agcccatcct ggaaaagatg gacggcaccg aggaactgct cgtgaagctg aacagagagg   2160
acctgctgcg gaagcagcgg accttcgaca acggcagcat ccccaccag atccacctgg    2220
gagagctgca cgccattctg cggcggcagg aagattttta cccattcctg aaggacaacc   2280
gggaaaagat cgagaagatc ctgaccttcc gcatccccta ctacgtgggc cctctggcca   2340
ggggaaacag cagattcgcc tggatgacca gaaagagcga ggaaaccatc accccctgga   2400
acttcgagga agtggtggac aagggcgctt ccgcccagag cttcatcgag cggatgacca   2460
acttcgataa gaacctgccc aacgagaagg tgctgcccaa gcacagcctg ctgtacgagt   2520
acttcaccgt gtataacgag ctgaccaaag tgaaatacgt gaccgaggga atgagaaagc   2580
ccgccttcct gagcggcgag cagaaaaagg ccatcgtgga cctgctgttc aagaccaacc   2640
ggaaagtgac cgtgaagcag ctgaaagagg actacttcaa gaaaatcgag tgcttcgact   2700
ccgtggaaat ctccggcgtg gaagatcggt tcaacgcctc cctgggcaca taccacgatc   2760
tgctgaaaat tatcaaggac aaggacttcc tggacaatga ggaaaacgag gacattctgg   2820
aagatatcgt gctgaccctg acactgtttg aggacagaga gatgatcgag aacggctgaa   2880
aaacctatgc ccacctgttc gacgacaaag tgatgaagca gctgaagcgg cggagataca   2940
ccggctgggg caggctgagc cggaagctga tcaacggcat ccgggacaag cagtccggca   3000
agacaatcct ggatttcctg aagtccgacg gcttcgccaa cagaaacttc atgcagctga   3060
tccacgacga cagcctgacc tttaagagg acatccagaa agcccaggtg tccggccagg   3120
gcgatagcct gcacgagcac attgccaatc tggccggcag ccccgccatt aagaagggca   3180
tcctgcagac agtgaaggtg gtggacgagc tcgtgaaagt gatgggccgg cacaagcccg   3240
```

| | |
|---|---|
| agaacatcgt gatcgaaatg gccagagaga accagaccac ccagaaggga cagaagaaca | 3300 |
| gccgcgagag aatgaagcgg atcgaagagg gcatcaaaga gctgggcagc cagatcctga | 3360 |
| aagaacaccc cgtggaaaac acccagctgc agaacgagaa gctgtacctg tactacctgc | 3420 |
| agaatgggcg ggatatgtac gtggaccagg aactggacat caaccggctg tccgactacg | 3480 |
| atgtggacca tatcgtgcct cagagctttc tgaaggacga ctccatcgac aacaaggtgc | 3540 |
| tgaccagaag cgacaagaac cggggcaaga gcgacaacgt gccctccgaa gaggtcgtga | 3600 |
| agaagatgaa gaactactgg cggcagctgc tgaacgccaa gctgattacc cagagaaagt | 3660 |
| tcgacaatct gaccaaggcc gagagaggcg gcctgagcga actggataag gccggcttca | 3720 |
| tcaagagaca gctggtggaa acccggcaga tcacaaagca cgtggcacag atcctggact | 3780 |
| cccggatgaa cactaagtac gacgagaatg acaagctgat ccggaagtg aaagtgatca | 3840 |
| ccctgaagtc caagctggtg tccgatttcc ggaaggattt ccagttttac aaagtgcgcg | 3900 |
| agatcaacaa ctaccaccac gcccacgacg cctacctgaa cgccgtcgtg ggaaccgccc | 3960 |
| tgatcaaaaa gtaccctaag ctggaaagcg agttcgtgta cggcgactac aaggtgtacg | 4020 |
| acgtgcggaa gatgatcgcc aagagcgagc aggaaatcgg caaggctacc gccaagtact | 4080 |
| tcttctacag caacatcatg aacttttca gaccgagat accctggcc aacggcgaga | 4140 |
| tccggaagcg gcctctgatc gagacaaacg gcgaaaccgg ggagatcgtg tgggataagg | 4200 |
| gccgggattt tgccaccgtg cggaaagtgc tgagcatgcc ccaagtgaat atcgtgaaaa | 4260 |
| agaccgaggt gcagacaggc ggcttcagca agagtctat cctgcccaag aggaacagcg | 4320 |
| ataagctgat cgccagaaag aaggactggg accctaagaa gtacggcggc ttcgacagcc | 4380 |
| ccaccgtggc ctattctgtg ctggtggtgg ccaaagtgga aaagggcaag tccaagaaac | 4440 |
| tgaagagtgt gaaagagctg ctggggatca ccatcatgga agaagcagc ttcgagaaga | 4500 |
| atcccatcga ctttctggaa gccaagggct acaaagaagt gaaaaaggac ctgatcatca | 4560 |
| agctgcctaa gtactccctg ttcgagctgg aaaacggccg gaagagaatg ctggcctctg | 4620 |
| ccggcgaact gcagaaggga acgaactggg ccctgccctc caaatatgtg aacttcctgt | 4680 |
| acctggccag ccactatgag aagctgaagg gctcccccga ggataatgag cagaaacagc | 4740 |
| tgtttgtgga acagcacaag cactacctgg acgagatcat cgagcagatc agcgagttct | 4800 |
| ccaagagagt gatcctggcc gacgctaatc tggacaaagt gctgtccgcc tacaacaagc | 4860 |
| accgggataa gcccatcaga gagcaggccg agaatatcat ccacctgttt accctgacca | 4920 |
| atctgggagc ccctgccgcc ttcaagtact ttgacaccac catcgaccgg aagaggtaca | 4980 |
| ccagcaccaa agaggtgctg gacgccaccc tgatccacca gagcatcacc ggcctgtacg | 5040 |
| agacacggat cgacctgtct cagctgggag gcgacaaaag gccggcggcc acgaaaaagg | 5100 |
| ccggccaggc aaaaaagaaa aagtaa | 5126 |

<210> SEQ ID NO 10
<211> LENGTH: 5742
<212> TYPE: DNA
<213> ORGANISM: Artificial Sequence
<220> FEATURE:
<223> OTHER INFORMATION: Synthetic

<400> SEQUENCE: 10

| | |
|---|---|
| aaggtcgggc aggaagaggg cctatttccc atgattcctt catatttgca tatacgatac | 60 |
| aaggctgtta gagagataat tagaattaat ttgactgtaa acacaaagat attagtacaa | 120 |
| aatacgtgac gtagaaagta ataatttctt gggtagtttg cagttttaaa attatgtttt | 180 |

```
aaaatggact atcatatgct taccgtaact tgaaagtatt tcgatttctt ggctttatat    240
atcttgtgga aaggacgaaa caccgggcac gggcagcttg ccgggtttta gagctagaaa    300
tagcaagtta aaataaggct agtccgttat caacttgaaa aagtggcacc gagtcggtgc    360
tttttttaag cttgggccgc tcgagcgcgt taacgggccc agcttcgata aaataaaaga    420
ttttatttag tctccagaaa aagggggaa tgaaagaccc cacctgtagg tttggcaagc    480
tagcttaagt aacgccattt tgcaaggcat ggaaaataca taactgagaa tagagaagtt    540
cagatcaagg ttaggaacag agagacagca gaatatgggc caaacaggat atctgtggta    600
agcagttcct gccccggctc agggccaaga acagatggtc cccagatgcg gtcccgccct    660
cagcagtttc tagagaacca tcagatgttt ccagggtgcc ccaaggacct gaaaatgacc    720
ctgtgcctta tttgaactaa ccaatcagtt cgcttctcgc ttctgttcgc gcgcttctgc    780
tccccgagct caataaaaga gcccacaacc cctcactcgg cgcgccagtc ctccgataga    840
ctgccggtgc caccatggac tataaggacc acgacggaga ctacaaggat catgatattg    900
attacaaaga cgatgacgat aagatggccc caaagaagaa gcggaaggtc ggtatccacg    960
gagtcccagc agccgacaag aagtacagca tcggcctgga catcggcacc aactctgtgg   1020
gctgggccgt gatcaccgac gagtacaagg tgcccagcaa gaaattcaag gtgctgggca   1080
acaccgaccg gcacagcatc aagaagaacc tgatcggagc cctgctgttc gacagcggcg   1140
aaacagccga ggccacccgg ctgaagagaa ccgccagaag aagatacacc agacggaaga   1200
accggatctg ctatctgcaa gagatcttca gcaacgagat ggccaaggtg gacgacagct   1260
tcttccacag actggaagag tccttcctgg tggaagagga taagaagcac gagcggcacc   1320
ccatcttcgg caacatcgtg gacgaggtgg cctaccacga gaagtacccc accatctacc   1380
acctgagaaa gaaactggtg gacagcaccg acaaggccga cctgcggctg atctatctgg   1440
ccctggccca catgatcaag ttccggggcc acttcctgat cgaggcgac ctgaaccccg   1500
acaacagcga cgtggacaag ctgttcatcc agctggtgca gacctacaac cagctgttcg   1560
aggaaaaccc catcaacgcc agcggcgtgg acgccaaggc catcctgtct gccagactga   1620
gcaagagcag acggctggaa aatctgatcg cccagctgcc cggcgagaag aagaatggcc   1680
tgttcggaaa cctgattgcc ctgagcctgg gcctgacccc caacttcaag agcaacttcg   1740
acctggccga ggatgccaaa ctgcagctga gcaaggacac ctacgacgac gacctggaca   1800
acctgctggc ccagatcggc gaccagtacg ccgacctgtt tctggccgcc aagaacctgt   1860
ccgacgccat cctgctgagc gacatcctga gagtgaacac cgagatcacc aaggcccccc   1920
tgagcgcctc tatgatcaag agatacgacg agcaccacca ggacctgacc ctgctgaaag   1980
ctctcgtgcg gcagcagctg cctgagaagt acaaagagat tttcttcgac cagagcaaga   2040
acggctacgc cggctacatt gacggcggag ccagccagga agagttctac aagttcatca   2100
agcccatcct ggaaaagatg gacggcaccg aggaactgct cgtgaagctg aacagagagg   2160
acctgctgcg gaagcagcgg accttcgaca acggcagcat cccccaccag atccacctgg   2220
gagagctgca cgccattctg cggcggcagg aagatttta cccattcctg aaggacaacc   2280
gggaaaagat cgaaagatc ctgaccttcc gcatccccta ctacgtgggc cctctggcca   2340
ggggaaacag cagattcgcc tggatgacca aaagagcga ggaaaccatc acccctgga   2400
acttcgagga agtggtggac aagggcgctt ccgcccagag cttcatcgag cggatgacca   2460
acttcgataa gaacctgccc aacgagaagg tgctgcccaa gcacagcctg ctgtacgagt   2520
```

```
acttcaccgt gtataacgag ctgaccaaag tgaaatacgt gaccgaggga atgagaaagc    2580
ccgccttcct gagcggcgag cagaaaaagg ccatcgtgga cctgctgttc aagaccaacc    2640
ggaaagtgac cgtgaagcag ctgaaagagg actacttcaa gaaaatcgag tgcttcgact    2700
ccgtggaaat ctccggcgtg gaagatcggt tcaacgcctc cctgggcaca taccacgatc    2760
tgctgaaaat tatcaaggac aaggacttcc tggacaatga ggaaaacgag gacattctgg    2820
aagatatcgt gctgaccctg acactgtttg aggacagaga gatgatcgag aacggctga    2880 aaacctatgc ccacctgttc gacgacaaag tgatgaagca gctgaagcgg cggagataca    2940
ccggctgggg caggctgagc cggaagctga tcaacggcat ccgggacaag cagtccggca    3000
agacaatcct ggatttcctg aagtccgacg gcttcgccaa cagaaacttc atgcagctga    3060
tccacgacga cagcctgacc tttaaagagg acatccagaa agcccaggtg tccggccagg    3120
gcgatagcct gcacgagcac attgccaatc tggccggcag ccccgccatt aagaagggca    3180
tcctgcagac agtgaaggtg gtggacgagc tcgtgaaagt gatgggccgg cacaagcccg    3240
agaacatcgt gatcgaaatg gccagagaga accagaccac ccagaaggga cagaagaaca    3300
gccgcgagag aatgaagcgg atcgaagagg gcatcaaaga gctgggcagc cagatcctga    3360
aagaacaccc cgtggaaaac acccagctgc agaacgagaa gctgtacctg tactacctgc    3420
agaatgggcg ggatatgtac gtggaccagg aactggacat caaccggctg tccgactacg    3480
atgtggacca tatcgtgcct cagagctttc tgaaggacga ctccatcgac aacaaggtgc    3540
tgaccagaag cgacaagaac cggggcaaga gcgacaacgt gccctccgaa gaggtcgtga    3600
agaagatgaa gaactactgg cggcagctgc tgaacgccaa gctgattacc cagagaaagt    3660
tcgacaatct gaccaaggcc gagagaggcg gcctgagcga actggataag gccggcttca    3720
tcaagagaca gctggtggaa acccggcaga tcacaaagca cgtggcacag atcctggact    3780
cccggatgaa cactaagtac gacgagaatg acaagctgat ccgggaagtg aaagtgatca    3840
ccctgaagtc caagctggtg tccgatttcc ggaaggattt ccagttttac aaagtgcgcg    3900
agatcaacaa ctaccaccac gcccacgacg cctacctgaa cgccgtcgtg ggaaccgccc    3960
tgatcaaaaa gtaccctaag ctggaaagcg agttcgtgta cggcgactac aaggtgtacg    4020
acgtgcggaa gatgatcgcc aagagcgagc aggaaatcgg caaggctacc gccaagtact    4080
tcttctacag caacatcatg aacttttca agaccgagat tacccctggcc aacggcgaga    4140 tccggaagcg gcctctgatc gagacaaacg gcgaaaccgg ggagatcgtg tgggataagg    4200
gccgggattt tgccaccgtg cggaaagtgc tgagcatgcc ccaagtgaat atcgtgaaaa    4260
agaccgaggt gcagacaggc ggcttcagca agagtctat cctgcccaag aggaacagcg    4320
ataagctgat cgccagaaag aaggactggg accctaagaa gtacggcggc ttcgacagcc    4380
ccaccgtggc ctattctgtg ctggtggtgg ccaaagtgga aaagggcaag tccaagaaac    4440
tgaagagtgt gaaagagctg ctggggatca ccatcatgga aagaagcagc ttcgagaaga    4500
atcccatcga ctttctggaa gccaagggct acaaagaagt gaaaaaggac ctgatcatca    4560
agctgcctaa gtactccctg ttcgagctgg aaaacggccg gaagagaatg ctggcctctg    4620
ccggcgaact gcagaaggga aacgaactgg ccctgcccte caaatatgtg aacttcctgt    4680
acctggccag ccactatgag aagctgaagg gctcccccga ggataatgag cagaaacagc    4740
tgtttgtgga acagcacaag cactacctgg acgagatcat cgagcagatc agcgagttct    4800
ccaagagagt gatcctggcc gacgctaatc tggacaaagt gctgtccgcc tacaacaagc    4860
accgggataa gcccatcaga gagcaggccg agaatatcat ccacctgttt accctgacca    4920
```

| | |
|---|---|
| atctgggagc ccctgccgcc ttcaagtact tgacaccac catcgaccgg aagaggtaca | 4980 |
| ccagcaccaa agaggtgctg gacgccaccc tgatccacca gagcatcacc ggcctgtacg | 5040 |
| agacacggat cgacctgtct cagctgggag gcgacaaaag gccggcggcc acgaaaaagg | 5100 |
| ccggccaggc aaaaaagaaa aagtaagaat tcgatgccgt aggccgcatc gataatcaac | 5160 |
| ctctggatta caaaatttgt gaaagattga ctggtattct taactatgtt gctccttta | 5220 |
| cgctatgtgg atacgctgct ttaatgcctt tgtatcatgc tattgcttcc cgtatggctt | 5280 |
| tcattttctc ctccttgtat aaatcctggt tgctgtctct ttatgaggag ttgtggcccg | 5340 |
| ttgtcaggca acgtggcgtg gtgtgcactg tgtttgctga cgcaaccccc actggttggg | 5400 |
| gcattgccac cacctgtcag ctcctttccg ggactttcgc tttcccctc cctattgcca | 5460 |
| cggcggaact catcgccgcc tgccttgccc gctgctggac aggggctcgg ctgttgggca | 5520 |
| ctgacaattc cgtggtgttg tcgggaaat catcgtcctt tccttggctg ctcgcctgtg | 5580 |
| ttgccacctg gattctgcgc gggacgtcct tctgctacgt cccttcggcc ctcaatccag | 5640 |
| cggaccttcc ttcccgcggc ctgctgccgg ctctgcggcc tcttccgcgt cttcgccttc | 5700 |
| gccctcagac gagtcggatc tcccttggg ccgcctcccc gc | 5742 |

<210> SEQ ID NO 11
<211> LENGTH: 1154
<212> TYPE: DNA
<213> ORGANISM: Artificial Sequence
<220> FEATURE:
<223> OTHER INFORMATION: Synthetic

<400> SEQUENCE: 11

| | |
|---|---|
| tagtctccag aaaaggggg gaatgaaaga ccccacctgt aggtttggca agctagctta | 60 |
| agtaacgcca ttttgcaagg catggaaaat acataactga gaatagagaa gttcagatca | 120 |
| aggttaggaa cagagagaca gcagaatatg ggccaaacag gatatctgtg gtaagcagtt | 180 |
| cctgccccgg ctcagggcca agaacagatg gtccccagat gcggtcccgc ctcagcagt | 240 |
| ttctagagaa ccatcagatg tttccagggt gccccaagga cctgaaaatg accctgtgcc | 300 |
| ttatttgaac taaccaatca gttcgcttct cgcttctgtt cgcgcgcttc tgctccccga | 360 |
| gctcaataaa agagcccaca acccctcact cggcgcgcca gtcctccgat agactgcgtc | 420 |
| gcccggtcgc caccatggtg agcaagggcg aggagctgtt caccggggtg gtgcccatcc | 480 |
| tggtcgagct ggacggcgac gtaaacggcc acaagttcag cgtgtccggc gagggcgagg | 540 |
| gcgatgccac ctacggcaag ctgaccctga agttcatctg caccaccggc aagctgcccg | 600 |
| tgccctggcc cacccttgtg accaccttcg gctacggcct gcagtgcttc gcccgctacc | 660 |
| ccgaccacat gaagcagcac gacttcttca gtccgccat gcccgaaggc tacgtccagg | 720 |
| agcgcaccat cttcttcaag gacgacggca actacaagac ccgcgccgag gtgaagttcg | 780 |
| agggcgacac cctggtgaac cgcatcgagc tgaagggcat cgacttcaag gaggacggca | 840 |
| acatcctggg gcacaagctg gagtacaact acaacagcca cacgtctat atcatggccg | 900 |
| acaagcagaa gaacggcatc aaggtgaact tcaagatccg ccacaacatc gaggacggca | 960 |
| gcgtgcagct cgccgaccac taccagcaga cacccccat cggcgacggc ccgtgctgc | 1020 |
| tgcccgacaa ccactacctg agctaccagt ccgccctgag caaagacccc aacgagaagc | 1080 |
| gcgatcacat ggtcctgctg gagttcgtga ccgccgccgg gatcactctc ggcatggacg | 1140 |
| agctgtacaa gtaa | 1154 |

<210> SEQ ID NO 12
<211> LENGTH: 364
<212> TYPE: DNA
<213> ORGANISM: Artificial Sequence
<220> FEATURE:
<223> OTHER INFORMATION: Synthetic

<400> SEQUENCE: 12

```
aaggtcgggc aggaagaggg cctatttccc atgattcctt catatttgca tatacgatac    60
aaggctgtta gagagataat tagaattaat ttgactgtaa acacaaagat attagtacaa   120
aatacgtgac gtagaaagta ataatttctt gggtagtttg cagttttaaa attatgtttt   180
aaaatggact atcatatgct taccgtaact tgaaagtatt tcgatttctt ggctttatat   240
atcttgtgga aaggacgaaa caccgggcac gggcagcttg ccgggtttta gagctagaaa   300
tagcaagtta aaataaggct agtccgttat caacttgaaa aagtggcacc gagtcggtgc   360
tttt                                                                364
```

<210> SEQ ID NO 13
<211> LENGTH: 1581
<212> TYPE: DNA
<213> ORGANISM: Artificial Sequence
<220> FEATURE:
<223> OTHER INFORMATION: Synthetic

<400> SEQUENCE: 13

```
aaggtcgggc aggaagaggg cctatttccc atgattcctt catatttgca tatacgatac    60
aaggctgtta gagagataat tagaattaat ttgactgtaa acacaaagat attagtacaa   120
aatacgtgac gtagaaagta ataatttctt gggtagtttg cagttttaaa attatgtttt   180
aaaatggact atcatatgct taccgtaact tgaaagtatt tcgatttctt ggctttatat   240
atcttgtgga aaggacgaaa caccgggcac gggcagcttg ccgggtttta gagctagaaa   300
tagcaagtta aaataaggct agtccgttat caacttgaaa aagtggcacc gagtcggtgc   360 ttttttaag cttgggccgc tcgagcgcgt taacgggccc agcttcgata aaataaaaga   420
ttttatttag tctccagaaa agggggggaa tgaaagaccc cacctgtagg tttggcaagc   480
tagcttaagt aacgccattt tgcaaggcat ggaaaataca taactgagaa tagagaagtt   540
cagatcaagg ttaggaacag agagacagca gaatatgggc caaacaggat atctgtggta   600
agcagttcct gccccggctc agggccaaga acagatggtc cccagatgcg gtcccgccct   660
cagcagtttc tagagaacca tcagatgttt ccagggtgcc ccaaggacct gaaaatgacc   720
ctgtgcctta tttgaactaa ccaatcagtt cgcttctcgc ttctgttcgc gcgcttctgc   780
tccccgagct caataaaaga gcccacaacc cctcactcgg cgcgccagtc ctccgataga   840
ctgcgtcgcc cggtcgccac catggtgagc aagggcgagg agctgttcac cggggtggtg   900
cccatcctgg tcgagctgga cggcgacgta aacggccaca gttcagcgt gtccggcgag   960 ggcgagggcg atgccaccta cggcaagctg accctgaagt tcatctgcac aacaggaaag  1020
ctgcctgtgc catggcccac cctcgtgacc accttcggct acggcctgca gtgcttcgcc  1080
cgctaccccg accacatgaa gcagcacgac ttcttcaagt ccgccatgcc cgaaggctac  1140
gtccaggagc gcaccatctt cttcaaggac gacggcaact acaagacccg cgccgaggtg  1200
aagttcgagg gcgacaccct ggtgaaccgc atcgagctga agggcatcga cttcaaggag  1260
gacggcaaca tcctggggca caagctggag tacaactaca acagccacaa cgtctatatc  1320
atggccgaca agcagaagaa cggcatcaag gtgaacttca agatccgcca caacatcgag  1380
```

```
gacggcagcg tgcagctcgc cgaccactac cagcagaaca ccccatcgg cgacggcccc    1440 gtgctgctgc ccgacaacca ctacctgagc taccagtccg ccctgagcaa agaccccaac    1500
gagaagcgcg atcacatggt cctgctggag ttcgtgaccg ccgccgggat cactctcggc    1560
atggacgagc tgtacaagta a                                              1581
```

<210> SEQ ID NO 14
<211> LENGTH: 1581
<212> TYPE: DNA
<213> ORGANISM: Artificial Sequence
<220> FEATURE:
<223> OTHER INFORMATION: Synthetic

<400> SEQUENCE: 14

```
aaggtcgggc aggaagaggg cctatttccc atgattcctt catatttgca tatacgatac     60
aaggctgtta gagagataat tagaattaat ttgactgtaa acacaaagat attagtacaa    120
aatacgtgac gtagaaagta ataatttct gggtagtttg cagttttaaa attatgtttt    180
aaaatggact atcatatgct taccgtaact tgaaagtatt tcgatttctt ggctttatat    240
atcttgtgga aaggacgaaa caccgggcac gggcagcttg ccgggtttta gagctagaaa    300
tagcaagtta aaataaggct agtccgttat caacttgaaa aagtggcacc gagtcggtgc    360 ttttttaag cttgggccgc tcgagcgcgt taacgggccc agcttcgata aaataaaaga    420
ttttatttag tctccagaaa aaggggggaa tgaaagaccc cacctgtagg tttggcaagc    480
tagcttaagt aacgccattt tgcaaggcat ggaaaataca taactgagaa tagagaagtt    540
cagatcaagg ttaggaacag agagacagca gaatatgggc caaacaggat atctgtggta    600
agcagttcct gccccggctc agggccaaga acagatggtc cccagatgcg gtcccgccct    660
cagcagtttc tagagaacca tcagatgttt ccagggtgcc caaggacct gaaaatgacc    720 ctgtgcctta tttgaactaa ccaatcagtt cgcttctcgc ttctgttcgc gcgcttctgc    780
tccccgagct caataaaaga gcccacaacc cctcactcgg cgcgccagtc ctccgataga    840
ctgcgtcgcc cggtcgccac catggtgagc aagggcgagg agctgttcac cggggtggtg    900
cccatcctgg tcgagctgga cggcgacgta aacggccaca agttcagcgt gtccggcgag    960
ggcgagggcg atgccaccta cggcaagctg accctgaagt tcatctgcac aacaggaaag   1020
ctgcctgtgc catggcccac cctcgtgacc accttcggct acggcctgca gtgcttcgcc   1080
cgctaccccg accacatgaa gcagcacgac ttcttcaagt ccgccatgcc cgaaggctac   1140
gtccaggagc gcaccatctt cttcaaggac gacggcaact acaagacccg cgccgaggtg   1200
aagttcgagg gcgacaccct ggtgaaccgc atcgagctga agggcatcga cttcaaggag   1260
gacggcaaca tcctggggca caagctggag tacaactaca acagccacaa cgtctatatc   1320
atggccgaca agcagaagaa cggcatcaag gtgaacttca agatccgcca caacatcgag   1380
gacggcagcg tgcagctcgc cgaccactac cagcagaaca ccccatcgg cgacggcccc    1440 gtgctgctgc ccgacaacca ctacctgagc taccagtccg ccctgagcaa agaccccaac   1500
gagaagcgcg atcacatggt cctgctggag ttcgtgaccg ccgccgggat cactctcggc   1560
atggacgagc tgtacaagta a                                             1581
```

<210> SEQ ID NO 15
<211> LENGTH: 364
<212> TYPE: DNA
<213> ORGANISM: Artificial Sequence
<220> FEATURE:

<223> OTHER INFORMATION: Synthetic

<400> SEQUENCE: 15

| | | | | | |
|---|---|---|---|---|---|
| aaggtcgggc | aggaagaggg | cctatttccc | atgattcctt | catatttgca | tatacgatac | 60 |
| aaggctgtta | gagagataat | tagaattaat | ttgactgtaa | acacaaagat | attagtacaa | 120 |
| aatacgtgac | gtagaaagta | ataatttctt | gggtagtttg | cagttttaaa | attatgtttt | 180 |
| aaaatggact | atcatatgct | taccgtaact | tgaaagtatt | tcgatttctt | ggctttatat | 240 |
| atcttgtgga | aaggacgaaa | caccgggcac | gggcagcttg | ccgggtttta | gagctagaaa | 300 |
| tagcaagtta | aaataaggct | agtccgttat | caacttgaaa | aagtggcacc | gagtcggtgc | 360 |
| tttt | | | | | | 364 |

<210> SEQ ID NO 16
<211> LENGTH: 1154
<212> TYPE: DNA
<213> ORGANISM: Artificial Sequence
<220> FEATURE:
<223> OTHER INFORMATION: Synthetic

<400> SEQUENCE: 16

| | | | | | |
|---|---|---|---|---|---|
| tagtctccag | aaaaaggggg | gaatgaaaga | ccccacctgt | aggtttggca | agctagctta | 60 |
| agtaacgcca | ttttgcaagg | catggaaaat | acataactga | gaatagagaa | gttcagatca | 120 |
| aggttaggaa | cagagagaca | gcagaatatg | ggccaaacag | gatatctgtg | gtaagcagtt | 180 |
| cctgccccgg | ctcagggcca | agaacagatg | gtccccagat | gcggtcccgc | cctcagcagt | 240 |
| ttctagaaga | ccatcagatg | tttccagggt | gccccaagga | cctgaaaatg | accctgtgcc | 300 |
| ttatttgaac | taaccaatca | gttcgcttct | cgcttctgtt | cgcgcgcttc | tgctccccga | 360 |
| gctcaataaa | agagcccaca | acccctcact | cggcgcgcca | gtcctccgat | agactgcgtc | 420 |
| gcccggtcgc | caccatggtg | agcaagggcg | aggagctgtt | caccggggtg | gtgcccatcc | 480 |
| tggtcgagct | ggacggcgac | gtaaacggcc | acaagttcag | cgtgtccggc | gagggcgagg | 540 |
| gcgatgccac | ctacggcaag | ctgaccctga | agttcatctg | cacaacagga | aagctgcctg | 600 |
| tgccatggcc | caccctcgtg | accaccttcg | gctacggcct | gcagtgcttc | gcccgctacc | 660 |
| ccgaccacat | gaagcagcac | gacttcttca | agtccgccat | gcccgaaggc | tacgtccagg | 720 |
| agcgcaccat | cttcttcaag | gacgacggca | actacaagac | ccgcgccgag | gtgaagttcg | 780 |
| agggcgacac | cctggtgaac | cgcatcgagc | tgaagggcat | cgacttcaag | gaggacggca | 840 |
| acatcctggg | gcacaagctg | gagtacaact | acaacagcca | caacgtctat | atcatggccg | 900 |
| acaagcagaa | gaacggcatc | aaggtgaact | tcaagatccg | ccacaacatc | gaggacggca | 960 |
| gcgtgcagct | cgccgaccac | taccagcaga | acacccccat | cggcgacggc | cccgtgctgc | 1020 |
| tgcccgacaa | ccactacctg | agctaccagt | ccgcccctgag | caaagacccc | aacgagaagc | 1080 |
| gcgatcacat | ggtcctgctg | gagttcgtga | ccgccgccgg | gatcactctc | ggcatggacg | 1140 |
| agctgtacaa | gtaa | | | | | 1154 |

<210> SEQ ID NO 17
<211> LENGTH: 364
<212> TYPE: DNA
<213> ORGANISM: Artificial Sequence
<220> FEATURE:
<223> OTHER INFORMATION: Synthetic

<400> SEQUENCE: 17

| | | | | | |
|---|---|---|---|---|---|
| aaggtcgggc | aggaagaggg | cctatttccc | atgattcctt | catatttgca | tatacgatac | 60 |

```
aaggctgtta gagagataat tagaattaat ttgactgtaa acacaaagat attagtacaa      120
aatacgtgac gtagaaagta ataatttctt gggtagtttg cagttttaaa attatgtttt      180
aaaatggact atcatatgct taccgtaact tgaaagtatt tcgatttctt ggctttatat      240
atcttgtgga aaggacgaaa caccgggcac gggcagcttg ccgggtttta gagctagaaa      300
tagcaagtta aaataaggct agtccgttat caacttgaaa aagtggcacc gagtcggtgc      360
tttt                                                                  364
```

<210> SEQ ID NO 18
<211> LENGTH: 1154
<212> TYPE: DNA
<213> ORGANISM: Artificial Sequence
<220> FEATURE:
<223> OTHER INFORMATION: Synthetic

<400> SEQUENCE: 18

```
tagtctccag aaaaaggggg gaatgaaaga ccccacctgt aggtttggca agctagctta       60
agtaacgcca ttttgcaagg catggaaaat acataactga gaatagagaa gttcagatca      120
aggttaggaa cagagagaca gcagaatatg ggccaaacag gatatctgtg gtaagcagtt      180
cctgccccgg ctcagggcca agaacagatg gtccccagat gcggtcccgc cctcagcagt      240
ttctagagaa ccatcagatg tttccagggt gccccaagga cctgaaaatg accctgtgcc      300
ttatttgaac taaccaatca gttcgcttct cgcttctgtt cgcgcgcttc tgctccccga      360
gctcaataaa agagcccaca acccctcact cggcgcgcca gtcctccgat agactgcgtc      420
gcccggtcgc caccatggtg agcaagggcg aggagctgtt caccggggtg gtgcccatcc      480
tggtcgagct ggacggcgac gtaaacggcc acaagttcag cgtgtccggc gagggcgagg      540
gcgatgccac ctacggcaag ctgaccctga agttcatctg cacaacagga aagctgcctg      600
tgccatggcc cacccttcgtg accaccttcg gctacggcct gcagtgcttc gcccgctacc      660
ccgaccacat gaagcagcac gacttcttca gtccgccat gcccgaaggc tacgtccagg      720
agcgcaccat cttcttcaag gacgacggca actacaagac ccgcgccgag gtgaagttcg      780
agggcgacac cctggtgaac cgcatcgagc tgaagggcat cgacttcaag gaggacggca      840
acatcctggg gcacaagctg gagtacaact acaacagcca caacgtctat atcatggccg      900
acaagcagaa gaacggcatc aaggtgaact tcaagatccg ccacaacatc gaggacggca      960
gcgtgcagct cgccgaccac taccagcaga cacccccat cggcgacggc cccgtgctgc     1020
tgcccgacaa ccactacctg agctaccagt ccgccctgag caaagacccc aacgagaagc     1080
gcgatcacat ggtcctgctg gagttcgtga ccgccgccgg gatcactctc ggcatggacg     1140
agctgtacaa gtaa                                                      1154
```

<210> SEQ ID NO 19
<211> LENGTH: 1154
<212> TYPE: DNA
<213> ORGANISM: Artificial Sequence
<220> FEATURE:
<223> OTHER INFORMATION: Synthetic

<400> SEQUENCE: 19

```
tagtctccag aaaaaggggg gaatgaaaga ccccacctgt aggtttggca agctagctta       60
agtaacgcca ttttgcaagg catggaaaat acataactga gaatagagaa gttcagatca      120
aggttaggaa cagagagaca gcagaatatg ggccaaacag gatatctgtg gtaagcagtt      180
```

| | |
|---|---|
| cctgccccgg ctcagggcca agaacagatg gtccccagat gcggtcccgc cctcagcagt | 240 |
| ttctagagaa ccatcagatg tttccagggt gccccaagga cctgaaaatg accctgtgcc | 300 |
| ttatttgaac taaccaatca gttcgcttct cgcttctgtt cgcgcgcttc tgctccccga | 360 |
| gctcaataaa agagcccaca acccctcact cggcgcgcca gtcctccgat agactgcgtc | 420 |
| gcccggtcgc caccatggtg agcaagggcg aggagctgtt caccggggtg gtgcccatcc | 480 |
| tggtcgagct ggacggcgac gtaaacggcc acaagttcag cgtgtccggc gagggcgagg | 540 |
| gcgatgccac ctacggcaag ctgaccctga agttcatctg cacaacagga aagctgcctg | 600 |
| tgccatggcc caccctcgtg accaccttcg gctacggcct gcagtgcttc gcccgctacc | 660 |
| ccgaccacat gaagcagcac gacttcttca gtccgccat gcccgaaggc tacgtccagg | 720 |
| agcgcaccat cttcttcaag gacgacggca actacaagac ccgcgccgag gtgaagttcg | 780 |
| agggcgacac cctggtgaac cgcatcgagc tgaagggcat cgacttcaag gaggacggca | 840 |
| acatcctggg gcacaagctg gagtacaact acaacagcca caacgtctat atcatggccg | 900 |
| acaagcagaa gaacggcatc aaggtgaact tcaagatccg ccacaacatc gaggacggca | 960 |
| gcgtgcagct cgccgaccac taccagcaga cacccccat cggcgacggc cccgtgctgc | 1020 |
| tgcccgacaa ccactacctg agctaccagt ccgccctgag caaagacccc aacgagaagc | 1080 |
| gcgatcacat ggtcctgctg gagttcgtga ccgccgccgg gatcactctc ggcatggacg | 1140 |
| agctgtacaa gtaa | 1154 |

<210> SEQ ID NO 20
<211> LENGTH: 1154
<212> TYPE: DNA
<213> ORGANISM: Artificial Sequence
<220> FEATURE:
<223> OTHER INFORMATION: Synthetic

<400> SEQUENCE: 20

| | |
|---|---|
| tagtctccag aaaaagggg gaatgaaaga ccccacctgt aggtttggca agctagctta | 60 |
| agtaacgcca ttttgcaagg catggaaaat acataactga gaatagagaa gttcagatca | 120 |
| aggttaggaa cagagagaca gcagaatatg ggccaaacag gatatctgtg gtaagcagtt | 180 |
| cctgccccgg ctcagggcca agaacagatg gtccccagat gcggtcccgc cctcagcagt | 240 |
| ttctagagaa ccatcagatg tttccagggt gccccaagga cctgaaaatg accctgtgcc | 300 |
| ttatttgaac taaccaatca gttcgcttct cgcttctgtt cgcgcgcttc tgctccccga | 360 |
| gctcaataaa agagcccaca acccctcact cggcgcgcca gtcctccgat agactgcgtc | 420 |
| gcccggtcgc caccatggtg agcaagggcg aggagctgtt caccggggtg gtgcccatcc | 480 |
| tggtcgagct ggacggcgac gtaaacggcc acaagttcag cgtgtccggc gagggcgagg | 540 |
| gcgatgccac ctacggcaag ctgaccctga agttcatctg cacaacagga aagctgcctg | 600 |
| tgccatggcc caccctcgtg accaccttcg gctacggcct gcagtgcttc gcccgctacc | 660 |
| ccgaccacat gaagcagcac gacttcttca gtccgccat gcccgaaggc tacgtccagg | 720 |
| agcgcaccat cttcttcaag gacgacggca actacaagac ccgcgccgag gtgaagttcg | 780 |
| agggcgacac cctggtgaac cgcatcgagc tgaagggcat cgacttcaag gaggacggca | 840 |
| acatcctggg gcacaagctg gagtacaact acaacagcca caacgtctat atcatggccg | 900 |
| acaagcagaa gaacggcatc aaggtgaact tcaagatccg ccacaacatc gaggacggca | 960 |
| gcgtgcagct cgccgaccac taccagcaga cacccccat cggcgacggc cccgtgctgc | 1020 |
| tgcccgacaa ccactacctg agctaccagt ccgccctgag caaagacccc aacgagaagc | 1080 |

```
gcgatcacat ggtcctgctg gagttcgtga ccgccgccgg gatcactctc ggcatggacg    1140
agctgtacaa gtaa                                                      1154

<210> SEQ ID NO 21
<211> LENGTH: 5126
<212> TYPE: DNA
<213> ORGANISM: Artificial Sequence
<220> FEATURE:
<223> OTHER INFORMATION: Synthetic

<400> SEQUENCE: 21
aaggtcgggc aggaagaggg cctatttccc atgattcctt catatttgca tatacgatac      60
aaggctgtta gagagataat tagaattaat ttgactgtaa acacaaagat attagtacaa     120
aatacgtgac gtagaaagta ataatttctt gggtagtttg cagttttaaa attatgtttt     180
aaaatggact atcatatgct taccgtaact tgaaagtatt tcgatttctt ggctttatat     240
atcttgtgga aaggacgaaa cacccttgcc ccacagggca gtaagtttta gagctagaaa     300
tagcaagtta aaataaggct agtccgttat caacttgaaa aagtggcacc gagtcggtgc     360
tttttttaag cttgggccgc tcgagcgcgt taacgggccc agcttcgata aaataaaaga     420
ttttatttag tctccagaaa aaggggggaa tgaaagaccc cacctgtagg tttggcaagc     480
tagcttaagt aacgccattt tgcaaggcat ggaaaataca taactgagaa tagagaagtt     540
cagatcaagg ttaggaacag agagacagca gaatatgggc caaacaggat atctgtggta     600
agcagttcct gccccggctc agggccaaga acagatggtc cccagatgcg gtcccgccct     660
cagcagtttc tagagaacca tcagatgttt ccagggtgcc ccaaggacct gaaaatgacc     720
ctgtgcctta tttgaactaa ccaatcagtt cgcttctcgc ttctgttcgc gcgcttctgc     780
tccccgagct caataaaaga gcccacaacc cctcactcgg cgcgccagtc ctccgataga     840
ctgccggtgc caccatggac tataaggacc acgacggaga ctacaaggat catgatattg     900
attacaaaga cgatgacgat aagatggccc aaagaagaa gcggaaggtc ggtatccacg     960
gagtcccagc agccgacaag aagtacagca tcggcctgga catcggcacc aactctgtgg    1020
gctgggccgt gatcaccgac gagtacaagg tgcccagcaa gaaattcaag gtgctgggca    1080
acaccgaccg gcacagcatc aagaagaacc tgatcggagc cctgctgttc gacagcggcg    1140
aaacagccga ggccacccgg ctgaagagaa ccgccagaag aagatacacc agacggaaga    1200
accggatctg ctatctgcaa gagatcttca gcaacgagat ggccaaggtg gacgacagct    1260
tcttccacag actggaagag tccttcctgg tggaagagga taagaagcac gagcggcacc    1320
ccatcttcgg caacatcgtg gacgaggtgg cctaccacga aaagtacccc accatctacc    1380
acctgagaaa gaaactggtg gacagcaccg acaaggccga cctgcggctg atctatctgg    1440
ccctggccca catgatcaag ttccggggcc acttcctgat cgagggcgac ctgaaccccg    1500
acaacagcga cgtggacaag ctgttcatcc agctggtgca gacctacaac cagctgttcg    1560
aggaaaaccc catcaacgcc agcggcgtgg acgccaaggc catcctgtct gccagactga    1620
gcaagagcag acggctggaa aatctgatcg cccagctgcc cggcgagaag aagaatggcc    1680
tgttcggaaa cctgattgcc ctgagcctgg gcctgacccc caacttcaag agcaacttcg    1740
acctggccga ggatgccaaa ctgcagctga gcaaggacac ctacgacgac gacctggaca    1800
acctgctggc ccagatcggc gaccagtacg ccgacctgtt tctggccgcc aagaacctgt    1860
ccgacgccat cctgctgagc gacatcctga gagtgaacac cgagatcacc aaggcccccc    1920
```

```
tgagcgcctc tatgatcaag agatacgacg agcaccacca ggacctgacc ctgctgaaag      1980
ctctcgtgcg gcagcagctg cctgagaagt acaaagagat tttcttcgac cagagcaaga      2040
acggctacgc cggctacatt gacggcggag ccagccagga agagttctac aagttcatca      2100
agcccatcct ggaaaagatg gacggcaccg aggaactgct cgtgaagctg aacagagagg      2160
acctgctgcg gaagcagcgg accttcgaca acggcagcat ccccaccag atccacctgg       2220
gagagctgca cgccattctg cggcggcagg aagatttta cccattcctg aaggacaacc       2280
gggaaaagat cgagaagatc ctgaccttcc gcatcccta ctacgtgggc cctctggcca       2340
ggggaaacag cagattcgcc tggatgacca gaaagagcga ggaaaccatc accccctgga      2400
acttcgagga agtggtggac aagggcgctt ccgcccagag cttcatcgag cggatgacca      2460
acttcgataa gaacctgccc aacgagaagg tgctgcccaa gcacagcctg ctgtacgagt      2520
acttcaccgt gtataacgag ctgaccaaag tgaaatacgt gaccgaggga atgagaaagc      2580
ccgccttcct gagcggcgag cagaaaaagg ccatcgtgga cctgctgttc aagaccaacc      2640
ggaaagtgac cgtgaagcag ctgaaagagg actacttcaa gaaaatcgag tgcttcgact      2700
ccgtggaaat ctccggcgtg gaagatcggt tcaacgcctc cctgggcaca taccacgatc      2760
tgctgaaaat tatcaaggac aaggacttcc tggacaatga ggaaaacgag gacattctgg      2820
aagatatcgt gctgaccctg acactgtttg aggacagaga gatgatcgag gaacggctga      2880
aaacctatgc ccacctgttc gacgacaaag tgatgaagca gctgaagcgg cggagataca      2940
ccggctgggg caggctgagc cggaagctga tcaacggcat ccgggacaag cagtccggca      3000
agacaatcct ggatttcctg aagtccgacg gcttcgccaa cagaaacttc atgcagctga      3060
tccacgacga cagcctgacc tttaaagagg acatccagaa agcccaggtg tccggccagg      3120
gcgatagcct gcacgagcac attgccaatc tggccgcag ccccgccatt aagaagggca      3180
tcctgcagac agtgaaggtg gtggacgagc tcgtgaaagt gatgggccgg cacaagcccg      3240
agaacatcgt gatcgaaatg gccagagaga accagaccac ccagaaggga cagaagaaca      3300
gccgcgagag aatgaagcgg atcgaagagg gcatcaaaga gctgggcagc cagatcctga      3360
aagaacaccc cgtggaaaac acccagctgc agaacgagaa gctgtacctg tactacctgc      3420
agaatgggcg ggatatgtac gtggaccagg aactggacat caaccggctg tccgactacg      3480
atgtggacca tatcgtgcct cagagctttc tgaaggacga ctccatcgac aacaaggtgc      3540
tgaccagaag cgacaagaac cggggcaaga gcgacaacgt gccctccgaa gaggtcgtga      3600
agaagatgaa gaactactgg cggcagctgc tgaacgccaa gctgattacc cagagaaagt      3660
tcgacaatct gaccaaggcc gagagaggcg gcctgagcga actggataag gccggcttca      3720
tcaagagaca gctggtggaa acccggcaga tcacaaagca cgtggcacag atcctggact      3780
cccggatgaa cactaagtac gacgagaatg acaagctgat ccgggaagtg aaagtgatca      3840
ccctgaagtc caagctggtg tccgatttcc ggaaggattt ccagttttac aaagtgcgcg      3900
agatcaacaa ctaccaccac gcccacgacg cctacctgaa cgccgtcgtg ggaaccgccc      3960
tgatcaaaaa gtaccctaag ctggaaagcg agttcgtgta cggcgactac aaggtgtacg      4020
acgtgcggaa gatgatcgcc aagagcgagc aggaaatcgg caaggctacc gccaagtact      4080
tcttctacag caacatcatg aactttttca agaccgagat taccctggcc aacggcgaga      4140
tccggaagcg gcctctgatc gagacaaacg gcgaaaccgg ggagatcgtg tgggataagg      4200
gccgggattt tgccaccgtg cggaaagtgc tgagcatgcc ccaagtgaat atcgtgaaaa      4260
agaccgaggt gcagacaggc ggcttcagca agagtctat cctgcccaag aggaacagcg      4320
```

```
ataagctgat cgccagaaag aaggactggg accctaagaa gtacggcggc ttcgacagcc   4380
ccaccgtggc ctattctgtg ctggtggtgg ccaaagtgga aaagggcaag tccaagaaac   4440
tgaagagtgt gaaagagctg ctggggatca ccatcatgga agaagcagc ttcgagaaga    4500 atcccatcga ctttctggaa gccaagggct acaaagaagt gaaaaggac ctgatcatca    4560 agctgcctaa gtactccctg ttcgagctgg aaaacggccg gaagagaatg ctggcctctg   4620
ccggcgaact gcagaaggga aacgaactgg ccctgccctc caaatatgtg aacttcctgt   4680
acctggccag ccactatgag aagctgaagg gctcccccga ggataatgag cagaaacagc   4740
tgtttgtgga acagcacaag cactacctgg acgagatcat cgagcagatc agcgagttct   4800
ccaagagagt gatcctggcc gacgctaatc tggacaaagt gctgtccgcc tacaacaagc   4860
accgggataa gcccatcaga gagcaggccg agaatatcat ccacctgttt accctgacca   4920
atctgggagc ccctgccgcc ttcaagtact ttgacaccac catcgaccgg aagaggtaca   4980
ccagcaccaa agaggtgctg gacgccaccc tgatccacca gagcatcacc ggcctgtacg   5040
agacacggat cgacctgtct cagctgggag gcgacaaaag gccggcggcc acgaaaaagg   5100
ccggccaggc aaaaaagaaa aagtaa                                       5126
```

<210> SEQ ID NO 22
<211> LENGTH: 5126
<212> TYPE: DNA
<213> ORGANISM: Artificial Sequence
<220> FEATURE:
<223> OTHER INFORMATION: Synthetic

<400> SEQUENCE: 22

```
aaggtcgggc aggaagaggg cctatttccc atgattcctt catatttgca tatacgatac     60
aaggctgtta gagagataat tagaattaat ttgactgtaa acacaaagat attagtacaa    120
aatacgtgac gtagaaagta ataatttctt gggtagtttg cagttttaaa attatgtttt    180
aaaatggact atcatatgct taccgtaact tgaaagtatt tcgatttctt ggctttatat    240
atcttgtgga aaggacgaaa cacctccaca tgcccagttt ctatgtttta gagctagaaa    300
tagcaagtta aaataaggct agtccgttat caacttgaaa aagtggcacc gagtcggtgc    360 ttttttttaag cttgggccgc tcgagcgcgt taacgggccc agcttcgata aaataaaaga   420
ttttatttag tctccagaaa aaggggggaa tgaaagaccc cacctgtagg tttggcaagc    480
tagcttaagt aacgccattt tgcaaggcat ggaaaataca taactgagaa tagagaagtt    540
cagatcaagg ttaggaacag agagacagca gaatatgggc caaacaggat atctgtggta    600
agcagttcct gccccggctc agggccaaga acagatggtc cccagatgcg gtcccgccct    660
cagcagtttc tagagaacca tcagatgttt ccagggtgcc ccaaggacct gaaaatgacc    720
ctgtgcctta tttgaactaa ccaatcagtt cgcttctcgc ttctgttcgc gcgcttctgc    780
tccccgagct caataaaaga gcccacaacc cctcactcgg cgcgccagtc ctccgataga    840
ctgccggtgc caccatggac tataaggacc acgacggaga ctacaaggat catgatattg    900
attacaaaga cgatgacgat aagatggccc caaagaagaa gcggaaggtc ggtatccacg    960
gagtcccagc agccgacaag aagtacagca tcggcctgga catcggcacc aactctgtgg   1020
gctgggccgt gatcaccgac gagtacaagg tgcccagcaa gaaattcaag gtgctgggca   1080
acaccgaccg gcacagcatc aagaagaacc tgatcggagc cctgctgttc gacagcggcg   1140
aaacagccga ggccacccgg ctgaagagaa ccgccagaag aagatacacc agacggaaga   1200
```

| | |
|---|---|
| accggatctg ctatctgcaa gagatcttca gcaacgagat ggccaaggtg gacgacagct | 1260 |
| tcttccacag actggaagag tccttcctgg tggaagagga taagaagcac gagcggcacc | 1320 |
| ccatcttcgg caacatcgtg gacgaggtgg cctaccacga gaagtacccc accatctacc | 1380 |
| acctgagaaa gaaactggtg gacagcaccg acaaggccga cctgcggctg atctatctgg | 1440 |
| ccctggccca catgatcaag ttccggggcc acttcctgat cgagggcgac ctgaaccccg | 1500 |
| acaacagcga cgtggacaag ctgttcatcc agctggtgca gacctacaac cagctgttcg | 1560 |
| aggaaaaccc catcaacgcc agcggcgtgg acgccaaggc catcctgtct gccagactga | 1620 |
| gcaagagcag acggctggaa aatctgatcg cccagctgcc cggcgagaag aagaatggcc | 1680 |
| tgttcggaaa cctgattgcc ctgagcctgg gcctgacccc caacttcaag agcaacttcg | 1740 |
| acctggccga ggatgccaaa ctgcagctga gcaaggacac ctacgacgac gacctggaca | 1800 |
| acctgctggc ccagatcggc gaccagtacg ccgacctgtt tctggccgcc aagaacctgt | 1860 |
| ccgacgccat cctgctgagc gacatcctga gagtgaacac cgagatcacc aaggcccccc | 1920 |
| tgagcgcctc tatgatcaag agatacgacg agcaccacca ggacctgacc ctgctgaaag | 1980 |
| ctctcgtgcg gcagcagctg cctgagaagt acaaagagat tttcttcgac cagagcaaga | 2040 |
| acggctacgc cggctacatt gacggcggag ccagccagga gagttctac aagttcatca | 2100 |
| agcccatcct ggaaaagatg gacggcaccg aggaactgct cgtgaagctg aacagagagg | 2160 |
| acctgctgcg gaagcagcgg accttcgaca acggcagcat cccccaccag atccacctgg | 2220 |
| gagagctgca cgccattctg cggcggcagg aagattttta cccattcctg aaggacaacc | 2280 |
| gggaaaagat cgaaaagatc ctgaccttcc gcatccccta ctacgtgggc cctctggcca | 2340 |
| ggggaaacag cagattcgcc tggatgacca gaaagagcga ggaaaccatc accccctgga | 2400 |
| acttcgagga agtggtggac aagggcgctt ccgcccagag cttcatcgag cggatgacca | 2460 |
| acttcgataa gaacctgccc aacgagaagg tgctgcccaa gcacagcctg ctgtacgagt | 2520 |
| acttcaccgt gtataacgag ctgaccaaag tgaaatacgt gaccgaggga atgagaaagc | 2580 |
| ccgccttcct gagcggcgag cagaaaaagg ccatcgtgga cctgctgttc aagaccaacc | 2640 |
| ggaaagtgac cgtgaagcag ctgaaagagg actacttcaa gaaaatcgag tgcttcgact | 2700 |
| ccgtggaaat ctccggcgtg gaagatcggt tcaacgcctc cctgggcaca taccacgatc | 2760 |
| tgctgaaaat tatcaaggac aaggacttcc tggacaatga ggaaaacgag gacattctgg | 2820 |
| aagatatcgt gctgaccctg acactgtttg aggacagaga gatgatcgag gaacggctga | 2880 |
| aaacctatgc ccacctgttc gacgacaaag tgatgaagca gctgaagcgg cggagataca | 2940 |
| ccggctgggg caggctgagc cggaagctga tcaacggcat ccgggacaag cagtccggca | 3000 |
| agacaatcct ggatttcctg aagtccgacg gcttcgccaa cagaaacttc atgcagctga | 3060 |
| tccacgacga cagcctgacc tttaaagagg acatccagaa agcccaggtg tccggccagg | 3120 |
| gcgatagcct gcacgagcac attgccaatc tggccggcag ccccgccatt aagaagggca | 3180 |
| tcctgcagac agtgaaggtg gtggacgagc tcgtgaaagt gatgggccgg cacaagcccg | 3240 |
| agaacatcgt gatcgaaatg gccagagaga accagaccac ccagaaggga cagaagaaca | 3300 |
| gccgcgagag aatgaagcgg atcgaagagg gcatcaaaga gctgggcagc cagatcctga | 3360 |
| aagaacaccc cgtggaaaac acccagctgc agaacgagaa gctgtacctg tactacctgc | 3420 |
| agaatgggcg ggatatgtac gtggaccagg aactggacat caaccggctg tccgactacg | 3480 |
| atgtggacca tatcgtgcct cagagctttc tgaaggacga ctccatcgac aacaaggtgc | 3540 |
| tgaccagaag cgacaagaac cggggcaaga gcgacaacgt gccctccgaa gaggtcgtga | 3600 |

```
agaagatgaa gaactactgg cggcagctgc tgaacgccaa gctgattacc cagagaaagt    3660
tcgacaatct gaccaaggcc gagagaggcg gcctgagcga actggataag gccggcttca    3720
tcaagagaca gctggtggaa acccggcaga tcacaaagca cgtggcacag atcctggact    3780 cccgatgaa cactaagtac gacgagaatg acaagctgat ccgggaagtg aaagtgatca    3840
ccctgaagtc caagctggtg tccgatttcc ggaaggattt ccagttttac aaagtgcgcg    3900
agatcaacaa ctaccaccac gcccacgacg cctacctgaa cgccgtcgtg ggaaccgccc    3960
tgatcaaaaa gtaccctaag ctggaaagcg agttcgtgta cggcgactac aaggtgtacg    4020
acgtgcggaa gatgatcgcc aagagcgagc aggaaatcgg caaggctacc gccaagtact    4080
tcttctacag caacatcatg aacttttca gaccgagat taccctggcc aacggcgaga    4140
tccggaagcg gcctctgatc gagacaaacg gcgaaaccgg ggagatcgtg tgggataagg    4200
gccgggattt tgccaccgtg cggaaagtgc tgagcatgcc ccaagtgaat atcgtgaaaa    4260
agaccgaggt gcagacaggc ggcttcagca agagtctat cctgcccaag aggaacagcg    4320
ataagctgat cgccagaaag aaggactggg accctaagaa gtacggcggc ttcgacagcc    4380
ccaccgtggc ctattctgtg ctggtggtgg ccaaagtgga aaaggcaag tccaagaaac    4440 tgaagagtgt gaaagagctg ctggggatca ccatcatgga agaagcagc ttcgagaaga    4500 atcccatcga ctttctggaa gccaagggct acaaagaagt gaaaaaggac ctgatcatca    4560
agctgcctaa gtactccctg ttcgagctgg aaaacggccg gaagagaatg ctggcctctg    4620
ccggcgaact gcagaaggga acgaactgg ccctgccctc caaatatgtg aacttcctgt    4680
acctggccag ccactatgag aagctgaagg gctccccga ggataatgag cagaaacagc    4740 tgttgtgga acagcacaag cactacctgg acgagatcat cgagcagatc agcgagttct    4800
ccaagagagt gatcctggcc gacgctaatc tggacaaagt gctgtccgcc tacaacaagc    4860
accgggataa gcccatcaga gagcaggccg agaatatcat ccacctgttt accctgacca    4920
atctgggagc ccctgccgcc ttcaagtact ttgacaccac catcgaccgg aagaggtaca    4980
ccagcaccaa agaggtgctg gacgccaccc tgatccacca gagcatcacc ggcctgtacg    5040
agacacggat cgacctgtct cagctgggag gcgacaaaag gccggcggcc acgaaaaagg    5100
ccggccaggc aaaaaagaaa aagtaa    5126
```

<210> SEQ ID NO 23
<211> LENGTH: 5126
<212> TYPE: DNA
<213> ORGANISM: Artificial Sequence
<220> FEATURE:
<223> OTHER INFORMATION: Synthetic

<400> SEQUENCE: 23

```
aaggtcgggc aggaagaggg cctatttccc atgattcctt catatttgca tatacgatac      60
aaggctgtta gagagataat tagaattaat ttgactgtaa acacaaagat attagtacaa     120
aatacgtgac gtagaaagta ataatttctt gggtagtttg cagttttaaa attatgtttt     180
aaaatggact atcatatgct taccgtaact tgaaagtatt tcgatttctt ggctttatat     240
atcttgtgga aggacgaaa caccaccaat agaaactggg catggtttta gagctagaaa     300
tagcaagtta aaataaggct agtccgttat caacttgaaa aagtggcacc gagtcggtgc     360 ttttttaag cttgggccgc tcgagcgcgt taacggccc agcttcgata aaataaaaga     420
ttttatttag tctccagaaa aaggggggaa tgaaagaccc cacctgtagg tttggcaagc     480
```

```
tagcttaagt aacgccattt tgcaaggcat ggaaaataca taactgagaa tagagaagtt      540
cagatcaagg ttaggaacag agagacagca gaatatgggc caaacaggat atctgtggta      600
agcagttcct gccccggctc agggccaaga acagatggtc cccagatgcg gtcccgccct      660
cagcagtttc tagagaacca tcagatgttt ccagggtgcc caaggacct gaaaatgacc       720 ctgtgcctta tttgaactaa ccaatcagtt cgcttctcgc ttctgttcgc gcgcttctgc      780
tccccgagct caataaaaga gcccacaacc cctcactcgg cgcgccagtc tccgataga       840 ctgccggtgc caccatggac tataaggacc acgacggaga ctacaaggat catgatattg      900
attacaaaga cgatgacgat aagatggccc caaagaagaa gcggaaggtc ggtatccacg      960
gagtcccagc agccgacaag aagtacagca tcggcctgga catcggcacc aactctgtgg     1020
gctgggccgt gatcaccgac gagtacaagg tgcccagcaa gaaattcaag gtgctgggca     1080
acaccgaccg gcacagcatc aagaagaacc tgatcggagc cctgctgttc gacagcggcg     1140
aaacagccga ggccacccgg ctgaagagaa ccgccagaag aagatacacc agacggaaga     1200
accggatctg ctatctgcaa gagatcttca gcaacgagtg gccaaggtg gacgacagct      1260 tcttccacag actggaagag tccttcctgg tggaagagga taagaagcac gagcggcacc     1320
ccatcttcgg caacatcgtg gacgaggtgg cctaccacga gaagtacccc accatctacc     1380
acctgagaaa gaaactggtg gacagcaccg acaaggccga cctgcggctg atctatctgg     1440
ccctggccca tatgatcaag ttccggggcc acttcctgat cgaggcgac ctgaaccccg       1500 acaacagcga cgtggacaag ctgttcatcc agctggtgca gacctacaac cagctgttcg     1560
aggaaacccc catcaacgcc agcggcgtgg acgccaaggc catcctgtct gccagactga     1620
gcaagagcag acggctggaa atctgatcg cccagctgcc cggcgagaag aagaatggcc       1680
tgttcggaaa cctgattgcc ctgagcctgg gcctgacccc caacttcaag agcaacttcg     1740
acctggccga ggatgccaaa ctgcagctga gcaaggacac ctacgacgac gacctggaca     1800
acctgctggc ccagatcggc gaccagtacg ccgacctgtt tctggccgcc aagaacctgt     1860
ccgacgccat cctgctgagc gacatcctga gagtgaacac cgagatcacc aaggcccccc     1920
tgagcgcctc tatgatcaag agatacgacg agcaccacca ggacctgacc ctgctgaaag     1980
ctctcgtgcg gcagcagctg cctgagaagt acaaagagat tttcttcgac cagagcaaga     2040
acggctacgc cggctacatt gacggcggag ccagccagga gagttctac aagttcatca       2100 agcccatcct ggaaaagatg gacggcaccg aggaactgct cgtgaagctg aacagagagg     2160
acctgctgcg gaagcagcgg accttcgaca acggcagcat cccccaccag atccacctgg     2220
gagagctgca cgccattctg cggcggcagg aagattttta cccattcctg aaggacaacc     2280
gggaaaagat cgagaagatc ctgacctttc gcatccccta ctacgtgggc cctctggcca     2340
ggggaaacag cagattcgcc tggatgacca gaaagagcga ggaaaccatc acccctgga      2400 acttcgagga agtggtggac aagggcgctt ccgcccagag cttcatcgag cggatgacca     2460
acttcgataa gaacctgccc aacgagaagg tgctgcccaa gcacagcctg ctgtacgagt     2520
acttcaccgt gtataacgag ctgaccaaag tgaaatacgt gaccgaggga atgagaaagc     2580
ccgccttcct gagcggcgag cagaaaaagg ccatcgtgga cctgctgttc aagaccaacc     2640
ggaaagtgac cgtgaagcag ctgaaagagg actacttcaa gaaaatcgag tgcttcgact     2700
ccgtggaaat ctccggcgtg gaagatcggt tcaacgcctc cctgggcaca taccacgatc     2760
tgctgaaaat tatcaaggac aaggacttcc tggacaatga ggaaaacgag gacattctgg     2820
aagatatcgt gctgaccctg acactgtttg aggacagaga gatgatcgag aacggctga      2880
```

```
aaacctatgc ccacctgttc gacgacaaag tgatgaagca gctgaagcgg cggagataca      2940
ccggctgggg caggctgagc cggaagctga tcaacggcat ccgggacaag cagtccggca      3000
agacaatcct ggatttcctg aagtccgacg gcttcgccaa cagaaacttc atgcagctga      3060
tccacgacga cagcctgacc tttaaagagg acatccagaa agcccaggtg tccggccagg      3120
gcgatagcct gcacgagcac attgccaatc tggccggcag ccccgccatt aagaagggca      3180
tcctgcagac agtgaaggtg gtggacgagc tcgtgaaagt gatgggccgg cacaagcccg      3240
agaacatcgt gatcgaaatg gccagagaga accagaccac ccagaaggga cagaagaaca      3300
gccgcgagag aatgaagcgg atcgaagagg gcatcaaaga gctgggcagc cagatcctga      3360
aggaacaccc cgtggaaaac acccagctgc agaacgagaa gctgtacctg tactacctgc      3420
agaatgggcg ggatatgtac gtggaccagg aactggacat caaccggctg tccgactacg      3480
atgtggacca tatcgtgcct cagagctttc tgaaggacga ctccatcgac aacaaggtgc      3540
tgaccagaag cgacaagaac cggggcaaga gcgacaacgt gcccctccga agggtcgtga      3600
agaagatgaa gaactactgg cggcagctgc tgaacgccaa gctgattacc cagagaaagt      3660
tcgacaatct gaccaaggcc gagagaggcg gcctgagcga actggataag gccggcttca      3720
tcaagagaca gctggtggaa acccggcaga tcacaaagca cgtggcacag atcctggact      3780
cccggatgaa cactaagtac gacgagaatg acaagctgat ccgggaagtg aaagtgatca      3840
ccctgaagtc caagctggtg tccgatttcc ggaaggattt ccagttttac aaagtgcgcg      3900
agatcaacaa ctaccaccac gcccacgacg cctacctgaa cgccgtcgtg ggaaccgccc      3960
tgatcaaaaa gtaccctaag ctggaaagcg agttcgtgta cggcgactac aaggtgtacg      4020
acgtgcggaa gatgatcgcc aagagcgagc aggaaatcgg caaggctacc gccaagtact      4080
tcttctacag caacatcatg aacttttttca agaccgagat taccctggcc aacggcgaga      4140
tccggaagcg gcctctgatc gagacaaacg gcgaaaccgg ggagatcgtg tgggataagg      4200
gccgggattt tgccaccgtg cggaaagtgc tgagcatgcc ccaagtgaat atcgtgaaaa      4260
agaccgaggt gcagacaggc ggcttcagca aagagtctat cctgcccaag aggaacagcg      4320
ataagctgat cgccagaaag aaggactggg accctaagaa gtacggcggc ttcgacagcc      4380
ccaccgtggc ctattctgtg ctggtggtgg ccaaagtgga aaagggcaag tccaagaaac      4440
tgaagagtgt gaaagagctg ctgggggatca ccatcatgga aagaagcagc ttcgagaaga      4500
atcccatcga ctttctggaa gccaagggct acaaagaagt gaaaaaggac ctgatcatca      4560
agctgcctaa gtactccctg ttcgagctgg aaaacggccg gaagagaatg ctggcctctg      4620
ccggcgaact gcagaaggga aacgaactgg ccctgccctc caaatatgtg aacttcctgt      4680
acctggccag ccactatgag aagctgaagg gctcccccga ggataatgag cagaaacagc      4740
tgtttgtgga acagcacaag cactacctgg acgagatcat cgagcagatc agcgagttct      4800
ccaagagagt gatcctggcc gacgctaatc tggacaaagt gctgtccgcc tacaacaagc      4860
accgggataa gcccatcaga gagcaggccg agaatatcat ccacctgttt accctgacca      4920
atctgggagc ccctgccgcc ttcaagtact ttgacaccac catcgaccgg aagaggtaca      4980
ccagcaccaa agaggtgctg gacgccaccc tgatccacca gagcatcacc ggcctgtacg      5040
agacacggat cgacctgtct cagctgggag gcgacaaaag gccggcggcc acgaaaaagg      5100
ccggccaggc aaaaaagaaa aagtaa                                          5126
```

<210> SEQ ID NO 24

<211> LENGTH: 5127
<212> TYPE: DNA
<213> ORGANISM: Artificial Sequence
<220> FEATURE:
<223> OTHER INFORMATION: Synthetic

<400> SEQUENCE: 24

| | | | | | |
|---|---|---|---|---|---|
| aaggtcgggc | aggaagaggg | cctatttccc | atgattcctt | catatttgca | tatacgatac | 60 |
| aaggctgtta | gagagataat | tagaattaat | ttgactgtaa | acacaaagat | attagtacaa | 120 |
| aatacgtgac | gtagaaagta | ataatttctt | gggtagtttg | cagttttaaa | attatgtttt | 180 |
| aaaatggact | atcatatgct | taccgtaact | tgaaagtatt | tcgatttctt | ggctttatat | 240 |
| atcttgtgga | aaggacgaaa | caccgcttgc | cccacagggc | agtaagtttt | agagctagaa | 300 |
| atagcaagtt | aaaataaggc | tagtccgtta | tcaacttgaa | aaagtggcac | cgagtcggtg | 360 |
| cttttttta | gcttgggccg | ctcgagcgcg | ttaacgggcc | cagcttcgat | aaaataaaag | 420 |
| attttattta | gtctccagaa | aaggggggga | atgaaagacc | ccacctgtag | gtttggcaag | 480 |
| ctagcttaag | taacgccatt | ttgcaaggca | tggaaaatac | ataactgaga | atagagaagt | 540 |
| tcagatcaag | gttaggaaca | gagagacagc | agaatatggg | ccaaacagga | tatctgtggt | 600 |
| aagcagttcc | tgccccggct | cagggccaag | aacagatggt | ccccagatgc | ggtcccgccc | 660 |
| tcagcagttt | ctagagaacc | atcagatgtt | tccagggtgc | cccaaggacc | tgaaaatgac | 720 |
| cctgtgcctt | atttgaacta | accaatcagt | tcgcttctcg | cttctgttcg | cgcgcttctg | 780 |
| ctccccgagc | tcaataaaag | agcccacaac | ccctcactcg | gcgcgccagt | cctccgatag | 840 |
| actgccggtg | ccaccatgga | ctataaggac | cacgacggag | actacaagga | tcatgatatt | 900 |
| gattacaaag | acgatgacga | taagatggcc | ccaaagaaga | agcggaaggt | cggtatccac | 960 |
| ggagtcccag | cagccgacaa | gaagtacagc | atcggcctgg | acatcggcac | caactctgtg | 1020 |
| ggctgggccg | tgatcaccga | cgagtacaag | gtgcccagca | gaaaattcaa | ggtgctgggc | 1080 |
| aacaccgacc | ggcacagcat | caagaagaac | ctgatcggag | ccctgctgtt | cgacagcggc | 1140 |
| gaaacagccg | aggccacccg | gctgaagaga | accgccagaa | gaagatacac | cagacggaag | 1200 |
| aaccggatct | gctatctgca | agagatcttc | agcaacgaga | tggccaaggt | ggacgacagc | 1260 |
| ttcttccaca | gactggaaga | gtccttcctg | gtggaagagg | ataagaagca | cgagcggcac | 1320 |
| cccatcttcg | gcaacatcgt | ggacgaggtg | gcctaccacg | agaagtaccc | caccatctac | 1380 |
| cacctgagaa | agaaactggt | ggacagcacc | gacaaggccg | acctgcggct | gatctatctg | 1440 |
| gccctggccc | acatgatcaa | gttccggggc | cacttcctga | tcgagggcga | cctgaacccc | 1500 |
| gacaacagcg | acgtggacaa | gctgttcatc | cagctggtgc | agacctacaa | ccagctgttc | 1560 |
| gaggaaaacc | ccatcaacgc | cagcggcgtg | gacgccaagg | ccatcctgtc | tgccagactg | 1620 |
| agcaagagca | gacggctgga | aaatctgatc | gcccagctgc | ccggcgagaa | gaagaatggc | 1680 |
| ctgttcggaa | acctgattgc | cctgagcctg | ggcctgaccc | caacttcaa | gagcaacttc | 1740 |
| gacctggccg | aggatgccaa | actgcagctg | agcaaggaca | cctacgacga | cgacctggac | 1800 |
| aacctgctgg | cccagatcgg | cgaccagtac | gccgacctgt | ttctggccgc | caagaacctg | 1860 |
| tccgacgcca | tcctgctgag | cgacatcctg | agagtgaaca | ccgagatcac | caaggccccc | 1920 |
| ctgagcgcct | ctatgatcaa | gagatacgac | gagcaccacc | aggacctgac | cctgctgaaa | 1980 |
| gctctcgtgc | ggcagcagct | gcctgagaag | tacaaagaga | ttttcttcga | ccagagcaag | 2040 |
| aacggctacg | ccggctacat | tgacggcgga | gccagccagg | aagagttcta | caagttcatc | 2100 |
| aagcccatcc | tggaaaagat | ggacggcacc | gaggaactgc | tcgtgaagct | gaacagagag | 2160 |

```
gacctgctgc ggaagcagcg gaccttcgac aacggcagca tccccacca gatccacctg   2220
ggagagctgc acgccattct gcggcggcag gaagattttt acccattcct gaaggacaac   2280
cgggaaaaga tcgagaagat cctgaccttc cgcatcccct actacgtggg ccctctggcc   2340
aggggaaaca gcagattcgc ctggatgacc agaaagagcg aggaaaccat cacccctgg    2400
aacttcgagg aagtggtgga caagggcgct tccgcccaga gcttcatcga gcggatgacc   2460
aacttcgata gaacctgcc caacgagaag gtgctgccca gcacagcct gctgtacgag     2520
tacttcaccg tgtataacga gctgaccaaa gtgaaatacg tgaccgaggg aatgagaaag   2580
cccgccttcc tgagcggcga gcagaaaaag gccatcgtgg acctgctgtt caagaccaac   2640
cggaaagtga ccgtgaagca gctgaaagag gactacttca gaaaatcga gtgcttcgac   2700
tccgtggaaa tctccggcgt ggaagatcgg ttcaacgcct ccctgggcac ataccacgat   2760
ctgctgaaaa ttatcaagga caaggacttc ctggacaatg aggaaaacga ggacattctg   2820
gaagatatcg tgctgacccc gacactgttt gaggacagag agatgatcga ggaacggctg   2880
aaaacctatg cccacctgtt cgacgacaaa gtgatgaagc agctgaagcg cggagatac    2940
accggctggg gcaggctgag ccggaagctg atcaacggca tccggacaa gcagtccggc    3000
aagacaatcc tggatttcct gaagtccgac ggcttcgcca cagaaactt catgcagctg    3060
atccacgacg acagcctgac ctttaaagag gacatccaga agcccaggt gtccggccag    3120
ggcgatagcc tgcacgagca cattgccaat ctggccggca gccccgccat taagaagggc   3180
atcctgcaga cagtgaaggt ggtggacgag ctcgtgaaag tgatgggccg gcacaagccc   3240
gagaacatcg tgatcgaaat ggccagagag aaccagacca cccagaaggg acagaagaac   3300
agccgcgaga gaatgaagcg gatcgaagag ggcatcaaag agctgggcag ccagatcctg   3360
aaagaacacc ccgtggaaaa cacccagctg cagaacgaga agctgtacct gtactacctg   3420
cagaatgggc gggatatgta cgtggaccag gaactggaca tcaaccggct gtccgactac   3480
gatgtggacc atatcgtgcc tcagagcttt ctgaaggacg actccatcga caacaaggtg   3540
ctgaccagaa gcgacaagaa ccggggcaag agcgacaacg tgccctccga agaggtcgtg   3600
aagaagatga aaaactactg gcggcagctg ctgaacgcca gctgattac ccagagaaag   3660
ttcgacaatc tgaccaaggc cgagagaggc ggcctgagcg aactggataa ggccggcttc   3720
atcaagagac agctggtgga aacccggcag atcacaaagc acgtggcaca gatcctggac   3780
tcccggatga acactaagta cgacgagaat gacaagctga tccgggaagt gaaagtgatc   3840
accctgaagt ccaagctggt gtccgatttc cggaaggatt tccagttta caaagtgcgc   3900
gagatcaaca actaccacca cgcccacgac gcctacctga acgccgtcgt gggaaccgcc   3960
ctgatcaaaa agtaccctaa gctggaaagc gagttcgtgt acggcgacta caaggtgtac   4020
gacgtgcgga agatgatcgc caagagcgag caggaaatcg gcaaggctac cgccaagtac   4080
ttcttctaca gcaacatcat gaactttttc aagaccgaga ttaccctggc caacggcgag   4140
atccggaagc ggcctctgat cgagacaaac ggcgaaaccg gggagatcgt gtgggataag   4200
ggccgggatt ttgccaccgt gcggaaagtg ctgagcatgc cccaagtgaa tatcgtgaaa   4260
aagaccgagg tgcagacagg cggcttcagc aaagagtcta tcctgcccaa gaggaacagc   4320
gataagctga tcgccagaaa gaaggactgg gaccctaaga gtacggcgg cttcgacagc   4380
cccaccgtgg cctattctgt gctggtggtg gccaaagtgg aaagggcaa gtccaagaaa   4440
ctgaagagtg tgaaagagct gctggggatc accatcatgg aaagaagcag cttcgagaag   4500
```

| | |
|---|---|
| aatcccatcg actttctgga agccaagggc tacaagaag tgaaaaagga cctgatcatc | 4560 |
| aagctgccta agtactccct gttcgagctg aaaacggcc ggaagagaat gctggcctct | 4620 |
| gccggcgaac tgcagaaggg aaacgaactg cccctgccct ccaaatatgt gaacttcctg | 4680 |
| tacctggcca gccactatga aagctgaag ggctcccccg aggataatga gcagaaacag | 4740 |
| ctgtttgtgg aacagcacaa gcactacctg gacgagatca tcgagcagat cagcgagttc | 4800 |
| tccaagagag tgatcctggc cgacgctaat ctggacaaag tgctgtccgc ctacaacaag | 4860 |
| caccgggata gcccatcag agagcaggcc gagaatatca tccacctgtt taccctgacc | 4920 |
| aatctgggag cccctgccgc cttcaagtac tttgacacca ccatcgaccg gaagaggtac | 4980 |
| accagcacca aagaggtgct ggacgccacc ctgatccacc agagcatcac cggcctgtac | 5040 |
| gagacacgga tcgacctgtc tcagctggga ggcgacaaaa ggccggcggc cacgaaaaag | 5100 |
| gccggccagg caaaaaagaa aaagtaa | 5127 |

<210> SEQ ID NO 25
<211> LENGTH: 5127
<212> TYPE: DNA
<213> ORGANISM: Artificial Sequence
<220> FEATURE:
<223> OTHER INFORMATION: Synthetic

<400> SEQUENCE: 25

| | |
|---|---|
| aaggtcgggc aggaagaggg cctatttccc atgattcctt catatttgca tatacgatac | 60 |
| aaggctgtta gagagataat tagaattaat ttgactgtaa acacaaagat attagtacaa | 120 |
| aatacgtgac gtagaaagta ataatttctt gggtagtttg cagttttaaa attatgtttt | 180 |
| aaaatggact atcatatgct taccgtaact tgaaagtatt tcgatttctt gctttatat | 240 |
| atcttgtgga aaggacgaaa caccgtccac atgcccagtt tctatgtttt agagctagaa | 300 |
| atagcaagtt aaaataaggc tagtccgtta tcaacttgaa aaagtggcac cgagtcggtg | 360 |
| cttttttaa gcttgggccg ctcgagcgcg ttaacgggcc cagcttcgat aaaataaaag | 420 |
| atttttattta gtctccagaa aaggggggga atgaaagacc ccacctgtag gtttggcaag | 480 |
| ctagcttaag taacgccatt ttgcaaggca tggaaaatac ataactgaga atagagaagt | 540 |
| tcagatcaag gttaggaaca gagagacagc agaatatggg ccaaacagga tatctgtggt | 600 |
| aagcagttcc tgccccggct cagggccaag aacagatggt ccccagatgc ggtcccgccc | 660 |
| tcagcagttt ctagagaacc atcagatgtt tccagggtgc cccaaggacc tgaaaatgac | 720 |
| cctgtgcctt atttgaacta accaatcagt tcgcttctcg cttctgttcg cgcgcttctg | 780 |
| ctccccgagc tcaataaaag agcccacaac ccctcactcg gcgcgccagt cctccgatag | 840 |
| actgccggtg ccaccatgga ctataaggac cacgacggag actacaagga tcatgatatt | 900 |
| gattacaaag acgatgacga taagatggcc ccaaagaaga gcggaaggt cggtatccac | 960 |
| ggagtcccag cagccgacaa gaagtacagc atcggcctgg acatcggcac caactctgtg | 1020 |
| ggctgggccg tgatcaccga cgagtacaag gtgcccagca gaaaattcaa ggtgctgggc | 1080 |
| aacaccgacc ggcacagcat caagaagaac ctgatcggag ccctgctgtt cgacagcggc | 1140 |
| gaaacagccg aggccacccg gctgaagaga accgccagaa agatacac cagacggaag | 1200 |
| aaccggatct gctatctgca agagatcttc agcaacgaga tggccaaggt ggacgacagc | 1260 |
| ttcttccaca gactggaaga gtccttcctg gtggaagagg ataagaagca cgagcggcac | 1320 |
| cccatcttcg gcaacatcgt ggacgaggtg gcctaccacg agaagtaccc caccatctac | 1380 |
| cacctgagaa agaaactggt ggacagcacc gacaaggccg acctgcggct gatctatctg | 1440 |

-continued

```
gccctggccc acatgatcaa gttccggggc cacttcctga tcgagggcga cctgaacccc      1500
gacaacagcg acgtggacaa gctgttcatc cagctggtgc agacctacaa ccagctgttc      1560
gaggaaaacc ccatcaacgc cagcggcgtg gacgccaagg ccatcctgtc tgccagactg      1620
agcaagagca gacggctgga aaatctgatc gcccagctgc ccggcgagaa gaagaatggc      1680
ctgttcggaa acctgattgc cctgagcctg ggcctgaccc ccaacttcaa gagcaacttc      1740
gacctggccg aggatgccaa actgcagctg agcaaggaca cctacgacga cgacctggac      1800
aacctgctgg cccagatcgg cgaccagtac gccgacctgt ttctggccgc caagaacctg      1860
tccgacgcca tcctgctgag cgacatcctg agagtgaaca ccgagatcac caaggccccc      1920
ctgagcgcct ctatgatcaa gagatacgac gagcaccacc aggacctgac cctgctgaaa      1980
gctctcgtgc ggcagcagct gcctgagaag tacaaagaga ttttcttcga ccagagcaag      2040
aacggctacg ccggctacat tgacggcgga gccagccagg aagagttcta caagttcatc      2100
aagcccatcc tggaaaagat ggacggcacc gaggaactgc tcgtgaagct gaacagagag      2160
gacctgctgc ggaagcagcg gaccttcgac aacggcagca tcccccacca gatccacctg      2220
ggagagctgc acgccattct gcggcggcag gaagatttt acccattcct gaaggacaac      2280
cgggaaaaga tcgagaagat cctgaccttc cgcatcccct actacgtggg ccctctggcc      2340
aggggaaaca gcagattcgc ctggatgacc agaaagagcg aggaaaccat cacccctgg      2400 aacttcgagg aagtggtgga caagggcgct tccgcccaga gcttcatcga gcggatgacc      2460
aacttcgata agaacctgcc caacgagaag gtgctgccca gcacagcct gctgtacgag      2520 tacttcaccg tgtataacga gctgaccaaa gtgaaatacg tgaccgaggg aatgagaaag      2580
cccgccttcc tgagcggcga gcagaaaaag gccatcgtgg acctgctgtt caagaccaac      2640
cggaaagtga ccgtgaagca gctgaaagag gactacttca gaaaaatcga gtgcttcgac      2700
tccgtggaaa tctccggcgt ggaagatcgg ttcaacgcct ccctgggcac ataccacgat      2760
ctgctgaaaa ttatcaagga caaggacttc ctggacaatg aggaaaacga ggacattctg      2820
gaagatatcg tgctgaccct gacactgttt gaggacagag agatgatcga ggaacggctg      2880
aaaacctatg cccacctgtt cgacgacaaa gtgatgaagc agctgaagcg gcggagatac      2940
accggctggg gcaggctgag ccggaagctg atcaacggca tccgggacaa gcagtccggc      3000
aagacaatcc tggatttcct gaagtccgac ggcttcgcca acagaaactt catgcagctg      3060
atccacgacg acagcctgac ctttaaagag gacatccaga aagcccaggt gtccggccag      3120
ggcgatagcc tgcacgagca cattgccaat ctggccggca gccccgccat taagaagggc      3180
atcctgcaga cagtgaaggt ggtggacgag ctcgtgaaag tgatgggccg gcacaagccc      3240
gagaacatcg tgatcgaaat ggccagagag aaccagacca cccagaaggg acagaagaac      3300
agccgcgaga gaatgaagcg gatcgaagag ggcatcaaag agctgggcag ccagatcctg      3360
aaagaacacc ccgtggaaaa cacccagctg cagaacgaga gctgtacct gtactacctg      3420 cagaatgggc gggatatgta cgtggaccag gaactggaca tcaaccggct gtccgactac      3480
gatgtggacc atatcgtgcc tcagagcttt ctgaaggacg actccatcga caacaaggtg      3540
ctgaccagaa gcgacaagaa ccggggcaag agcgacaacg tgccctccga agaggtcgtg      3600
aagaagatga aaaactactg gcggcagctg ctgaacgcca agctgattac ccagagaaag      3660
ttcgacaatc tgaccaaggc cgagagaggc ggcctgagcg aactggataa ggccggcttc      3720
atcaagagac agctggtgga aacccggcag atcacaaagc acgtggcaca gatcctggac      3780
```

```
tcccggatga acactaagta cgacgagaat gacaagctga tccgggaagt gaaagtgatc    3840
accctgaagt ccaagctggt gtccgatttc cggaaggatt ccagttttta caaagtgcgc    3900
gagatcaaca actaccacca cgcccacgac gcctacctga acgccgtcgt gggaaccgcc    3960
ctgatcaaaa agtaccctaa gctggaaagc gagttcgtgt acggcgacta caaggtgtac    4020
gacgtgcgga agatgatcgc caagagcgag caggaaatcg gcaaggctac cgccaagtac    4080
ttcttctaca gcaacatcat gaactttttc aagaccgaga ttaccctggc caacggcgag    4140
atccggaagc ggcctctgat cgagacaaac ggcgaaaccg gggagatcgt gtgggataag    4200
ggccgggatt ttgccaccgt gcggaaagtg ctgagcatgc ccaagtgaa tatcgtgaaa    4260
aagaccgagg tgcagacagg cggcttcagc aaagagtcta tcctgcccaa gaggaacagc    4320
gataagctga tcgccagaaa gaaggactgg gaccctaaga gtacggcgg cttcgacagc    4380
cccaccgtgg cctattctgt gctggtggtg gccaaagtgg aaaagggcaa gtccaagaaa    4440
ctgaagagtg tgaaagagct gctggggatc accatcatgg aaagaagcag cttcgagaag    4500
aatcccatcg actttctgga agccaagggc tacaagaag tgaaaaagga cctgatcatc    4560
aagctgccta gtactccct gttcgagctg aaaacggcc ggaagagaat gctggcctct    4620
gccggcgaac tgcagaaggg aaacgaactg gccctgccct ccaaatatgt gaacttcctg    4680
tacctggcca gccactatga aagctgaag gctcccccg aggataatga gcagaaacag    4740
ctgtttgtgg aacagcacaa gcactacctg gacgagatca tcgagcagat cagcgagttc    4800
tccaagagag tgatcctggc cgacgctaat ctggacaaag tgctgtccgc ctacaacaag    4860
caccgggata agcccatcag agagcaggcc gagaatatca tccacctgtt taccctgacc    4920
aatctgggag ccctgccgc cttcaagtac tttgacacca ccatcgaccg gaagaggtac    4980
accagcacca agaggtgct ggacgccacc ctgatccacc agagcatcac cggcctgtac    5040
gagacacgga tcgacctgtc tcagctggga ggcgacaaaa ggccggcggc cacgaaaaag    5100
gccggccagg caaaaaagaa aaagtaa                                        5127
```

<210> SEQ ID NO 26
<211> LENGTH: 5127
<212> TYPE: DNA
<213> ORGANISM: Artificial Sequence
<220> FEATURE:
<223> OTHER INFORMATION: Synthetic

<400> SEQUENCE: 26

```
aaggtcgggc aggaagaggg cctatttccc atgattcctt catatttgca tatacgatac      60
aaggctgtta gagagataat tagaattaat ttgactgtaa acacaaagat attagtacaa     120
aatacgtgac gtagaaagta ataatttctt gggtagtttg cagttttaaa attatgtttt     180
aaaatggact atcatatgct taccgtaact tgaaagtatt tcgatttctt ggctttatat     240
atcttgtgga aggacgaaa caccgaccaa tagaaactgg gcatggtttt agagctagaa     300
atagcaagtt aaaataaggc tagtccgtta tcaacttgaa aaagtggcac cgagtcggtg     360
ctttttttaa gcttgggccg ctcgagcgcg ttaacgggcc cagcttcgat aaaataaaag     420
attttattta gtctccagaa aaaggggggga atgaaagacc ccacctgtag gtttggcaag     480
ctagcttaag taacgccatt ttgcaaggca tggaaaatac ataactgaga atagagaagt     540
tcagatcaag gttaggaaca gagagacagc agaatatggg ccaaacagga tatctgtggt     600
aagcagttcc tgccccggct cagggccaag aacagatggt cccagatgc ggtcccgccc     660
tcagcagttt ctagagaacc atcagatgtt tccagggtgc cccaaggacc tgaaaatgac     720
```

```
cctgtgcctt atttgaacta accaatcagt tcgcttctcg cttctgttcg cgcgcttctg    780
ctccccgagc tcaataaaag agcccacaac ccctcactcg gcgcgccagt cctccgatag    840
actgccggtg ccaccatgga ctataaggac cacgacggag actacaagga tcatgatatt    900
gattacaaag acgatgacga taagatggcc caaagaagaa gcggaaggt cggtatccac    960
ggagtcccag cagccgacaa gaagtacagc atcggcctgg acatcggcac caactctgtg   1020
ggctgggccg tgatcaccga cgagtacaag gtgcccagca gaaaattcaa ggtgctgggc   1080
aacaccgacc ggcacagcat caagaagaac ctgatcggag ccctgctgtt cgacagcggc   1140
gaaacagccg aggccacccg gctgaagaga accgccagaa gaagatacac cagacggaag   1200
aaccggatct gctatctgca agagatcttc agcaacgaga tggccaaggt ggacgacagc   1260
ttcttccaca gactggaaga gtccttcctg gtggaagagg ataagaagca cgagcggcac   1320
cccatcttcg gcaacatcgt ggacgaggtg gcctaccacg agaagtaccc caccatctac   1380
cacctgagaa agaaactggt ggacagcacc gacaaggccg acctgcggct gatctatctg   1440
gccctggccc acatgatcaa gttccggggc cacttcctga tcgagggcga cctgaacccc   1500
gacaacagcg acgtggacaa gctgttcatc cagctggtgc agacctacaa ccagctgttc   1560
gaggaaaacc ccatcaacgc cagcggcgtg gacgccaagg ccatcctgtc tgccagactg   1620
agcaagagca cggctggaa aaatctgatc gcccagctgc ccggcgagaa gaagaatggc   1680
ctgttcggaa acctgattgc cctgagcctg ggcctgaccc ccaacttcaa gagcaacttc   1740
gacctggccg aggatgccaa actgcagctg agcaaggaca cctacgacga cgacctggac   1800
aacctgctgg cccagatcgg cgaccagtac gccgacctgt ttctggccgc caagaacctg   1860
tccgacgcca tcctgctgag cgacatcctg agagtgaaca ccgagatcac caaggccccc   1920
ctgagcgcct ctatgatcaa gagatacgac gagcaccacc aggacctgac cctgctgaaa   1980
gctctcgtgc ggcagcagct gcctgagaag tacaaagaga ttttcttcga ccagagcaag   2040
aacggctacg ccggctacat tgacggcgga gccagccagg aagagttcta caagttcatc   2100
aagcccatcc tggaaaagat ggacggcacc gaggaactgc tcgtgaagct gaacagagag   2160
gacctgctgc ggaagcagcg gaccttcgac aacggcagca tcccccacca gatccacctg   2220
ggagagctgc acgccattct gcggcggcag gaagattttt acccattcct gaaggacaac   2280
cgggaaaaga tcgagaagat cctgaccttc cgcatcccct actacgtggg ccctctggcc   2340
aggggaaaca gcagattcgc ctggatgacc agaaagagcg aggaaaccat cacccctgg   2400
aacttcgagg aagtggtgga caagggcgct tccgcccaga gcttcatcga gcggatgacc   2460
aacttcgata agaacctgcc caacgagaag gtgctgccca gcacagcct gctgtacgag   2520
tacttcaccg tgtataacga gctgaccaaa gtgaaatacg tgaccgaggg aatgagaaag   2580
cccgccttcc tgagcggcga gcagaaaaag gccatcgtgg acctgctgtt caagaccaac   2640
cggaaagtga ccgtgaagca gctgaaagag gactacttca gaaaatcga gtgcttcgac   2700
tccgtggaaa tctccggcgt ggaagatcgg ttcaacgcct ccctgggcac ataccacgat   2760
ctgctgaaaa ttatcaagga caaggacttc ctggacaatg aggaaaacga ggacattctg   2820
gaagatatcg tgctgaccct gacactgttt gaggacagag agatgatcga ggaacggctc   2880
aaaacctatg cccacctgtt cgacgacaaa gtgatgaagc agctgaagcg gcggagatac   2940
accggctggg gcaggctgag ccggaagctg atcaacggca tccggacaa gcagtccggc   3000
aagacaatcc tggatttcct gaagtccgac ggcttcgcca acagaaactt catgcagctg   3060
```

```
atccacgacg acagcctgac ctttaaagag gacatccaga aagcccaggt gtccggccag    3120
ggcgatagcc tgcacgagca cattgccaat ctggccggca gccccgccat taagaagggc    3180
atcctgcaga cagtgaaggt ggtggacgag ctcgtgaaag tgatgggccg gcacaagccc    3240
gagaacatcg tgatcgaaat ggccagagag aaccagacca cccagaaggg acagaagaac    3300
agccgcgaga gaatgaagcg gatcgaagag ggcatcaaag agctgggcag ccagatcctg    3360
aaagaacacc ccgtggaaaa cacccagctg cagaacgaga gctgtacct gtactacctg    3420
cagaatgggc gggatatgta cgtggaccag gaactggaca tcaaccggct gtccgactac    3480
gatgtggacc atatcgtgcc tcagagcttt ctgaaggacg actccatcga caacaaggtg    3540
ctgaccagaa gcgacaagaa ccggggcaag agcgacaacg tgccctccga agaggtcgtg    3600
aagaagatga gaactactg gcggcagctg ctgaacgcca agctgattac ccagagaaag    3660
ttcgacaatc tgaccaaggc cgagagaggc ggcctgagcg aactggataa ggccggcttc    3720
atcaagagac agctggtgga aacccggcag atcacaaagc acgtggcaca gatcctggac    3780
tcccggatga acactaagta cgacgagaat gacaagctga tccgggaagt gaaagtgatc    3840
accctgaagt ccaagctggt gtccgatttc cggaaggatt tccagtttta caaagtgcgc    3900
gagatcaaca actaccacca cgcccacgac gcctacctga acgccgtcgt gggaaccgcc    3960
ctgatcaaaa agtaccctaa gctggaaagc gagttcgtgt acggcgacta caaggtgtac    4020
gacgtgcgga agatgatcgc caagagcgag caggaaatcg gcaaggctac cgccaagtac    4080
ttcttctaca gcaacatcat gaactttttc aagaccgaga ttaccctggc caacggcgag    4140
atccggaagc ggcctctgat cgagacaaac ggcgaaaccg gggagatcgt gtgggataag    4200
ggccgggatt ttgccaccgt gcggaaagtg ctgagcatgc ccaagtgaa tatcgtgaaa    4260
aagaccgagg tgcagacagg cggcttcagc aaagagtcta tcctgcccaa gaggaacagc    4320
gataagctga tcgccagaaa gaaggactgg gaccctaaga agtacggcgg cttcgacagc    4380
cccaccgtgg cctattctgt gctggtggtg gccaaagtgg aaaagggcaa gtccaagaaa    4440
ctgaagagtg tgaaagagct gctggggatc accatcatgg aaagaagcag cttcgagaag    4500
aatcccatcg actttctgga agccaagggc tacaaagaag tgaaaaagga cctgatcatc    4560
aagctgccta agtactccct gttcgagctg gaaaacggcc ggaagagaat gctggcctct    4620
gccggcgaac tgcagaaggg aaacgaactg gccctgccct ccaaatatgt gaacttcctg    4680
tacctggcca gccactatga aagctgaag gctcccccg aggataatga gcagaaacag    4740
ctgtttgtgg aacagcacaa gcactacctg gacgagatca tcgagcagat cagcgagttc    4800
tccaagagag tgatcctggc cgacgctaat ctggacaaag tgctgtccgc ctacaacaag    4860
caccgggata gcccatcag agagcaggcc gagaatatca tccacctgtt taccctgacc    4920
aatctgggag cccctgccgc cttcaagtac tttgacacca ccatcgaccg gaagaggtac    4980
accagcacca agaggtgct ggacgccacc ctgatccacc agagcatcac cggcctgtac    5040
gagacacgga tcgacctgtc tcagctggga ggcgacaaaa ggccggcggc cacgaaaaag    5100
gccggccagg caaaaaagaa aaagtaa                                        5127
```

<210> SEQ ID NO 27
<211> LENGTH: 3412
<212> TYPE: DNA
<213> ORGANISM: Artificial Sequence
<220> FEATURE:
<223> OTHER INFORMATION: Synthetic

<400> SEQUENCE: 27

```
gaattctttg ccaaagtgat gggccagcac acagaccagc acgttgccca ggagctgtgg      60
gaggaagata agaggtatga acatgattag caaaagggcc tagcttggac tcagaataat     120
ccagccttat cccaaccata aaataaaagc agaatggtag ctggattgta gctgctatta     180
gcaatatgaa acctcttaca tcagttacaa tttatatgca gaaatattta tatgcagaga     240
tattgctatt gccttaaccc agaaattatc actgttattc tttagaatgg tgcaaagagg     300
catgatacat tgtatcatta ttgccctgaa agaaagagat tagggaaagt attagaaata     360
agataaacaa aaaagtatat taaaagaaga aagcattttt taaaattaca aatgcaaaat     420
taccctgatt tggtcaatat gtgtacacat attaaaacat tacactttaa cccataaata     480
tgtataatga ttatgtatca attaaaaata aagaaaata aagtagggag attatgaata       540
tgcaaataag cacacatata ttccaaatag taatgtacta gcagactgt gtaaagtttt       600 tttttaagtt acttaatgta tctcagagat atttccttt gttatacaca atgttaaggc       660
attaagtata atagtaaaaa ttgcggagaa gaaaaaaaaa gaaagcaaga attaaacaaa     720
agaaaacaat tgttatgaac agcaaataaa agaaactaaa acgatcctga gcttccaca      780 ctgatgcaat cattcgtctg tttcccattc taaactgtac cctgttactt atccccttcc     840
tatgacatga acttaaccat agaaaagaag gggaaagaaa acatcaagcg tcccatagac     900
tcaccctgaa gttctcagga tccacgtgca gcttgtcaca gtgcagctca ctcagtgtgg     960
caaaggtgcc cttgaggttg tccaggtgag ccaggccatc actaaaggca ccgagcactt    1020
tcttgccatg agccttcacc ttagggttgc ccataacagc atcaggagtg acagatccc     1080 caaaggactc aaagaacctc tgggtccaag ggtagaccac cagcagccta agggtgggaa    1140
aatagaccaa taggcagaga gagtcagtgc ctatcagaaa cccaagagtc ttctctgtct    1200
ccagatcgat aagcttgata tcgaattgta cctagtggaa ccggaaccct taaacatgta    1260
taacttcgta taatgtatgc tatacgaagt tattaggtcc ctcgacgaat tgtgtcagtc    1320
ctgctcctcg gccacgaagt gcacgcagtt gccggccggg tcgcgcaggg cgaactcccg    1380
cccccacggc tgctcgccga tctcggtcat ggccggcccg gaggcgtccc ggaagttcgt    1440
ggacacgacc tccgaccact cggcgtacag ctcgtccagg ccgcgcaccc acacccaggc    1500
cagggtgttg tccggcacca cctggtcctg gaccgcgctg atgaacaggg tcacgtcgtc    1560
ccggaccaca ccggcgaagt cgtcctccac gaagtcccgg gagaacccga gccggtcggt    1620
ccagaactcg accgctccgg cgacgtcgcg cgcggtgagc accggaacgg cactggtcaa    1680
cttggccttg tacagctcgt ccatgccgag agtgatcccg gcggcggtca cgaactccag    1740
caggaccatg tgatcgcgct tctcgttggg gtctttgctc agggcggact gggtgctcag    1800
gtagtggttg tcgggcagca gcacgggcc gtcgccgatg ggggtgttct gctggtagtg      1860
gtcggcgagc tgcacgctgc cgtcctcgat gttgtggcgg atcttgaagt tcaccttgat    1920
gccgttcttc tgcttgtcgg ccatgatata gacgttgtgg ctgttgtagt tgtactccag    1980
cttgtgcccc aggatgttgc cgtcctcctt gaagtcgatg cccttcagct cgatgcggtt    2040
caccagggtg tcgccctcga acttcacctc ggcgcgggtc ttgtagttgc cgtcgtcctt    2100
gaagaagatg gtgcgctcct ggacgtagcc ttcgggcatg cgcggacttga agaagtcgtg   2160 ctgcttcatg tggtcggggt agcggctgaa gcactgcacg ccgtaggtca gggtggtcac    2220
gagggtgggc cagggcacgg gcagcttgcc ggtggtgcag atgaacttca gggtcagctt    2280
gccgtaggtg gcatcgccct cgccctcgcc ggacacgctg aacttgtggc cgtttacgtc    2340
```

```
gccgtccagc tcgaccagga tgggcaccac cccggtgaac agctcctcgc ccttgctcac    2400
catggtggcg ggatccgggc gactcagtca atcggaggac tggcgcgccg agtgaggggt    2460
tgtgagctct tttatagagc tcgggaagca gaagcgcgcg aacagaagcg agaagcaggc    2520
tgattggtta attcaaataa ggcgcagggt catttcaggt ccttggggga gcctggaaac    2580
atctgatggg tcttaagaaa ctgctgaggg ttgggccata tctggggacc atctgttctt    2640
ggcctcgggc cggggccgaa actgcggtga ccatctgttc ttggcccccgg gccggggccg    2700 aaactgctca ccgcagatat cctgtttggc ccaacgttag ctattttcat gtacccgccc    2760
ttgatctgaa cttctctatt cttggtttgg tattttccca tgccttgcaa aatggcgtta    2820
ctgcagctag cttgccaaac ctacaggtgg ggtctttcag cggccgctta agcttggaac    2880
ccttaatata acttcgtata atgtatgcta tacgaagtta ttaggtccct cgacctgctg    2940
gaatctcgtg aagcgagctt atcgatctgg tctccttaaa cctgtcttgt aaccttgata    3000
ccaacctgcc cagggcctca ccaccaactt catccacgtt caccttgccc cacagggcag    3060
taacggcaga cttctcctca ggagtcaggt gcaccatggt gtctgtttga ggttgctagt    3120
gaacacagtt gtgtcagaag caaatgtaag caatagatgg ctctgccctg acttttatgc    3180
ccagccctgg ctcctgccct ccctgctcct gggagtagat tggccaaccc tagggtgtgg    3240
ctccacaggg tgaggtctaa gtgatgacag ccgtacctgt ccttggctct tctggcactg    3300
gcttaggagt tggacttcaa accctcagcc ctccctctaa gatatatctc ttggccccat    3360
accatcagta caaattgcta ctaaaaacat cctcctttgc aagtgtattt ac            3412
```

<210> SEQ ID NO 28
<211> LENGTH: 3669
<212> TYPE: DNA
<213> ORGANISM: Artificial Sequence
<220> FEATURE:
<223> OTHER INFORMATION: Synthetic

<400> SEQUENCE: 28

```
gaattctttg ccaaagtgat gggccagcac acagaccagc acgttgccca ggagctgtgg     60
gaggaagata agaggtatga acatgattag caaaagggcc tagcttggac tcagaataat    120
ccagccttat cccaaccata aaataaaagc agaatggtag ctggattgta gctgctatta    180
gcaatatgaa acctcttaca tcagttacaa tttatatgca gaaatattta tatgcagaga    240
tattgctatt gccttaaccc agaaattatc actgttattc tttagaatgg tgcaaagagg    300
catgatacat tgtatcatta ttgccctgaa agaaagagat tagggaaagt attagaaata    360
agataaacaa aaaagtatat taaaagaaga aagcattttt taaaattaca aatgcaaaat    420
taccctgatt tggtcaatat gtgtacacat attaaaacat tacactttaa cccataaata    480
tgtataatga ttatgtatca attaaaaata aagaaaata aagtagggag attatgaata    540
tgcaaataag cacacatata ttccaaatag taatgtacta ggcagactgt gtaaagtttt    600
tttttaagtt acttaatgta tctcagagat atttccttttt gttatacaca atgttaaggc    660
attaagtata atagtaaaaa ttgcggagaa gaaaaaaaaa gaaagcaaga attaaacaaa    720
agaaaacaat tgttatgaac agcaaataaa agaaactaaa acgatcctga acttccaca     780 ctgatgcaat cattcgtctg tttcccattc taaactgtac cctgttactt atccccttcc    840
tatgacatga acttaaccat agaaaagaag gggaaagaaa acatcaagcg tcccatagac    900
tcaccctgaa gttctcagga tccacgtgca gcttgtcaca gtgcagctca ctcagtgtgg    960
caaaggtgcc cttgaggttg tccaggtgag ccaggccatc actaaaggca ccgagcactt   1020
```

```
tcttgccatg agccttcacc ttagggttgc ccataacagc atcaggagtg gacagatccc    1080
caaaggactc aaagaacctc tgggtccaag ggtagaccac cagcagccta agggtgggaa    1140
aatagaccaa taggcagaga gagtcagtgc ctatcagaaa cccaagagtc ttctctgtct    1200
ccagatcgat aagcttgata tcgaattgta cctagtggaa ccggaaccct aaacatgta     1260 taacttcgta taatgtatgc tatacgaagt tattaggtcc ctcgacgaat tcagacatga    1320
taagatacat tgatgagttt ggacaaacca caactagaat gcagtgaaaa aaatgcttta    1380
tttgtgaaat ttgtgatgct attgctttat ttgtaaccat tataagctgc aataaacaag    1440
ttggggtggg cgaagaactc cagcatgaga tccccgcgct ggaggatcat ccagccggcg    1500
tcccggaaaa cgattccgaa gcccaacctt tcatagaagg cggcggtgga atcgaaatct    1560
cgtagcacgt gtcagtcctg ctcctcggcc acgaagtgca cgcagttgcc ggccgggtcg    1620
cgcagggcga actcccgccc ccacggctgc tcgccgatct cggtcatggc cggcccggag    1680
gcgtcccgga agttcgtgga cacgacctcc gaccactcgg cgtacagctc gtccaggccg    1740
cgcacccaca cccaggccag ggtgttgtcc ggcaccacct ggtcctggac cgcgctgatg    1800
aacagggtca cgtcgtcccg gaccacaccg gcgaagtcgt cctccacgaa gtcccgggag    1860
aacccgagcc ggtcggtcca gaactcgacc gctccggcga cgtcgcgcgc ggtgagcacc    1920
ggaacggcac tggtcaactt ggccttgtac agctcgtcca tgccgagagt gatcccggcg    1980
gcggtcacga actccagcag gaccatgtga tcgcgcttct cgttgggggtc tttgctcagg    2040 gcggactggg tgctcaggta gtggttgtcg ggcagcagca cggggccgtc gccgatgggg    2100
gtgttctgct ggtagtggtc ggcgagctgc acgctgccgt cctcgatgtt gtggcggatc    2160
ttgaagttca ccttgatgcc gttcttctgc ttgtcggcca tgatatagac gttgtggctg    2220
ttgtagttgt actccagctt gtgccccagg atgttgccgt cctccttgaa gtcgatgccc    2280
ttcagctcga tgcggttcac cagggtgtcg ccctcgaact tcacctcggc gcgggtcttg    2340
tagttgccgt cgtccttgaa gaagatggtg cgctcctgga cgtagccttc gggcatggcg    2400
gacttgaaga agtcgtgctg cttcatgtgg tcggggtagc ggctgaagca ctgcacgccg    2460
taggtcaggg tggtcacgag ggtgggccag ggcacgggca gcttgccggt ggtgcagatg    2520
aacttcaggg tcagcttgcc gtaggtggca tcgccctcgc cctcgccgga cacgctgaac    2580
ttgtggccgt ttacgtcgcc gtccagctcg accaggatgg caccaccccc ggtgaacagc    2640
tcctcgccct gctcaccat ggtggcggga tccgggcgac tcagtcaatc ggaggactgg     2700 cgcgccagt gagggttgt gagctctttt atagagctcg ggaagcagaa gcgcgcgaac      2760
agaagcgaga agcaggctga ttggttaatt caaataaggc gcagggtcat ttcaggtcct    2820
tgggggagcc tggaaacatc tgatgggtct taagaaactg ctgagggttg gccatatct     2880 ggggaccatc tgttcttggc ctcgggccgg ggccgaaact gcggtgacca tctgttcttg    2940
gccccgggcc ggggccgaaa ctgctcaccg cagatatcct gtttggccca acgttagcta    3000
ttttcatgta cccgcccttg atctgaactt ctctattctt ggtttggtat ttttccatgc    3060
cttgcaaaat ggcgttactg cagctagctt gccaaaccta caggtggggt ctttcagcgg    3120
ccgcttaagc ttggaaccct taatataact tcgtataatg tatgctatac gaagttatta    3180
ggtccctcga cctgctggaa tctcgtgaag cgagcttatc gatctggtct ccttaaacct    3240
gtcttgtaac cttgatacca acctgccagg ggcctcacca ccaacttcat ccacgttcac    3300
cttgccccac agggcagtaa cggcagactt ctcctcagga gtcaggtgca ccatggtgtc    3360
```

| | |
|---|---|
| tgtttgaggt tgctagtgaa cacagttgtg tcagaagcaa atgtaagcaa tagatggctc | 3420 |
| tgccctgact tttatgccca gccctggctc ctgccctccc tgctcctggg agtagattgg | 3480 |
| ccaaccctag ggtgtggctc cacagggtga ggtctaagtg atgacagccg tacctgtcct | 3540 |
| tggctcttct ggcactggct taggagttgg acttcaaacc ctcagccctc cctctaagat | 3600 |
| atatctcttg gccccatacc atcagtacaa attgctacta aaaacatcct cctttgcaag | 3660 |
| tgtatttac | 3669 |

<210> SEQ ID NO 29
<211> LENGTH: 5127
<212> TYPE: DNA
<213> ORGANISM: Artificial Sequence
<220> FEATURE:
<223> OTHER INFORMATION: Synthetic

<400> SEQUENCE: 29

| | |
|---|---|
| aaggtcgggc aggaagaggg cctatttccc atgattcctt catatttgca tatacgatac | 60 |
| aaggctgtta gagagataat tagaattaat ttgactgtaa acacaaagat attagtacaa | 120 |
| aatacgtgac gtagaaagta ataatttctt gggtagtttg cagttttaaa attatgtttt | 180 |
| aaaatggact atcatatgct taccgtaact tgaaagtatt tcgatttctt ggctttatat | 240 |
| atcttgtgga aggacgaaa caccgaccaa tagaaactgg gcatggtttt agagctagaa | 300 |
| atagcaagtt aaaataaggc tagtccgtta tcaacttgaa aaagtggcac cgagtcggtg | 360 |
| cttttttaa gcttgggccg ctcgagcgcg ttaacgggcc cagcttcgat aaaataaaag | 420 |
| attttattta gtctccagaa aaaggggggga atgaaagacc ccacctgtag gtttggcaag | 480 |
| ctagcttaag taacgccatt ttgcaaggca tggaaaatac ataactgaga atagagaagt | 540 |
| tcagatcaag gttaggaaca gagagacagc agaatatggg ccaaacagga tatctgtggt | 600 |
| aagcagttcc tgccccggct cagggccaag aacagatggt ccccagatgc ggtcccgccc | 660 |
| tcagcagttt ctagagaacc atcagatgtt tccaggtgc cccaaggacc tgaaaatgac | 720 |
| cctgtgcctt atttgaacta accaatcagt tcgcttctcg cttctgttcg cgcgcttctg | 780 |
| ctccccgagc tcaataaaag agcccacaac ccctcactcg gcgcgccagt cctccgatag | 840 |
| actgccggtg ccaccatgga ctataaggac cacgacggag actacaagga tcatgatatt | 900 |
| gattacaaag acgatgacga taagatggcc caaagaagaa gcggaaggt cggtatccac | 960 |
| ggagtcccag cagccgacaa gaagtacagc atcggcctgg acatcggcac caactctgtg | 1020 |
| ggctgggccg tgatcaccga cgagtacaag gtgcccagca gaaaattcaa ggtgctgggc | 1080 |
| aacaccgacc ggcacagcat caagaagaac ctgatcggag ccctgctgtt cgacagcggc | 1140 |
| gaaacagccg aggccaccccg gctgaagaga accgccagaa agatacac cagacggaag | 1200 |
| aaccggatct gctatctgca agagatcttc agcaacgaga tggccaaggt ggacgacagc | 1260 |
| ttcttccaca gactgaaga gtccttcctg gtggaagagg ataagaagca cgagcggcac | 1320 |
| cccatcttcg gcaacatcgt ggacgaggtg gcctaccacg agaagtaccc caccatctac | 1380 |
| cacctgagaa agaaactggt ggacagcacc gacaaggccg acctgcggct gatctatctg | 1440 |
| gccctggccc acatgatcaa gttccggggc cacttcctga tcgagggcga cctgaacccc | 1500 |
| gacaacagcg acgtggacaa gctgttcatc cagctggtgc agacctacaa ccagctgttc | 1560 |
| gaggaaaacc ccatcaacgc cagcggcgtg gacgccaagg ccatcctgtc tgccagactg | 1620 |
| agcaagagca gacggctgga aaatctgatc gcccagctgc ccggcgagaa gaagaatggc | 1680 |
| ctgttcggaa acctgattgc cctgagcctg ggcctgaccc ccaacttcaa gagcaacttc | 1740 |

```
gacctggccg aggatgccaa actgcagctg agcaaggaca cctacgacga cgacctggac    1800
aacctgctgg cccagatcgg cgaccagtac gccgacctgt ttctggccgc caagaacctg    1860
tccgacgcca tcctgctgag cgacatcctg agagtgaaca ccgagatcac caaggccccc    1920
ctgagcgcct ctatgatcaa agagatacgac gagcaccacc aggacctgac cctgctgaaa    1980
gctctcgtgc ggcagcagct gcctgagaag tacaaagaga ttttcttcga ccagagcaag    2040
aacggctacg ccggctacat tgacggcgga gccagccagg aagagttcta caagttcatc    2100
aagcccatcc tggaaaagat ggacggcacc gaggaactgc tcgtgaagct gaacagagag    2160
gacctgctgc ggaagcagcg gaccttcgac aacggcagca tcccccacca gatccacctg    2220
ggagagctgc acgccattct gcggcggcag gaagattttt acccattcct gaaggacaac    2280
cgggaaaaga tcgagaagat cctgaccttc cgcatcccct actacgtggg ccctctggcc    2340
aggggaaaca gcagattcgc ctggatgacc agaaagagcg aggaaaccat caccccctgg    2400
aacttcgagg aagtggtgga caagggcgct tccgcccaga gcttcatcga gcggatgacc    2460
aacttcgata agaacctgcc caacgagaag gtgctgccca gcacagcct gctgtacgag    2520 tacttcaccg tgtataacga gctgaccaaa gtgaaatacg tgaccgaggg aatgagaaag    2580
cccgccttcc tgagcggcga gcagaaaaag gccatcgtgg acctgctgtt caagaccaac    2640
cggaaagtga ccgtgaagca gctgaaagag gactacttca gaaaaatcga gtgcttcgac    2700
tccgtggaaa tctccggcgt ggaagatcgg ttcaacgcct ccctgggcac ataccacgat    2760
ctgctgaaaa ttatcaagga caaggacttc ctggacaatg aggaaaacga ggacattctg    2820
gaagatatcg tgctgaccct gacactgttt gaggacagag agatgatcga ggaacggctg    2880
aaaacctatg cccacctgtt cgacgacaaa gtgatgaagc agctgaagcg gcggagatac    2940
accggctggg gcaggctgag ccggaagctg atcaacggca tccgggacaa gcagtccggc    3000
aagacaatcc tggatttcct gaagtccgac ggcttcgcca acagaaactt catgcagctg    3060
atccacgacg acagcctgac ctttaaagag gacatccaga aagcccaggt gtccggccag    3120
ggcgatagcc tgcacgagca cattgccaat ctggccggca gccccgccat taagaagggc    3180
atcctgcaga cagtgaaggt ggtggacgag ctcgtgaaag tgatgggccg gcacaagccc    3240
gagaacatcg tgatcgaaat ggccagagag aaccagacca cccagaaggg acagaagaac    3300
agccgcgaga gaatgaagcg gatcgaagag ggcatcaaag agctgggcag ccagatcctg    3360
aaagaacacc ccgtggaaaa cacccagctg cagaacgaga gctgtacct gtactacctg    3420 cagaatgggc gggatatgta cgtggaccag gaactggaca tcaaccggct gtccgactac    3480
gatgtggacc atatcgtgcc tcagagcttt ctgaaggacg actccatcga caacaaggtg    3540
ctgaccagaa gcgacaagaa ccggggcaag agcgacaacg tgccctccga agaggtcgtg    3600
aagaagatga aaaactactg gcggcagctg ctgaacgcca agctgattac cagagaaag    3660 ttcgacaatc tgaccaaggc cgagagaggc ggcctgagcg aactggataa ggccggcttc    3720
atcaagagac agctggtgga aacccggcag atcacaaagc acgtggcaca gatcctggac    3780
tcccggatga acactaagta cgacgagaat gacaagctga tccgggaagt gaaagtgatc    3840
accctgaagt ccaagctggt gtccgatttc cggaaggatt tccagtttta caaagtgcgc    3900
gagatcaaca actaccacca cgcccacgac gcctacctga acgccgtcgt gggaaccgcc    3960
ctgatcaaaa agtaccctaa gctggaaagc gagttcgtgt acggcgacta caaggtgtac    4020
gacgtgcgga agatgatcgc caagagcgag caggaaatcg gcaaggctac cgccaagtac    4080
```

| | |
|---|---|
| ttcttctaca gcaacatcat gaactttttc aagaccgaga ttaccctggc caacggcgag | 4140 |
| atccggaagc ggcctctgat cgagacaaac ggcgaaaccg gggagatcgt gtgggataag | 4200 |
| ggccgggatt ttgccaccgt gcggaaagtg ctgagcatgc cccaagtgaa tatcgtgaaa | 4260 |
| aagaccgagg tgcagacagg cggcttcagc aaagagtcta tcctgcccaa gaggaacagc | 4320 |
| gataagctga tcgccagaaa gaaggactgg gaccctaaga agtacggcgg cttcgacagc | 4380 |
| cccaccgtgg cctattctgt gctggtggtg gccaaagtgg aaaagggcaa gtccaagaaa | 4440 |
| ctgaagagtg tgaaagagct gctggggatc accatcatgg aaagaagcag cttcgagaag | 4500 |
| aatcccatcg actttctgga agccaagggc tacaagaag tgaaaaagga cctgatcatc | 4560 |
| aagctgccta agtactccct gttcgagctg gaaaacggcc ggaagagaat gctggcctct | 4620 |
| gccggcgaac tgcagaaggg aaacgaactg gccctgccct ccaaatatgt gaacttcctg | 4680 |
| tacctggcca gccactatga aagctgaag ggctcccccg aggataatga gcagaaacag | 4740 |
| ctgtttgtgg aacagcacaa gcactacctg gacgagatca tcgagcagat cagcgagttc | 4800 |
| tccaagagag tgatcctggc cgacgctaat ctggacaaag tgctgtccgc ctacaacaag | 4860 |
| caccgggata gcccatcag agagcaggcc gagaatatca tccacctgtt taccctgacc | 4920 |
| aatctgggag cccctgccgc cttcaagtac tttgacacca ccatcgaccg gaagaggtac | 4980 |
| accagcacca agaggtgct ggacgccacc ctgatccacc agagcatcac cggcctgtac | 5040 |
| gagacacgga tcgacctgtc tcagctggga ggcgacaaaa ggccggcggc cacgaaaaag | 5100 |
| gccggccagg caaaaaagaa aaagtaa | 5127 |

<210> SEQ ID NO 30
<211> LENGTH: 3412
<212> TYPE: DNA
<213> ORGANISM: Artificial Sequence
<220> FEATURE:
<223> OTHER INFORMATION: Synthetic

<400> SEQUENCE: 30

| | |
|---|---|
| gaattctttg ccaaagtgat gggccagcac acagaccagc acgttgccca ggagctgtgg | 60 |
| gaggaagata gaggtatga acatgattag caaaagggcc tagcttggac tcagaataat | 120 |
| ccagccttat cccaaccata aaataaaagc agaatggtag ctggattgta gctgctatta | 180 |
| gcaatatgaa acctcttaca tcagttacaa tttatatgca gaaatattta tatgcagaga | 240 |
| tattgctatt gccttaaccc agaaattatc actgttattc tttagaatgg tgcaaagagg | 300 |
| catgatacat tgtatcatta ttgccctgaa agaaagagat tagggaaagt attagaaata | 360 |
| agataaacaa aaaagtatat taaaagaaga aagcattttt taaaattaca aatgcaaaat | 420 |
| taccctgatt tggtcaatat gtgtacacat attaaaacat tacactttaa cccataaata | 480 |
| tgtataatga ttatgtatca attaaaaata aagaaaata agtagggag attatgaata | 540 |
| tgcaaataag cacacatata ttccaaatag taatgtacta gcagactgt gtaaagtttt | 600 |
| tttttaagtt acttaatgta tctcagagat atttcctttt gttatacaca atgttaaggc | 660 |
| attaagtata atagtaaaaa ttgcggagaa gaaaaaaaaa gaaagcaaga attaaacaaa | 720 |
| agaaaacaat tgttatgaac agcaaataaa gaaactaaa acgatcctga gcttccaca | 780 |
| ctgatgcaat cattcgtctg tttcccattc taaactgtac cctgttactt atcccttcc | 840 |
| tatgacatga acttaaccat agaaaagaag gggaaagaaa acatcaagcg tcccatagac | 900 |
| tcaccctgaa gttctcagga tccacgtgca gcttgtcaca gtgcagctca ctcagtgtgg | 960 |
| caaaggtgcc cttgaggttg tccaggtgag ccaggccatc actaaaggca ccgagcactt | 1020 |

```
tcttgccatg agccttcacc ttagggttgc ccataacagc atcaggagtg gacagatccc    1080
caaaggactc aaagaacctc tgggtccaag ggtagaccac cagcagccta agggtgggaa    1140
aatagaccaa taggcagaga gagtcagtgc ctatcagaaa cccaagagtc ttctctgtct    1200
ccagatcgat aagcttgata tcgaattgta cctagtggaa ccggaaccct aaacatgta    1260 taacttcgta taatgtatgc tatacgaagt tattaggtcc ctcgacgaat tgtgtcagtc    1320
ctgctcctcg gccacgaagt gcacgcagtt gccggccggg tcgcgcaggg cgaactcccg    1380
cccccacggc tgctcgccga tctcggtcat ggccggcccg gaggcgtccc ggaagttcgt    1440
ggacacgacc tccgaccact cggcgtacag ctcgtccagg ccgcgcaccc acacccaggc    1500
cagggtgttg tccggcacca cctggtcctg gaccgcgctg atgaacaggg tcacgtcgtc    1560
ccggaccaca ccgcgaagt cgtcctccac gaagtcccgg gagaacccga ccggtcggt    1620 ccagaactcg accgctccgg cgacgtcgcg cgcggtgagc accggaacgg cactggtcaa    1680
cttggccttg tacagctcgt ccatgccgag agtgatcccg gcggcggtca cgaactccag    1740
caggaccatg tgatcgcgct tctcgttggg gtctttgctc agggcggact gggtgctcag    1800
gtagtggttg tcgggcagca gcacggggcc gtcgccgatg ggggtgttct gctggtagtg    1860
gtcggcgagc tgcacgctgc cgtcctcgat gttgtggcgg atcttgaagt tcaccttgat    1920
gccgttcttc tgcttgtcgg ccatgatata gacgttgtgg ctgttgtagt tgtactccag    1980
cttgtgcccc aggatgttgc cgtcctcctt gaagtcgatg cccttcagct cgatgcggtt    2040
caccagggtg tcgccctcga acttcacctc ggcgcgggtc ttgtagttgc cgtcgtcctt    2100
gaagaagatg gtgcgctcct ggacgtagcc ttcgggcatg gcggacttga agaagtcgtg    2160
ctgcttcatg tggtcggggt agcggctgaa gcactgcacg ccgtaggtca gggtggtcac    2220
gagggtgggc caggcacgg gcagcttgcc ggtggtgcag atgaacttca gggtcagctt    2280
gccgtaggtg gcatcgccct cgccctcgcc ggacacgctg aacttgtggc cgtttacgtc    2340
gccgtccagc tcgaccagga tgggcaccac cccggtgaac agctcctcgc ccttgctcac    2400
catggtggcg ggatccgggc gactcagtca atcggaggac tggcgcgccg agtgaggggt    2460
tgtgagctct tttatagagc tcgggaagca gaagcgcgcg aacagaagcg agaagcaggc    2520
tgattggtta attcaaataa ggcgcagggt catttcaggt ccttggggga gcctggaaac    2580
atctgatggg tcttaagaaa ctgctgaggg ttgggccata tctggggacc atctgttctt    2640
ggcctcgggc cggggccgaa actgcggtga ccatctgttc ttggccccgg gccggggccg    2700
aaactgctca ccgcagatat cctgtttggc ccaacgttag ctattttcat gtacccgccc    2760
ttgatctgaa cttctctatt cttggtttgg tattttttcca tgccttgcaa aatggcgtta    2820
ctgcagctag cttgccaaac ctacaggtgg ggtctttcag cggccgctta agcttggaac    2880
ccttaatata acttcgtata atgtatgcta tacgaagtta ttaggtccct cgacctgctg    2940
gaatctcgtg aagcgagctt atcgatctgg tctccttaaa cctgtcttgt aaccttgata    3000
ccaacctgcc cagggcctca ccaccaactt catccacgtt caccttgccc cacagggcag    3060
taacggcaga cttctcctca ggagtcaggt gcaccatggt gtctgtttga ggttgctagt    3120
gaacacagtt gtgtcagaag caaatgtaag caatagatgg ctctgccctg acttttatgc    3180
ccagccctgg ctcctgccct ccctgctcct gggagtagat tggccaaccc tagggtgtgg    3240
ctccacaggt tgaggtctaa gtgatgacag ccgtacctgt ccttggctct tctggcactg    3300
gcttaggagt tggacttcaa accctcagcc ctccctctaa gatatatctc ttggccccat    3360
```
accatcagta caaattgcta ctaaaaacat cctcctttgc aagtgtattt ac         3412

<210> SEQ ID NO 31
<211> LENGTH: 365
<212> TYPE: DNA
<213> ORGANISM: Artificial Sequence
<220> FEATURE:
<223> OTHER INFORMATION: Synthetic

<400> SEQUENCE: 31
aaggtcgggc aggaagaggg cctatttccc atgattcctt catatttgca tatacgatac   60
aaggctgtta gagagataat tagaattaat ttgactgtaa acacaaagat attagtacaa   120
aatacgtgac gtagaaagta ataatttctt gggtagtttg cagttttaaa attatgtttt   180
aaaatggact atcatatgct taccgtaact tgaaagtatt tcgatttctt ggctttatat   240
atcttgtgga aaggacgaaa caccgaccaa tagaaactgg gcatggtttt agagctagaa   300
atagcaagtt aaaataaggc tagtccgtta tcaacttgaa aaagtggcac cgagtcggtg   360
cttttt                                                             365

<210> SEQ ID NO 32
<211> LENGTH: 3412
<212> TYPE: DNA
<213> ORGANISM: Artificial Sequence
<220> FEATURE:
<223> OTHER INFORMATION: Synthetic

<400> SEQUENCE: 32
gaattctttg ccaaagtgat gggccagcac acagaccagc acgttgccca ggagctgtgg    60
gaggaagata gaggtatga acatgattag caaagggcc tagcttggac tcagaataat     120
ccagccttat cccaaccata aaataaaagc agaatggtag ctggattgta gctgctatta   180
gcaatatgaa acctcttaca tcagttacaa tttatatgca gaaatattta tatgcagaga   240
tattgctatt gccttaaccc agaaattatc actgttattc tttagaatgg tgcaaagagg   300
catgatacat tgtatcatta ttgccctgaa agaaagagat tagggaaagt attagaaata   360
agataaacaa aaaagtatat taaaagaaga aagcattttt taaaattaca aatgcaaaat   420
taccctgatt tggtcaatat gtgtacacat attaaaacat tacactttaa cccataaata   480
tgtataatga ttatgtatca attaaaaata aagaaaata aagtagggag attatgaata   540
tgcaaataag cacacatata ttccaaatag taatgtacta ggcagactgt gtaaagtttt   600
tttttaagtt acttaatgta tctcagagat atttccttt gttatacaca atgttaaggc    660
attaagtata atagtaaaaa ttgcggagaa gaaaaaaaa gaaagcaaga attaaacaaa    720
agaaaacaat tgttatgaac agcaaataaa agaaactaaa acgatcctga gcttccaca    780 ctgatgcaat cattcgtctg tttcccattc taaactgtac cctgttactt atcccttcc    840 tatgacatga acttaaccat agaaaagaag gggaaagaaa acatcaagcg tcccatagac   900
tcaccctgaa gttctcagga tccacgtgca gcttgtcaca gtgcagctca ctcagtgtgg   960
caaaggtgcc cttgaggttg tccaggtgag ccaggccatc actaaaggca ccgagcactt  1020
tcttgccatg agccttcacc ttaggggttgc ccataacagc atcaggagtg acagatccc   1080 caaaggactc aaagaacctc tgggtccaag ggtagaccac cagcagccta agggtgggaa  1140
aatagaccaa taggcagaga gagtcagtgc ctatcagaaa cccaagagtc ttctctgtct  1200
ccagatcgat aagcttgata tcgaattgta cctagtggaa ccggaaccct aaacatgta   1260 taacttcgta taatgtatgc tatacgaagt tattaggtcc ctcgacgaat tgtgtcagtc  1320

-continued

```
ctgctcctcg gccacgaagt gcacgcagtt gccggccggg tcgcgcaggg cgaactcccg    1380
cccccacggc tgctcgccga tctcggtcat ggccggcccg gaggcgtccc ggaagttcgt    1440
ggacacgacc tccgaccact cggcgtacag ctcgtccagg ccgcgcaccc acacccaggc    1500
cagggtgttg tccggcacca cctggtcctg gaccgcgctg atgaacaggg tcacgtcgtc    1560
ccggaccaca ccggcgaagt cgtcctccac gaagtcccgg gagaacccga gccggtcggt    1620
ccagaactcg accgctccgg cgacgtcgcg cgcggtgagc accggaacgg cactggtcaa    1680
cttggccttg tacagctcgt ccatgccgag agtgatcccg gcggcggtca cgaactccag    1740
caggaccatg tgatcgcgct tctcgttggg gtctttgctc agggcggact gggtgctcag    1800
gtagtggttg tcgggcagca gcacggggcc gtcgccgatg ggggtgttct gctggtagtg    1860
gtcggcgagc tgcacgctgc cgtcctcgat gttgtggcgg atcttgaagt tcaccttgat    1920
gccgttcttc tgcttgtcgg ccatgatata gacgttgtgg ctgttgtagt tgtactccag    1980
cttgtgcccc aggatgttgc cgtcctcctt gaagtcgatg cccttcagct cgatgcggtt    2040
caccagggtg tcgccctcga acttcacctc ggcgcgggtc ttgtagttgc cgtcgtcctt    2100
gaagaagatg gtgcgctcct ggacgtagcc ttcgggcatg gcggacttga agaagtcgtg    2160
ctgcttcatg tggtcggggt agcggctgaa gcactgcacg ccgtaggtca gggtggtcac    2220
gagggtgggc cagggcacgg gcagcttgcc ggtggtgcag atgaacttca gggtcagctt    2280
gccgtaggtg gcatcgccct cgccctcgcc ggacacgctg aacttgtggc cgtttacgtc    2340
gccgtccagc tcgaccagga tgggcaccac cccggtgaac agctcctcgc ccttgctcac    2400
catggtggcg ggatccgggc gactcagtca atcggaggac tggcgcgccg agtgaggggt    2460
tgtgagctct tttatagagc tcgggaagca gaagcgcgcg aacagaagcg agaagcaggc    2520
tgattggtta attcaaataa ggcgcagggt catttcaggt ccttggggga gcctggaaac    2580
atctgatggg tcttaagaaa ctgctgaggg ttgggccata tctggggacc atctgttctt    2640
ggcctcgggc cggggccgaa actgcggtga ccatctgttc ttggccccgg gccggggccg    2700
aaactgctca ccgcagatat cctgtttggc ccaacgttag ctattttcat gtacccgccc    2760
ttgatctgaa cttctctatt cttggttttgg tattttttcca tgccttgcaa aatggcgtta    2820
ctgcagctag cttgccaaac ctacaggtgg ggtctttcag cggccgctta agcttggaac    2880
ccttaatata acttcgtata atgtatgcta tacgaagtta ttaggtccct cgacctgctg    2940
gaatctcgtg aagcgagctt atcgatctgg tctccttaaa cctgtcttgt aaccttgata    3000
ccaacctgcc cagggcctca ccaccaactt catccacgtt caccttgccc cacagggcag    3060
taacggcaga cttctcctca ggagtcaggt gcaccatggt gtctgtttga ggttgctagt    3120
gaacacagtt gtgtcagaag caaatgtaag caatagatgg ctctgccctg acttttatgc    3180
ccagccctgg ctcctgccct ccctgctcct gggagtagat tggccaaccc tagggtgtgg    3240
ctccacaggg tgaggtctaa gtgatgacag ccgtacctgt ccttggctct tctggcactg    3300
gcttaggagt tggacttcaa accctcagcc ctccctctaa gatatatctc ttggccccat    3360
accatcagta caaattgcta ctaaaaacat cctcctttgc aagtgtattt ac            3412
```

<210> SEQ ID NO 33
<211> LENGTH: 365
<212> TYPE: DNA
<213> ORGANISM: Artificial Sequence
<220> FEATURE:
<223> OTHER INFORMATION: Synthetic

<400> SEQUENCE: 33

```
aaggtcgggc aggaagaggg cctatttccc atgattcctt catatttgca tatacgatac    60
aaggctgtta gagagataat tagaattaat ttgactgtaa acacaaagat attagtacaa   120
aatacgtgac gtagaaagta ataatttctt gggtagtttg cagttttaaa attatgtttt   180
aaaatggact atcatatgct taccgtaact tgaaagtatt tcgatttctt ggctttatat   240
atcttgtgga aaggacgaaa caccgaccaa tagaaactgg gcatggtttt agagctagaa   300
atagcaagtt aaaataaggc tagtccgtta tcaacttgaa aaagtggcac cgagtcggtg   360
ctttt                                                               365
```

<210> SEQ ID NO 34
<211> LENGTH: 3412
<212> TYPE: DNA
<213> ORGANISM: Artificial Sequence
<220> FEATURE:
<223> OTHER INFORMATION: Synthetic

<400> SEQUENCE: 34

```
gaattctttg ccaaagtgat gggccagcac acagaccagc acgttgccca ggagctgtgg    60
gaggaagata gaggtatgaa acatgattag caaaagggcc tagcttggac tcagaataat   120
ccagccttat cccaaccata aataaaaagc agaatggtag ctggattgta gctgctatta   180
gcaatatgaa acctcttaca tcagttacaa tttatatgca gaatatttta tatgcagaga   240
tattgctatt gccttaaccc agaaattatc actgttattc tttagaatgg tgcaaagagg   300
catgatacat tgtatcatta ttgccctgaa agaaagagat tagggaaagt attagaaata   360
agataaacaa aaaagtatat taaagaagaa agcatttttt taaaattaca aatgcaaaat   420
taccctgatt tggtcaatat gtgtacacat attaaaacat tacactttaa cccataaata   480
tgtataatga ttatgtatca attaaaaata aaagaaaata agtagggag attatgaata   540
tgcaaataag cacacatata ttccaaatag taatgtacta ggcagactgt gtaaagtttt   600
ttttttaagtt acttaatgta tctcagagat atttccttt gttatacaca atgttaaggc   660
attaagtata atagtaaaaa ttgcggagaa gaaaaaaaaa gaaagcaaga attaaacaaa   720
agaaaacaat tgttatgaac agcaaataaa agaaactaaa acgatcctga gacttccaca   780
ctgatgcaat cattcgtctg tttcccattc taaactgtac cctgttactt atccccttcc   840
tatgacatga acttaaccat agaaaagaag gggaaagaaa acatcaagcg tcccatagac   900
tcaccctgaa gttctcagga tccacgtgca gcttgtcaca gtgcagctca ctcagtgtgg   960
caaaggtgcc cttgaggttg tccaggtgag ccaggccatc actaaaggca ccgagcactt  1020
tcttgccatg agccttcacc ttaggggttgc ccataacagc atcaggagtg acagatccc  1080
caaaggactc aaagaacctc tgggtccaag ggtagaccac cagcagccta agggtgggaa  1140
aatagaccaa taggcagaga gagtcagtgc ctatcagaaa cccaagagtc ttctctgtct  1200
ccagatcgat aagcttgata tcgaattgta cctagtggaa ccggaaccct taaacatgta  1260
taacttcgta taatgtatgc tatacgaagt tattaggtcc ctcgacgaat tgtgtcagtc  1320
ctgctcctcg gccacgaagt gcacgcagtt gccggccggg tcgcgcaggg cgaactcccg  1380
cccccacggc tgctcgccga tctcggtcat ggccggcccg gaggcgtccc ggaagttcgt  1440
ggacacgacc tccgaccact cggcgtacag ctcgtccagg ccgcgcaccc acacccaggc  1500
cagggtgttg tccggcacca cctggtcctg gaccgcgctg atgaacaggg tcacgtcgtc  1560
ccggaccaca ccggcgaagt cgtcctccac gaagtcccgg gagaacccga gccggtcggt  1620
```

| | |
|---|---|
| ccagaactcg accgctccgg cgacgtcgcg cgcggtgagc accggaacgg cactggtcaa | 1680 |
| cttggccttg tacagctcgt ccatgccgag agtgatcccg gcgcggtca cgaactccag | 1740 |
| caggaccatg tgatcgcgct tctcgttggg gtctttgctc agggcggact gggtgctcag | 1800 |
| gtagtggttg tcgggcagca gcacggggcc gtcgccgatg ggggtgttct gctggtagtg | 1860 |
| gtcggcgagc tgcacgctgc cgtcctcgat gttgtggcgg atcttgaagt tcaccttgat | 1920 |
| gccgttcttc tgcttgtcgg ccatgatata gacgttgtgg ctgttgtagt tgtactccag | 1980 |
| cttgtgcccc aggatgttgc cgtcctcctt gaagtcgatg cccttcagct cgatgcggtt | 2040 |
| caccagggtg tcgccctcga acttcacctc ggcgcgggtc ttgtagttgc cgtcgtcctt | 2100 |
| gaagaagatg gtgcgctcct ggacgtagcc ttcgggcatg gcggacttga agaagtcgtg | 2160 |
| ctgcttcatg tggtcggggt agcggctgaa gcactcacg ccgtaggtca gggtggtcac | 2220 |
| gagggtgggc cagggcacgg gcagcttgcc ggtggtgcag atgaacttca gggtcagctt | 2280 |
| gccgtaggtg gcatcgccct cgccctcgcc ggacacgctg aacttgtggc cgtttacgtc | 2340 |
| gccgtccagc tcgaccagga tgggcaccac cccggtgaac agctcctcgc ccttgctcac | 2400 |
| catggtggcg ggatccgggc gactcagtca atcggaggac tggcgcgccg agtgaggggt | 2460 |
| tgtgagctct tttatagagc tcgggaagca gaagcgcgcg aacagaagcg agaagcaggc | 2520 |
| tgattggtta attcaaataa ggcgcagggt catttcaggt ccttgggga gcctggaaac | 2580 |
| atctgatggg tcttaagaaa ctgctgaggg ttgggccata tctggggacc atctgttctt | 2640 |
| ggcctcgggc cggggccgaa actgcggtga ccatctgttc ttggccccgg gccggggccg | 2700 |
| aaactgctca ccgcagatat cctgtttggc ccaacgttag ctattttcat gtacccgccc | 2760 |
| ttgatctgaa cttctctatt cttggtttgg tatttttcca tgccttgcaa aatggcgtta | 2820 |
| ctgcagctag cttgccaaac ctacaggtgg ggtctttcag cggccgctta agcttggaac | 2880 |
| ccttaatata acttcgtata atgtatgcta tacgaagtta ttaggtccct cgacctgctg | 2940 |
| gaatctcgtg aagcgagctt atcgatctgg tctccttaaa cctgtcttgt aaccttgata | 3000 |
| ccaacctgcc cagggcctca ccaccaactt catccacgtt caccttgccc cacagggcag | 3060 |
| taacggcaga cttctcctca ggagtcaggt gcaccatggt gtctgtttga ggttgctagt | 3120 |
| gaacacagtt gtgtcagaag caaatgtaag caatagatgg ctctgccctg acttttatgc | 3180 |
| ccagccctgg ctcctgccct ccctgctcct gggagtagat tggccaaccc tagggtgtgg | 3240 |
| ctccacaggg tgaggtctaa gtgatgacag ccgtacctgt ccttggctct tctggcactg | 3300 |
| gcttaggagt tggacttcaa accctcagcc ctccctctaa gatatatctc ttggcccat | 3360 |
| accatcagta caaattgcta ctaaaaacat cctcctttgc aagtgtattt ac | 3412 |

<210> SEQ ID NO 35
<211> LENGTH: 3807
<212> TYPE: DNA
<213> ORGANISM: Artificial Sequence
<220> FEATURE:
<223> OTHER INFORMATION: Synthetic

<400> SEQUENCE: 35

| | |
|---|---|
| aaggtcgggc aggaagaggg cctatttccc atgattcctt catatttgca tatacgatac | 60 |
| aaggctgtta gagagataat tagaattaat ttgactgtaa acacaaagat attagtacaa | 120 |
| aatacgtgac gtagaaagta ataatttctt gggtagtttg cagttttaaa attatgtttt | 180 |
| aaaatggact atcatatgct taccgtaact tgaaagtatt tcgatttctt ggctttatat | 240 |

```
atcttgtgga aaggacgaaa caccgaccaa tagaaactgg gcatggtttt agagctagaa    300
atagcaagtt aaaataaggc tagtccgtta tcaacttgaa aaagtggcac cgagtcggtg    360
cttttttaa gcttgggccg ctcgagcgcg ttaacgaatt ctttgccaaa gtgatgggcc     420
agcacacaga ccagcacgtt gcccaggagc tgtgggagga agataagagg tatgaacatg    480
attagcaaaa gggcctagct tggactcaga ataatccagc cttatcccaa ccataaaata    540
aaagcagaat ggtagctgga ttgtagctgc tattagcaat atgaaacctc ttacatcagt    600
tacaatttat atgcagaaat atttatatgc agagatattg ctattgcctt aacccagaaa    660
ttatcactgt tattctttag aatggtgcaa agaggcatga tacattgtat cattattgcc    720
ctgaaagaaa gagattaggg aaagtattag aaataagata acaaaaaag tatattaaaa     780
gaagaaagca ttttttaaaa ttacaaatgc aaaattaccc tgatttggtc aatatgtgta    840
cacatattaa aacattacac tttaacccat aaatatgtat aatgattatg tatcaattaa    900
aaataaaaga aaataaagta gggagattat gaatatgcaa ataagcacac atatattcca    960
aatagtaatg tactaggcag actgtgtaaa gtttttttttt aagttactta atgtatctca  1020
gagatatttc cttttgttat acacaatgtt aaggcattaa gtataatagt aaaaattgcg   1080
gagaagaaaa aaaagaaag caagaattaa acaaaagaaa acaattgtta tgaacagcaa    1140
ataaagaaa ctaaaacgat cctgagactt ccacactgat gcaatcattc gtctgtttcc    1200
cattctaaac tgtaccctgt tacttatccc cttcctatga catgaactta accatagaaa   1260
agaagggaa agaaaacatc aagcgtccca tagactcacc ctgaagttct caggatccac    1320
gtgcagcttg tcacagtgca gctcactcag tgtggcaaag gtgccccttga ggttgtccag  1380
gtgagccagg ccatcactaa aggcaccgag cactttcttg ccatgagcct tcaccttagg   1440
gttgcccata acagcatcag gagtggacag atcccccaaag gactcaaaga acctctgggt  1500
ccaagggtag accaccagca gcctaagggt gggaaaatag accaataggc agagagagtc   1560
agtgcctatc agaaacccaa gagtcttctc tgtctccaga tcgataagct tgatatcgaa   1620
ttgtacctag tggaaccgga acccttaaac atgtataact tcgtataatg tatgctatac   1680
gaagttatta ggtccctcga cgaattgtgt cagtcctgct cctcggccac gaagtgcacg   1740
cagttgccgg ccgggtcgcg cagggcgaac tcccgccccc acggctgctc gccgatctcg   1800
gtcatggccg gccggaggc gtcccggaag ttcgtggaca cgacctccga ccactcggcg    1860
tacagctcgt ccaggccgcg cacccacacc caggccaggg tgttgtccgg caccacctgg   1920
tcctggaccg cgctgatgaa cagggtcacg tcgtcccgga ccacaccggc gaagtcgtcc   1980
tccacgaagt cccgggagaa cccgagccgg tcggtccaga actcgaccgc tccggcgacg   2040
tcgcgcgcgg tgagcaccgg aacggcactg gtcaacttgg ccttgtacag ctcgtccatg   2100
ccgagagtga tcccggcggc ggtcacgaac tccagcagga ccatgtgatc gcgcttctcg   2160
ttgggtctt tgctcagggc ggactgggtg ctcaggtagt ggttgtcggg cagcagcacg    2220
gggccgtcgc cgatgggggt gttctgctgg tagtggtcgg cgagctgcac gctgccgtcc   2280
tcgatgttgt ggcggatctt gaagttcacc ttgatgccgt tcttctgctt gtcggccatg   2340
atatagacgt tgtggctgtt gtagttgtac tccagcttgt gccccaggat gttgccgtcc   2400
tccttgaagt cgatgccctt cagctcgatg cggttcacca gggtgtcgcc ctcgaacttc   2460
acctcggcgc gggtcttgta gttgccgtcg tccttgaaga agatggtgcg ctcctggacg   2520
tagccttcgg gcatggcgga cttgaagaag tcgtgctgct tcatgtggtc ggggtagcgg   2580
ctgaagcact gcacgccgta ggtcagggtg gtcacgaggg tgggccaggg cacgggcagc   2640
```

```
ttgccggtgg tgcagatgaa cttcagggtc agcttgccgt aggtggcatc gccctcgccc    2700
tcgccggaca cgctgaactt gtggccgttt acgtcgccgt ccagctcgac caggatgggc    2760
accaccccgg tgaacagctc ctcgcccttg ctcaccatgg tggcgggatc cgggcgactc    2820
agtcaatcgg aggactggcg cgccgagtga ggggttgtga gctcttttat agagctcggg    2880
aagcagaagc gcgcgaacag aagcgagaag caggctgatt ggttaattca ataaggcgc     2940 agggtcattt caggtccttg ggggagcctg gaaacatctg atgggtctta agaaactgct    3000
gagggttggg ccatatctgg gaccatctg ttcttggcct cgggccgggg ccgaaactgc     3060
ggtgaccatc tgttcttggc cccgggccgg ggccgaaact gctcaccgca gatatcctgt    3120
ttggcccaac gttagctatt ttcatgtacc cgcccttgat ctgaacttct ctattcttgg    3180
tttggtattt ttccatgcct tgcaaaatgg cgttactgca gctagcttgc caaacctaca    3240
ggtggggtct ttcagcggcc gcttaagctt ggaacccttta atataacttc gtataatgta    3300
tgctatacga agttattagg tccctcgacc tgctggaatc tcgtgaagcg agcttatcga    3360
tctggtctcc ttaaacctgt cttgtaacct tgataccaac ctgcccaggg cctcaccacc    3420
aacttcatcc acgttcacct tgccccacag ggcagtaacg gcagacttct cctcaggagt    3480
caggtgcacc atggtgtctg tttgaggttg ctagtgaaca cagttgtgtc agaagcaaat    3540
gtaagcaata gatggctctg ccctgacttt tatgcccagc cctggctcct gccctccctg    3600
ctcctgggag tagattggcc aaccctaggg tgtggctcca cagggtgagg tctaagtgat    3660
gacagccgta cctgtccttg gctcttctgg cactggctta ggagttggac ttcaaaccct    3720
cagccctccc tctaagatat atctcttggc cccataccat cagtacaaat gctactaaa     3780 aacatcctcc tttgcaagtg tatttac                                       3807
```

<210> SEQ ID NO 36
<211> LENGTH: 1805
<212> TYPE: DNA
<213> ORGANISM: Artificial Sequence
<220> FEATURE:
<223> OTHER INFORMATION: Synthetic

<400> SEQUENCE: 36

```
aaggtcgggc aggaagaggg cctatttccc atgattcctt catatttgca tatacgatac     60
aaggctgtta gagagataat tagaattaat ttgactgtaa acacaaagat attagtacaa    120
aatacgtgac gtagaaagta ataatttctt gggtagtttg cagttttaaa attatgtttt    180
aaaatggact atcatatgct taccgtaact tgaaagtatt tcgatttctt ggctttatat    240
atcttgtgga aggacgaaa caccgggcac gggcagcttg ccgggtttta gagctagaaa    300
tagcaagtta aaataaggct agtccgttat caacttgaaa aagtggcacc gagtcggtgc    360 ttttttttaag cttgggccgc tcgagcgcgt taacaccggt gggcacgggc agcttgccgg    420
gttttagagc tagaaatagc aagttaaaat aaggctagtc cgttatcaac ttgaaaaagt    480
ggcaccgagt cggtgctttt tttaaacacc gggcacgggc agcttgccgg gttttagagc    540
tagaaatagc aagttaaaat aaggctagtc cgttatcaac ttgaaaaagt ggcaccgagt    600
cggtgctttt tttccaacgg gcccagcttc gataaaataa agattttat ttagtctcca     660 gaaaagggg ggaatgaaag accccacctg taggtttggc aagctagctt aagtaacgcc     720
attttgcaag gcatggaaaa tacataactg agaatagaga agttcagatc aaggttagga    780
acagagagac agcagaatat gggccaaaca ggatatctgt ggtaagcagt tcctgccccg    840
```

| gctcagggcc aagaacagat ggtccccaga tgcggtcccg ccctcagcag tttctagaga | 900 |
| accatcagat gtttccaggg tgccccaagg acctgaaaat gaccctgtgc cttatttgaa | 960 |
| ctaaccaatc agttcgcttc tcgcttctgt tcgcgcgctt ctgctccccg agctcaataa | 1020 |
| aagagcccac aaccccctcac tcggcgcgcc agtcctccga tagactgcgt cgcccggtcg | 1080 |
| ccaccatggt gagcaagggc gaggagctgt tcaccggggt ggtgcccatc ctggtcgagc | 1140 |
| tggacggcga cgtaaacggc cacaagttca gcgtgtccgg cgagggcgag ggcgatgcca | 1200 |
| cctacggcaa gctgaccctg aagttcatct gcacaacagg aaagctgcct gtgccatggc | 1260 |
| ccaccctcgt gaccaccttc ggctacggcc tgcagtgctt cgcccgctac cccgaccaca | 1320 |
| tgaagcagca cgacttcttc aagtccgcca tgcccgaagg ctacgtccag gagcgcacca | 1380 |
| tcttcttcaa ggacgacggc aactacaaga cccgcgccga ggtgaagttc gagggcgaca | 1440 |
| ccctggtgaa ccgcatcgag ctgaagggca tcgacttcaa ggaggacggc aacatcctgg | 1500 |
| ggcacaagct ggagtacaac tacaacagcc acaacgtcta tatcatggcc gacaagcaga | 1560 |
| agaacggcat caaggtgaac ttcaagatcc gccacaacat cgaggacggc agcgtgcagc | 1620 |
| tcgccgacca ctaccagcag aacacccccca tcggcgacgg ccccgtgctg ctgcccgaca | 1680 |
| accactacct gagctaccag tccgcccctga gcaaagaccc caacgagaag cgcgatcaca | 1740 |
| tggtcctgct ggagttcgtg accgccgccg ggatcactct cggcatggac gagctgtaca | 1800 |
| agtaa | 1805 |

<210> SEQ ID NO 37
<211> LENGTH: 2015
<212> TYPE: DNA
<213> ORGANISM: Artificial Sequence
<220> FEATURE:
<223> OTHER INFORMATION: Synthetic

<400> SEQUENCE: 37

| aaggtcgggc aggaagaggg cctatttccc atgattcctt catatttgca tatacgatac | 60 |
| aaggctgtta gagagataat tagaattaat ttgactgtaa acacaaagat attagtacaa | 120 |
| aatacgtgac gtagaaagta ataatttctt gggtagtttg cagttttaaa attatgtttt | 180 |
| aaaatggact atcatatgct taccgtaact tgaaagtatt tcgatttctt ggctttatat | 240 |
| atcttgtgga aaggacgaaa caccgggcac gggcagcttg ccgggtttta gagctagaaa | 300 |
| tagcaagtta aaataaggct agtccgttat caacttgaaa aagtggcacc gagtcggtgc | 360 |
| ttttttttaag cttgggccgc tcgagcgcgt taacaccggg ggcacgggca gcttgccggg | 420 |
| ttttagagct agaaatagca agttaaaata aggctagtcc gttatcaact tgaaaaagtg | 480 |
| gcaccgagtc ggtgcttttt ttaaacaccg gcacgggca gcttgccggg ttttagagct | 540 |
| agaaatagca agttaaaata aggctagtcc gttatcaact tgaaaaagtg gcaccgagtc | 600 |
| ggtgcttttt ttaccgggca cgggcagctt gccgggtttt agagctagaa atagcaagtt | 660 |
| aaaataaggc tagtccgtta tcaacttgaa aaagtggcac cgagtcggtg cttttttttaa | 720 |
| acaccgggca cgggcagctt gccgggtttt agagctagaa atagcaagtt aaaataaggc | 780 |
| tagtccgtta tcaacttgaa aaagtggcac cgagtcggtg cttttttttgg cccagcttc | 840 |
| gataaaataa aagatttat ttagtctcca gaaaagggg ggaatgaaag accccacctg | 900 |
| taggtttggc aagctagctt aagtaacgcc attttgcaag gcatggaaaa tacataactg | 960 |
| agaatagaga agttcagatc aaggttagga acagagagac agcagaatat gggccaaaca | 1020 |
| ggatatctgt ggtaagcagt tcctgccccg gctcagggcc aagaacagat ggtccccaga | 1080 |

```
tgcggtcccg ccctcagcag tttctagaga accatcagat gtttccaggg tgccccaagg   1140
acctgaaaat gaccctgtgc cttatttgaa ctaaccaatc agttcgcttc tcgcttctgt   1200
tcgcgcgctt ctgctccccg agctcaataa aagagcccac aaccccctcac tcggcgcgcc  1260 agtcctccga tagactgcgt cgcccggtcg ccaccatggt gagcaagggc gaggagctgt   1320
tcaccggggt ggtgcccatc ctggtcgagc tggacggcga cgtaaacggc cacaagttca   1380
gcgtgtccgg cgagggcgag ggcgatgcca cctacggcaa gctgaccctg aagttcatct   1440
gcacaacagg aaagctgcct gtgccatggc ccaccctcgt gaccaccttc ggctacggcc   1500
tgcagtgctt cgcccgctac cccgaccaca tgaagcagca cgacttcttc aagtccgcca   1560
tgcccgaagg ctacgtccag gagcgcacca tcttcttcaa ggacgacggc aactacaaga   1620
cccgcgccga ggtgaagttc gagggcgaca ccctggtgaa ccgcatcgag ctgaagggca   1680
tcgacttcaa ggaggacggc aacatcctgg ggcacaagct ggagtacaac tacaacagcc   1740
acaacgtcta tatcatggcc gacaagcaga agaacggcat caaggtgaac ttcaagatcc   1800
gccacaacat cgaggacggc agcgtgcagc tcgccgacca ctaccagcag aacaccccca   1860
tcggcgacgg ccccgtgctg ctgcccgaca ccactacct gagctaccag tccgccctga   1920
gcaaagaccc caacgagaag cgcgatcaca tggtcctgct ggagttcgtg accgccgccg   1980
ggatcactct cggcatggac gagctgtaca agtaa                              2015

<210> SEQ ID NO 38
<211> LENGTH: 2231
<212> TYPE: DNA
<213> ORGANISM: Artificial Sequence
<220> FEATURE:
<223> OTHER INFORMATION: Synthetic

<400> SEQUENCE: 38
aaggtcgggc aggaagaggg cctatttccc atgattcctt catatttgca tatacgatac     60
aaggctgtta gagagataat tagaattaat ttgactgtaa acacaaagat attagtacaa    120
aatacgtgac gtagaaagta ataatttctt gggtagtttg cagttttaaa attatgtttt    180
aaaatggact atcatatgct taccgtaact tgaaagtatt tcgatttctt ggctttatat    240
atcttgtgga aaggacgaaa caccgggcac gggcagcttg ccgggtttta gagctagaaa    300
tagcaagtta aaataaggct agtccgttat caacttgaaa aagtggcacc gagtcggtgc    360 ttttttttaag cttgggccgc tcgagcgcgt taacaccggt gggcacgggc agcttgccgg    420
gttttagagc tagaaatagc aagttaaaat aaggctagtc cgttatcaac ttgaaaaagt    480
ggcaccgagt cggtgctttt tttaaacacc gggcacgggc agcttgccgg gttttagagc    540
tagaaatagc aagttaaaat aaggctagtc cgttatcaac ttgaaaaagt ggcaccgagt    600
cggtgctttt tttccgggca cgggcagctt gccgggtttt agagctagaa atagcaagtt    660
aaaataaggc tagtccgtta tcaacttgaa aaagtggcac cgagtcggtg cttttttta    720 acaccgggca cgggcagctt gccgggtttt agagctagaa atagcaagtt aaaataaggc    780
tagtccgtta tcaacttgaa aaagtggcac cgagtcggtg cttttttta cgggcacggg    840 cagcttgccg gttttagag ctagaaatag caagttaaaa taaggctagt ccgttatcaa    900
cttgaaaaag tggcaccgag tcggtgcttt ttaaacac cgggcacggg cagcttgccg      960
ggttttagag ctagaaatag caagttaaaa taaggctagt ccgttatcaa cttgaaaaag   1020
tggcaccgag tcggtgcttt ttttgggccc agcttcgata aaataaaaga tttttatttag  1080
```

```
tctccagaaa aagggggaa tgaaagaccc cacctgtagg tttggcaagc tagcttaagt     1140
aacgccattt tgcaaggcat ggaaaataca taactgagaa tagagaagtt cagatcaagg    1200
ttaggaacag agagacagca gaatatgggc caaacaggat atctgtggta agcagttcct   1260
gccccggctc agggccaaga acagatggtc cccagatgcg gtcccgccct cagcagtttc   1320
tagagaacca tcagatgttt ccagggtgcc ccaaggacct gaaaatgacc ctgtgcctta   1380
tttgaactaa ccaatcagtt cgcttctcgc ttctgttcgc gcgcttctgc tccccgagct   1440
caataaaaga gcccacaacc cctcactcgg cgcgccagtc ctccgataga ctgcgtcgcc   1500
cggtcgccac catggtgagc aagggcgagg agctgttcac cggggtggtg cccatcctgg   1560
tcgagctgga cggcgacgta aacggccaca agttcagcgt gtccggcgag ggcgagggcg   1620
atgccaccta cggcaagctg accctgaagt tcatctgcac aacaggaaag ctgcctgtgc   1680
catggcccac cctcgtgacc accttcggct acggcctgca gtgcttcgcc cgctaccccg   1740
accacatgaa gcagcacgac ttcttcaagt ccgccatgcc cgaaggctac gtccaggagc   1800
gcaccatctt cttcaaggac gacggcaact acaagacccg cgccgaggtg aagttcgagg   1860
gcgacaccct ggtgaaccgc atcgagctga agggcatcga cttcaaggag gacggcaaca   1920
tcctggggca caagctggag tacaactaca acagccacaa cgtctatatc atggccgaca   1980
agcagaagaa cggcatcaag gtgaacttca gatccgcca caacatcgag gacggcagcg   2040
tgcagctcgc cgaccactac cagcagaaca ccccccatcgg cgacggcccc gtgctgctgc   2100
ccgacaacca ctacctgagc taccagtccg ccctgagcaa agaccccaac gagaagcgcg   2160
atcacatggt cctgctggag ttcgtgaccg ccgccgggat cactctcggc atggacgagc   2220
tgtacaagta a                                                         2231
```

<210> SEQ ID NO 39  
<211> LENGTH: 2564  
<212> TYPE: DNA  
<213> ORGANISM: Artificial Sequence  
<220> FEATURE:  
<223> OTHER INFORMATION: Synthetic
<400> SEQUENCE: 39

```
aaggtcgggc aggaagaggg cctatttccc atgattcctt catatttgca tatacgatac     60
aaggctgtta gagagataat tagaattaat ttgactgtaa acacaaagat attagtacaa    120
aatacgtgac gtagaaagta ataatttctt gggtagtttg cagttttaaa attatgtttt    180
aaaatggact atcatatgct taccgtaact tgaaagtatt tcgatttctt ggctttatat    240
atcttgtgga aaggacgaaa caccgggcac gggcagcttg ccgggtttta gagctagaaa    300
tagcaagtta aaataaggct agtccgttat caacttgaaa aagtggcacc gagtcggtgc    360
tttttttaag cttgggccgc tcgagcgcgt taacaccggt gggcacgggc agcttgccgg    420
gttttagagc tagaaatagc aagttaaaat aaggctagtc cgttatcaac ttgaaaaagt    480
ggcaccgagt cggtgctttt tttaaacacc gggcacgggc agcttgccgg ttttagagc    540
tagaaatagc aagttaaaat aaggctagtc cgttatcaac ttgaaaaagt ggcaccgagt    600
cggtgctttt tttcctgcag gggcacgggc agcttgccgg ttttagagc tagaaatagc    660
aagttaaaat aaggctagtc cgttatcaac ttgaaaaagt ggcaccgagt cggtgctttt    720
tttaaacacc gggcacgggc agcttgccgg ttttagagc tagaaatagc aagttaaaat    780
aaggctagtc cgttatcaac ttgaaaaagt ggcaccgagt cggtgctttt tttaaacacc    840
gggcacgggc agcttgccgg ttttagagc tagaaatagc aagttaaaat aaggctagtc    900
```

```
cgttatcaac ttgaaaaagt ggcaccgagt cggtgctttt tttaccgcgg gcacgggcag    960
cttgccgggt tttagagcta gaaatagcaa gttaaaataa ggctagtccg ttatcaactt   1020
gaaaaagtgg caccgagtcg gtgcttttt  taaacaccgg gcacgggcag cttgccgggt   1080
tttagagcta gaaatagcaa gttaaaataa ggctagtccg ttatcaactt gaaaaagtgg   1140
caccgagtcg gtgcttttt  taccgggcac gggcagcttg ccgggtttta gagctagaaa   1200
tagcaagtta aaataaggct agtccgttat caacttgaaa aagtggcacc gagtcggtgc   1260 ttttttaaa  caccgggcac gggcagcttg ccgggtttta gagctagaaa tagcaagtta   1320
aaataaggct agtccgttat caacttgaaa aagtggcacc gagtcggtgc ttttttggg    1380 cccagcttcg ataaaataaa agattttatt tagtctccag aaaaaggggg gaatgaaaga   1440
ccccacctgt aggtttggca agctagctta agtaacgcca ttttgcaagg catggaaaat   1500
acataactga gaatagagaa gttcagatca aggttaggaa cagagagaca gcagaatatg   1560
ggccaaacag gatatctgtg gtaagcagtt cctgccccgg ctcagggcca agaacagatg   1620
gtccccagat gcggtcccgc cctcagcagt ttctagagaa ccatcagatg tttccagggt   1680
gccccaagga cctgaaaatg accctgtgcc ttatttgaac taaccaatca gttcgcttct   1740
cgcttctgtt cgcgcgcttc tgctccccga gctcaataaa agagcccaca cccctcact   1800 cggcgcgcca gtcctccgat agactgcgtc gcccggtcgc caccatggtg agcaagggcg   1860
aggagctgtt caccggggtg gtgcccatcc tggtcgagct ggacggcgac gtaaacggcc   1920
acaagttcag cgtgtccggc gagggcgagg gcgatgccac ctacggcaag ctgaccctga   1980
agttcatctg cacaacagga aagctgcctg tgccatggcc caccctcgtg accaccttcg   2040
gctacggcct gcagtgcttc gcccgctacc ccgaccacat gaagcagcac gacttcttca   2100
agtccgccat gcccgaaggc tacgtccagg agcgcaccat cttcttcaag gacgacggca   2160
actacaagac ccgcgccgag gtgaagttcg agggcgacac cctggtgaac cgcatcgagc   2220
tgaagggcat cgacttcaag gaggacggca acatcctggg gcacaagctg gagtacaact   2280
acaacagcca caacgtctat atcatggccg acaagcagaa gaacggcatc aaggtgaact   2340
tcaagatccg ccacaacatc gaggacggca gcgtgcagct cgccgaccac taccagcaga   2400
acacccccat cggcgacggc cccgtgctgc tgcccgacaa ccactacctg agctaccagt   2460
ccgccctgag caaagacccc aacgagaagc gcgatcacat ggtcctgctg gagttcgtga   2520
ccgccgccgg gatcactctc ggcatggacg agctgtacaa gtaa               2564
```

LENTIVIRAL PROTEIN DELIVERY SYSTEM FOR RNA-GUIDED GENOME EDITING

CROSS-REFERENCE TO RELATED APPLICATIONS

This patent application is a continuation-in-part of International Patent Application No. PCT/US2016/054759, filed Sep. 30, 2016, which claims the benefit of U.S. Provisional Patent Application No. 62/236,223, filed Oct. 2, 2015, each of which is incorporated herein by reference in its entirety.

STATEMENT REGARDING FEDERALLY SPONSORED RESEARCH AND DEVELOPMENT

This invention was made with Government support under project number Z01HL006008 by the National Institutes of Health, National Heart, Lung and Blood Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 278,050 Byte ASCII (Text) file named "738712_ST25.txt," created on Mar. 28, 2018.

BACKGROUND OF THE INVENTION

Gene correction is an attractive gene therapy strategy for hereditary diseases, particularly diseases caused by a defect in a single gene such as sickle cell disease. Recently, new technologies for targeted genome editing have been developed, including designer zinc fingers (ZFs) (see, e.g., Sander et al., Nat. Methods, 8: 67 (2011); and Wood et al., Science, 333: 307 (2011)), transcription activator-like effectors (TALEs) (see, e.g., Zhang et al., Nat. Biotechnol., 29: 149 (2011); and Reyon et al., Nat. Biotechnol., 30: 460 (2012)), and homing meganucleases (see, e.g., Stoddard, Q., Rev. Biophys., 38: 49 (2005); Popplewell et al., Human Gene Ther., 24: 692-701 (2013); and Cai et al., eLife, 3: e01911 (2014)). Many of these approaches, however, are time consuming, costly, and suffer from limited precision, which can lead to unpredictable off-target effects.

Target-specific gene correction strategies based on the bacterial CRISPR (clustered regularly interspaced short palindromic repeats)/CRISPR-associated (Cas) system have been developed (see, e.g., Cong et al., Science, 339: 819-823 (2013); Xiao-Jie et al., J. Med. Genet., 52(5): 289-96 (2015); U.S. Pat. No. 8,697,359; Xie et al., Genome Res., 24(9): 1526-1533 (2014); Huang et al., Stem Cells, 33(5): 1470-1479 (2015); Smith et al., Molecular Therapy, 23(3): 570-577 (2015); and U.S. Patent Application Publication 2014/0068797). In bacteria and archaea, CRISPR-Cas systems provide immunity by incorporating fragments of invading phage and plasmid DNA into CRISPR loci and using the corresponding CRISPR RNAs (crRNAs) to guide the degradation of homologous sequences (Mali et al., Nat. Methods, 10(10): 957-963 (2013); and Terns M P and Terns R M., Curr. Opin. Microbiol.; 14: 321-327 (2011)). Gene editing using CRISPR/Cas9 technology in eukaryotic cells is in its infancy, however, and further development and refinement of the technology is necessary in order to realize the full therapeutic potential of CRISPR/Cas9.

There remains a need for more efficient, affordable, and rapid systems and methods that enable precise targeting and modification of nucleic acid sequences in eukaryotic cells. The invention provides such systems and methods.

BRIEF SUMMARY OF THE INVENTION

In an embodiment, the invention provides a system comprising (a) a lentivirus vector particle comprising a lentiviral genome which encodes at least one guide RNA sequence that is complementary to a first DNA sequence in a host cell genome, (b) a Cas9 protein, and optionally (c) a donor nucleic acid molecule comprising a second DNA sequence. In addition, the invention provides a host cell comprising the foregoing system, as well as a method of altering a DNA sequence in a host cell comprising contacting a host cell with the foregoing system.

In an embodiment, the present invention provides a system comprising: (a) a lentivirus vector particle comprising a lentiviral genome which encodes at least two guide RNA sequences that are each complementary to a first DNA sequence in a host cell genome, (b) a Cas9 protein, and optionally (c) a donor nucleic acid molecule comprising a second DNA sequence.

In an embodiment, the invention also provides a fusion protein comprising a Cas9 protein and a cyclophilin A (CypA) protein, wherein the fusion protein binds to a lentivirus vector particle. In addition, the invention provides a lentiviral vector particle comprising such a fusion protein.

In an embodiment, the invention also is directed to sequences of vectors that can be used in the system and method.

BRIEF DESCRIPTION OF THE SEVERAL VIEWS OF THE DRAWING(S)

FIG. 1 is a schematic diagram illustrating the lentiviral vector constructs described in Example 1, in accordance with embodiments of the invention.

FIG. 2 is a graph depicting experimental results illustrating % GFP in cells transduced with the lentiviral vectors described in Example 1 which encode both guide RNA specific for green fluorescent protein (GFP) and Cas9 endonuclease, in accordance with embodiments of the invention. The data shown is 12 days after lentiviral transduction (multiplicity of infection (MOI)=5) in GFP+HEL cells (**p<0.01 evaluated by Dunnett's test).

FIG. 3 is a schematic diagram illustrating the YFP template vector construct described in Example 1, in accordance with embodiments of the invention.

FIG. 4 is a graph depicting experimental results illustrating % GFP or % YFP in cells transduced with a donor nucleic acid sequence encoding YFP following induction of double strand breaks by the lentiviral vectors described in Example 1, in accordance with embodiments of the invention (top bar: GFP+YFP−; middle bar, when present: GFP+YFP+; bottom bar: GFP−YFP+). The data shown is 9 days after non-integrating vector transduction (template) in GFP+HEL cells with lentiviral transduction (guide RNA/Cas9) (**p<0.01, *p<0.05 evaluated by Dunnett's test).

Figure 8:
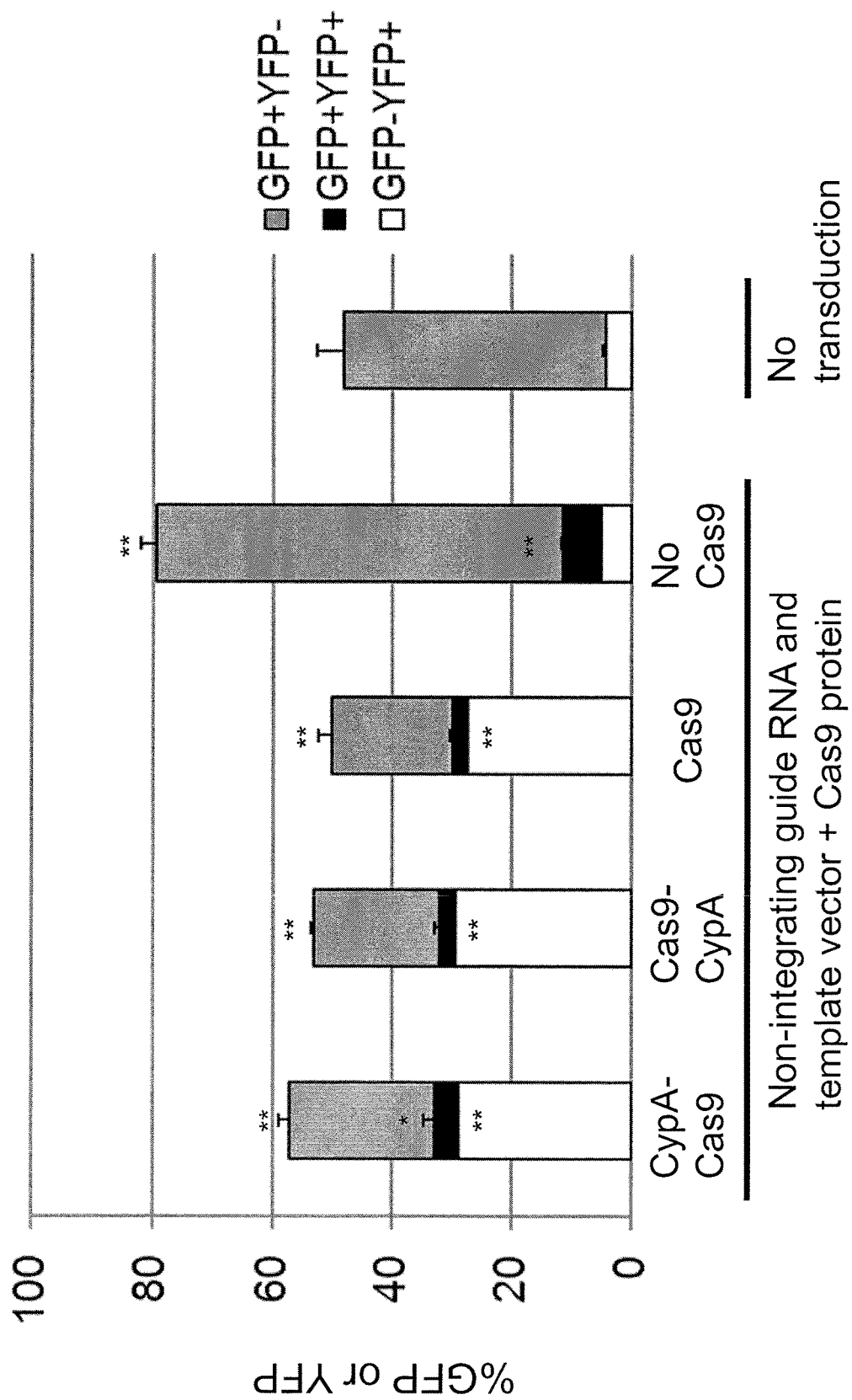

FIG. 8 is a graph depicting experimental results illustrating % GFP or % YFP in cells modified with a donor nucleic acid sequence encoding YFP following induction of double strand breaks by the non-integrating lentiviral vectors described in Example 3, in accordance with embodiments of the invention (top bar: GFP+YFP−; middle bar, when present: GFP+YFP+; bottom bar: GFP−YFP+). The data shown is 15 days after non-integrating vector transduction (MOI=5) in GFP+HEL cells (**p<0.01, *p<0.05 evaluated by Dunnett's test).

FIGS. 9A and 9B are schematic diagrams illustrating the lentiviral vector constructs described in Example 4, in accordance with embodiments of the invention.

Figure 10:
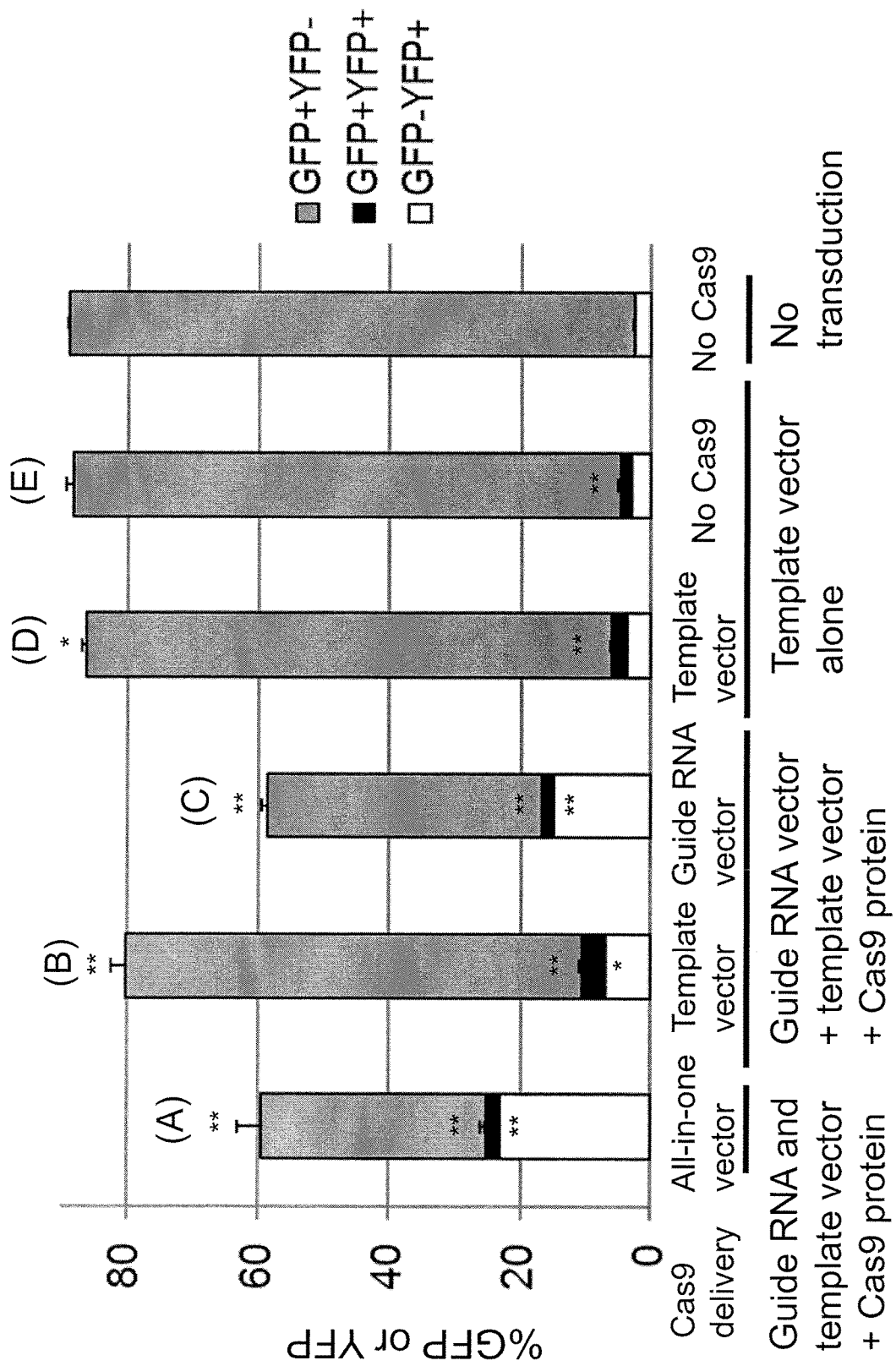

FIG. 10 is a graph depicting experimental results illustrating % GFP or % YFP in cells transduced with vectors described in Example 4, in accordance with embodiments of the invention (top bar: GFP+YFP−; middle bar, when present: GFP+YFP+; bottom bar: GFP−YFP+). The data shown is 9 days after non-integrating vector transduction (MOI=5) in GFP+HEL cells (**p<0.01, *p<0.05 evaluated by Dunnett's test).

Figure 11:
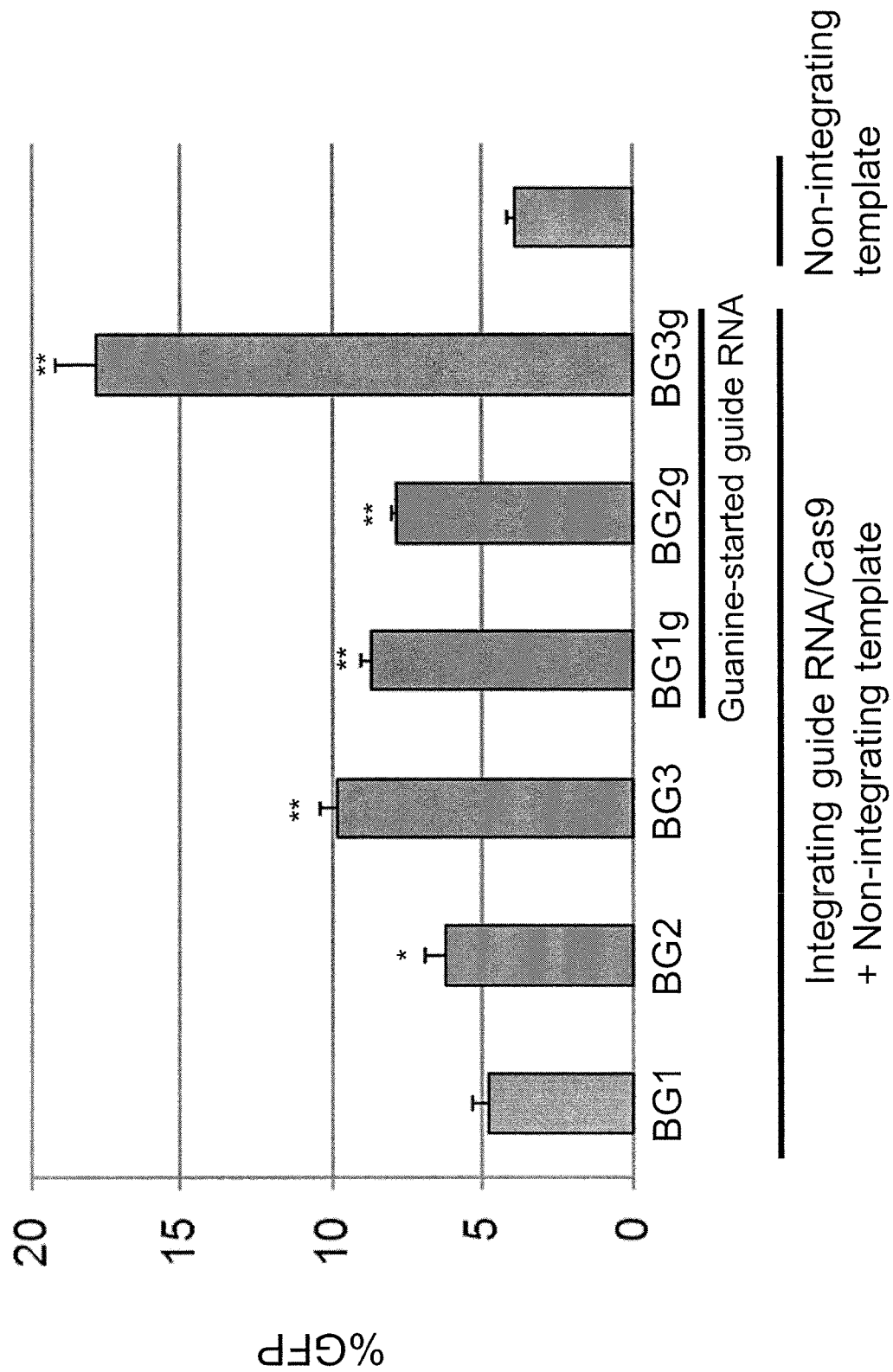

FIG. 11 is a graph depicting experimental results illustrating % GFP in cells transduced with vectors described in Example 5, in accordance with embodiments of the invention. The data shown is 11 days after transduction (MOI=5) in K562 cells (**p<0.01, *p<0.05 evaluated by Dunnett's test).

FIG. 12 is a schematic diagram illustrating the lentiviral vector constructs described in Example 5, in accordance with embodiments of the invention. Both templates contain a chimeric gene of GFP and Sh ble gene (GFP/Zeo). The first template contains no polyadenylation signal, which allows for GFP/Zeo expression in the corrected gene but not in the vector. The second template contains a polyadenylation signal, which allows for GFP/Zeo expression in both vector and corrected gene. In addition, the second template vector may have lower viral titers since a polyadenylation signal can interfere with viral genomic RNA production. For vector (a), the GFP/Zeo signals are produced by the corrected gene (with recombination in β-globin gene); the GFP-positive cells can be selected by Zeocin treatment; and the GFP/Zeo expression cassette can be removed by a Cre recombinase. For vector (b), the GFP/Zeo signals are produced by vector (without recombination) and corrected gene (with recombination); the GFP-positive cells can be selected by Zeocin treatment; and the GFP/Zeo expression cassette can be removed by a Cre recombinase. LoxP: Locus of Crossover in P1; GFP/Zeo: chimeric DNA of GFP and Sh ble gene; P: spleen focus forming virus promoter; pA: simian virus 40 polyadenylation signal.

FIG. 13 is a graph depicting experimental results illustrating % GFP in cells transduced with vectors described in Example 5, in accordance with embodiments of the invention. The data shown is 5 days after transduction (MOI=5) in K562 cells (**p<0.01 evaluated by Dunnett's test).

FIGS. 14A and 14B are schematic diagrams illustrating the lentiviral vector constructs described in Example 6, in accordance with embodiments of the invention.

Figure 15:
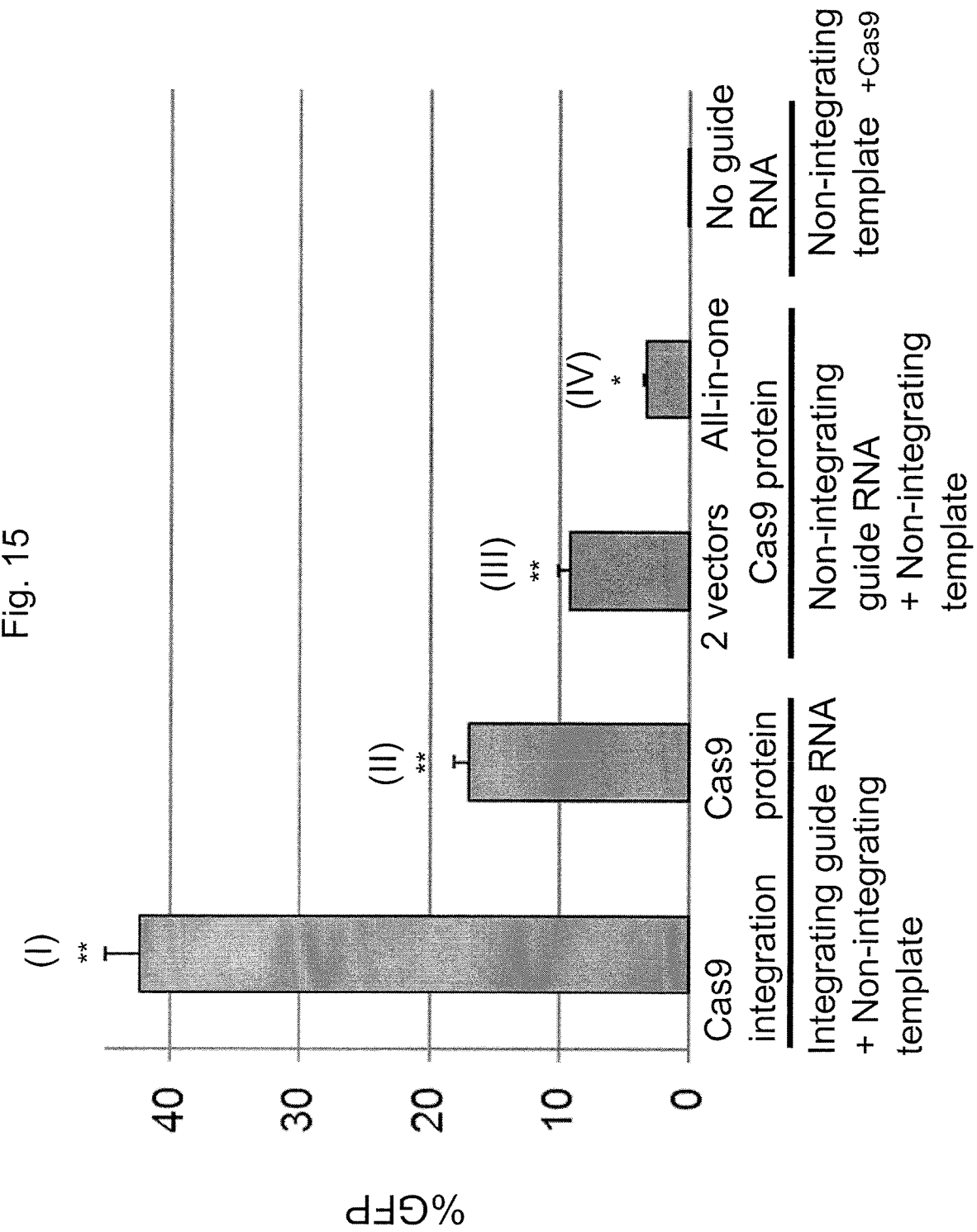

FIG. 15 is a graph depicting experimental results illustrating % GFP in cells transduced with vectors described in Example 6, in accordance with embodiments of the invention. The data shown is 7 days after transduction (MOI=5) in K562 cells (**p<0.01, *p<0.05 evaluated by Dunnett's test).

FIGS. 16A and 16B present schematic diagrams illustrating the lentiviral vector constructs described in Example 7, in accordance with embodiments of the invention.

Figure 17:
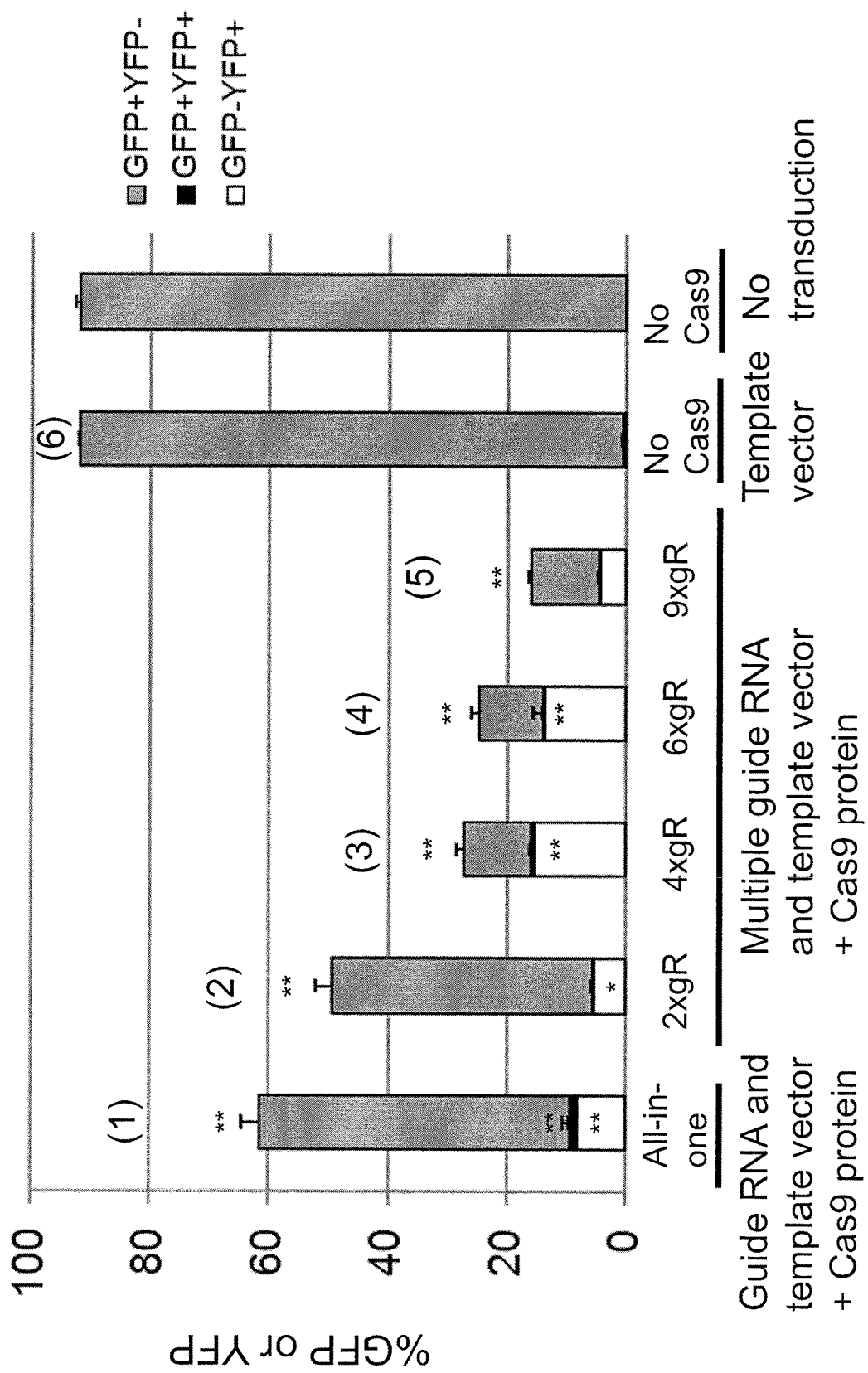
Figure 18:
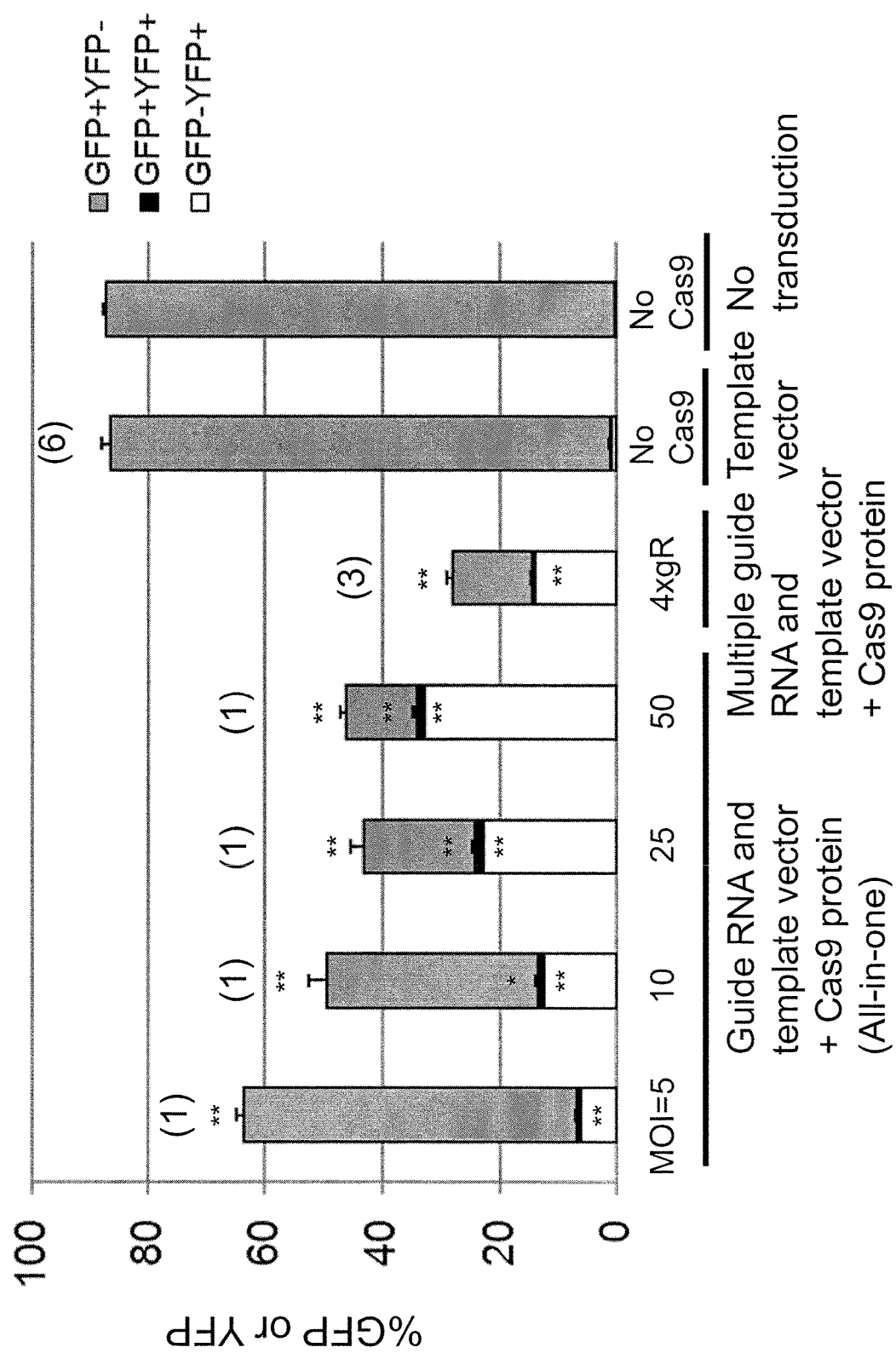

FIGS. 17 and 18 are graphs depicting experimental results illustrating % GFP or YFP in cells transduced with vectors described in Example 7, in accordance with embodiments of the invention.

DETAILED DESCRIPTION OF THE INVENTION

The invention is predicated, in part, on the discovery that CRISPR/Cas9 gene editing can be achieved using a vector that does not encode the Cas9 protein as part of its genome, rather, gene editing can be performed using a lentivirus vector particle physically associated to the Cas9 protein, either alone or as part of a fusion protein.

The invention provides a system comprising (a) a lentivirus vector particle comprising a lentiviral genome which encodes at least one guide RNA sequence that is complementary to a first DNA sequence in a host cell genome, (b) a Cas9 protein, and optionally (c) a donor nucleic acid molecule comprising a second DNA sequence.

Lentiviruses are a subclass of Retroviruses. Lentiviruses resemble γ-retroviruses (γ-RV) in their ability to stably integrate into the target cell genome, resulting in persistent expression of the gene of interest. However, in contrast to γ-retroviruses, lentiviruses also can transduce nondividing cells, which has led to their wide use as gene transfer vectors. The lentivirus genome is monopartite, linear, dimeric, positive-strand single-stranded RNA ("ssRNA(+)") of 9.75 kb, with a 5'-cap and a 3'poly-A tail. The lentiviral genome is flanked by the 5' and 3' long terminal repeat (LTR) sequences which have promoter/enhancer activity and are essential for the correct expression of the full-length lentiviral vector transcript. The LTRs also have an important role in reverse transcription and integration of the vector into the target cell genome. Upon viral entry into a cell, the RNA genome is reverse-transcribed into double-stranded DNA, which is then inserted into the genome at a random position by the viral integrase enzyme. The lentivirus, now called a provirus, remains in the genome and is passed on to the progeny of the cell when it divides. Species of lentivirus include, for example, human immunodeficiency virus 1 (HIV-1), human immunodeficiency virus 2 (HIV-2), simian immunodeficiency virus (SIV), bovine immunodeficiency virus (BIV), and feline immunodeficiency virus (FIV). The lentiviral vector of the invention can be based on any lentivirus species. Preferably, the lentiviral vector is based on a human immunodeficiency virus (e.g., HIV-1 or HIV-2), most preferably HIV-1.

Lentiviral vectors typically are generated by trans-complementation in packaging cells that are co-transfected with a plasmid containing the vector genome and the packaging constructs that encode only the proteins essential for lentiviral assembly and function. A self-inactivating (SIN) lentiviral vector can be generated by abolishing the intrinsic promoter/enhancer activity of the HIV-1 LTR, which reduces the likelihood of aberrant expression of cellular coding sequences located adjacent to the vector integration site (see, e.g., Vigna et al., J. Gene Med., 2: 308-316 (2000); Naldini et al., Science, 272: 263-267 (1996); and Mátrai et al., Molecular Therapy, 18(3): 477-490 (2010)). The most common procedure to generate lentiviral vectors is to cotransfect cell lines (e.g., 293T human embryonic kidney cells) with a lentiviral vector plasmid and three packaging constructs encoding the viral Gag-Pol, Rev-Tat, and envelope (Env) proteins. The lentiviral vector particle can integrate its genome into a host cell genome. In some applications, however, it may be desirable to avoid potential insertional mutagenesis induced by an integrating lentivirus vector. In such cases, the lentiviral vector particle does not integrate its genome into a host cell genome (also referred to as a "non-integrating" vector). Non-integrating lentiviral vectors typically are generated by mutating the lentiviral integrase gene or by modifying the attachment sequences of the LTRs (see, e.g., Sarkis et al., *Curr. Gene. Ther.,* 6: 430-437 (2008)).

CRISPR/Cas gene editing systems have been developed to enable targeted modifications to a specific gene of interest in eukaryotic cells. CRISPR/Cas gene editing systems are based on the RNA-guided Cas9 nuclease from the type II prokaryotic clustered regularly interspaced short palindromic repeats (CRISPR) adaptive immune system (see, e.g., Jinek et al., *Science,* 337: 816 (2012); Gasiunas et al., *Proc. Natl. Acad. Sci. U.S.A.,* 109, E2579 (2012); Garneau et al., *Nature,* 468: 67 (2010); Deveau et al., *Annu. Rev. Microbiol.,* 64: 475 (2010); Horvath and Barrangou, *Science,* 327: 167 (2010); Makarova et al., *Nat. Rev. Microbiol.,* 9, 467 (2011); Bhaya et al., *Annu. Rev. Genet.,* 45, 273 (2011); and Cong et al., *Science,* 339: 819-823 (2013)). In bacteria and archaea, CRISPR/Cas systems provide immunity by incorporating fragments of invading phage, virus, and plasmid DNA into CRISPR loci and using corresponding CRISPR RNAs ("crRNAs") to guide the degradation of homologous sequences. Each CRISPR locus encodes acquired "spacers" that are separated by repeat sequences. Transcription of a CRISPR locus produces a "pre-crRNA," which is processed to yield crRNAs containing spacer-repeat fragments that guide effector nuclease complexes to cleave dsDNA sequences complementary to the spacer.

The type II CRISPR locus comprises four genes, including the gene encoding the Cas9 protein, two noncoding crRNAs: trans-activating crRNA (tracrRNA) and a precursor crRNA (pre-crRNA) array containing nuclease guide sequences (also referred to as "spacers") interspaced by identical direct repeats (DRs) (Cong et al., supra). tracrRNA is important for processing the pre-crRNA and formation of the Cas9 complex. CRISPR-guided degradation of pathogenic sequences occurs in three steps. First, tracrRNAs hybridize to repeat regions of the pre-crRNA. Second, endogenous RNaseIII cleaves the hybridized crRNA-tracrRNAs, and a second event removes the 5' end of each spacer, yielding mature crRNAs that remain associated with both the tracrRNA and Cas9. Third, each mature complex locates a target double stranded DNA (dsDNA) sequence and cleaves both strands.

To engineer CRISPR/Cas systems for use in eukaryotic cells, the crRNA-tracrRNA-Cas9 complex must be reconstituted. For use in human cells, for example, the Cas9 amino acid sequence is codon-optimized and modified to include an appropriate nuclear localization signal, and the crRNA and tracrRNA sequences are expressed individually or as a single chimeric molecule via an RNA polymerase II promoter. Typically, the crRNA and tracrRNA sequences are expressed as a chimera, and are referred to collectively as "guide RNA" (gRNA) or single guide RNA (sgRNA). In CRISPR/Cas9 systems, the guide RNA contains a 20 nucleotide guide sequence followed by a trinucleotide (5'-NGG-3') protospacer adjacent motif (PAM) that directs Cas9 via Watson-Crick base pairing to a target sequence (Deveau et al., *Annu. Rev. Microbiol.,* 64: 475-493 (2010); Jinek et al., *Science,* 337: 816-821 (2012); and Xie et al., *Genome Res.,* 24(9): 1526-1533 (2014)).

Any suitable CRISPR/Cas system can be used in the context of the invention. The term "CRISPR/Cas system," as used herein, generally refers collectively to transcripts and other elements involved in the expression of or directing the activity of CRISPR-associated ("Cas") genes, including nucleic acid sequences encoding a Cas protein (e.g., Cas9), a trans-activating CRISPR ("tracr") sequence (e.g. tracrRNA), a guide RNA sequence (also referred to as a "spacer" in the context of an endogenous CRISPR system), or other nucleic acid sequences and transcripts from a CRISPR locus. In some embodiments, one or more elements of a CRISPR/Cas system is derived from a type I, type II, or type III CRISPR system.

A CRISPR/Cas system is characterized by elements that promote the formation of a CRISPR complex at the site of a target sequence (also referred to as a protospacer in the context of an endogenous CRISPR system). The term "target sequence," as used herein, refers to a nucleic acid sequence in a host cell to which a guide sequence (e.g., a guide RNA) is designed to have complementarity, wherein hybridization between the target sequence and a guide sequence promotes the formation of a CRISPR complex. The target sequence and guide sequence need not exhibit complete complementarity, provided that there is sufficient complementarity to cause hybridization and promote formation of a CRISPR complex. A target sequence may comprise any polynucleotide, such as DNA or RNA. In an embodiment of the invention, the target sequence is a first DNA sequence in a host cell genome, and the lentivirus vector particle of the inventive system comprises a lentiviral genome which encodes at least one guide RNA sequence that is complementary to a first DNA sequence (i.e., target sequence) in a host cell genome.

The terms "complementary" and "complementarity" refer to the ability of a nucleic acid to form hydrogen bond(s) with another nucleic acid sequence by either traditional Watson-Crick base-paring or other non-traditional types of pairing. The degree of complementarity between two nucleic acid sequences can be indicated by the percentage of nucleotides in a nucleic acid sequence which can form hydrogen bonds (e.g., Watson-Crick base pairing) with a second nucleic acid sequence (e.g., 50%, 60%, 70%, 80%, 90%, and 100% complementary). Two nucleic acid sequences are "perfectly complementary" if all the contiguous nucleotides of a nucleic acid sequence will hydrogen bond with the same number of contiguous nucleotides in a second nucleic acid sequence. Two nucleic acid sequences are "substantially complementary" if the degree of complementarity between the two nucleic acid sequences is at least 60% (e.g., 65%, 70%, 75%, 80%, 85%, 90%, 95%. 97%, 98%, 99%, or 100%) over a region of at least 8 nucleotides (e.g., 9, 10, 11, 12, 13, 14, 15, 16, 17, 18, 19, 20, 21, 22, 23, 24, 25, 30, 35, 40, 45, 50, or more nucleotides), or if the two nucleic acid sequences hybridize under at least moderate, preferably high, stringency conditions. Exemplary moderate stringency conditions include overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C., or substantially similar conditions, e.g., the moderately stringent conditions described in Sambrook et al., infra. High stringency conditions are conditions that use, for example (1) low ionic strength and high temperature for washing, such as 0.015 M sodium chloride/0.0015 M sodium citrate/0.1% sodium dodecyl sulfate (SDS) at 50° C., (2) employ a denaturing agent during hybridization, such as formamide, for example, 50% (v/v) formamide with 0.1% bovine serum albumin (BSA)/0.1% Ficoll/0.1% polyvinylpyrrolidone (PVP)/50 mM sodium phosphate buffer at pH 6.5 with 750 mM sodium chloride and 75 mM sodium citrate at 42° C., or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at (i) 42° C. in 0.2×SSC, (ii) 55° C. in 50% formamide, and (iii) 55° C. in 0.1×SSC (preferably in combination with EDTA). Additional details and an explanation of stringency of hybridization reactions are provided in, e.g., Sambrook et al., *Molecular Cloning: A Laboratory Manual*, 3$^{rd}$ ed., Cold Spring Harbor Press, Cold Spring Harbor, N.Y. (2001); and Ausubel et al., *Current Protocols in Molecular Biology, Greene Publishing Associates and* John Wiley & Sons, *New York* (1994).

In one embodiment, the inventive system comprises a lentivirus vector particle comprising a lentiviral genome which encodes at least one guide RNA sequence that is complementary to a first DNA sequence in a host cell genome. As discussed above, the "first DNA sequence" in a host cell functions as the target sequence to which the guide RNA sequence binds, promoting the formation of a CRISPR complex at the site of the first DNA sequence. The terms "guide RNA," "single guide RNA," and "synthetic guide RNA," are used interchangeably herein and refer to a nucleic acid sequence comprising a tracrRNA and a pre-crRNA array containing a guide sequence. The terms "guide sequence," "guide," and "spacer," are used interchangeably herein and refer to the about 20 nucleotide sequence within a guide RNA that specifies the target site.

In an embodiment, the present invention provides a system comprising: (a) a lentivirus vector particle comprising a lentiviral genome which encodes at least two guide RNA sequences that are each complementary to a first DNA sequence in a host cell genome, (b) a Cas9 protein, and optionally (c) a donor nucleic acid molecule comprising a second DNA sequence. In an embodiment, the lentiviral genome encodes 2-20 guide RNA sequences. In an embodiment, the lentiviral genome encodes 1, 2, 3, 4, 5, 6, 7, 8, 9, 10, 11, 12, 13, 14, 15, 16, 17, 18, 19, or 20 guide RNA sequences.

Without wishing to be limited by theory, it is believed that the additional guide RNAs provide for greater delivery of Cas9 through binding the guide RNAs, which results in an increase of the delivery of the Cas9 protein and thus an increase in the efficiency of Cas9, resulting in a strong increase of DNA breakage and a slight increase in gene correction. To improve gene correction, more DNA template can be added to improve gene correction, which can be achieved by increasing the amount of vector, e.g., by 2-, 3-, 4-, 5-, 6-, 7-, 8-, 9-, or 10-fold.

In an embodiment, the inventive system also comprises a Cas protein. Any suitable Cas protein (or homolog or modified version thereof) can be included in the inventive system. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. Cas protein families are described in further detail in, e.g., Haft et al., *PLoS Comput. Biol.*, 1(6): e60 (2005). In one embodiment, the Cas protein is a Cas9 protein. The Cas9 protein can be obtained from any suitable microorganism, but preferably is obtained from *S. pyogenes* or *S. pneumonia*. The Cas9 protein is further described in, e.g., Mali et al., *Nat Methods*, 10(10): 957-963 (2013), and the amino acid sequence of the Cas9 protein is available through the UniProt database (Accession No. Q99ZW2) and provided herein as SEQ ID NO: 1.

The Cas9 protein can be included in the system separate from, associated with, or encoded by, the lentivirus vector particle. When the Cas9 protein is included in the system separate from the lentiviral vector particle, preferably it is included in a single composition (e.g., a pharmaceutical composition) with the lentiviral vector particle and is not physically or chemically bound to the lentiviral vector. The Cas9 protein is "associated" with the lentiviral vector if it is physically or chemically linked or bound to the lentiviral vector particle, such that a complex between the Cas9 protein and lentiviral vector particle is formed. The Cas9 protein can be associated with the lentiviral vector particle using any suitable method for protein-protein linking or protein-virus linking known in the art. Preferably, the Cas9 protein is associated with a capsid protein of the lentivirus vector particle. In another embodiment, the Cas9 protein can be packaged into the lentivirus vector particle. Alternatively, the Cas9 protein can be provided in the inventive system as a fusion protein with a second protein that can bind to a lentivirus vector particle. In this regard, for example, the Cas9 protein can be provided as a fusion protein comprising a Cas9 protein and a cyclophilin A (CypA) protein. CypA is a ubiquitously expressed protein belonging to the immunophilin family. CypA has peptidyl prolyl cis-trans isomerase (PPIase) activity, and is believed to play important roles in many biological conditions including protein folding, trafficking, and T-cell activation (Nigro et al., *Cell Death and Disease*, 4: e888; doi:10.1038/cddis.2013.410 (2013)). CypA also has been shown to bind to capsid proteins of several viruses, including lentiviruses (see, e.g., Luban et al., *Cell*, 73(6): 1067-1078 (1993); Qing et al., *PLoS Pathog.*, 10(10): e1004422 (2014); and He et al., *Gene Therapy*, 21: 759-766 (2014); and Mascarenhas and Musier-Forsyth, *FEBS J.*, 276(21): 6118-27 (2009)). As such, the Cas9-CypA fusion protein binds to a capsid protein of the lentivirus vector particle via the CypA portion of the fusion protein. The Cas9-CypA fusion protein can be produced using routine molecular biology techniques, such as those described in He et al., supra. Moreover, the fusion protein can be generated with the Cas9 and CypA proteins in any suitable orientation, i.e., CypA to Cas9 or Cas9 to CypA. An amino acid sequence of a CypA-Cas9 fusion protein suitable for use in the inventive system comprises, for example, SEQ ID NO: 2, while an amino acid sequence of a Cas9-CypA fusion protein suitable for use in the inventive system comprises, for example, SEQ ID NO: 3.

In another embodiment, the Cas9 protein can be encoded by the lentivirus vector. In this regard, the lentivirus vector comprises a nucleic acid sequence integrated into its genome that encodes the Cas9 protein. The lentivirus vector of the inventive system can be engineered to incorporate an exogenous nucleic acid sequence (e.g., a transgene), using routine molecular biology techniques known in the art, such as those described herein with respect to lentiviral vector generations, and in, e.g., Logan et al., *Curr. Opin. Biotechnol.*, 13(5): 429-36 (2002).

CRISPR/Cas technology has been used in the art as an efficient method for introducing mutations into a variety of eukaryotic cells, including yeast, mouse, human, roundworms, silkworms, fruit flies, zebrafish, frogs, mice, rats, rabbits, rice, wheat, sorghum, tobacco, and thale cress (see, e.g., Sander and Joung, *Nat. Biotechnol.*, 32(4): 347-355 (2014)). Any element of any suitable CRISPR/Cas gene editing system known in the art can be incorporated into the inventive system, particularly as part of the lentiviral vector particle, as appropriate. CRISPR/Cas gene editing technology is described in detail in, for example, Cong et al., supra; Xie et al., supra; U.S. Patent Application Publication 2014/0068797; U.S. Pat. Nos. 8,697,359; 8,771,945; and 8,945,839. Lentiviral vectors have been employed to deliver elements of the CRISPR/Cas system to eukaryotic cells (see, e.g., Kabadi et al., *Nucleic Acids Res.*, 42(19): e147 (2014); and Abrahimi et al., *Circulation Res.*, pii: CIRCRESAHA.115.306290 (2015) [Epub ahead of print]).

The inventive system optionally comprises a donor nucleic acid molecule which comprises a second DNA sequence. The donor nucleic acid molecule can be incorporated into the lentiviral genome, or alternatively, the donor nucleic acid sequence can be included in the inventive system as a separate molecule distinct from the lentiviral vector particle and the Cas9 protein (e.g., on a plasmid). In one embodiment, the second DNA sequence of the donor nucleic acid molecule is different from the first DNA sequence. In this respect, the first DNA sequence can comprise one or more mutations (e.g., deletion or insertion of one more nucleotides), the expression of which produces a defective protein product, and the second DNA sequence encodes a wild-type version of the defective protein. The term "wild-type," as used herein, refers to an organism, strain, gene, protein, or characteristic that prevails among individuals in nature and is distinct from an atypical mutant or variant form. The term "defective protein," as used herein, refers to a protein whose function has been obliterated or impaired (e.g., such that the function of the protein is reduced by at least about 2-fold, 5-fold, 10-fold, 20-fold, 30-fold, or 50-fold). In another embodiment, the first DNA sequence can encode an entirely different protein than the second DNA sequence of the donor nucleic acid molecule.

The first DNA sequence and second DNA can encode defective and corresponding wild-type versions, respectively, of any suitable protein. In one embodiment, the first DNA sequence can comprise a gene, the mutation of which causes a particular disease (i.e., "single-gene" or "monogenic" disorders). There are more than 6,000 known monogenic diseases, which occur in about 1 out of every 200 births. Examples of genes responsible for monogenic disorders include, but are not limited to, adenosine deaminase, α-1 antitrypsin, cystic fibrosis transmembrane conductance regulator (CFTR), β-hemoglobin (HBB), oculocutaneous albinism II (OCA2), Huntingtin (HTT), dystrophia myotonica-protein kinase (DMPK), low-density lipoprotein receptor (LDLR), apolipoprotein B (APOB), neurofibromin 1 (NF1), polycystic kidney disease 1 (PKD1), polycystic kidney disease 2 (PKD2), coagulation factor VIII (F8), dystrophin (DMD), phosphate-regulating endopeptidase homologue, X-linked (PHEX), methyl-CpG-binding protein 2 (MECP2), and ubiquitin-specific peptidase 9Y, Y-linked (USP9Y). Other single gene or monogenic diseases are known in the art and described in, e.g, Chial, H. Rare Genetic Disorders: Learning About Genetic Disease Through Gene Mapping, SNPs, and Microarray Data. Nature Education 1(1):192 (2008); Online Mendelian Inheritance in Man (OMIM) (www.ncbi.nim.nih.gov/entrez/query.fcgi?db=OMIM); and the Human Gene Mutation Database (HGMD) (www.hgmd.cf.ac.uk). In another embodiment, the first DNA sequence can comprise a gene, the mutation of which contributes to a particular disease in combination with mutations in other genes. Diseases caused by the contribution of multiple genes which lack simple (i.e., Mendelian) inheritance patterns are referred to in the art as a "multifactorial" or "polygenic" disease. Examples of multifactorial or polygenic diseases include, but are not limited to, asthma, diabetes, epilepsy, hypertension, bipolar disorder, and schizophrenia. Certain developmental abnormalities also can be inherited in a multifactorial or polygenic pattern and include, for example, cleft lip/palate, congenital heart defects, and neural tube defects.

In one embodiment, the first DNA sequence encodes a defective human β-globin protein and the second DNA sequence encodes a wild-type human β-globin protein. The human β-globin protein (also referred to herein as HBB or β-globin) is 146 amino acids long and has a molecular weight of 15,867 Da. β-globin, together with the human α-globin protein, make up hemoglobin A, which is the most common form of hemoglobin in adult humans. Hemoglobin A (HbA) comprises over 97% of the total red blood cell hemoglobin, and consists of two α-globin chains and two β-globin chains.

More than 1000 natural variants of the β-globin gene have been identified. A single point mutation in the β-globin (HBB) gene leads to sickle cell disease. This mutation results in the production of an abnormal version of β-globin called hemoglobin S (HbS). In sickle cell disease, hemoglobin S replaces both β-globin subunits in hemoglobin. The point mutation results in replacement of a GAG codon with GTG, which substitutes a glutamic acid residue with a valine residue at position 6 in the β-globin protein. Replacing glutamic acid with valine causes the abnormal hemoglobin S subunits to stick together and form long, rigid molecules. The rigid hemoglobin S molecules bend red blood cells into a sickle, or crescent, shape. The sickle-shaped cells die prematurely, which can lead to sickle cell disease. The sickle-shaped cells also can block small blood vessels, causing pain and organ damage.

Thalassemia is an autosomal recessive disorder that is caused by mutations in the α-globin gene (α-thalassemia), the β-globin gene (β-thalassemia), or less commonly, the δ-globin gene (δ-thalassemia). Both α- and β-thalassemia can occur in two forms: thalassemia major or thalassemia minor. Inheritance of two mutant globin genes, one from each parent, results in thalassemia major. Inheritance of only one mutant globin gene from one parent results in thalassemia minor. Humans with thalassemia minor are carriers of the disease and typically do not exhibit disease symptoms.

More than 250 mutations in the β-globin gene have been found to cause β-thalassemia. Most of the mutations involve a change in a single nucleotide within or near the β-globin gene. Other mutations insert or delete a small number of nucleotides in the HBB gene. β-globin gene mutations that decrease β-globin production result in a type of thalassemia called β-plus (B+) thalassemia. Mutations that prevent cells from producing any β-globin result in β-zero (B0) thalassemia. Without proper amounts of β-globin, sufficient hemoglobin cannot be formed. A lack of hemoglobin disrupts the normal development of red blood cells. Mutations in the β-globin gene can cause other abnormalities in β-globin, leading to other types of sickle cell disease or thalassemias.

In one embodiment, the first DNA sequence encodes a defective β-globin protein, such as any of the aforementioned defective β-globin proteins resulting from particular mutations in the β-globin gene. The second DNA sequence desirably encodes a wild-type human β-globin protein, or a human β-globin protein that is resistant to sickling (also referred to as an "anti-sickling" β-globin protein). Recombinant nucleic acid sequences encoding anti-sickling β-globin protein have been generated and can be used as the second DNA sequence in the inventive system (see, e.g., Romero et al., *J. Clin. Invest.*, 123(8): 3317-3330 (2013); Oh et al., *Exp. Hematol.*, 32(5): 461-469 (2004); Levasseur et al., *J. Biol. Chem.*, 279: 27518-27524 (2004); and U.S. Pat. No. 5,861,488). In addition, a human γ-globin resistant to sickling (Persons et al., *Blood*, 101(6): 2175-83 (2003); and Hargrove et al., *Mol. Ther.*, 16(3): 525-33 (2008)) can be used in the inventive lentiviral vector. The γ-globin genes (HBG1 and HBG2) are normally expressed in the fetal liver, spleen, and bone marrow. Two gamma chains together with two alpha chains constitute fetal hemoglobin (HbF), which is normally replaced by adult hemoglobin (HbA) at birth. HbF has been shown to protect against many of the complications of sickle-cell anemia (see, e.g., Steinberg, M. H. and Sebastiani P., *Am. J. Hematol.*, 87: 795-803 (2012)). Preferably, the nucleic acid sequence encodes a wild-type human β-globin protein or a wild-type human γ-globin protein. The wild-type nucleic acid sequence of the human β-globin gene locus is publicly available via the National Center for Biotechnology Information (NCBI) (NCBI Reference Sequence: NG_000007.3). SEQ ID NO: 4 provides the sequence for the human β-globin gene locus. SEQ ID NO: 5 provides the sequence for the human β-globin gene (HBB). The wild-type nucleic acid sequences of the human A-γ-globin gene (HBG1) and G-γ-globin gene (HBG2) also are publicly available via the NCBI (GenBank Accession No. NC_000011), and are disclosed in, e.g., Slighthom et al., *Cell*, 21(3): 627-38 (1980). SEQ ID NO: 6 provides the sequence for HBG1, and SEQ ID NO: 7 provides the sequence for HBG2.

The lentivirus vector particle of the inventive system preferably comprises expression control sequences, such as promoters, enhancers, polyadenylation signals, transcription terminators, internal ribosome entry sites (IRES), and the like, that provide for the expression of the guide RNA sequence and/or a nucleic acid sequence encoding the Cas9 protein (if included in the lentivirus vector genome). Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art and can be used in the invention. In one embodiment, an RNA Pol III promoter can be operatively linked to the guide RNA sequence and/or the nucleic acid sequence encoding the Cas9 protein (if included in the lentivirus vector) to control expression of such sequences. RNA Pol III promoters are frequently used to express small RNAs, such as small interfering RNA (siRNA)/short hairpin RNA (shRNA) and guide RNA sequences used in CRISPR-Cas9 systems (see, e.g., Ma et al., *Molecular Therapy Nucleic Acids*, 3: e161; doi:10.1038/mtna.2014.12 (2014)). Examples of RNA Pol III promoters that can be used in the invention include, but are not limited to, the U6 promoter and the H1 promoter, which are described in, for example Goomer and Kunkel, *Nucl. Acids Res.*, 20 (18): 4903-4912 (1992), and Myslinski et al., *Nucleic Acids Res.*, 29(12): 2502-9 (2001), respectively.

In another embodiment, the guide RNA sequence and/or the nucleic acid sequence encoding the Cas9 protein (if included in the lentivirus vector genome) is operably linked to a woodchuck hepatitis virus post-transcriptional regulatory element (WPRE). The WPRE is a tripartite cis-acting RNA element that is required for the cytoplasmic accumulation of woodchuck hepatitis virus (WHV) surface RNAs which has been shown to enhance transgene expression from retroviral vectors and improve their performance (see, e.g., Donello et al., *J. Virol.*, 72(6): 5085-5092 (1998); and Zufferey et al., *J. Virol.*, 73(4): 2886-2892 (1999)). The WPRE is two to three times more active than the bipartite post-transcriptional regulatory element of the closely related hepatitis B virus (HBVPRE) (Donello et al., supra).

In addition to the guide RNA sequence, the nucleic acid sequence encoding the Cas9 protein (if included in the lentivirus vector genome), and the optional donor nucleic acid sequence (if present and integrated into the lentiviral genome), the lentiviral vector desirably comprises other elements necessary for viral replication and packaging. Such elements include long terminal repeats (LTRs) (e.g., self-inactivating LTRs (SIN-LTRs)), a packaging signal, and a 3' untranslated region. The LTRs, including SIN-LTRs, are identical sequences of DNA that flank the ends of the retroviral genome and are necessary for integration of the double-stranded viral genome into the host chromosome. The packaging signal (also referred to as a "packaging sequence" or "Psi (Ψ)-sequence") is located in the 5' LTR and is necessary for packaging viral RNA into virus capsids. The 3' untranslated region (3'UTR) is a sequence transcribed into RNA but not translated into protein, and typically contains regulatory regions that influence post-transcriptional gene expression.

When a donor nucleic acid molecule is included in the inventive system as part of the lentiviral genome and comprises a second DNA sequence that encodes the β-globin protein, the lentivirus vector also comprises a locus control region (LCR). An LCR is a nucleic acid sequence that is operationally defined by its ability to enhance the expression of linked genes to physiological levels in a tissue-specific and copy number-dependent manner at ectopic chromatin sites. LCRs have been identified in a large number of mammalian genes, including the human β-globin locus (see, e.g., Li et al., *Blood*, 100(9): 3077-3086 (2002); and Li et al., *Trends Genet.*, 15(10): 403-8 (1999)). The β-globin LCR is a 5 kb regulatory element 10-60 kb upstream of the globin structural genes. The LCR encompasses six highly conserved subdomains, HS1, HS2, HS3, HS4, HS5, and 3'HS1, which were originally identified as DNase I hypersensitive sites (HSs) (see, e.g., Reik et al., *Mol. Cell. Biol.*, 18: 5992-6000 (1998); Hardison et al., *Gene*, 205, 73-94 (1997); Forrester et al., *Proc. Natl Acad. Sci. USA*, 83: 1359-1363 (1986); Tuan et al., *Proc. Natl Acad. Sci. USA*, 82: 6384-6388 (1985); and Jackson et al., *Nucleic Acids Res.*, 31(4): 1180-1190 (2003)).

Methods for generating lentiviral vectors are well-known in the art, and the inventive lentiviral vector can be constructed using any suitable such method. As discussed above, lentiviral vectors typically are produced by co-transfecting 293T human embryonic kidney cells with several different plasmid constructs, which separately contain the lentiviral cis-acting sequences and trans-acting factors that are required for viral particle production, infection, and integration. Lentiviral vector production systems typically include four plasmids. The transfer vector contains the transgene be delivered in a lentiviral backbone containing all of the cis-acting sequences required for genomic RNA production and packaging. Three additional provide the trans-acting factors required for packaging, namely Gag-Pol, Rev-Tat, and the envelope protein VSVG, respectively. When these four plasmids are transfected into 293T human embryonic kidney cells, viral particles accumulate in the supernatant, and the viral product can be concentrated by ultracentrifugation. Lentiviral production protocols are further described in, for example, Tiscornia et al., *Nature Protocols*, 1: 241-245 (2006); Stevenson, M., *Curr. Top. Microbiol. Immunol.*, 261: 1-30 (2002); Cronin et al., *Curr. Gene Ther.*, 5: 387-398 (2005); Sandrin et al., *Curr. Top. Microbiol. Immunol.*, 281: 137-178 (2003); Zufferey, R., *Curr. Top. Microbiol. Immunol.*, 261: 107-121 (2002); Sinn et al., *Gene Ther.*, 12: 1089-1098 (2005); and Saenz, D. T. and Poeschla, E. M., *J. Gene Med.*, 6: S95-S104 (2004). Other methods for producing lentiviral vectors are known in the art and described in, for example, U.S. Patent Application Publications 2008/0254008 and 2010/0003746; and Yang et al., *Hum Gene Ther. Methods*, 23(2): 73-83 (2012).

In other embodiments, the invention provides a vector having the sequence of any one of SED ID NOS: 8-39.

The invention provides a composition comprising the system described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the system comprising a lentivirus vector particle, a Cas9 protein, and optionally a donor nucleic acid molecule. Any suitable carrier can be used within the context of the invention, and such carriers are well known in the art. The choice of carrier will be determined, in part, by the particular use of the composition (e.g., administration to an animal) and the particular method used to administer the composition. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the inventive system is part of a composition formulated to protect the lentiviral vector from damage prior to administration. For example, the composition can be formulated to reduce loss of the lentiviral vector on devices used to prepare, store, or administer lentiviral vector, such as glassware, syringes, or needles. The composition can be formulated to decrease the light sensitivity and/or temperature sensitivity of the system. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the system, and facilitate its administration. Formulations for lentiviral-containing compositions are further described in, for example, Ausubel et al., *Bioprocess Int.*, 10(2): 32-43 (2012), U.S. Pat. No. 7,575,924, and International Patent Application Publication WO 2013/139300.

In an embodiment, the invention provides a host cell comprising the system described herein or a composition comprising the inventive system. In this respect, the invention provides a host cell transduced with the lentivirus vector particle, Cas9 protein, and optionally a donor nucleic acid molecule as described herein or a composition comprising the aforementioned components. Preferred host cells are those that can be easily and reliably grown, have reasonably fast growth rates, have well characterized expression systems, and can be transformed, transfected, or transduced easily and efficiently with a lentiviral vector. The host cell can be any suitable eukaryotic cell known in the art including, for example, yeast cells, insect cells, and mammalian cells. Preferably, mammalian cells are utilized in the invention. In one embodiment, the host cells are packaging cells used for producing lentiviral vector particles, including, for example, 293T cells (ATCC No. CRL-3216) and HT1080 cells (ATCC No. CCL-121). In another embodiment, the host cell is a hematopoietic stem cell. Hematopoietic stem cells (HSCs) are multipotent, self-renewing progenitor cells that develop from mesodermal hemangioblast cells. All differentiated blood cells (i.e., myelocytes, lymphocytes, erythrocytes, and platelets) arise from HSCs. HSCs can be found in adult bone marrow, peripheral blood, and umbilical cord blood. In another embodiment, the host cell is a cell that expresses the CD34 protein, which is also referred to as a "CD34+" cell. CD34 is a cell surface glycoprotein that functions as a cell-cell adhesion factor and may also mediate the attachment of stem cells to bone marrow extracellular matrix or directly to stromal cells. CD34 is a marker for primitive blood- and bone marrow-derived progenitor cells, especially for HSCs.

Hematopoietic stem cells can be harvested from bone marrow, peripheral blood, or umbilical cord blood of the mammal (e.g., a human) using methods known in the art, such as those described in, for example, Wognum et al., *Arch Med Res.*, 34(6): 461-75 (2003); Ng et al., *Methods Mol. Biol.*, 506: 13-21 (2009); Weissman and Shizuru, *Blood*, 112(9): 3543-3553 (2008); Frisch and Calvi, *Skeletal Development and Repair Methods in Molecular Biology*, 1130: 315-324 (2014); and U.S. Pat. No. 8,383,404. For example, HSCs can be harvested from the pelvis, at the iliac crest, using a needle and syringe. Alternatively, HSCs can be isolated from circulating peripheral blood by injecting the mammal (or allogeneic donor) with a cytokine, such as granulocyte-colony stimulating factor (G-CSF), that induce cells to leave the bone marrow and circulate in the blood vessels.

In another embodiment, the host cell is a somatic cell. The term "somatic cell," as used herein, refers to any cell forming the body of an organism other than a gamete, germ cell, gametocyte, or undifferentiated stem cell. Any cells, other than germ cells, of mammalian origin (e.g., humans, mice, monkey, swine, rat etc.) can be harvested from an organism and used as a somatic cell in the context of the invention. Examples of somatic cells include, but are not limited to, keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., bacillary cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells thereof (tissue progenitor cells), and the like. There is no limitation on the degree of cell differentiation, age of animal from which cells are collected and the like. Furthermore, undifferentiated progenitor cells (including somatic stem cells) and finally differentiated mature cells can be used as sources of somatic cells in the present invention. Examples of undifferentiated progenitor cells include tissue stem cells (somatic stem cells) such as nerve stem cells, hematopoietic stem cells (discussed above), mesenchymal stem cells, and dental pulp stem cells.

The harvested HSCs or somatic cells can be "autologous" or "allogeneic." Autologous HSCs or somatic cells are removed from a mammal, stored (and optionally modified), and returned back to the same mammal. Allogeneic HSCs or somatic cells are removed from a mammal, stored (and optionally modified), and transplanted into a genetically similar, but not identical, recipient. Preferably, the cells are autologous to the mammal.

In an embodiment, the inventive system comprising a lentivirus vector particle, or composition comprising the inventive system, may be introduced into a host cell by "transfection," "transformation," or "transduction." The terms "transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols*, Humana Press (1991)); DEAE-dextran; electroporation; cationic liposome-mediated transfection; tungsten particle-facilitated microparticle bombardment (Johnston, *Nature*, 346: 776-777 (1990)); and strontium phosphate DNA co-precipitation (Brash et al., *Mol. Cell Biol.*, 7: 2031-2034 (1987)). Lentiviral vectors typically are introduced into host cells after growth of infectious particles in suitable packaging cells.

The host cells may be transduced with the lentiviral vector in vivo or in vitro, depending on the ultimate application. When the host cells are HSCs, the HSCs preferably are transduced in vitro with the inventive system or composition comprising the inventive system followed by infusion of the transduced stem cells into the mammal. In this embodiment, the human stem cell can be removed from a human patient using methods well known in the art and transduced as described above. The transduced HSCs are then reintroduced into the same (autologous) or different mammal (allogeneic).

Once harvested and transduced with the inventive system or composition in vitro, HSCs can be cultured under suitable conditions known in the art. The HSCs are cultured under conditions in which the one or more guide RNAs, Cas9 protein (if encoded by the lentiviral vector), and donor nucleic acid molecule (if included) are expressed. HSCs can be cultured using methods known in the art, such as those described in, for example, Csaszar et al., *Cell Stem Cell.*, 10(2): 218-29 (2012); Madlambayan et al., *Biol Blood Marrow Transplant.*, 12(10): 1020-1030 (2006); Woods et al., *Stem Cells*, 29(7): 1158-1164 (2011); U.S. Patent Application Publications 2002/0061293 and 2012/0071397; and International Patent Application Publication WO 2014/043131; or using commercially available systems, such as those available from, for example, Life Technologies Corp., Carlsbad, Calif. and Stem Cell Technologies, Inc., Vancouver, BC.

In embodiments where the host cell is a somatic cell, the somatic cell preferably is transduced in vitro with the inventive system or composition comprising the inventive system and cultured under conditions to generate induced pluripotent stem cells (also known as iPS cells or iPSCs). An iPS cell is a type of pluripotent stem cell that can be generated directly from somatic (typically adult) cells by introducing appropriate reprogramming factors into somatic cells. A "reprogramming factor" refers to any substance(s) capable of inducing an iPS cell from a somatic cell, and can be a proteinaceous molecule, a nucleic acid sequence encoding same, or a low-molecular compound. Reprogramming factors typically used to generate iPS cells include, but are not limited to, the four genes Oct3/4, Sox2, Klf4, and c-Myc (see, e.g., U.S. Pat. No. 8,951,801, International Patent Application Publication WO 2007/069666; and Takahashi, K. and Yamanaka, S., *Cell*, 126: 663-676 (2006)).

In another embodiment, the host cell can be a mammalian induced pluripotent stem (iPS) cell that can be derived from various types of somatic cells, such as those described herein. The iPS cell preferably is transduced in vitro with the inventive system or composition comprising the inventive system and can be differentiated into hematopoietic stem cells, red blood cells, or other suitable cell type.

Somatic cells separated from a mammal such as mouse or human can be pre-cultured using any suitable medium known in the art, depending on the cell type. Examples of such media include, but are not limited to, a minimal essential medium (MEM) comprising about 5 to 20% fetal calf serum, Dulbecco's modified Eagle medium (DMEM), RPMI1640 medium, 199 medium, F12 medium, and the like. When a transfer reagent such as cationic liposome, for example, is used for mediating contact between the somatic cell and a reprogramming factor, the medium can be exchanged with a serum-free medium in order to prevent reductions in transfer efficiency. Methods for culturing somatic cells to produce iPS cells are described in, for example, U.S. Pat. No. 8,951,801, International Patent Application Publication WO 2007/069666; and Takahashi, K. and Yamanaka, S., supra).

The invention provides a method of altering a DNA sequence in a host cell, which method comprises contacting a host cell comprising a first DNA sequence with the system described herein, wherein (a) the at least one guide RNA sequence is expressed in the host cell and binds to the first DNA sequence in the host cell genome, and (b) the Cas9 protein induces a double strand break in the first DNA sequence, thereby altering a DNA sequence in a host cell. Descriptions of the lentivirus vector, the guide RNA sequence, the host cell, and the Cas9 protein set forth above in connection with the inventive system also are applicable to the inventive method of altering a DNA sequence in a host cell.

The phrase "altering a DNA sequence," as used herein, refers to modifying at least one physical feature of a wild-type DNA sequence of interest. DNA alterations include, for example, single or double strand DNA breaks, deletion or insertion of one or more nucleotides, and other modifications that affect the structural integrity or nucleotide sequence of the DNA sequence. In one embodiment, the inventive method introduces a single strand or double strand break in the first DNA sequence. In this respect, the Cas9 protein directs cleavage of one or both strands of a target sequence (e.g., the first DNA sequence), such as within the target sequence and/or within the complement of the target sequence. In some embodiments, the Cas9 protein directs cleavage of one or both strands of a target sequence within about 1, 2, 3, 4, 5, 6, 7, 8, 9, 10, 15, 20, 25, 50, 100, 200, 500, or more base pairs from the first or last nucleotide of a target sequence. In one embodiment, the Cas9 protein can be mutated with respect to a corresponding wild-type Cas9 protein such that the mutated Cas9 enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase that cleaves a single DNA strand. Other examples of mutations that render Cas9 a nickase include, without limitation, H840A, N854A, and N863A. Desirably, the inventive method alters a first DNA sequence in a host cell so as to modulate expression of the first DNA sequence, i.e., expression of the first DNA sequence is increased or decreased.

In one embodiment, the Cas9 protein cleaves a target sequence, such as the first DNA sequence of the host cell, to produce double strand DNA breaks. The double strand breaks can be repaired by the host cell by either non-homologous end joining (NHEJ) or homologous recombination. In NHEJ, the double-strand breaks are repaired by direct ligation of the break ends to one another. As such, no new nucleic acid material is inserted into the DNA break location; however, some nucleic acid material may be lost, resulting in a deletion. In homologous recombination repair, a donor nucleic acid molecule comprising a second DNA sequence with homology to the cleaved target DNA sequence is used as a template for repair of the cleaved target DNA sequence, resulting in the transfer of genetic information from the donor nucleic acid molecule to the target DNA. As a result, new nucleic acid material is inserted/copied into the DNA break site. The modifications of the target sequence due to NHEJ and/or homologous recombination repair lead to, for example, gene correction, gene replacement, gene tagging, transgene insertion, nucleotide deletion, gene disruption, gene mutation, gene knock-down, and the like.

As discussed above, in some embodiments the inventive system further comprises a donor nucleic acid molecule comprising a second DNA sequence, which can be different from the first DNA sequence. In the context of the inventive method, the first DNA sequence of the host cell is replaced with the second DNA sequence by homologous recombination following Cas9-mediated cleavage of the first DNA sequence. When the inventive method is used to correct one or more defects or mutations in a gene (referred to as "gene correction"), the first DNA sequence encodes a defective protein and the second DNA sequence encodes a wild-type version of the defective protein. In such cases, the first and second DNA sequences encode defective and wild-type versions, respectively, of any suitable protein. Preferably the first DNA sequence is a "disease-associated" gene, which refers to any gene or polynucleotide whose gene products are expressed at an abnormal level or in an abnormal form in cells obtained from a disease-affected individual as compared with tissues or cells obtained from an individual not affected by the disease. A disease-associated gene may be expressed at an abnormally high level or at an abnormally low level, where the altered expression correlates with the occurrence and/or progression of the disease. A disease-associated gene also refers to a gene, the mutation or genetic variation of which is directly responsible or is in linkage disequilibrium with a gene(s) that is responsible for the etiology of a disease. Examples of genes responsible for such "single gene" or "monogenic" diseases are described above and can be employed in the lentivirus vector system of the inventive method.

In another embodiment, the inventive method can be used to delete nucleic acids from a target sequence in a host cell by cleaving the target sequence and allowing the host cell to repair the cleaved sequence in the absence of an exogenously provided donor nucleic acid molecule. Deletion of a nucleic acid sequence in this manner can be used in a variety of applications, such as, for example, to remove disease-causing trinucleotide repeat sequences in neurons, to create gene knock-outs or knock-downs, and to generate mutations for disease models in research. For example, the inventive method can be used to knock-down the BCL11A gene in hematopoietic cells to induce the production of fetal hemoglobin as a potential therapy for sickle cell disease. BCL11A plays a role in regulating the expression of fetal hemoglobin (HbF) in humans, as down-regulation of BCL11A expression in primary adult erythroid cells leads to robust fetal hemoglobin (HbF) expression (see, e.g., Sankaran et al., *Science*, 322(5909): 1839-1842 (2008)).

Alternatively, if the inventive system is administered to host cells along with a donor nucleic acid molecule that includes a second DNA sequence that includes at least a portion of homology with the first (i.e., target) DNA sequence, the second DNA sequence of the donor nucleic acid molecule is inserted into the host cell genome at the location of the double strand break in the first (i.e., target) DNA sequence (e.g. to "knock-in" a nucleic acid that encodes for a protein, an siRNA, an miRNA, etc.) to add a tag (e.g., 6×His, a fluorescent protein, hemagglutinin (HA), FLAG, etc.), to add a regulatory sequence to a gene (e.g., a promoter, polyadenylation signal, internal ribosome entry sequence (IRES), 2A peptide, start codon, stop codon, splice signal, localization signal, etc.), to modify a nucleic acid sequence (e.g., introduce a mutation), and the like.

In this regard, for example, the inventive method can be used for gene correction in somatic cells obtained from a human patient, which can then be converted to induced pluripotent stem (iPS) cells. For example, a somatic cell comprising a first DNA sequence encoding a defective protein, as described herein, can be contacted with the inventive system and a donor nucleic acid molecule comprising a second DNA sequence that encodes a wild-type version the defective protein. For example, the second DNA sequence can encode a wild-type version of the β-globin protein to correct a mutation responsible for a hemoglobinopathy, such as sickle cell disease. iPS cells can then be generated by introducing one or more reprogramming factors, such as, for example, an Oct4 protein, a Sox2 protein, a Klf4 protein, and/or a c-Myc protein, into a gene-corrected somatic cell using any suitable method known in the art, such as those described in, e.g., see, e.g., U.S. Pat. No. 8,951,801, International Patent Application Publication WO 2007/069666; and Takahashi, K. and Yamanaka, S., Cell, 126: 663-676 (2006). The gene-corrected iPS cells can be differentiated into various types of cells, including hematopoietic stem cells, red blood cells, or any other suitable cell type.

The host cell can be any suitable eukaryotic host cell described herein, such as, for example, a hematopoetic stem cell (HSC), a somatic cell, or an iPS cell, and the host cell may be transduced with the inventive system in vivo or in vitro, depending on the ultimate application as described above. In one embodiment, the host cell is harvested from a mammal and transplanted into the mammal after the DNA sequence has been altered. The cell can be harvested from a mammal using any suitable method known in the art and described herein, modified by the inventive method to alter a DNA sequence in the host cell, and then transplanted back into the mammal using any suitable method known in the art and described herein.

The following includes certain aspects of the invention.

Aspect 1. A system comprising:
(a) a lentivirus vector particle comprising a lentiviral genome which encodes at least one guide RNA sequence that is complementary to a first DNA sequence in a host cell genome,
(b) a Cas9 protein, and optionally
(c) a donor nucleic acid molecule comprising a second DNA sequence.

Aspect 2. The system of aspect 1, wherein the first DNA sequence encodes a defective protein.

Aspect 3. The system of aspect 1 or 2, wherein the first DNA sequence encodes a defective human β-globin protein.

Aspect 4. The system of aspect 1, which comprises a donor nucleic acid molecule comprising a second DNA sequence.

Aspect 5. The system of aspect 4, wherein the second DNA sequence is different from the first DNA sequence.

Aspect 6. The system of aspect 4 or aspect 5, wherein the donor nucleic acid molecule is incorporated into the lentiviral genome.

Aspect 7. The system of any one of aspects 4-6, wherein the first DNA sequence encodes a defective protein and the second DNA sequence encodes a wild-type version of the defective protein.

Aspect 8. The system of aspect 7, wherein the first DNA sequence encodes a defective human β-globin protein and the second DNA sequence encodes a wild-type human β-globin protein.

Aspect 9. The system of any one of aspects 1-8, wherein the lentiviral vector particle integrates its genome into a host cell genome.

Aspect 10. The system of any one of aspects 1-8, wherein the lentiviral vector particle does not integrate its genome into a host cell genome.

Aspect 11. The system of any one of aspects 1-10, wherein the Cas9 protein is provided as a fusion protein comprising a Cas9 protein and a cyclophilin A (CypA) protein.

Aspect 12. The system of aspect 11, wherein the fusion protein binds to a capsid protein of the lentivirus vector particle via the CypA portion of the fusion protein.

Aspect 13. The system of aspect 11 or aspect 12, wherein the fusion protein comprises the amino acid sequence of SEQ ID NO: 2 or SEQ ID NO: 3.

Aspect 14. A host cell comprising the system of any one of aspects 1-13.

Aspect 15. The host cell of aspect 15, wherein the at least one guide RNA sequence is expressed in the host cell and binds to the first DNA sequence in the host cell genome that is complementary to the at least one guide RNA sequence, and the Cas9 protein cleaves the first DNA sequence.

Aspect 16. The host cell of aspect 14 or aspect 15, which is a mammalian hematopoietic cell, a mammalian somatic cell, or a mammalian induced pluripotent stem (iPS) cell.

Aspect 17. A method of altering a DNA sequence in a host cell, which method comprises contacting a host cell comprising a first DNA sequence with the system of any one of aspects 1-16, wherein:

(a) the at least one guide RNA sequence is expressed in the host cell and binds to the first DNA sequence in the host cell genome,
(b) the Cas9 protein induces a double strand break in the first DNA sequence, thereby altering a DNA sequence in a host cell.

Aspect 18. The method of aspect 17, wherein the system comprises a donor nucleic acid molecule comprising a second DNA sequence.

Aspect 19. The method of aspect 18, wherein the second DNA sequence of the donor nucleic acid molecule is different from the first DNA sequence.

Aspect 20. The method of aspect 18 or aspect 19, wherein the first DNA sequence is replaced with the second DNA sequence after step (b).

Aspect 21. The method of aspect 20, wherein the first DNA sequence is replaced with the second DNA sequence by homologous recombination.

Aspect 22. The method of any one of aspects 18-21, wherein the first DNA sequence encodes a defective protein and the second DNA sequence encodes a wild-type version of the defective protein.

Aspect 23. The method of aspect 22, wherein the first DNA sequence encodes a defective human β-globin protein and the second DNA sequence encodes a wild-type human β-globin protein.

Aspect 24. The method of aspect 18, wherein the second DNA sequence of the donor nucleic acid molecule is inserted into the host cell genome at the location of the double strand break in the first DNA sequence.

Aspect 25. The method of aspect 17, wherein the first DNA sequence encodes a BCL11A protein.

Aspect 26. The method of any one of aspects 17-25, wherein the host cell is in vivo.

Aspect 27. The method of any one of aspects 17-25, wherein the host cell is in vitro.

Aspect 28. The method of aspect 25, wherein the host cell is harvested from a mammal and transplanted into the mammal after the DNA sequence has been altered.

Aspect 29. The method of any one of aspects 17-28, wherein the host cell is a mammalian hematopoietic stem cell, a mammalian somatic cell, or a mammalian induced pluripotent stem (iPS) cell.

Aspect 30. A fusion protein comprising a Cas9 protein and a cyclophilin A (CypA) protein, wherein the fusion protein binds to a lentivirus vector particle.

Aspect 31. The fusion protein of aspect 30, which comprises the amino acid sequence of SEQ ID NO: 2 or SEQ ID NO: 3.

Aspect 32. A lentivirus vector particle bound to the fusion protein of aspect 30 or 31 comprising a lentiviral genome which encodes at least one guide RNA sequence that is complementary to a first DNA sequence in a host cell genome and optionally comprises a donor nucleic acid molecule comprising a second DNA sequence, wherein the fusion protein binds to a capsid protein of the lentivirus vector particle via the CypA portion of the fusion protein.

Aspect 33. The lentivirus vector particle of aspect 32, wherein the lentiviral genome comprises a donor nucleic acid molecule comprising a second DNA sequence.

Aspect 34. The lentivirus vector particle of aspect 33, wherein the second DNA sequence of the donor nucleic acid molecule is different from the first DNA sequence.

Aspect 35. A vector having the sequence of any one of SEQ ID NOS: 8-39.

Aspect 36. A system comprising:

(a) a lentivirus vector particle comprising a lentiviral genome which encodes at least two guide RNA sequences that are each complementary to a first DNA sequence in a host cell genome, (b) a Cas9 protein, and optionally (c) a donor nucleic acid molecule comprising a second DNA sequence.

Aspect 37. The system of aspect 36, wherein the first DNA sequence encodes a defective human β-globin protein.

Aspect 38. The system of aspect 36, which comprises a donor nucleic acid molecule comprising a second DNA sequence.

Aspect 39. The system of aspect 38, wherein the second DNA sequence encodes a wild-type human β-globin protein.

Aspect 40. The system of aspect 36, wherein the Cas9 protein is provided as a fusion protein comprising a Cas9 protein and a cyclophilin A (CypA) protein.

Aspect 41. The system of aspect 40, wherein the fusion protein comprises the amino acid sequence of SEQ ID NO: 2 or SEQ ID NO: 3.

Aspect 42. The system of aspect 36, wherein the lentiviral genome encodes 3, 5, 7, or 10 guide RNA sequences.

Aspect 43. A host cell comprising the system of aspect 36.

Aspect 44. The host cell of aspect 43, which is a mammalian hematopoietic cell, a mammalian somatic cell, or a mammalian induced pluripotent stem (iPS) cell.

Aspect 45. A method of altering a DNA sequence in a host cell, which method comprises contacting a host cell comprising a first DNA sequence with the system of aspect 36, wherein:

(a) the at least one guide RNA sequence is expressed in the host cell and binds to the first DNA sequence in the host cell genome, (b) the Cas9 protein induces a double strand break in the first DNA sequence, thereby altering a DNA sequence in a host cell.

The following examples further illustrate the invention but, of course, should not be construed as in any way limiting its scope.

Example 1

This example demonstrates the generation of a lentivirus vector system for delivering CRISPR/Cas9 elements to eukaryotic cells.

To deliver both guide RNA and Cas9 endonuclease into target cells, an HIV-1 based lentiviral vector system, SJ1 (Hanawa et al., Mol Ther., 5(3):242-51 (2002)), was used, which allows for efficient gene delivery in various cells, including hematopoietic stem cells and embryonic stem (ES) cells or induced pluripotent stem (iPS) cells. In this system, transgene expression cassettes can be integrated into genomic DNA in target cells, which allows for long-term transgene expression. Three types of lentiviral vectors were generated by co-transfection of Gag-Pol, Rev-Tat, vesicular stomatitis virus G glycoprotein envelope, and lentiviral vector plasmids, where each of the lentiviral plasmids encoded both guide RNA specific for green fluorescent protein (GFP) and Cas9 endonuclease. The H1 promoter or U6 promoter was used to control guide RNA expression in the lentiviral vectors, and a woodchuck hepatitis virus post-transcriptional regulatory element (WPRE) was added to one lentiviral vector construct to enhance Cas9 expression. Schematic diagrams of each lentiviral vector are depicted in FIG. 1 (LTR: long terminal repeat, and Mp: murine stem cell virus promoter), where vector (1) has the sequence at SEQ ID NO: 8, vector (2) has the sequence at SEQ ID NO: 9, and vector (3) has the sequence at SEQ ID NO: 10.

Figure 2:
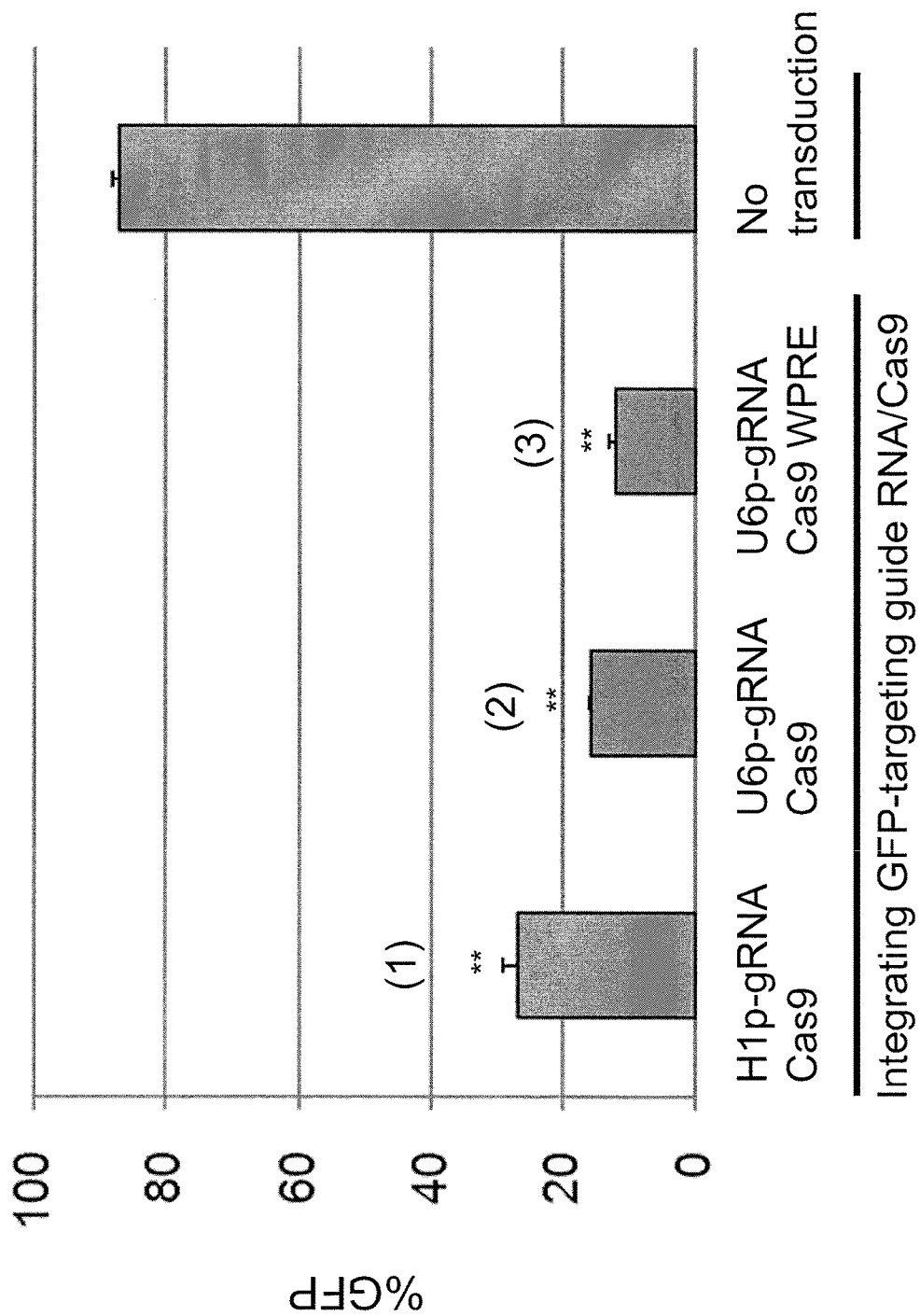

To compare the CRISPR/Cas9 function of GFP DNA breakage, a GFP+HEL cell line (a human erythroleukemia cell line including a copy of lentiviral vector encoding GFP integrated into the cell genome) was separately transduced with each of the guide RNA/Cas9 lentiviral vectors and 12 days later reduction of the GFP-positivity (% GFP) was evaluated in transduced cells. % GFP was strongly reduced with all guide RNA/Cas9 vectors (12-27%, p<0.01), as compared to no transduction control (87%), as shown in FIG. 2 and numbered as in FIG. 1. These data suggest that the guide RNA/Cas9 lentiviral vectors induced GFP DNA double strand breaks.

Figure 3:
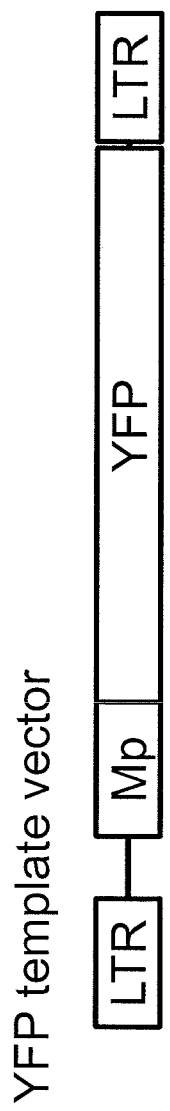
Figure 4:
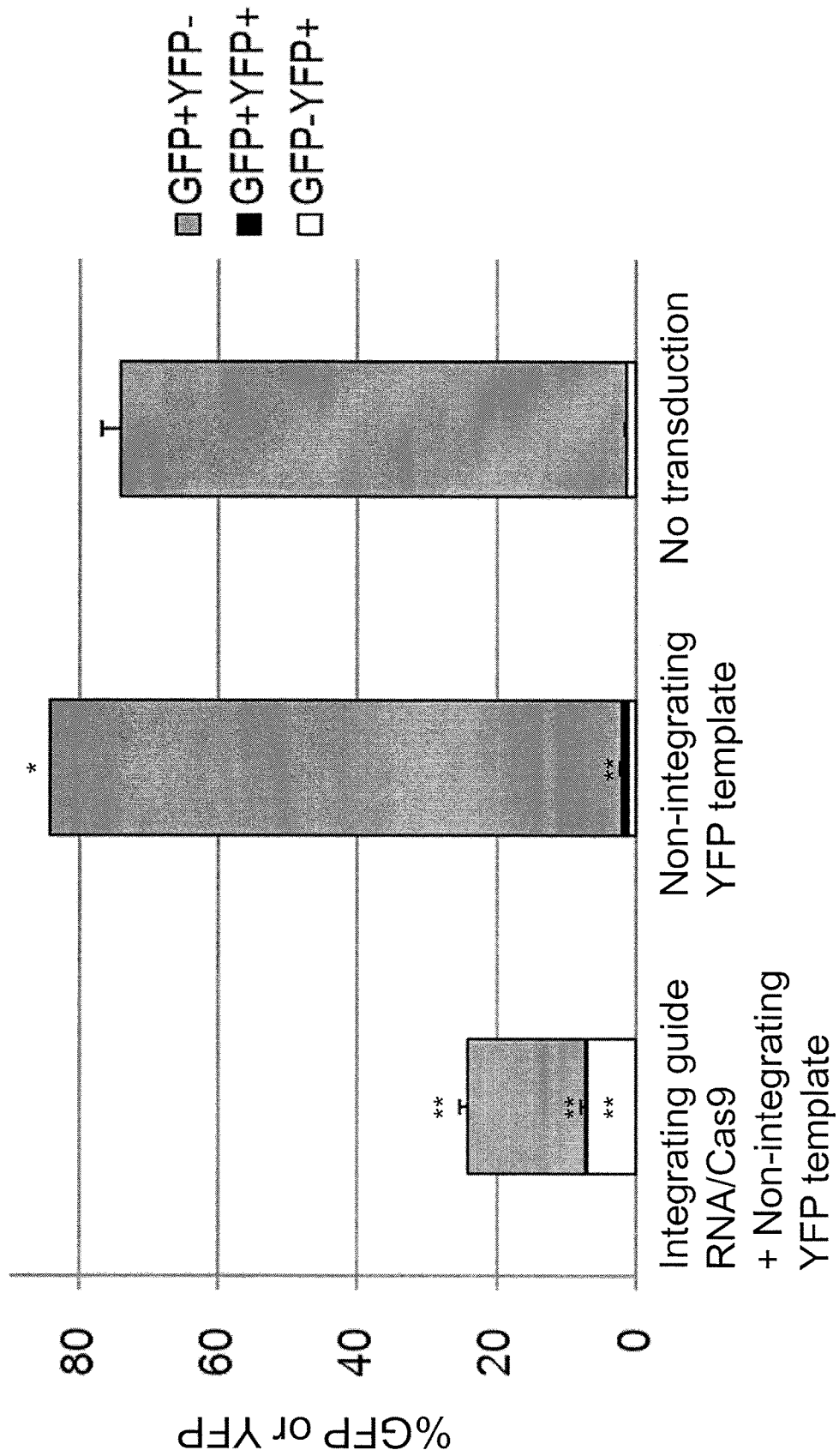

To evaluate whether site-specific DNA breaks improved homologous recombination, a yellow fluorescent protein (YFP) gene template (the YFP gene had an original sequence; vector sequence at SEQ ID NO: 11) was transferred into a GFP+HEL cell line using a non-integrating lentiviral vector (D64V integrase deficient; see FIG. 3) following induction of a DNA break in the GFP sequence mediated by GFP-targeting guide RNA/Cas9 transduction using the vector (2) of FIG. 1. After nine days, higher % YFP (6.9%, p<0.01) and lower % GFP (17%, p<0.01) were observed in treated cells, as compared to YFP template alone control (YFP 1.0%) and no transduction control (YFP 1.3%), as shown in FIG. 4. These data suggest that a GFP DNA break improves homologous recombination-based gene correction, resulting in the replacement of the GFP gene with the YFP gene.

The results of this example demonstrate a method of altering a DNA sequence in a host cell in accordance with the inventive method involving delivery of a CRISPR/Cas9 system.

Example 2

This example describes the generation of a lentivirus vector system in which the Cas9 protein is provided as a packaged fusion protein comprising a Cas9 endonuclease and a cyclophilin A (CypA) protein.

Cells transduced with the guide RNA/Cas9 system described in Example 1 continuously express Cas9 endonuclease even after completing site-specific DNA break and gene correction, which may result in DNA damage in target cells by off-target effects. In addition, the size of the Cas9 gene may be too large to ensure efficient lentiviral packaging in some cases, possibly resulting in reduced transduction efficiency in target cells. To address these issues, a fusion protein containing Cas9 and cyclophilin A was generated. The cyclophilin A (CypA) protein has been shown to bind to lentiviral capsids; thus, it was hypothesized that fusion proteins between Cas9 and CypA could be packaged in lentiviral particles.

Figure 5:
FIG. 5 is a schematic diagram illustrating the guide RNA vector construct described in Example 2, in accordance with embodiments of the invention.
Figure 6:
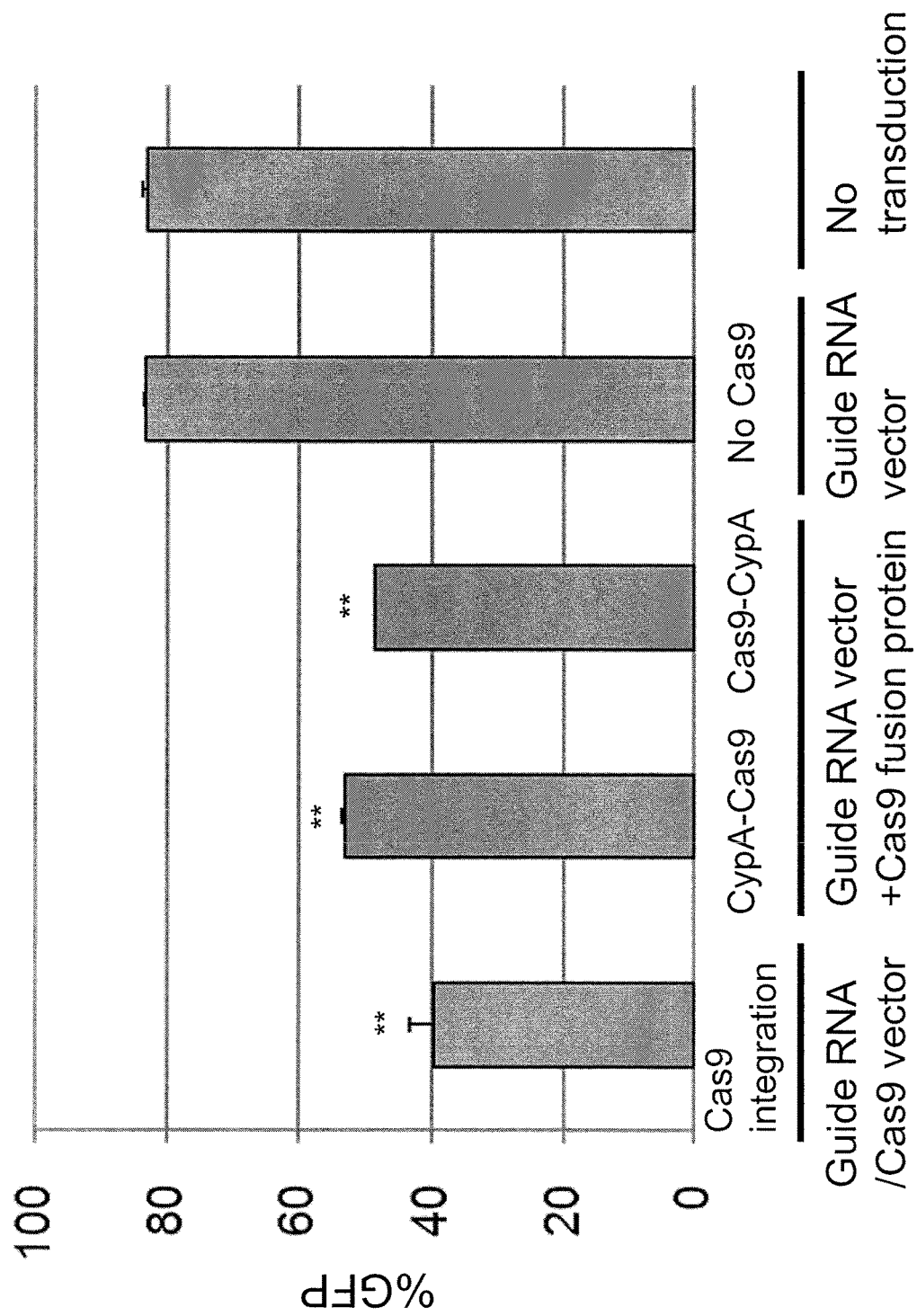
FIG. 6 is a graph depicting experimental results illustrating % GFP in cells transduced with guide RNA-encoding lentiviral vectors described in Example 2 in combination with a Cas9/CypA fusion protein or with a Cas9 protein alone, in accordance with embodiments of the invention. The data shown is 14 days after lentiviral transduction (MOI=5) in GFP+HEL cells (**p<0.01 evaluated by Dunnett's test).

Two Cas9/CypA fusion proteins were designed: "CypA to Cas9" and "Cas9 to CypA." Lentiviral vectors encoding a GFP-targeting guide RNA with the fusion proteins were prepared (vector schematic diagram is at FIG. 5; sequence at SEQ ID NO: 12). A GFP+HEL cell line was separately transduced with the GFP-targeting guide RNA lentiviral vector in combination with the CypA to Cas9 fusion protein or the Cas9 to CypA fusion protein (the proteins packaged in the lentiviral vectors). As shown in FIG. 6, after 14 days % GFP was reduced after transduction with a lentiviral vector in combination with either Cas9/CypA fusion protein (48-53%, p<0.01) as compared to guide RNA alone vector control (83%) and no transduction control (83%), and was comparable to guide RNA/Cas9 integrating vector (2) as in FIG. 1 (40%).

The results of this example suggest that Cas9/CypA fusion proteins can be delivered with lentiviral particles, and the Cas9 fusion proteins have an endonuclease function to induce DNA double strand breaks.

Example 3

This example describes the generation of an embodiment of the inventive lentivirus vector system in which the Cas9 protein is provided to a host cell.

Figure 7:
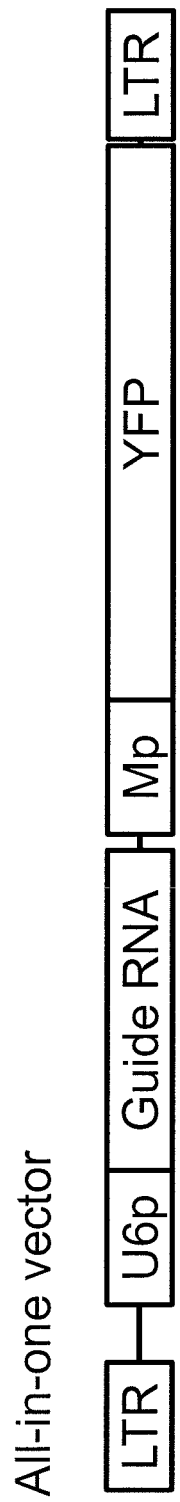
FIG. 7 is a schematic diagram illustrating the all-in-one vector construct described in Example 3, in accordance with embodiments of the invention.

A non-integrating lentivirus vector particle encoding both a GFP-targeting guide RNA and a YFP gene template (i.e., a donor nucleic acid molecule) was generated, and this vector contained all of the essential components for gene correction in a single vector (guide RNA, Cas9 protein, and template; see FIG. 7; sequence at SEQ ID NO: 13). Silent mutations in the target site of YFP template were required to produce the gene correction vector in order for the guide RNA to not target the YFP template. A GFP+HEL cell line was separately transduced with the lentiviral vector in combination with either a Cas9/CypA fusion protein (described in Example 2) or the Cas9 protein itself as a control (the proteins packaged in the lentiviral vectors). Unexpectedly, a higher % YFP (29-30%, p<0.01) and lower % GFP (20-24%, p<0.01) was observed for both the lentiviral vector+Cas9/CypA fusion protein and the lentiviral vector+Cas9, as compared to no Cas9 control (YFP 4.9%) and no transduction control (YFP 4.3%), as shown in FIG. 8. The GFP to YFP gene correction was confirmed by DNA sequencing. In addition, no increase of % YFP by addition of the YFP template was observed six days after Cas9 protein delivery, suggesting that Cas9 function diminished over the short term (<6 days).

The results of this example suggest that the Cas9 protein alone can be delivered with lentiviral particles in accordance with the inventive method, and Cas9 protein delivery allows for efficient one-time gene correction with a non-integrating lentiviral vector encoding both guide RNA and a donor nucleic acid molecule.

Example 4

This example demonstrates Cas9 protein binds to guide RNA sequence in lentiviral RNA genome.

A GFP+HEL cell line was separately transduced with the following Cas9 protein delivery gene correction vectors: (A) an all-in-one vector (both guide RNA and YFP template-encoding vector with Cas9 protein delivery (packaged in the viral vectors)) (SEQ ID NO: 14), (B) a guide RNA-encoding vector (without Cas9) (SEQ ID NO: 15) and a YFP template-encoding vector with Cas9 protein delivery (packaged in the viral vectors) (SEQ ID NO: 16), (C) a guide RNA-encoding vector with Cas9 protein delivery (packaged in the viral vectors) (SEQ ID NO: 17) and a YFP template-encoding vector (without Cas9) (SEQ ID NO: 18), (D) a YFP template-encoding vector with Cas9 protein delivery (packaged in the viral vectors) (SEQ ID NO: 19), and (E) a YFP template-encoding vector (without Cas9) (SEQ ID NO: 20), as depicted in FIGS. 9A and 9B. More efficient GFP to YFP gene correction was observed with the all-in-one vector (YFP 23% and GFP 34%) and guide RNA-encoding vector with Cas9 protein delivery (YFP 14% and GFP 42%), as compared to the template-encoding vector with Cas9 protein delivery (YFP 7% and GFP 70%) and no transduction control (YFP 3% and GFP 86%) (FIG. 10).

These data suggest that the Cas9 protein is dominantly delivered with guide RNA sequence encoded in lentiviral genome.

Example 5

This experiment demonstrates optimization of both β-globin targeting guide RNA sequence and β-globin gene template sequence.

Integrating lentiviral vectors encoding both guide RNA and Cas9 were used since the β-globin gene requires higher efficiency of genome editing than GFP to YFP gene correction.

Three guide RNAs targeting β-globin gene (BG1 (SEQ ID NO: 21), BG2 (SEQ ID NO: 22), and BG3 (SEQ ID NO: 23)) were designed. It was observed that efficient DNA breakage was dependent on the optimal target site and the guide RNA sequence should be started by guanine (BG1g (SEQ ID NO: 24), BG2g (SEQ ID NO: 25), and BG3g (SEQ ID NO: 26)) (FIG. 11).

In addition, a recombination-specific β-globin gene template vector was designed (vector (a) of FIG. 12 with sequence at SEQ ID NO: 27); the vector contains an expression cassette for GFP marker (and drug selection) gene without a polyadenylation signal in the 1st intron. Lower background GFP levels in a recombination-specific template was observed, as compared to a control template containing a GFP expression cassette with a polyadenylation signal (vector (b) of FIG. 12 with sequence at SEQ ID NO: 28) (FIG. 13), suggesting that the recombination-specific template results in more specific and sensitive detection of β-globin gene correction.

Example 6

This example demonstrates Cas9 protein delivery in lentiviral vectors encoding an optimal guide RNA targeting β-globin gene and a β-globin gene template containing a GFP marker gene.

A K562 cell line was separately transduced with the following β-globin gene correction vectors: (I) an integrating vector encoding both guide RNA and Cas9 (SEQ ID NO: 29) and a non-integrating template vector (SEQ ID NO: 30), (II) an integrating guide RNA-encoding vector with Cas9 protein delivery (packaged in the viral vectors) (SEQ ID NO: 31) and a non-integrating template vector (SEQ ID NO: 32), (III) a non-integrating template vector (SEQ ID NO: 33) and a non-integrating guide RNA-encoding vector with Cas9 protein delivery (packaged in the viral vectors) (SEQ ID NO: 34), and (IV) a non-integrating vector encoding both guide RNA and template with Cas9 protein delivery (protein packaged in the viral vectors) (all-in-one vector) (SEQ ID NO: 35), depicted in FIGS. 14A and 14B. In this gene correction model, β-globin gene correction can be evaluated as GFP positivity. Higher % GFP was observed among all 3-globin gene correction vectors (3-42%), as compared to a template only control (0%) (FIG. 15). In this setting, transduction with two separated non-integrating vectors encoding guide RNA or template resulted in more efficient β-globin gene correction (9%), as compared to a non-integrating all-in-one vector (3%). More efficient gene correction was observed in an integrating vector encoding both guide RNA and Cas9 (42%), as compared to a guide RNA-encoding integrating vector with Cas9 protein delivery (17%).

These data demonstrate that the Cas9 protein delivery lentiviral vector system allows for β-globin gene correction in a cell line model.

Example 7

This example demonstrates improved efficiency of Cas9 delivery through the use of multiple guide RNA sequences in the lentiviral vector and increased MOIs.

Multiple "pseudo" guide RNA sequences (without transcription from the vector) were added to an all-in-one vector (encoding both GFP-targeting guide RNA (1×) and YFP template with Cas9 protein delivery). See FIGS. 16A and 16B. In this manner, the pseudo guide RNAs should allow for Cas9 protein delivery but not for guide RNA transcription (due to no promoter).

Increasing numbers of pseudo guide RNA sequences (2×, SEQ ID NO: 36; 4×, SEQ ID NO: 37; 6×, SEQ ID NO: 38; or 9×, SEQ ID NO: 39) resulted in lower vector titers among all-in-one vectors with Cas9 protein delivery (p<0.01), while a multiple pseudo guide RNA vector titer (9×) was increased by removing the Cas9 protein. These data suggest that too much Cas9 protein packaging interferes with lentiviral preparation in multiple pseudo guide RNA vectors.

A GFP+ stable cell line was transduced with multiple pseudo guide RNA vectors, resulting in a strong reduction of % GFP (DNA break) by increasing numbers of pseudo guide RNA (p<0.01), while a maximal increase of % YFP (gene correction) was observed in 4× and 6×pseudo guide RNA vectors (p<0.01). See FIG. 17. These data suggest that multiple pseudo guide RNA vectors enhance DNA breakage, probably mediated by greater amounts of Cas9 protein delivery; however, gene correction was only slightly improved maybe due to insufficient template DNA.

To improve Cas9 protein delivery as well as template DNA delivery, the amounts of all-in-one vector were increased (MOIs 5, 10, 25, and 50) for transduction. Strikingly, lower % GFP and higher % YFP were observed by increasing MOIs (p<0.01). The % GFP reduction in the high MOI transduction (MOI 50) was similar to a 4× pseudo guide RNA vector, while % YFP in the high MOI transduction increased more than the 4× pseudo guide RNA vector. See FIG. 18. These data suggest that multiple pseudo guide RNA enhances DNA break in the all-in-one vector, while improvement of Cas9 protein as well as template DNA delivery is required for efficient gene correction with the all-in-one vector.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

The invention claimed is:

1. A method of forming a system, the system comprising:
   (a) a lentivirus vector particle comprising a lentiviral genome which does not contain a Cas9 gene and encodes at least one guide RNA sequence that is complementary to a first DNA sequence in a host cell genome, wherein the first DNA sequence encodes a defective human β-globin protein, and
   (b) a Cas9 protein within the lentivirus vector particle;
   the method comprising:
   (1) obtaining the Cas9 protein as a non-fusion protein, and
   (2) packaging the non-fusion Cas9 protein into the lentivirus vector particle.

2. The method of claim 1, wherein the system further comprises a donor nucleic acid molecule comprising a second DNA sequence.

3. The method of claim 2, wherein the second DNA sequence encodes a wild-type human β-globin protein.

4. A method of making an isolated host cell, the method comprising forming the system of claim 1 within the isolated host cell.

5. The method of claim 4, wherein the host cell is a mammalian hematopoietic stem cell, a mammalian somatic stem cell, or a mammalian induced pluripotent stem (iPS) cell.

6. A method of altering a DNA sequence in a host cell, which method comprises contacting a host cell comprising a first DNA sequence with the system formed according to the method of claim 1, wherein:
   (a) the at least one guide RNA sequence is expressed in the host cell and binds to the first DNA sequence in the host cell genome, and
   (b) the Cas9 protein induces a double strand break in the first DNA sequence, thereby altering a DNA sequence in a host cell.

7. A vector having the sequence of SEQ ID NO: 35.

8. A method of forming a system, the system comprising:
(a) a lentivirus vector particle comprising a lentiviral genome which does not contain a Cas9 gene and encodes at least two guide RNA sequences that are each complementary to a first DNA sequence in a host cell genome, and
(b) a Cas9 protein within the lentivirus vector particle;
the method comprising:
(1) obtaining the Cas9 protein as a non-fusion protein, and
(2) packaging the non-fusion Cas9 protein into the lentivirus vector particle.

9. The method of claim 8, wherein the first DNA sequence encodes a defective human (β-globin protein.

10. The method of claim 8, wherein the system further comprises a donor nucleic acid molecule comprising a second DNA sequence.

11. The method of claim 10, wherein the second DNA sequence encodes a wild-type human (β-globin protein.

12. The method of claim 8, wherein the lentiviral genome encodes 3, 5, 7, or 10 guide RNA sequences.

13. A method of making an isolated host cell, the method comprising forming the system of claim 8 within the isolated host cell.

14. The method of claim 13, wherein the host cell is a mammalian hematopoietic stem cell, a mammalian somatic stem cell, or a mammalian induced pluripotent stem (iPS) cell.

15. A method of altering a DNA sequence in a host cell, which method comprises contacting a host cell comprising a first DNA sequence with the system formed according to the method of claim 8, wherein:
(a) at least one guide RNA sequence is expressed in the host cell and binds to the first DNA sequence in the host cell genome, and
(b) the Cas9 protein induces a double strand break in the first DNA sequence, thereby altering a DNA sequence in a host cell.

16. A system comprising:
(a) a lentivirus vector particle comprising a lentiviral genome which encodes at least one guide RNA sequence that is complementary to a first DNA sequence in a host cell genome, and
(b) a Cas9 protein associated with the lentivirus vector, wherein the Cas9 protein is provided as a fusion protein comprising a Cas9 protein and a cyclophilin A (CypA) protein, and wherein the fusion protein comprises the amino acid sequence of SEQ ID NO: 2 or SEQ ID NO: 3.

17. The system of claim 16, wherein the first DNA sequence encodes a defective human (β-globin protein.

18. The system of claim 16, wherein the lentiviral genome does not contain a Cas9 gene.

19. The system of claim 16, wherein the lentiviral genome encodes at least two guide RNA sequences that are each complementary to a first DNA sequence in a host cell genome.

20. The system of claim 17, wherein the lentiviral genome encodes at least two guide RNA sequences that are each complementary to a first DNA sequence in a host cell genome.

* * * * *